the(12) United States Patent
Chao et al.

(10) Patent No.: US 7,741,317 B2
(45) Date of Patent: Jun. 22, 2010

(54) LXR MODULATORS

(75) Inventors: Hannguang J. Chao, Pennington, NJ (US); Huji Tuerdi, Pennington, NJ (US); Ellen K. Kick, Pennington, NJ (US); Wu Yang, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 356 days.

(21) Appl. No.: 11/582,673

(22) Filed: Oct. 18, 2006

(65) Prior Publication Data

US 2007/0093470 A1 Apr. 26, 2007

Related U.S. Application Data

(60) Provisional application No. 60/728,964, filed on Oct. 21, 2005.

(51) Int. Cl.
*A01N 43/00* (2006.01)
*A61K 31/55* (2006.01)
*C07D 223/14* (2006.01)

(52) U.S. Cl. .................... 514/213.01; 540/576

(58) Field of Classification Search ............... None
See application file for complete search history.

(56) References Cited

U.S. PATENT DOCUMENTS 4,107,303 A * 8/1978 Aldrich et al. ........... 514/183
5,141,935 A 8/1992 Takenaka et al.

FOREIGN PATENT DOCUMENTS

| EP | 0149974 | | 7/1985 |
|---|---|---|---|
| EP | 0196570 | | 10/1986 |
| EP | 0272914 | | 12/1987 |
| FR | 1472839 A | * | 4/1965 |
| WO | WO 89/08654 | | 9/1989 |
| WO | WO 00/54759 | * | 9/2000 |
| WO | WO 0054759 | * | 9/2000 |
| WO | WO 03/014075 | | 2/2003 |
| WO | WO 03/041641 | | 5/2003 |
| WO | WO 03/063576 | | 8/2003 |
| WO | WO 03068753 | * | 8/2003 |
| WO | WO 2004/014388 | | 2/2004 |
| WO | WO 2004/072042 | | 8/2004 |
| WO | WO 2005019188 | * | 3/2005 |
| WO | WO 2005/090282 | | 9/2005 |
| WO | WO 2005/105791 | | 11/2005 |
| WO | WO 2006/050054 | | 5/2006 |

OTHER PUBLICATIONS

Augustine et al. Journal of Organic Chemistry, 1969, 34(7), 2235-37.*
Hassner et al. Tetrahedron Letters, 1977, 35, 3023-6.*
Meyers et al. Journal of Organic Chemistry, 1993, 58(24), 6538-40.*
Hassner et al. Journal of Organic Chemistry, 2003, 68, 6853-58.*
Hamamoto, Hiromi et al., Chemical & Pharmaceutical Bulletin, vol. 52, No. 10, pp. 1231-1234 (2004).
Hoshino, Osamu et al., Tetrahedron, vol. 57, No. 2, pp. 265-271 (2001).
Hoye, Thomas et al., Journal of Organic Chemistry, vol. 64, No. 19, pp. 7184-7201 (1999).
Kupchan, S. Morris et al., Journal of Organic Chemistry, vol. 43, No. 12, pp. 2521-2529 (1978).
Kupchan, S. Morris et al., Journal of Organic Chemistry, vol. 41, No. 25, pp. 4047-4049 (1976).
Coudert, G. et al., "A new Synthesis of 3,4-Dihydro-2H-1,4-benzoxazines using Solid-Liquid Phase-Transfer Catalysis", Synthesis, vol. 7, pp. 541-543 (1979).
Salvador, A. et al., "Preliminary Studies of Supercritical-Fluid Chromatography on Porous Graphitic Carbon with Methylated Cyclodextrin as Chiral Selector", Chromatographia, vol. 53, No. 3/4, pp. 207-209 (2001).
Sawada, Y. et al., "Synthesis and insecticidal activity of benzoheterocyclic analogues of N-benzoyl-N-(tert-butyl)benzohydrazide: Part 1. Design of benzoheterocyclic analogues", Pest Management Science, vol. 59, No. 1, pp. 25-35 (2003).
Zhou, Y. et al., "Synthesis and Highly Enantioselective Hydrogenation of Exocyclic Enamides: (Z)-3-Arylidene-4-acetyl-3,4-dihydro-2H-1,4-benzoxazines", J. Org, Chem., vol. 70, pp. 1679-1683 (2005).

* cited by examiner

*Primary Examiner*—James O Wilson
*Assistant Examiner*—Noble Jarrell
(74) *Attorney, Agent, or Firm*—Terence J. Bogie

(57) ABSTRACT

A compound of formula I

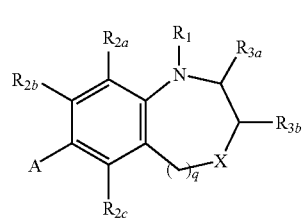

wherein A, X, q, $R_1$, $R_{2a}$, $R_{2b}$, $R_{2c}$, $R_{3a}$, and $R_{3b}$ are defined herein.

17 Claims, No Drawings

LXR MODULATORS

RELATED APPLICATION

This application claims the benefit of U.S. Provisional Application No. 60/728,964, filed on Oct. 21, 2005, incorporated herein by reference in its entirety.

FIELD OF THE INVENTION

The present invention provides for heteroaryl compounds, such as thiazinyl, tetrahydrobenzazepinyl, and related compounds, useful as modulators of nuclear receptors, including liver X receptor (LXR), and to pharmaceutical compositions containing such compounds. The present invention further provides for methods of using such compounds in the treatment and prevention of diseases or disorders mediated by or in which nuclear receptor activity, including LXR and/or orphan nuclear receptor activity.

BACKGROUND OF THE INVENTION

Nuclear receptors are a superfamily of regulatory proteins that are structurally and functionally related and are receptors for, e.g., steroids, retinoids, vitamin D and thyroid hormones (see, e.g., Evans (1988) Science 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) Endocr. Rev. 15:391-407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptors or PPARs) and ecdysone, bind to HREs as heterodimers with a common partner, the retinoid X receptors (i.e., RXRs, also known as the 9-cis retinoic acid receptors; see, e.g., Levin et al. (1992) Nature 355:359-361 and Heyman et al. (1992) Cell 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) Cell 83:841-850). The latter receptors, termed the class II nuclear receptor subfamily, include many which are established or implicated as important regulators of gene expression. There are three RXR genes (see, e.g., Mangelsdorf et al. (1992) Genes Dev. 6:329-344), coding for RXRα, -β, and -γ, all of which are able to heterodimerize with any of the class II receptors, although there appear to be preferences for distinct RXR subtypes by partner receptors in vivo (see, e.g., Chiba et al. (1997) Mol. Cell. Biol. 17:3013-3020). In the adult liver, RXRα is the most abundant of the three RXRs (see, e.g., Mangelsdorf et al. (1992) Genes Dev. 6:329-344), suggesting that it might have a prominent role in hepatic functions that involve regulation by class II nuclear receptors. See also, Wan et al. (2000) Mol. Cell. Biol. 20:4436-4444.

Included in the nuclear receptor superfamily of regulatory proteins are nuclear receptors for whom the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for farnesoid X receptor (FXR).

LXRα is found predominantly in the liver, with lower levels found in kidney, intestine, spleen and adrenal tissue (see, e.g., Willy, et al. (1995) Gene Dev. 9(9):1033-1045). LXRβ is ubiquitous in mammals and was found in nearly all tissues examined. LXRs are activated by certain naturally occurring, oxidized derivatives of cholesterol (see, e.g., Lehmann, et al. (1997) J. Biol. Chem. 272(6):3137-3140). LXRα is activated by oxycholesterol and promotes cholesterol metabolism (Peet et al. (1998) Cell 93:693-704). Thus, LXRs appear to play a role in, e.g., cholesterol metabolism (see, e.g., Janowski, et al. (1996) Nature 383:728-731).

Nuclear receptor activity has been implicated in a variety of diseases and disorders, including, but not limited to, hypercholesterolemia (see, e.g., International Patent Application Publication No. WO 00/57915), osteoporosis and vitamin deficiency (see, e.g., U.S. Pat. No. 6,316,503), hyperlipoproteinemia (see, e.g., International Patent Application Publication No. WO 01/60818), hypertriglyceridemia, lipodystrophy, hyperglycemia and diabetes mellitus (see, e.g., International Patent Application Publication No. WO 01/82917), atherosclerosis and gallstones (see, e.g., International Patent Application Publication No. WO 00/37077), disorders of the skin and mucous membranes (see, e.g., U.S. Pat. Nos. 6,184,215 and 6,187,814, and International Patent Application Publication No. WO 98/32444), acne (see, e.g., International Patent Application Publication No. WO 00/49992), and cancer, Parkinson's disease and Alzheimer's disease (see, e.g., International Patent Application Publication No. WO 00/17334). Activity of nuclear receptors, including LXRs, FXR and PPAR, and orphan nuclear receptors, has been implicated in physiological processes including, but not limited to, bile acid biosynthesis, cholesterol metabolism or catabolism, and modulation of cholesterol 7.alpha-hydroxylase gene (CYP7A1) transcription (see, e.g., Chiang et al. (2000) J. Biol. Chem. 275:10918-10924), HDL metabolism (see, e.g., Urizar et al. (2000) J. Biol. Chem. 275:39313-39317 and International Patent Application Publication No. WO 01/03705), and increased cholesterol efflux and increased expression of ATP binding cassette transporter protein (ABC1) (see, e.g., International Patent Application Publication No. WO 00/78972).

Thus, there is a need for compounds, compositions and methods of modulating the activity of nuclear receptors, including LXRs, FXR, PPAR and orphan nuclear receptors. Such compounds are useful in the treatment, prevention, or amelioration of one or more symptoms of diseases or disorders in which nuclear receptor activity is implicated.

SUMMARY OF THE INVENTION

In accordance with the present invention, thiazinyl compounds, tetrahydrobenzazepinyl compounds and related compounds are provided that have the general structure of formula I:

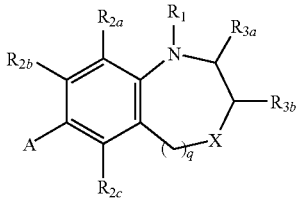

I wherein A, X, q, $R_1$, $R_{2a}$, $R_{2b}$, $R_{2c}$, $R_{3a}$, and $R_{3b}$ are defined below.

By use of a respective effective amount of at least one compound described herein, provided are methods of modulating liver X receptors (LXRα and LXRβ), FXR, PPAR and/or orphan nuclear receptors.

Also provided are pharmaceutical compositions comprising a therapeutically effective amount of at least one compound described herein and a pharmaceutically acceptable vehicle or carrier thereof. Such compositions can further comprise one or more other agent(s). For example, at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as razaxaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

DEFINITIONS

The terms "alk" or "alkyl" refer to straight or branched chain hydrocarbon groups having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described in the definition of $R_{50}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described in the definition of $R_{50}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described in the definition of $R_{50}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described in the definition of $R_{50}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocylcic ring groups of 3 to 15 carbon atoms which are, respectively, fully saturated and partially unsaturated. The rings of multi-ring cycloalkyl groups may be either fused, bridged and/or joined through one or more spiro unions. The term "substituted cycloalkyl" refers to a cycloalkyl group substituted with one or more groups (such as by groups described in the definition of $R_{50}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

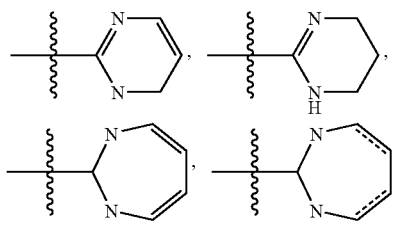

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

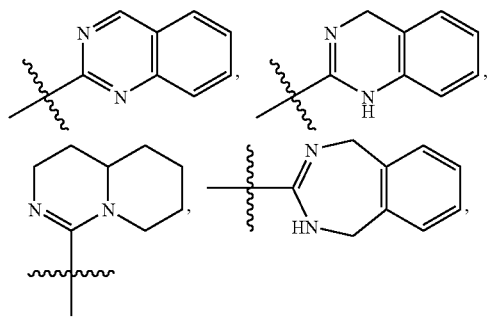

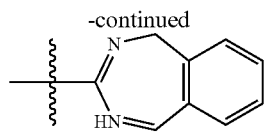

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described in the definition of $R_{50}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

Throughout the specification, groups and substituents thereof may be chosen to provide stable moieties and compounds.

The compounds of formula I form salts or solvates which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
  a) *The Practice of Medicinal Chemistry*, Camille G. Wermuth et al., Ch. 31 (Academic Press, 1996);
  b) *Design of Prodrugs*, edited by H. Bundgaard (Elsevier, 1985);
  c) *A Textbook of Drug Design and Development*, P. Krogsgaard-Larson and H. Bundgaard, eds. Ch. 5, pp. 113-191 (Harwood Academic Publishers, 1991); and
  d) *Hydrolysis in Drug and Prodrug Metabolism*, Bernard Testa and Joachim M. Mayer, (Wiley-VCH, 2003).

Said references are incorporated herein by reference.

In addition, compounds of the formula I are, subsequent to their preparation, may be isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers.

The terms "including", "such as", "for example" and the like are intended to refer to exemplary embodiments and not to limit the scope of the present invention.

DETAILED DESCRIPTION OF THE INVENTION

It will be understood that any given exemplary embodiment can be combined with one or more additional exemplary embodiments.

In accordance with the present invention, compounds of formula I are provided

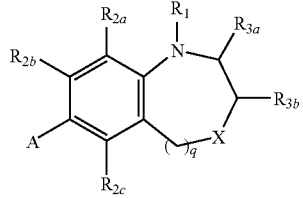

or stereoisomers or pharmaceutically acceptable salts or N-oxides thereof, wherein:

A is

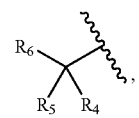

—C(O)NR$_{28}$R$_{29}$, —CO$_2$(C$_1$-C$_6$)-alkyl, or heterocyclyl, wherein the alkyl and heterocyclyl may be optionally substituted with one or more R$_{10a}$'s;

X is O, S, NR$_{19}$ or CR$_{20}$R$_{20}$;

R$_1$ is —C(O)R$_7$, —C(O)OR$_7$, —S(O)$_n$R$_7$, —C(O)C(O)R$_7$, —C(O)NR$_{28}$R$_{29}$, (C$_1$-C$_3$)alkylaryl or (C$_1$-C$_3$)alkylheteroaryl, wherein the alkylaryl and alkylheteroaryl may be optionally substituted with one or more R$_{10b}$'s;

R$_{2a}$, R$_{2b}$ and R$_{2c}$ are independently hydrogen, halo, —OH, —(C$_1$-C$_6$)-alkyl, —O(C$_1$-C$_6$)-alkyl, halo(C$_1$-C$_6$)-alkyl-, halo (C$_1$-C$_6$)-alkyloxy-, cyano, or nitro;

R$_{3a}$ is hydrogen, (C$_1$-C$_8$)alkyl, aryl or heteroaryl, wherein the alkyl, aryl and heteroaryl may be optionally substituted with one or more R$_{10b}$'s;

R$_{3b}$ is (a) hydrogen, (b) —OH, (c) —O[(C=O)]$_s$(C$_1$-C$_6$)-alkyl, (d) —O[(C=O)]$_s$(C$_2$-C$_6$)-alkenyl, (e) R$_{46}$—S(O)$_n$—, (f) R$_{46}$—S(O)$_n$—O—, (g) aryl-(C$_1$-C$_6$)alkyloxy-, which may optionally be substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_2$-C$_6$)-alkenyl, (C$_2$-C$_6$)-alkynyl, (C$_1$-C$_6$)-alkyloxy, (OH)—(C$_1$-C$_6$)-alkyl-, R$_{46}$—S(O)$_n$—, cyano, nitro, —COOH, —(C$_1$-C$_6$)-alkylCOOH, —(C$_1$-C$_6$)-alkylheterocyclyl, —(C$_1$-C$_6$)-alkyl-CONHS(O)$_2$—(C$_1$-C$_6$)-alkyl, —(C$_1$-C$_6$)-alkyl(NH$_2$)COOH, —CO(C$_1$-C$_6$)-alkyl, —(C$_1$-C$_6$)-alkyl-CO$_2$(C$_1$-C$_6$)-alkyl, —CO$_2$(C$_1$-C$_6$)-alkyl, —CONR$_{28a}$R$_{29a}$, —NR$_{28a}$R$_{29a}$, —O(C=O)—(C$_1$-C$_6$)-alkyl, —O(C$_1$-C$_6$-alkylaryl, —O(C=O)NR$_{28a}$R$_{29a}$, aryl, which may be optionally substituted with one or more R$_{50}$'s; heteroaryl, which may be optionally substituted with one or more R$_{50}$'s, and heterocyclo, which may be optionally substituted with one or more R$_{50}$'s; (h) heteroaryl-(C$_1$-C$_6$)alkyloxy-, which may optionally be substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_2$-C$_6$)-alkenyl, (C$_2$-C$_6$)-alkynyl, (C$_1$-C$_6$)-alkyloxy, (OH)—(C$_1$-C$_6$)-alkyl-, $R_{46}$—S(O)$_n$—, cyano, nitro, —COOH, —($C_1$-$C_6$)-alkyl-COOH, —($C_1$-$C_6$)-alkylheterocyclyl, —($C_1$-$C_6$)-alkyl-CONHS(O)$_2$—($C_1$-$C_6$)-alkyl, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —CONR$_{28a}$R$_{29a}$, —NR$_{28a}$R$_{29a}$, —O(C=O)—($C_1$-$C_6$)-alkyl, —O($C_1$-$C_6$)-alkylaryl, —O(C=O)NR$_{28a}$R$_{29a}$, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (i) cyano, (j) —NR$_{28a}$R$_{29a}$, (k) —O(CO)NR$_{28a}$R$_{29a}$, (l) —COOH, (m) —CO($C_1$-$C_6$)-alkyl, (n) —CO$_2$($C_1$-$C_6$)-alkyl, (o) —CONR$_{28a}$R$_{29a}$, (p) aryl which may optionally be substituted with one or more substituents selected from the group consisting of: halo, —OH, ($C_1$-$C_6$)-alkyl, halo($C_1$-$C_6$) alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkylheterocyclyl, —($C_1$-$C_6$)-alkyl-CONHS(O)$_2$—($C_1$-$C_6$)-alkyl, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —CONR$_{28a}$R$_{29a}$, —NR$_{28a}$R$_{29a}$, —O(C=O)—($C_1$-$C_6$)-alkyl, —($C_1$-$C_6$)-alkylaryl, —O(C=O)NR$_{28a}$R$_{29a}$, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (q) heteroaryl optionally substituted with one or more substituents selected from the group consisting of: halo, —OH, ($C_1$-$C_6$)-alkyl, halo($C_1$-$C_6$) alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkylheterocyclyl, —($C_1$-$C_6$)-alkyl-CONHS(O)$_2$—($C_1$-$C_6$)-alkyl, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —CONR$_{28a}$R$_{29a}$, —NR$_{28a}$R$_{29a}$, —O(C=O)—($C_1$-$C_6$)-alkyl, —O($C_1$-$C_6$)-alkylaryl, —O(C=O)NR$_{28a}$R$_{29a}$, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (r) ($C_2$-$C_8$)-alkenyl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkylheterocyclyl, —($C_1$-$C_6$)-alkyl-CONHS(O)$_2$—($C_1$-$C_6$)-alkyl, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —CONR$_{28a}$R$_{29a}$, —NR$_{28a}$R$_{29a}$, —O(C=O)—($C_1$-$C_6$)-alkyl, —O($C_1$-$C_6$)-alkylaryl, —O(C=O)NR$_{28a}$R$_{29a}$, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (s) ($C_2$-$C_8$)-alkynyl wherein alkynyl is optionally substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkylheterocyclyl, —($C_1$-$C_6$)-alkyl-CONHS(O)$_2$—($C_1$-$C_6$)-alkyl, —($C_1$-$C_6$)-alkyl(NH$_2$)COOH, —CO($C_1$-$C_6$)-alkyl, —C($C_1$-$C_6$)-alkyl-CO$_2$($C_1$-$C_6$)-alkyl, —CO$_2$($C_1$-$C_6$)-alkyl, —CONR$_{28a}$R$_{29a}$, —NR$_{28a}$R$_{29a}$, —O(C=O)—($C_1$-$C_6$)-alkyl, —O($C_1$-$C_6$)-alkylaryl, —O(C=O)NR$_{28a}$R$_{29a}$, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (t) —($C_1$-$C_8$)-alkyl, which may optionally be substituted with one or more substituents selected from the group consisting of: halo, —OH, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, ($C_1$-$C_6$)-alkyl-S(O)$_n$—, $R_{46}$—S(O)$_n$—, cyano, ($C_3$-$C_6$)-cycloalkyl, —COOH, —($C_1$-$C_6$)-alkylCOOH, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —CONR$_{28a}$R$_{29a}$, —NR$_{28a}$R$_{29a}$, —O(C=O)—($C_1$-$C_6$)-alkyl, —O($C_1$-$C_6$)-alkylaryl, —O(C=O)NR$_{28a}$R$_{29a}$, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (u) —O[(C=O)]$_s$aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkylheterocyclyl, —($C_1$-$C_6$)-alkyl-CONHS(O)$_2$—($C_1$-$C_6$)-alkyl, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —CONR$_{28a}$R$_{29a}$, NR$_{28a}$R$_{29a}$, —O(C=O)—($C_1$-$C_6$)-alkyl, —O($C_1$-$C_6$)-alkylaryl, —O(C=O)NR$_{28a}$R$_{29a}$, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (v) —O[(C=O)]$_s$heteroaryl, which may optionally be substituted with one or more substituents selected from the group consisting of: halo, —OH, ($C_1$-$C_6$)-alkyl, halo($C_1$-$C_6$) alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkylheterocyclyl, —($C_1$-$C_6$)-alkyl-CONHS(O)$_2$—($C_1$-$C_6$)-alkyl, —($C_1$-$C_6$)-alkyl(NH$_2$)COOH, —CO($C_1$-$C_6$)-alkyl, —C($C_1$-$C_6$)-alkyl-CO$_2$($C_1$-$C_6$)-alkyl, —CO$_2$($C_1$-$C_6$)-alkyl, —CONR$_{28a}$R$_{29a}$, —NR$_{28a}$R$_{29a}$, —O(C=O)—($C_1$-$C_6$)-alkyl, —O($C_1$-$C_6$)-alkylaryl, —O(C=O)NR$_{28a}$R$_{29a}$, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (w) —O[(C=O)]$_s$($C_3$-$C_6$)-cycloalkyl, which may optionally be substituted with one or more substituents selected from the group consisting of: halo, —OH, ($C_1$-$C_6$)-alkyl, halo($C_1$-$C_6$) alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkylheterocyclyl, —($C_1$-$C_6$)-alkyl-CONHS(O)$_2$—($C_1$-$C_6$)-alkyl, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —CONR$_{28a}$R$_{29a}$, —NR$_{28a}$R$_{29a}$, —O(C=O)—($C_1$-$C_6$)-alkyl, —O($C_1$-$C_6$)-alkylaryl, —O(C=O)NR$_{28a}$R$_{29a}$, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_4$, $R_5$ and $R_6$ are independently hydrogen, hydroxy, ($C_1$-$C_4$)-alkyl, or halo($C_1$-$C_4$)-alkyl; provided that (i) only one of $R_4$, $R_5$ or $R_6$ is hydroxy, (ii) $R_5$ and $R_6$ are not both hydrogen when $R_4$ is hydroxy, and (iii) $R_5$ and $R_6$ are halo($C_1$-$C_4$)-alkyl when $R_{3a}$ and $R_{3b}$ are hydrogen and $R_4$ is hydroxy;

$R_7$ is alkyl, cycloalkyl, alkenyl, aryl or heterocyclyl, wherein the alkyl, cycloalkyl, aryl, or heterocyclyl may be optionally substituted with one or more $R_{10b}$'s;

$R_{10a}$ is halo, —OH, —O[(C═O)]$_s$(C$_1$-C$_6$)-alkyl, —O[(C═O)]$_s$(C$_2$-C$_6$)-alkenyl, cyano, nitro, —NR$_{28b}$R$_{29b}$, —COOH, —CO(C$_1$-C$_6$)-alkyl, —CO$_2$(C$_1$-C$_6$)-alkyl, —(C$_1$-C$_6$)-haloalkyl, ═O, —(C$_3$-C$_6$)-cycloalkyl or —(C$_1$-C$_6$)-alkyl;

$R_{10b}$ is (a) halo; (b) —OH; (c) —O[(C═O)]$_s$(C$_1$-C$_6$)-alkyl; (d) —O[(C═O)]$_s$(C$_1$-C$_6$)-alkylaryl; (e) —O[(C═O)]$_s$(C$_2$-C$_6$)-alkenyl; (f) —O[(C═O)]$_s$heteroaryl; (g) R$_{46}$—S(O)$_n$—; (h) aryl-(C$_1$-C$_6$)alkyloxy-; (i) cyano; (j) nitro; (k) —NR$_{28b}$R$_{29b}$; (l) —O(CO)NR$_{28b}$R$_{29b}$; (m) —CO(C$_1$-C$_6$)-alkyl; (n) —CO$_2$(C$_1$-C$_6$)-alkyl; (o) —CONR$_{28b}$R$_{29b}$; (p) aryl, which may optionally be substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_2$-C$_6$)-alkenyl, (C$_2$-C$_6$)-alkynyl, (C$_1$-C$_6$)-alkyloxy, (OH)—(C$_1$-C$_6$)-alkyl-, (C$_1$-C$_6$)-alkyl-S(O)$_n$—, cyano, nitro, —CO(C$_1$-C$_6$)-alkyl, —(C$_1$-C$_3$)-alkyl-CO$_2$(C$_1$-C$_6$)-alkyl, —CO$_2$(C$_1$-C$_6$)-alkyl, —CONR$_{28b}$R$_{29b}$, —NR$_{28b}$R$_{29b}$, —O(C═O)—(C$_1$-C$_6$)-alkyl, —O(C$_1$-C$_6$)-alkylaryl, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (q) heteroaryl optionally substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_2$-C$_6$)-alkenyl, (C$_2$-C$_6$)-alkynyl, (C$_1$-C$_6$)-alkyloxy, (OH)—(C$_1$-C$_6$)-alkyl-(C$_1$-C$_6$)-alkyl-S(O)$_n$—, cyano, nitro, —CO(C$_1$-C$_6$)-alkyl, —(C$_1$-C$_3$)-alkyl-CO$_2$(C$_1$-C$_6$)-alkyl, —CO$_2$(C$_1$-C$_6$)-alkyl, —CONR$_{28b}$R$_{29b}$, —NR$_{28b}$R$_{29b}$, —O(C═O)—(C$_1$-C$_6$)-alkyl, —O(C$_1$-C$_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (r) heterocyclo other than heteroaryl which is optionally substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_2$-C$_6$)-alkenyl, (C$_2$-C$_6$)-alkynyl, (C$_1$-C$_6$)-alkyloxy, (OH)—(C$_1$-C$_6$)-alkyl-(C$_1$-C$_6$)-alkyl-S(O)$_n$—, cyano, nitro, —CO(C$_1$-C$_6$)-alkyl, —(C$_1$-C$_3$)-alkyl-CO$_2$(C$_1$-C$_6$)-alkyl, —CO$_2$(C$_1$-C$_6$)-alkyl, —CONR$_{28b}$R$_{29b}$, —NR$_{28b}$R$_{29b}$, —O(C═O)—(C$_1$-C$_6$)-alkyl, —O(C$_1$-C$_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (s) (C$_2$-C$_6$)-alkenyl, which may optionally be substituted with one or more substituents selected from the group consisting of: halo, —OH, (C$_1$-C$_6$)-alkyl, halo(C$_1$-C$_3$)alkyl, halo(C$_1$-C$_3$)alkyloxy, (C$_1$-C$_3$)-alkyloxy, (OH)—(C$_1$-C$_6$)-alkyl- or cyano; (t) (C$_2$-C$_{10}$)-alkynyl wherein alkynyl is optionally substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_1$-C$_6$)-alkyloxy, (OH)—(C$_1$-C$_6$)-alkyl-, cyano, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (u) —(C$_1$-C$_6$)-alkyl, which may optionally be substituted with one or more substituents selected from the group consisting of: halo, —OH, halo(C$_1$-C$_6$)alkyloxy, (C$_1$-C$_6$)-alkyloxy, cyano, —CO(C$_1$-C$_6$)-alkyl, —CO$_2$(C$_1$-C$_6$)-alkyl, —CONR$_{28b}$R$_{29b}$, —NR$_{28b}$R$_{29b}$, —O(C═O)—(C$_1$-C$_6$)-alkyl, —O(C═O)NR$_{28c}$R$_{29c}$, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (v) ═O, (w) —(C$_3$-C$_8$)-cycloalkyl, which may optionally be substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_1$-C$_6$)-alkyloxy, (OH)—(C$_1$-C$_6$)-alkyl-, (C$_1$-C$_6$)-alkyl-S(O)$_n$—, cyano, nitro, —CO(C$_1$-C$_6$)-alkyl, —(C$_1$-C$_6$)-alkyl-CO$_2$(C$_1$-C$_6$)-alkyl, —CO$_2$(C$_1$-C$_6$)-alkyl, —CONR$_{28b}$R$_{29b}$, —NR$_{28b}$R$_{29b}$, —O(C═O)—(C$_1$-C$_6$)-alkyl, —O(C$_1$-C$_6$)-alkylaryl, —O(C═O)NR$_{28b}$R$_{29b}$, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (x) —O[(C═O)]$_s$aryl, which may optionally be substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_2$-C$_6$)-alkenyl, (C$_2$-C$_6$)-alkynyl, (C$_1$-C$_6$)-alkyloxy, (OH)—(C$_1$-C$_6$)-alkyl-, (C$_1$-C$_3$)-alkyl-S(O)$_n$—, cyano, nitro, —CO(C$_1$-C$_6$)-alkyl, —(C$_1$-C$_6$)-alkyl-CO$_2$(C$_1$-C$_6$)-alkyl, —CO$_2$(C$_1$-C$_6$)-alkyl, —CONR$_{28b}$R$_{29b}$, —NR$_{28b}$R$_{29b}$, —O(C═O)—(C$_1$-C$_6$)-alkyl, and —O(C═O)NR$_{28b}$R$_{29b}$; or (y) halo(C$_1$-C$_6$)alkyloxy;

$R_{19}$ is hydrogen, (C$_1$-C$_4$)-alkyl or —CO(C$_1$-C$_6$)-alkyl;

$R_{20}$ is hydrogen, or (C$_1$-C$_4$)-alkyl; or the two $R_{20}$'s are taken together with the carbon atom to which they are attached to form a 3- to 6-membered ring;

$R_{28}$ and $R_{29}$ are independently hydrogen, aryl, (C$_1$-C$_6$) alkyl, halo(C$_1$-C$_6$)alkyl, aryl(C$_1$-C$_3$)alkyl or heterocyclyl, wherein the aryl, alkyl, arylalkyl and heterocyclyl may be optionally substituted with one or more $R_{50a}$'s;

or $R_{28}$ and $R_{29}$ are taken together with the nitrogen to which both are attached to form a 3- to 8-membered ring, which may optionally contain 1-4 heteroatoms selected from N, O, and S and be optionally substituted with one or more $R_{50a}$'s;

$R_{28a}$ and $R_{29a}$ are independently hydrogen, —[(C═O)O$_r$]$_s$aryl, —[(C═O)O$_r$]$_s$heteroaryl, —[(C═O)O$_r$]$_s$(C$_2$-C$_8$)-alkenyl, —[(C═O)O$_r$]$_s$(C$_1$-C$_8$)alkyl, —[(C═O)O$_r$]$_s$alkylaryl, —[(C═O)O$_r$]$_s$alkylheteroaryl, —S(O)$_p$(C$_1$-C$_8$)alkyl, —S(O)$_p$aryl, —S(O)$_p$heteroaryl, —S(O)$_p$NR$_{36}$R$_{37}$, —C(═NR$_{38}$)(NR$_{36}$R$_{37}$) or heterocyclyl, wherein the aryl, heteroaryl, alkenyl, alkyl and heterocyclyl may be optionally substituted with one or more $R_{50}$'s;

or $R_{28a}$ and $R_{29a}$ are taken together with the nitrogen to which both are attached to form a 3- to 8-membered ring, which may optionally contain 1-4 heteroatoms selected from N, O, and S and be optionally substituted with one or more $R_{50}$'s;

$R_{28b}$ and $R_{29b}$ are independently hydrogen, alkyl or haloalkyl;

$R_{28c}$ and $R_{29c}$ are independently alkyl or haloalkyl;

$R_{36}$ and $R_{37}$ are independently (a) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (b) heteroaryl optionally substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, benzyl-S(O)$_n$—, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (c) heterocyclo, other than heteroaryl, which is optionally substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, —O(C=O)NR$_{28a}$R$_{29a}$, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (d) $(C_2-C_{10})$-alkenyl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, benzyl-S(O)$_n$—, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (e) $(C_2-C_{10})$-alkynyl wherein alkynyl is optionally substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, benzyl-S(O)$_n$—, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (f) —$(C_1-C_{10})$-alkyl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, benzyl-S(O)$_n$—, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

or $R_{36}$ and $R_{37}$ are taken together with the nitrogen to which both are attached to form a 3- to 8-membered ring, which may optionally contain 1-4 heteroatoms selected from N, O, and S and be optionally substituted with one or more $R_{50}$'s;

$R_{38}$ is cyano, —COR$_{46}$ or —SO$_2$R$_{46}$;

$R_{46}$ is (a) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —$(C_1-C_6)$-alkylheterocyclyl, —$(C_1-C_6)$-alkyl-CONHS(O)$_2$—$(C_1-C_6)$alkyl, —O$(C_1-C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (b) heteroaryl optionally substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —$(C_1-C_6)$-alkylheterocyclyl, —$(C_1-C_6)$-alkyl-CONHS(O)$_2$—$(C_1-C_6)$alkyl, —O$(C_1-C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (c) heterocyclo, other than heteroaryl, which is optionally substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —$(C_1-C_6)$-alkylheterocyclyl, —$(C_1-C_6)$-alkyl-CONHS(O)$_2$—$(C_1-C_6)$alkyl, —O$(C_1-C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (d) —$(C_1-C_{10})$-alkyl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, $(C_1-C_6)$-alkyl-S(O)$_n$—, cyano, nitro, —COOH, —$(C_1-C_6)$-alkylCOOH, —$(C_1-C_6)$-alkyl(NH$_2$)COOH, CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —$(C_1-C_6)$-alkylheterocyclyl, —$(C_1-C_6)$-alkyl-CONHS(O)$_2$—$(C_1-C_6)$alkyl, —O$(C_1-C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (e) —$(C_3$-$C_8)$-cycloalkyl, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-, $(C_1$-$C_6)$-alkyl-S(O)$_n$—, cyano, nitro, —COOH, —$(C_1$-$C_6)$-alkylCOOH, —$(C_1$-$C_6)$-alkyl(NH$_2$)COOH, —CO$(C_1$-$C_6)$-alkyl, —$(C_1$-$C_6)$-alkyl-CO$_2(C_1$-$C_6)$-alkyl, —CO$_2(C_1$-$C_6)$-alkyl, —O(C=O)—$(C_1$-$C_6)$-alkyl, —$(C_1$-$C_6)$-alkylheterocyclyl, —$(C_1$-$C_6)$-alkyl-CONHS(O)$_2$—$(C_1$-$C_6)$alkyl, —O$(C_1$-$C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_{50}$ is (a) hydrogen, (b) halo, (c) —OH, (d) $(C_1$-$C_6)$-alkyl, (e) halo$(C_1$-$C_6)$-alkyl, (f) halo$(C_1$-$C_6)$-alkyloxy, (g) —O[(C=O)]$_s(C_1$-$C_6)$-alkyl, (h) $R_{51}$—S(O)$_n$—, (i) cyano, (j) nitro, (k) —NR$_{51}$R$_{52}$, (l) —O(CO)NR$_{51}$R$_{52}$, (m) —COOH, (n) —CO$(C_1$-$C_6)$-alkyl, (o) —CO$_2(C_1$-$C_6)$-alkyl, (p) —CONR$_{51}$R$_{52}$, (q) (OH)—$(C_1$-$C_6)$-alkyl-, (r) —$(C_1$-$C_6)$-alkylCOOH, (s) —$(C_1$-$C_6)$-alkyl-heteroaryl, (t) —$(C_1$-$C_6)$-alkyl-heterocyclyl, (u) —$(C_1$-$C_6)$-alkyl-CONHS(O)$_2$—$R_{51}$, (v) —$(C_1$-$C_6)$-alkyl(NH$_2$)COOH, (w) —$(C_1$-$C_6)$-alkyl-CO$_2$$(C_1$-$C_6)$-alkyl, (x) =O; or (y) —$(C_3$-$C_{10})$-cycloalkyl;

$R_{50a}$ is halo, —OH, —O[(C=O)]$_s(C_1$-$C_6)$-alkyl, cyano, nitro, —NR$_{51}$R$_{52}$, —COOH, —CO$(C_1$-$C_6)$-alkyl, —CO$_2(C_1$-$C_6)$-alkyl, —$(C_1$-$C_6)$-haloalkyl, =O, —$(C_3$-$C_6)$-cycloalkyl, or —$(C_1$-$C_6)$-alkyl;

$R_{51}$ and $R_{52}$, at each occurrence, are independently hydrogen, —$(C_1$-$C_6)$-alkyl, —$(C_3$-$C_8)$-cycloalkyl, or -halo$(C_1$-$C_6)$-alkyl;

n is 0 to 2;

p is 1 or 2;

q is 0 or 1, provided that q is 1 when X is other than S;

r is 0 or 1; and s is 0 or 1.

In another embodiments of the invention, compounds of formula I are provided wherein X is O, S or CH$_2$.

In yet another embodiment, compounds of formula I are provided wherein A is

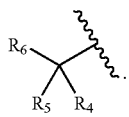

In one embodiment, compounds of formula I are provide wherein:

A is

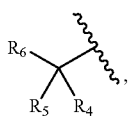

—C(O)NR$_{28}$R$_{29}$, —CO$_2(C_1$-$C_6)$-alkyl, or heterocyclyl, wherein the alkyl and heterocyclyl may be optionally substituted with one or more $R_{10a}$'s;

X is O, S or CR$_{20}$R$_{20}$;

$R_1$ is —C(O)R$_7$, —C(O)OR$_7$, —S(O)$_n$R$_7$, —C(O)NR$_{28}$R$_{29}$, $(C_1$-$C_3)$alkylaryl or $(C_1$-$C_3)$alkylheteroaryl, wherein the alkylaryl and alkylheteroaryl may be optionally substituted with one or more $R_{10b}$'s;

$R_{2a}$, $R_{2b}$ and $R_{2c}$ are independently hydrogen, halo, —OH, —$(C_1$-$C_6)$-alkyl, —O$(C_1$-$C_6)$-alkyl, halo$(C_1$-$C_6)$-alkyl-, halo$(C_1$-$C_6)$-alkyloxy- or cyano;

$R_{3a}$ is hydrogen, $(C_1$-$C_8)$alkyl, aryl or heteroaryl, wherein the alkyl, aryl and heteroaryl may be optionally substituted with one or more $R_{10b}$'s;

$R_{3b}$ is (a) hydrogen, (b) —OH, (c) $R_{46}$—S(O)$_n$—, (d) cyano, (e) aryl-$(C_1$-$C_6)$alkyloxy-, which may optionally be substituted with one or more substituents selected from the group consisting of: halo, —OH, $(C_1$-$C_6)$-alkyl, halo$(C_1$-$C_6)$ alkyl, halo$(C_1$-$C_6)$alkyloxy, $(C_2$-$C_6)$-alkenyl, $(C_2$-$C_6)$-alkynyl, $(C_1$-$C_6)$-alkyloxy, (OH)—$(C_1$-$C_6)$-alkyl-, $R_{46}$—S(O)$_n$—, cyano, nitro, —COOH, —$(C_1$-$C_6)$-alkylCOOH, —$(C_1$-$C_6)$-alkyl(NH$_2$)COOH, —CO$(C_1$-$C_6)$-alkyl, —$(C_1$-$C_6)$-alkyl-CO$_2(C_1$-$C_6)$-alkyl, —CO$_2(C_1$-$C_6)$-alkyl, —O(C=O)—$(C_1$-$C_6)$-alkyl, —O$(C_1$-$C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (f) heteroaryl-$(C_1$-$C_6)$alkyloxy-, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_2$-$C_6)$-alkenyl, $(C_2$-$C_6)$-alkynyl, $(C_1$-$C_6)$-alkyloxy, (OH)—$(C_1$-$C_6)$-alkyl-, $R_{46}$—S(O)$_n$—, cyano, nitro, —COOH, —$(C_1$-$C_6)$-alkylCOOH, —$(C_1$-$C_6)$-alkyl(NH$_2$)COOH, —CO$(C_1$-$C_6)$-alkyl, —$(C_1$-$C_6)$-alkyl-CO$_2(C_1$-$C_6)$-alkyl, —CO$_2(C_1$-$C_6)$-alkyl, —O(C=O)—$(C_1$-$C_6)$-alkyl, —O$(C_1$-$C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (g) aryl, which may optionally be substituted with one or more substituents selected from the group consisting of: halo, —OH, $(C_1$-$C_6)$-alkyl, halo$(C_1$-$C_6)$alkyl, halo$(C_1$-$C_6)$ alkyloxy, $(C_2$-$C_6)$-alkenyl, $(C_2$-$C_6)$-alkynyl, $(C_1$-$C_6)$-alkyloxy, (OH)—$(C_1$-$C_6)$-alkyl-, cyano, nitro, —COOH, —$(C_1$-$C_6)$-alkylCOOH, —$(C_1$-$C_6)$-alkyl(NH$_2$)COOH, —CO$(C_1$-$C_6)$-alkyl, —$(C_1$-$C_6)$-alkyl-CO$_2(C_1$-$C_6)$-alkyl, —CO$_2(C_1$-$C_6)$-alkyl, —O(C=O)—$(C_1$-$C_6)$-alkyl, —O$(C_1$-$C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (h) heteroaryl optionally substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_2$-$C_6)$-alkenyl, $(C_2$-$C_6)$-alkynyl, $(C_1$-$C_6)$-alkyloxy, (OH)—$(C_1$-$C_6)$-alkyl-, cyano, nitro, —COOH, —$(C_1$-$C_6)$-alkylCOOH, —$(C_1$-$C_6)$-alkyl(NH$_2$)COOH, —CO$(C_1$-$C_6)$-alkyl, —$(C_1$-$C_6)$-alkyl-CO$_2(C_1$-$C_6)$-alkyl, —CO$_2(C_1$-$C_6)$-alkyl, —O(C=O)—$(C_1$-$C_6)$-alkyl, —O$(C_1$-$C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (i) —$(C_1$-$C_8)$-alkyl, which may optionally be substituted with one or more substituents selected from the group consisting of: halo, —OH, halo$(C_1$-$C_6)$alkyloxy, $(C_2$-$C_6)$-alkenyl, $(C_2$-$C_6)$-alkynyl, $(C_1$-$C_6)$-alkyloxy, (OH)—$(C_1$-$C_6)$-alkyl-, cyano, $(C_3$-$C_6)$-cycloalkyl, —COOH, —$(C_1$-$C_6)$-alkylCOOH, —$(C_1$-$C_6)$-alkyl(NH$_2$)COOH, —CO$(C_1$-$C_6)$-alkyl, —$(C_1$-$C_6)$-alkyl-CO$_2(C_1$-$C_6)$-alkyl, —CO$_2(C_1$-$C_6)$-alkyl, —O(C=O)—$(C_1$-$C_6)$-alkyl, —O$(C_1$-$C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (j) —O[(C=O)]$_s$aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (k) —O[(C=O)]$_s$heteroaryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, cyano, nitro, —COOH, —$(C_1-C_6)$-alkylCOOH, —$(C_1-C_6)$-alkyl(NH$_2$)COOH, —CO$(C_1-C_6)$-alkyl, —$(C_1-C_6)$-alkyl-CO$_2(C_1-C_6)$-alkyl, —CO$_2(C_1-C_6)$-alkyl, —(C=O)—$(C_1-C_6)$-alkyl, —O$(C_1-C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_4$, $R_5$ and $R_6$ are independently hydroxy, $(C_1-C_4)$-alkyl, or halo$(C_1-C_4)$-alkyl; provided that (i) only one of $R_4$, $R_5$ or $R_6$ is hydroxy and (ii) $R_5$ and $R_6$ are halo$(C_1-C_4)$-alkyl when $R_{3a}$ and $R_{3b}$ are hydrogen and $R_4$ is hydroxy;

$R_7$ is alkyl, cycloalkyl, alkenyl, aryl or heterocyclyl, wherein the alkyl, cycloalkyl, aryl, or heterocyclyl may be optionally substituted with one or more $R_{10b}$'s;

$R_{10a}$ is halo, —OH, —O[(C=O)]$_s(C_1-C_6)$-alkyl, —O[(C=O)]$_s(C_2-C_6)$-alkenyl, cyano, nitro, —NR$_{28b}$R$_{29b}$, —COOH, —CO$(C_1-C_6)$-alkyl, —CO$_2(C_1-C_6)$-alkyl, —$(C_1-C_6)$-haloalkyl, —$(C_3-C_6)$-cycloalkyl or —$(C_1-C_6)$-alkyl;

$R_{10b}$ is (a) halo; (b) —OH; (c) —O[(C=O)]$_s(C_1-C_6)$-alkyl; (d) —O[(C=O)]$_s(C_1-C_6)$-alkylaryl; (e) $R_{46}$—S(O)$_n$—; (f) cyano; (g) nitro; (h) —NR$_{28b}$R$_{29b}$; (i) —CO$(C_1-C_6)$-alkyl; (j) —CO$_2(C_1-C_6)$-alkyl; (k) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, $(C_1-C_6)$-alkyl-S(O)$_n$—, cyano, nitro, —CO$(C_1-C_6)$-alkyl, —$(C_1-C_3)$-alkyl-CO$_2(C_1-C_6)$-alkyl, —CO$_2(C_1-C_6)$-alkyl, —NR$_{28b}$R$_{29b}$, —O(C=O)—$(C_1-C_6)$-alkyl, —O$(C_1-C_6)$-alkylaryl, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (l) heteroaryl optionally substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, cyano, nitro, —CO$(C_1-C_6)$-alkyl, —$(C_1-C_3)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (m) heterocyclo, other than heteroaryl, which is optionally substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, cyano, nitro, —CO$(C_1-C_6)$-alkyl, —$(C_1-C_3)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (n) —$(C_1-C_6)$-alkyl, which may optionally be substituted with one or more substituents selected from the group consisting of: halo, —OH, halo$(C_1-C_6)$alkyloxy, $(C_1-C_6)$-alkyloxy, cyano, —CO$(C_1-C_6)$-alkyl, —CO$_2(C_1-C_6)$-alkyl, —O(C=O)—$(C_1-C_6)$-alkyl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (o) =O, (p) —$(C_3-C_8)$-cycloalkyl, which may optionally be substituted with one or more substituents selected from the group consisting of: halo, —OH, $(C_1-C_6)$-alkyl, halo$(C_1-C_6)$alkyl, halo $(C_1-C_6)$alkyloxy, $(C_1-C_6)$-alkyloxy, (OH)—$(C_1-C_6)$-alkyl-, cyano, nitro, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (q) —O[(C=O)]$_s$aryl, which may optionally be substituted with one or more substituents selected from the group consisting of: halo, —OH, $(C_1-C_6)$-alkyl, halo$(C_1-C_6)$alkyl, halo $(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, cyano, nitro, —CO$(C_1-C_6)$-alkyl, —$(C_1-C_6)$-alkyl-CO$_2(C_1-C_6)$-alkyl, —CO$_2(C_1-C_6)$-alkyl, and —O(C=O)—$(C_1-C_6)$-alkyl; or (r) halo$(C_1-C_6)$alkyloxy;

$R_{20}$ is hydrogen, or $(C_1-C_4)$-alkyl; or the two $R_{20}$'s are taken together with the carbon atom to which they are attached to form a 3- to 6-membered ring;

$R_{28}$ and $R_{29}$ are independently hydrogen, aryl, $(C_1-C_6)$ alkyl, halo$(C_1-C_6)$alkyl, aryl$(C_1-C_3)$alkyl or heterocyclyl, wherein the aryl, alkyl, arylalkyl and heterocyclyl may be optionally substituted with one or more $R_{50a}$'s;

or $R_{28}$ and $R_{29}$ are taken together with the nitrogen to which both are attached to form a 3- to 8-membered ring, which may optionally contain 1-4 heteroatoms selected from N, O, and S and be optionally substituted with one or more $R_{50a}$'s;

$R_{28a}$ and $R_{29a}$ are independently hydrogen, —[(C=O)O$_r$]$_s$aryl, —[(C=O)O$_r$]$_s$heteroaryl, —[(C=O)O$_r$]$_s$(C$_2$-C$_8$)-alkenyl, —[(C=O)O$_r$]$_s$(C$_1$-C$_8$)alkyl, —S(O)$_p$(C$_1$-C$_8$)alkyl, —S(O)$_p$aryl, —S(O)$_p$heteroaryl or heterocyclyl, wherein the aryl, heteroaryl, alkenyl, alkyl and heterocyclyl may be optionally substituted with one or more $R_{50}$'s;

or $R_{28a}$ and $R_{29a}$ are taken together with the nitrogen to which both are attached to form a 3- to 8-membered ring, which may optionally contain 1-4 heteroatoms selected from N, O, and S and be optionally substituted with one or more $R_{50}$'s;

$R_{28b}$ and $R_{29b}$ are independently hydrogen, alkyl or haloalkyl;

$R_{46}$ is (a) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, cyano, nitro, —COOH, —$(C_1-C_6)$-alkylCOOH, —$(C_1-C_6)$-alkyl$(NH_2)$COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (b) heteroaryl optionally substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, cyano, nitro, —COOH, —$(C_1-C_6)$-alkylCOOH, —$(C_1-C_6)$-alkyl$(NH_2)$COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (c) heterocyclo, other than heteroaryl, which is optionally substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, cyano, nitro, —COOH, —$(C_1-C_6)$-alkylCOOH, —$(C_1-C_6)$-alkyl$(NH_2)$COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (d) —$(C_1-C_{10})$-alkyl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, cyano, nitro, —COOH, —$(C_1-C_6)$-alkylCOOH, —$(C_1-C_6)$-alkyl$(NH_2)$COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_{50}$ is (a) hydrogen, (b) halo, (c) —OH, (d) $(C_1-C_6)$-alkyl, (e) halo$(C_1-C_6)$-alkyl, (f) halo$(C_1-C_6)$-alkyloxy, (g) —O[(C=O)]$_s(C_1-C_6)$-alkyl, (h) cyano, (i) nitro, (j) —COOH, (k) —CO$(C_1-C_6)$-alkyl, (l) —CO$_2(C_1-C_6)$-alkyl, (m) (OH)—$(C_1-C_6)$-alkyl-, (n) —$(C_1-C_6)$-alkylCOOH, (o) —$(C_1-C_6)$-alkyl-heteroaryl, (p) —$(C_1-C_6)$-alkyl-heterocyclyl, (q) —$(C_1-C_6)$-alkyl$(NH_2)$COOH, (r) —$(C_1-C_6)$-alkyl-CO$_2(C_1-C_6)$-alkyl, or (s) —$(C_3-C_6)$-cycloalkyl;

$R_{50a}$ is halo, —OH, —O[(C=O)]$_s(C_1-C_6)$-alkyl, cyano, nitro, —NR$_{51}$R$_{52}$, —COOH, —CO$(C_1-C_6)$-alkyl, —CO$_2(C_1-C_6)$-alkyl, —$(C_1-C_6)$-haloalkyl, —$(C_3-C_6)$-cycloalkyl or —$(C_1-C_6)$-alkyl;

$R_{51}$ and $R_{52}$, at each occurrence, are independently hydrogen, —$(C_1-C_6)$-alkyl, —$(C_3-C_8)$-cycloalkyl, or -halo$(C_1-C_6)$-alkyl;

n is 0 to 2;
p is 1 or 2;
q is 0 or 1, provided that q is 1 when X is other than S;
r is 0 or 1; and
s is 0 or 1.

In another embodiment, compounds of formula I are provided wherein:

A is

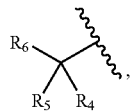

—CO$_2(C_1-C_6)$-alkyl, or heterocyclyl, wherein the alkyl and heterocyclyl may be optionally substituted with one or more $R_{10a}$'s;

X is O, S or CR$_{20}$R$_{20}$;

$R_1$ is —C(O)R$_7$, —C(O)OR$_7$, —S(O)$_n$R$_7$, —C(O)NR$_{28}$R$_{29}$, or $(C_1-C_3)$alkylaryl, wherein the alkylaryl may be optionally substituted with one or more $R_{10b}$'s;

$R_{2a}$, $R_{2b}$ and $R_{2c}$ are independently hydrogen, halo, —$(C_1-C_6)$-alkyl, —O$(C_1-C_6)$-alkyl, halo$(C_1-C_6)$-alkyl- or halo$(C_1-C_6)$-alkyloxy-;

$R_{3a}$ is hydrogen, $(C_1-C_8)$alkyl, aryl or heteroaryl, wherein the alkyl, aryl and heteroaryl may be optionally substituted with one or more $R_{10b}$'s;

$R_{3b}$ is (a) hydrogen, (b) —OH, (c) $R_{46}$—S(O)$_n$—, (d) aryl-$(C_1-C_6)$alkyloxy-, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alkynyl, $(C_1-C_6)$-alkyloxy, (OH)—$(C_1-C_6)$-alkyl-, $R_{46}$—S(O)$_n$—, cyano, nitro, —COOH, —$(C_1-C_6)$-alkylCOOH, —$(C_1-C_6)$-alkyl$(NH_2)$COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (e) heteroaryl-$(C_1-C_6)$alkyloxy-, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_2-C_6)$-alkenyl, $(C_2-C_6)$-alklynyl, $(C_1-C_6)$-alkyloxy, (OH)—$(C_1-C_6)$-alkyl-, $R_{46}$—S(O)$_n$—, cyano, nitro, —COOH, —$(C_1-C_6)$-alkyl-COOH, —$(C_1-C_6)$-alkyl$(NH_2)$COOH, —CO$(C_1-C_6)$-alkyl, —$(C_1-C_6)$-alkyl-CO$_2(C_1-C_6)$-alkyl, —CO$_2(C_1-C_6)$-alkyl, —O(C=O)—$(C_1-C_6)$-alkyl, —O$(C_1-C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s (f) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, cyano, nitro, —COOH, —$(C_1-C_6)$-alkylCOOH, —$(C_1-C_6)$-alkyl$(NH_2)$COOH, —CO$(C_1-C_6)$-alkyl, —CO$_2(C_1-C_6)$-alkyl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (g) heteroaryl optionally substituted with one or more substituents selected from the group consisting of: halo, —OH, $(C_1-C_6)$- alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl(NH$_2$)COOH, —CO($C_1$-$C_6$)-alkyl, —CO$_2$($C_1$-$C_6$)-alkyl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (h) —($C_1$-$C_8$)-alkyl, which may optionally be substituted with one or more substituents selected from the group consisting of: halo, —OH, halo($C_1$-$C_6$)alkyloxy, ($C_1$-$C_6$)-alkyloxy, (OH)—($C_1$-$C_6$)-alkyl-, cyano, ($C_3$-$C_6$)-cycloalkyl, —COOH, —($C_1$-$C_6$)-alkylCOOH, —($C_1$-$C_6$)-alkyl(NH$_2$)COOH, —CO($C_1$-$C_6$)-alkyl, —CO$_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (i) —O[(C=O)]$_s$aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl(NH$_2$)COOH, —($C_1$-$C_6$)-alkyl-CO$_2$($C_1$-$C_6$)-alkyl, —CO$_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (j) —O[(C=O)]$_s$heteroaryl, which may optionally be substituted with one or more substituents selected from the group consisting of: halo, —OH, ($C_1$-$C_6$)-alkyl, halo($C_1$-$C_6$) alkyl, halo($C_1$-$C_6$)alkyloxy, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl(NH$_2$)COOH, —($C_1$-$C_6$)-alkyl-CO$_2$($C_1$-$C_6$)-alkyl, —CO$_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_4$, $R_5$ and $R_6$ are independently hydroxy, ($C_1$-$C_4$)-alkyl, or halo($C_1$-$C_4$)-alkyl; provided that (i) only one of $R_4$, $R_5$ or $R_6$ is hydroxy and (ii) $R_5$ and $R_6$ are halo($C_1$-$C_4$)-alkyl when $R_{3a}$ and $R_{3b}$ are hydrogen and $R_4$ is hydroxy;

$R_7$ is alkyl, cycloalkyl, alkenyl, aryl or heterocyclyl, wherein the alkyl, cycloalkyl, aryl, or heterocyclyl may be optionally substituted with one or more $R_{10b}$'s;

$R_{10a}$ is halo, —OH, —O[(C=O)]$_s$($C_1$-$C_6$)-alkyl, —O[(C=O)]$_s$($C_2$-$C_6$)-alkenyl, cyano, nitro, —COOH, —CO($C_1$-$C_6$)-alkyl, —CO$_2$($C_1$-$C_6$)-alkyl, —($C_1$-$C_6$)-haloalkyl, —($C_3$-$C_6$)-cycloalkyl or —($C_1$-$C_6$)-alkyl;

$R_{10b}$ is (a) halo; (b) —OH; (c) —O[(C=O)]$_s$($C_1$-$C_6$)-alkyl; (d) —O[(C=O)]$_s$($C_1$-$C_6$)-alkylaryl; (e) $R_{46}$—S(O)$_n$—; (f) cyano; (g) nitro; (h) —NR$_{28b}$R$_{29b}$; (i) —CO($C_1$-$C_6$)-alkyl; (j) —CO$_2$($C_1$-$C_6$)-alkyl; (k) aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-($C_1$-$C_6$)-alkyl-S(O)$_n$—, cyano, nitro, —NR$_{28b}$R$_{29b}$, —O($C_1$-$C_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (l) heteroaryl optionally substituted with one or more substituents selected from the group consisting of: halo, —OH, ($C_1$-$C_6$)-alkyl, halo($C_1$-$C_6$) alkyl, halo($C_1$-$C_6$)alkyloxy, ($C_1$-$C_6$)-alkyloxy, (OH)—($C_1$-$C_6$)-alkyl-, cyano, nitro, —O($C_1$-$C_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (m) heterocyclo, other than heteroaryl, which is optionally substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, —CO($C_1$-$C_6$)-alkyl, —O($C_1$-$C_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; —($C_1$-$C_6$)-alkyl, which may optionally be substituted with one or more substituents selected from the group consisting of: halo, —OH, halo($C_1$-$C_6$)alkyloxy, ($C_1$-$C_6$)-alkyloxy, cyano, —CO$_2$($C_1$-$C_6$)-alkyl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; —($C_3$-$C_8$)-cycloalkyl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, —CO$_2$($C_1$-$C_6$)-alkyl, —O($C_1$-$C_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; —O[(C=O)]$_s$aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, and —CO$_2$($C_1$-$C_6$)-alkyl; or halo($C_1$-$C_6$)alkyloxy;

$R_{20}$ is hydrogen, or ($C_1$-$C_4$)-alkyl; or the two $R_{20}$'s are taken together with the carbon atom to which they are attached to form a 3- to 6-membered ring;

$R_{28}$ and $R_{29}$ are independently hydrogen, aryl, ($C_1$-$C_6$) alkyl, halo($C_1$-$C_6$)alkyl, aryl($C_1$-$C_3$)alkyl or heterocyclyl, wherein the aryl, alkyl, arylalkyl and heterocyclyl may be optionally substituted with one or more $R_{50a}$'s;

or $R_{28}$ and $R_{29}$ are taken together with the nitrogen to which both are attached to form a 3- to 8-membered ring, which may optionally contain 1-4 heteroatoms selected from N, O, and S and be optionally substituted with one or more $R_{50a}$'s;

$R_{28a}$ and $R_{29a}$ are independently hydrogen, —[(C=O)O$_r$]$_s$ aryl, —[(C=O)O$_r$]$_s$($C_1$-$C_8$)alkyl or heterocyclyl, wherein the aryl, alkyl and heterocyclyl may be optionally substituted with one or more $R_{50}$'s;

or $R_{28a}$ and $R_{29a}$ are taken together with the nitrogen to which both are attached to form a 3- to 8-membered ring, which may optionally contain 1-4 heteroatoms selected from N, O, and S and be optionally substituted with one or more $R_{50}$'s;

$R_{28b}$ and $R_{29b}$ are independently hydrogen, alkyl or haloalkyl;

$R_{46}$ is (a) aryl, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, —COOH, —$(C_1$-$C_6)$-alkylCOOH, —$(C_1$-$C_6)$-alkyl(NH$_2$)COOH, —$(C_1$-$C_6)$-alkyl-CO$_2(C_1$-$C_6)$-alkyl, —CO$_2(C_1$-$C_6)$-alkyl, —O$(C_1$-$C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (b) heteroaryl optionally substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, —COOH, —$(C_1$-$C_6)$-alkylCOOH, —$(C_1$-$C_6)$-alkyl(NH$_2$)COOH, —$(C_1$-$C_6)$-alkyl-CO$_2(C_1$-$C_6)$-alkyl, —CO$_2(C_1$-$C_6)$-alkyl, —O$(C_1$-$C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (c) —$(C_1$-$C_{10})$-alkyl, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, —COOH, —$(C_1$-$C_6)$-alkylCOOH, —$(C_1$-$C_6)$-alkyl(NH$_2$)COOH, —$(C_1$-$C_6)$-alkyl-CO$_2(C_1$-$C_6)$-alkyl, —CO$_2(C_1$-$C_6)$-alkyl, —$(C_1$-$C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_{50}$ is (a) hydrogen, (b) halo, (c) —OH, (d) $(C_1$-$C_6)$-alkyl, (e) halo$(C_1$-$C_6)$-alkyl, (f) —O[(C=O)]$_s(C_1$-$C_6)$-alkyl, (g) cyano, (h) nitro, (i) —COOH, (j) —CO$(C_1$-$C_6)$-alkyl, (k) —CO$_2(C_1$-$C_6)$-alkyl, (l) (OH)—$(C_1$-$C_6)$-alkyl-, (m) —$(C_1$-$C_6)$-alkylCOOH, (n) —$(C_1$-$C_6)$-alkyl(NH$_2$)COOH, or (o) —$(C_3$-$C_6)$-cycloalkyl;

$R_{50a}$ is halo, —OH, —O[(C=O)]$_s(C_1$-$C_6)$-alkyl, cyano, nitro, —COOH, —CO$(C_1$-$C_6)$-alkyl, —CO$_2(C_1$-$C_6)$-alkyl, —$(C_1$-$C_6)$-haloalkyl, —$(C_3$-$C_6)$-cycloalkyl or —$(C_1$-$C_6)$-alkyl;

n is 0 to 2;

q is 0 or 1, provided that q is 1 when X is other than S;

r is 0 or 1; and s is 0 or 1.

In yet another embodiment, compounds of formula I are provided wherein:

A is

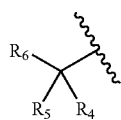

or heterocyclyl, which may be optionally substituted with one or more $R_{10a}$'s;

X is O, S or CR$_{20}$R$_{20}$;

$R_1$ is —C(O)R$_7$, —C(O)OR$_7$, —S(O)$_n$R$_7$ or —C(O)NR$_{28}$R$_{29}$;

$R_{2a}$, $R_{2b}$ and $R_{2c}$ are independently hydrogen, halo, —$(C_1$-$C_6)$-alkyl or halo$(C_1$-$C_6)$-alkyl-;

$R_{3a}$ is hydrogen, $(C_1$-$C_8)$alkyl or aryl, wherein the alkyl and aryl may be optionally substituted with one or more halo, alkyl, haloalkyl, OH, alkyloxy, haloalkyoxy, cyano, or nitro;

$R_{3b}$ is (a) hydrogen, (b) —OH, (c) $R_{46}$—S(O)$_n$—, (d) aryl, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (e) —$(C_1$-$C_8)$-alkyl, which may optionally be substituted with one or more substituents selected from the group consisting of: halo, —OH, halo$(C_1$-$C_6)$alkyloxy, $(C_1$-$C_6)$-alkyloxy, (OH)—$(C_1$-$C_6)$-alkyl-, cyano, $(C_3$-$C_6)$-cycloalkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (f) —O[(C=O)]$_s$aryl, which may optionally be substituted with one or more substituents selected from the group consisting of: halo, $(C_1$-$C_6)$-alkyl, halo$(C_1$-$C_6)$alkyl, halo$(C_1$-$C_6)$alkyloxy, $(C_1$-$C_6)$-alkyloxy, —COOH, —$(C_1$-$C_6)$-alkylCOOH, —$(C_1$-$C_6)$-alkyl(NH$_2$)COOH, —$(C_1$-$C_6)$-alkyl-CO$_2(C_1$-$C_6)$-alkyl, —CO$_2(C_1$-$C_6)$-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (g) —O[(C=O)]$_s$heteroaryl, which may optionally be substituted with one or more substituents selected from the group consisting of: halo, $(C_1$-$C_6)$-alkyl, halo$(C_1$-$C_6)$alkyl, halo$(C_1$-$C_6)$alkyloxy, $(C_1$-$C_6)$-alkyloxy, —COOH, —$(C_1$-$C_6)$-alkylCOOH, —$(C_1$-$C_6)$-alkyl(NH$_2$)COOH, —$(C_1$-$C_6)$-alkyl-CO$_2(C_1$-$C_6)$-alkyl, —CO$_2(C_1$-$C_6)$-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_4$, $R_5$ and $R_6$ are independently hydroxy or halo$(C_1$-$C_4)$-alkyl; provided that (i) only one of $R_4$, $R_5$ or $R_6$ is hydroxy and (ii) $R_5$ and $R_6$ are halo$(C_1$-$C_4)$-alkyl when $R_{3a}$ and $R_{3b}$ are hydrogen and $R_4$ is hydroxy;

$R_7$ is alkyl, cycloalkyl, aryl or heterocyclyl, wherein the alkyl, cycloalkyl, aryl, or heterocyclyl may be optionally substituted with one or more $R_{10b}$'s;

$R_{10a}$ is halo, —OH, —O[(C=O)]$_s(C_1$-$C_6)$-alkyl, cyano, nitro, —COOH, —CO$(C_1$-$C_6)$-alkyl, —CO$_2(C_1$-$C_6)$-alkyl, —$(C_1$-$C_6)$-haloalkyl, —$(C_3$-$C_6)$-cycloalkyl or —$(C_1$-$C_6)$-alkyl;

$R_{10b}$ is (a) halo; (b) —OH; (c) —O[(C=O)]$_s(C_1$-$C_6)$-alkyl; (d) —O[(C=O)]$_s(C_1$-$C_6)$-alkylaryl; (e) $R_{46}$—S(O)$_n$—; (f) —CO$_2(C_1$-$C_6)$-alkyl; (g) aryl, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-$(C_1$-$C_6)$-alkyl-S(O)$_n$—, cyano, nitro, —O$(C_1$-$C_6)$-alkylaryl, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (h) heteroaryl optionally substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, —O$(C_1-C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (i) heterocyclo, other than heteroaryl, which is optionally substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (j) —$(C_1-C_6)$-alkyl, which may optionally be substituted with one or more substituents selected from the group consisting of: halo, —OH, halo$(C_1-C_6)$alkyloxy, $(C_1-C_6)$-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (k) —$(C_3-C_8)$-cycloalkyl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; or (l) —O[(C=O)]$_s$aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, and (OH)—$(C_1-C_6)$-alkyl-;

$R_{20}$ is hydrogen or $(C_1-C_4)$-alkyl;

$R_{28}$ and $R_{29}$ are independently hydrogen, aryl, $(C_1-C_6)$ alkyl, halo$(C_1-C_6)$alkyl, aryl$(C_1-C_3)$alkyl or heterocyclyl, wherein the aryl, alkyl, arylalkyl and heterocyclyl may be optionally substituted with one or more $R_{50a}$'s;

or $R_{28}$ and $R_{29}$ are taken together with the nitrogen to which both are attached to form a 3- to 8-membered ring, which may optionally contain 1-4 heteroatoms selected from N, O, and S and be optionally substituted with one or more $R_{50a}$'s;

$R_{46}$ is (a) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, —COOH, —$(C_1-C_6)$-alkylCOOH, —$(C_1-C_6)$-alkyl(NH$_2$)COOH, —$(C_1-C_6)$-alkyl-CO$_2$$(C_1-C_6)$-alkyl, —CO$_2$$(C_1-C_6)$-alkyl, aryl, which may be optionally substituted with one or more $R_{50}$; heteroaryl, which may be optionally substituted with one or more $R_{50}$'s, and heterocyclo, which may be optionally substituted with one or more $R_{50}$'s; (b) heteroaryl optionally substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, —COOH, —$(C_1-C_6)$-alkylCOOH, —$(C_1-C_6)$-alkyl(NH$_2$)COOH, —$(C_1-C_6)$-alkyl-CO$_2$$(C_1-C_6)$-alkyl, —CO$_2$$(C_1-C_6)$-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (c) —$(C_1-C_{10})$-alkyl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, —COOH, —$(C_1-C_6)$-alkylCOOH, —$(C_1-C_6)$-alkyl(NH$_2$)COOH, —$(C_1-C_6)$-alkyl-CO$_2$$(C_1-C_6)$-alkyl, —CO$_2$$(C_1-C_6)$-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_{50}$ is (a) hydrogen, (b) halo, (c) —OH, (d) $(C_1-C_6)$-alkyl, (e) halo$(C_1-C_6)$-alkyl, (f) —O[(C=O)]$_s$$(C_1-C_6)$-alkyl, or (g) (OH)—$(C_1-C_6)$-alkyl-;

$R_{50a}$ is halo, —OH, —O[(C=O)]$_s$$(C_1-C_6)$-alkyl, cyano, nitro, —COOH, —CO$(C_1-C_6)$-alkyl, —CO$_2$$(C_1-C_6)$-alkyl, —$(C_1-C_6)$-haloalkyl, —$(C_3-C_6)$-cycloalkyl or —$(C_1-C_6)$-alkyl;

n is 0 to 2;

q is 0 or 1, provided that q is 1 when X is other than S; and s is 0 or 1.

In one embodiment, compounds of formula I are provided wherein:

A is

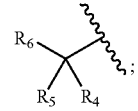

X is O, S or CH$_2$;

$R_1$ is —C(O)R$_7$, —C(O)OR$_7$ or —S(O)$_n$R$_7$;

$R_{2a}$, $R_{2b}$ and $R_{2c}$ are independently hydrogen, halo or —$(C_1-C_6)$-alkyl;

$R_{3a}$ is hydrogen, $(C_1-C_8)$alkyl or aryl, wherein the alkyl and aryl may be optionally substituted with one or more halo, alkyl, haloalkyl, OH, alkyloxy, haloalkyoxy, cyano, or nitro;

$R_{3b}$ is (a) hydrogen, (b) —OH, (c) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, cyano, nitro, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (d) —$(C_1-C_8)$-alkyl, which may optionally be substituted with one or more substituents selected from the group consisting of: halo, —OH, halo$(C_1-C_6)$alkyloxy, $(C_1-C_6)$-alkyloxy, (OH)—$(C_1-C_6)$-alkyl-, cyano, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (e) —O[(C=O)]$_s$aryl, which may optionally be substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, —COOH, —$(C_1-C_6)$-alkylCOOH, —$(C_1-C_6)$-alkyl-CO$_2$$(C_1-C_6)$-alkyl, —CO$_2$$(C_1-C_6)$-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (f) —O[(C═O)]$_s$heteroaryl, which may optionally be substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, —COOH, —$(C_1-C_6)$-alkylCOOH, —$(C_1-C_6)$-alkyl-$CO_2$$(C_1-C_6)$-alkyl, —$CO_2(C_1-C_6)$-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (g) $R_{46}$—S(O)$_n$—;

$R_4$, $R_5$ and $R_6$ are independently hydroxy or halo$(C_1-C_4)$-alkyl; provided that (i) only one of $R_4$, $R_5$ or $R_6$ is hydroxy and (ii) $R_5$ and $R_6$ are halo$(C_1-C_4)$-alkyl when $R_{3a}$ and $R_{3b}$ are hydrogen and $R_4$ is hydroxy;

$R_7$ is alkyl, cycloalkyl, aryl or heterocyclyl, wherein the alkyl, cycloalkyl, aryl, or heterocyclyl may be optionally substituted with one or more $R_{10b}$'s;

$R_{10b}$ is (a) halo; (b) —OH; (c) —O[(C═O)]$_s$$(C_1-C_6)$-alkyl; (d) —O[(C═O)]$_s$$(C_1-C_6)$-alkylaryl; (e) $R_{46}$—S(O)$_n$—; (f) —$CO_2(C_1-C_6)$-alkyl; (g) aryl, which may optionally be substituted with one or more substituents selected from the group consisting of: halo, $(C_1-C_6)$-alkyl, halo$(C_1-C_6)$alkyl, $(C_1-C_6)$-alkyloxy, halo$(C_1-C_6)$alkyloxy, cyano, nitro, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (h) heteroaryl optionally substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, cyano, nitro, —O$(C_1-C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (i) —$(C_1-C_6)$-alkyl, which may optionally be substituted with one or more substituents selected from the group consisting of: halo, halo$(C_1-C_6)$alkyloxy, $(C_1-C_6)$-alkyloxy, aryl, which may optionally be substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (j) —$(C_3-C_8)$-cycloalkyl, which may optionally be substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; or —O[(C═O)]$_s$aryl, which may optionally be substituted with one or more substituents selected from the group consisting of: halo, $(C_1-C_6)$-alkyl, halo$(C_1-C_6)$alkyl, halo$(C_1-C_6)$alkyloxy, and $(C_1-C_6)$-alkyloxy;

$R_{46}$ is (a) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, —COOH, —$(C_1-C_6)$-alkylCOOH, —$(C_1-C_6)$-alkyl(NH$_2$)COOH, —$(C_1-C_6)$-alkyl-$CO_2(C_1-C_6)$-alkyl, —$CO_2(C_1-C_6)$-alkyl, aryl, heteroaryl, and heterocyclo; (b) heteroaryl optionally substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, —COOH, —$(C_1-C_6)$-alkylCOOH, —$(C_1-C_6)$-alkyl(NH$_2$)COOH, —$(C_1-C_6)$-alkyl-$CO_2(C_1-C_6)$-alkyl, —$CO_2(C_1-C_6)$-alkyl, aryl, heteroaryl and heterocyclo; or (c) —$(C_1-C_{10})$-alkyl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, aryl, heteroaryl, and heterocyclo;

$R_{50}$ is (a) hydrogen, (b) halo, (c) —OH, (d) $(C_1-C_6)$-alkyl, (e) halo$(C_1-C_6)$-alkyl, (f) —O[(C═O)]$_s$$(C_1-C_6)$-alkyl, or (g) (OH)—$(C_1-C_6)$-alkyl-;

n is 0 to 2;

q is 0 or 1, provided that q is 1 when X is other than S; and s is 0 or 1.

In yet another embodiment, compounds of formula I are provided wherein:

A is

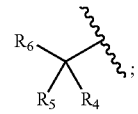

X is O, S or CH$_2$;

$R_1$ is —C(O)$R_7$ or —S(O)$_n$$R_7$;

$R_{2a}$, $R_{2b}$ and $R_2$ are independently hydrogen, halo or —$(C_1-C_6)$-alkyl;

$R_{3a}$ is hydrogen, $(C_1-C_8)$alkyl or aryl, wherein the alkyl and aryl may be optionally substituted with one or more halo, alkyl, haloalkyl, OH, alkyloxy, haloalkyoxy, cyano, or nitro;

$R_{3b}$ is (a) hydrogen, (b) —OH, (c) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, cyano, nitro, aryl, heteroaryl, and heterocyclo; (d) —$(C_1-C_8)$-alkyl, which may optionally be substituted with one or more substituents selected from the group consisting of: halo, —OH, halo$(C_1-C_6)$alkyloxy, $(C_1-C_6)$-alkyloxy, (OH)—$(C_1-C_6)$-alkyl-, cyano, aryl, heteroaryl, and heterocyclo; (e) —O[(C═O)]$_s$aryl, which may optionally be substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, —COOH, —$(C_1-C_6)$-alkylCOOH, —$(C_1-C_6)$-alkyl-$CO_2(C_1-C_6)$-alkyl, —$CO_2(C_1-C_6)$-alkyl, aryl, heteroaryl and heterocyclo; (f) —O[(C═O)]$_s$heteroaryl, which may optionally be substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, —COOH, —$(C_1-C_6)$-alkylCOOH, —$(C_1-C_6)$-alkyl-$CO_2(C_1-C_6)$-alkyl, —$CO_2(C_1-C_6)$-alkyl, aryl, heteroaryl, and heterocyclo; or (g) $R_{46}$—S(O)$_n$—;

$R_4$ and $R_6$ are halo$(C_1-C_4)$-alkyl;

$R_5$ is hydroxy;

R$_7$ is alkyl, cycloalkyl, aryl or heterocyclyl, wherein the alkyl, cycloalkyl, aryl, or heterocyclyl may be optionally substituted with one or more R$_{10b}$'s;

R$_{10b}$ is (a) halo; (b) —OH; (c) —O[(C=O)]$_s$(C$_1$-C$_6$)-alkyl; (d) —O[(C=O)]$_s$(C$_1$-C$_6$)-alkylaryl; (e) —CO$_2$(C$_1$-C$_6$)-alkyl; (f) aryl, which may optionally be substituted with one or more substituents selected from the group consisting of: halo, (C$_1$-C$_6$)-alkyl, halo(C$_1$-C$_6$)alkyl, (C$_1$-C$_6$)-alkyloxy, halo(C$_1$-C$_6$)alkyloxy, cyano, nitro, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (g) heteroaryl optionally substituted with one or more substituents selected from the group consisting of: halo, (C$_1$-C$_6$)-alkyl, halo(C$_1$-C$_6$)alkyl, OH, halo (C$_1$-C$_6$)alkyloxy, (C$_1$-C$_6$)-alkyloxy, cyano, nitro, —O(C$_1$-C$_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (h) —(C$_1$-C$_6$)-alkyl, which may optionally be substituted with one or more substituents selected from the group consisting of: halo, halo(C$_1$-C$_6$)alkyloxy, (C$_1$-C$_6$)-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (i) —(C$_3$-C$_8$)-cycloalkyl, which may optionally be substituted with one or more substituents selected from the group consisting of: halo, (C$_1$-C$_6$)-alkyl, halo(C$_1$-C$_6$)alkyl, halo(C$_1$-C$_6$)alkyloxy, (C$_1$-C$_6$)-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; or (O) —O[(C=O)]$_s$aryl, which may optionally be substituted with one or more substituents selected from the group consisting of: halo, (C$_1$-C$_6$)-alkyl, halo(C$_1$-C$_6$)alkyl, halo(C$_1$-C$_6$)alkyloxy, and (C$_1$-C$_6$)-alkyloxy;

R$_{46}$ is (a) aryl, which may optionally be substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_1$-C$_6$)-alkyloxy, (OH)—(C$_1$-C$_6$)-alkyl-, aryl, heteroaryl, and heterocyclo; (b) heteroaryl optionally substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_1$-C$_6$)-alkyloxy, (OH)—(C$_1$-C$_6$)-alkyl-, aryl, heteroaryl and heterocyclo; or (c) —(C$_1$-C$_{10}$)-alkyl, which may optionally be substituted with one or more substituents selected from the group consisting of: halo, —OH, (C$_1$-C$_6$)-alkyl, halo(C$_1$-C$_6$)alkyl, halo(C$_1$-C$_6$)alkyloxy, (C$_1$-C$_6$)-alkyloxy, (OH)—(C$_1$-C$_6$)-alkyl-, aryl, heteroaryl, and heterocyclo;

n is 0 to 2;

q is 0 or 1, provided that q is 1 when X is other than S; and s is 0 or 1.

In yet another embodiment, compounds of formula I are provided wherein:

A is

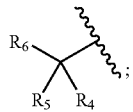

X is O, S or CH$_2$;

R$_1$ is —C(O)R$_7$;

R$_{2a}$, R$_{2b}$ and R$_{2c}$ are independently hydrogen or —(C$_1$-C$_6$)-alkyl;

R$_{3a}$ is hydrogen, (C$_1$-C$_8$)alkyl or aryl, wherein the alkyl and aryl may be optionally substituted with one or more halo, alkyl, haloalkyl, OH, alkyloxy, haloalkyoxy, cyano, or nitro;

R$_{3b}$ is (a) hydrogen, (b) —OH, (c) aryl, which may optionally be substituted with one or more substituents selected from the group consisting of: halo, (C$_1$-C$_6$)-alkyl, halo(C$_1$-C$_6$)alkyl, (C$_1$-C$_6$)-alkyloxy, cyano and nitro; (d) —(C$_1$-C$_8$)-alkyl, which may optionally be substituted with one or more substituents selected from the group consisting of: halo, —OH, halo(C$_1$-C$_6$)alkyloxy, (C$_1$-C$_6$)-alkyloxy, aryl and heteroaryl; (e) —O[(C=O)]$_s$aryl, which may optionally be substituted with one or more substituents selected from the group consisting of: halo, (C$_1$-C$_6$)-alkyl, halo (C$_1$-C$_6$)alkyl, (C$_1$-C$_6$)-alkyloxy, —COOH, —(C$_1$-C$_6$)-alkylCOOH, —(C$_1$-C$_6$)-alkyl-CO$_2$(C$_1$-C$_6$)-alkyl, —CO$_2$(C$_1$-C$_6$)-alkyl and aryl; or (f) —O[(C=O)]$_s$heteroaryl, which may optionally be substituted with one or more substituents selected from the group consisting of: halo, (C$_1$-C$_6$)-alkyl, halo(C$_1$-C$_6$)alkyl, (C$_1$-C$_6$)-alkyloxy, —COOH, —(C$_1$-C$_6$)-alkylCOOH, —(C$_1$-C$_6$)-alkyl-CO$_2$(C$_1$-C$_6$)-alkyl, —CO$_2$(C$_1$-C$_6$)-alkyl and aryl;

R$_4$ and R$_6$ are halo(C$_1$-C$_4$)-alkyl;

R$_5$ is hydroxy;

R$_7$ is alkyl, aryl or heterocyclyl, wherein the alkyl, aryl, or heterocyclyl may be optionally substituted with one or more R$_{10b}$'s;

R$_{3a}$ is (a) halo; (b) —OH; (c) —O[(C=O)]$_s$(C$_1$-C$_6$)-alkyl; (d) —O[(C=O)]$_s$(C$_1$-C$_6$)-alkylaryl; (e) —CO$_2$(C$_1$-C$_6$)-alkyl; (f) aryl, which may optionally be substituted with one or more substituents selected from the group consisting of: halo, (C$_1$-C$_6$)-alkyl, halo(C$_1$-C$_6$)alkyl, (C$_1$-C$_6$)-alkyloxy, halo(C$_1$-C$_6$)-alkyloxy, cyano, nitro, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, cyano, or nitro; (g) heteroaryl optionally substituted with one or more substituents selected from the group consisting of: halo, (C$_1$-C$_6$)-alkyl, halo(C$_1$-C$_6$)alkyl, —OH, (C$_1$-C$_6$)-alkyloxy, halo (C$_1$-C$_6$)-alkyloxy, cyano, nitro, —O(C$_1$-C$_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (h) —(C$_1$-C$_6$)-alkyl, which may optionally be substituted with one or more substituents selected from the group consisting of: halo, halo(C$_1$-C$_6$)alkyloxy, (C$_1$-C$_6$)-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (i) —($C_3$-$C_8$)-cycloalkyl, which may optionally be substituted with one or more substituents selected from the group consisting of: halo, ($C_1$-$C_6$)-alkyl, halo($C_1$-$C_6$)alkyl, halo($C_1$-$C_6$)alkyloxy, ($C_1$-$C_6$)-alkyloxy, aryl, which may be optionally substituted with one or more halo, alkyl, haloalkyl, OH, alkyloxy, haloalkyloxy, cyano, or nitro; heteroaryl, which may be optionally substituted with one or more which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; or (j) —O[(C=O)]$_s$aryl, which may optionally be substituted with one or more substituents selected from the group consisting of: halo, ($C_1$-$C_6$)-alkyl, halo($C_1$-$C_6$)alkyl, halo($C_1$-$C_6$)alkyloxy, and ($C_1$-$C_6$)-alkyloxy;

q is 0 or 1, provided that q is 1 when X is other than S; and s is 0 or 1.

In yet another embodiment, compounds of formula I are provided wherein:

A is

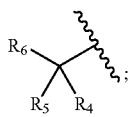

X is O, S or $CH_2$;
$R_1$ is —C(O)$R_7$;
$R_{2a}$, $R_{2b}$ and $R_{2c}$ are hydrogen;
$R_{3a}$ is hydrogen, ($C_1$-$C_8$)alkyl or aryl, wherein the alkyl and aryl may be optionally substituted with one or more halo, alkyl, haloalkyl, OH, alkyloxy, haloalkyoxy, cyano, or nitro;
$R_{3b}$ is (a) hydrogen, (b) —OH, (c) aryl, which may optionally be substituted with one or more substituents selected from the group consisting of: halo, ($C_1$-$C_6$)-alkyl, halo($C_1$-$C_6$)alkyl, and ($C_1$-$C_6$)-alkyloxy; (d) —($C_1$-$C_8$)-alkyl; (e) —Oaryl, which may optionally be substituted with one or more substituents selected from the group consisting of: halo, ($C_1$-$C_6$)-alkyl, halo($C_1$-$C_6$)alkyl, ($C_1$-$C_6$)-alkyloxy, —COOH, —($C_1$-$C_6$)-alkylCOOH, —($C_1$-$C_6$)-alkyl-$CO_2$($C_1$-$C_6$)-alkyl, —$CO_2$($C_1$-$C_6$)-alkyl and aryl; or (f) —Oheteroaryl, which may optionally be substituted with one or more substituents selected from the group consisting of: halo, ($C_1$-$C_6$)-alkyl, halo($C_1$-$C_6$)alkyl, ($C_1$-$C_6$)-alkyloxy, —COOH, —($C_1$-$C_6$)-alkylCOOH, —($C_1$-$C_6$)-alkyl-$CO_2$($C_1$-$C_6$)-alkyl, —$CO_2$($C_1$-$C_6$)-alkyl and aryl;

$R_4$ and $R_6$ are halo($C_1$-$C_4$)-alkyl;
$R_5$ is hydroxy;
$R_7$ is alkyl or aryl, wherein the alkyl or aryl may be optionally substituted with one or more $R_{10b}$'s;
$R_{10b}$ is (a) halo; (b) —OH; (c) —O($C_1$-$C_6$)-alkyl; (d) —$CO_2$($C_1$-$C_6$)-alkyl; (e) aryl, which may optionally be substituted with one or more substituents selected from the group consisting of: halo, ($C_1$-$C_6$)-alkyl, halo($C_1$-$C_6$)alkyl, ($C_1$-$C_6$)-alkyloxy, halo($C_1$-$C_6$)-alkyloxy, cyano, nitro, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, cyano, or nitro; (f) heteroaryl which may be optionally substituted with one or more halo, ($C_1$-$C_6$)-alkyl, halo($C_1$-$C_6$) alkyl, —OH, ($C_1$-$C_6$)-alkyloxy, halo($C_1$-$C_6$)-alkyloxy, cyano or nitro; (g) —($C_1$-$C_6$)-alkyl, which may optionally be substituted with one or more substituents selected from the group consisting of: halo, halo($C_1$-$C_6$)alkyloxy, and ($C_1$-$C_6$)-alkyloxy; (h) —($C_3$-$C_8$)-cycloalkyl; or (i) —Oaryl; and q is 1.

In another embodiment, compounds of the present invention are selected from the compounds exemplified in the examples.

In another embodiment, compounds of the present invention are selected from the group consisting of:

3-Phenyl-1-[7-(2,2,2-trifluoro-1-hydroxy-1-trifluoromethyl-ethyl)-2,3,4,5-tetrahydro-1-benzazepin-1-yl]-propan-1-one;

2-Phenyl-1-[7-(2,2,2-trifluoro-1-hydroxy-1-trifluoromethyl-ethyl)-2,3,4,5-tetrahydro-1-benzazepin-1-yl]-ethanone;

2-Cyclopentyl-1-[7-(2,2,2-trifluoro-1-hydroxy-1-trifluoromethyl-ethyl)-2,3,4,5-tetrahydro-1-benzazepin-1-yl]-ethanone;

(R)-2-Hydroxy-2-phenyl-1-[7-(2,2,2-trifluoro-1-hydroxy-1-trifluoromethyl-ethyl)-2,3,4,5-tetrahydro-1-benzazepin-1-yl]-ethanone;

Phenyl-[7-(2,2,2-trifluoro-1-hydroxy-1-trifluoromethyl-ethyl)-2,3,4,5-tetrahydro-1-benzazepin-1-yl]-methanone;

(R)-2-Phenyl-1-[7-(2,2,2-trifluoro-1-hydroxy-1-trifluoromethyl-ethyl)-2,3,4,5-tetrahydro-1-benzazepin-1-yl]-butan-1-one;

m-Tolyl-[7-(2,2,2-trifluoro-1-hydroxy-1-trifluoromethyl-ethyl)-2,3,4,5-tetrahydro-1-benzazepin-1-yl]-methanone;

2-Thiophen-2-yl-1-[7-(2,2,2-trifluoro-1-hydroxy-1-trifluoromethyl-ethyl)-2,3,4,5-tetrahydro-1-benzazepin-1-yl]-ethanone;

Furan-2-yl-[7-(2,2,2-trifluoro-1-hydroxy-1-trifluoromethyl-ethyl)-2,3,4,5-tetrahydro-1-benzazepin-1-yl]-methanone;

2-Phenoxy-1-[7-(2,2,2-trifluoro-1-hydroxy-1-trifluoromethyl-ethyl)-2,3,4,5-tetrahydro-1-benzazepin-1-yl]-ethanone;

(2-Methoxy-phenyl)-[7-(2,2,2-trifluoro-1-hydroxy-1-trifluoromethyl-ethyl)-2,3,4,5-tetrahydro-1-benzazepin-1-yl]-methanone;

3-Cyclopentyl-1-[7-(2,2,2-trifluoro-1-hydroxy-1-trifluoromethyl-ethyl)-2,3,4,5-tetrahydro-1-benzazepin-1-yl]-propan-1-one;

Thiophen-2-yl-[7-(2,2,2-trifluoro-1-hydroxy-1-trifluoromethyl-ethyl)-2,3,4,5-tetrahydro-1-benzazepin-1-yl]-methanone;

2-(3-Methoxy-phenyl)-1-[7-(2,2,2-trifluoro-1-hydroxy-1-trifluoromethyl-ethyl)-2,3,4,5-tetrahydro-1-benzazepin-1-yl]-ethanone;

2-(4-Methoxy-phenyl)-1-[7-(2,2,2-trifluoro-1-hydroxy-1-trifluoromethyl-ethyl)-2,3,4,5-tetrahydro-1-benzazepin-1-yl]-ethanone;

2-Phenylsulfanyl-1-[7-(2,2,2-trifluoro-1-hydroxy-1-trifluoromethyl-ethyl)-2,3,4,5-tetrahydro-1-benzazepin-1-yl]-ethanone;

2-(4-Fluoro-phenyl)-1-[7-(2,2,2-trifluoro-1-hydroxy-1-trifluoromethyl-ethyl)-2,3,4,5-tetrahydro-1-benzazepin-1-yl]-ethanone;

2-(4-Chloro-phenyl)-1-[7-(2,2,2-trifluoro-1-hydroxy-1-trifluoromethyl-ethyl)-2,3,4,5-tetrahydro-1-benzazepin-1-yl]-ethanone;

2-(2-Bromo-phenyl)-1-[7-(2,2,2-trifluoro-1-hydroxy-1-trifluoromethyl-ethyl)-2,3,4,5-tetrahydro-1-benzazepin-1-yl]-ethanone;

2-(3,5-Difluoro-phenyl)-1-[7-(2,2,2-trifluoro-1-hydroxy-1-trifluoromethyl-ethyl)-2,3,4,5-tetrahydro-1-benzazepin-1-yl]-ethanone;

Furan-3-yl-[7-(2,2,2-trifluoro-1-hydroxy-1-trifluoromethyl-ethyl)-2,3,4,5-tetrahydro-1-benzazepin-1-yl]-methanone;

2-(2,4-Dichloro-phenyl)-1-[7-(2,2,2-trifluoro-1-hydroxy-1-trifluoromethyl-ethyl)-2,3,4,5-tetrahydro-1-benzazepin-1-yl]-ethanone;

Bicyclo[4.2.0]octa-1(6),2,4-trien-7-yl-[7-(2,2,2-trifluoro-1-hydroxy-1-trifluoromethyl-ethyl)-2,3,4,5-tetrahydro-1-benzazepin-1-yl]-methanone;

2-Cyclohexyl-1-[7-(2,2,2-trifluoro-1-hydroxy-1-trifluoromethyl-ethyl)-2,3,4,5-tetrahydro-1-benzazepin-1-yl]-ethanone;

(2,6-Difluoro-phenyl)-[7-(2,2,2-trifluoro-1-hydroxy-1-trifluoromethyl-ethyl)-2,3,4,5-tetrahydro-1-benzazepin-1-yl]-methanone;

(R)-2-Methoxy-2-phenyl-1-[7-(2,2,2-trifluoro-1-hydroxy-1-trifluoromethyl-ethyl)-2,3,4,5-tetrahydro-1-benzazepin-1-yl]-ethanone;

2-(2,6-Dichloro-phenyl)-1-[7-(2,2,2-trifluoro-1-hydroxy-1-trifluoromethyl-ethyl)-2,3,4,5-tetrahydro-1-benzazepin-1-yl]-ethanone;

2-(2-Methoxy-phenyl)-1-[7-(2,2,2-trifluoro-1-hydroxy-1-trifluoromethyl-ethyl)-2,3,4,5-tetrahydro-1-benzazepin-1-yl]-ethanone;

2-o-Tolyl-1-[7-(2,2,2-trifluoro-1-hydroxy-1-trifluoromethyl-ethyl)-2,3,4,5-tetrahydro-1-benzazepin-1-yl]-ethanone;

2-m-Tolyl-1-[7-(2,2,2-trifluoro-1-hydroxy-1-trifluoromethyl-ethyl)-2,3,4,5-tetrahydro-1-benzazepin-1-yl]-ethanone;

2-(4-Ethoxy-phenyl)-1-[7-(2,2,2-trifluoro-1-hydroxy-1-trifluoromethyl-ethyl)-2,3,4,5-tetrahydro-1-benzazepin-1-yl]-ethanone;

2-Methyl-2-phenyl-1-[7-(2,2,2-trifluoro-1-hydroxy-1-trifluoromethyl-ethyl)-2,3,4,5-tetrahydro-1-benzazepin-1-yl]-propan-1-one;

2-(3,5-Dimethoxy-phenyl)-1-[7-(2,2,2-trifluoro-1-hydroxy-1-trifluoromethyl-ethyl)-2,3,4,5-tetrahydro-1-benzazepin-1-yl]-ethanone;

2-(4-Isopropyl-phenyl)-1-[7-(2,2,2-trifluoro-1-hydroxy-1-trifluoromethyl-ethyl)-2,3,4,5-tetrahydro-1-benzazepin-1-yl]-ethanone;

2-(2,3-Dimethoxy-phenyl)-1-[7-(2,2,2-trifluoro-1-hydroxy-1-trifluoromethyl-ethyl)-2,3,4,5-tetrahydro-1-benzazepin-1-yl]-ethanone;

(R)-2-Phenyl-1-[7-(2,2,2-trifluoro-1-hydroxy-1-trifluoromethyl-ethyl)-2,3,4,5-tetrahydro-1-benzazepin-1-yl]-propan-1-one;

(S)-2-Methoxy-2-phenyl-1-[7-(2,2,2-trifluoro-1-hydroxy-1-trifluoromethyl-ethyl)-2,3,4,5-tetrahydro-1-benzazepin-1-yl]-ethanone;

4,4,4-Trifluoro-1-[7-(2,2,2-trifluoro-1-hydroxy-1-trifluoromethyl-ethyl)-2,3,4,5-tetrahydro-1-benzazepin-1-yl]-butan-1-one;

2-(1R,4S)-Bicyclo[2.2.1]hept-2-yl-1-[7-(2,2,2-trifluoro-1-hydroxy-1-trifluoromethyl-ethyl)-2,3,4,5-tetrahydro-1-benzazepin-1-yl]-ethanone;

2-(4-Hydroxymethyl-phenyl)-1-[7-(2,2,2-trifluoro-1-hydroxy-1-trifluoromethyl-ethyl)-2,3,4,5-tetrahydro-1-benzazepin-1-yl]-ethanone;

7-(2,2,2-Trifluoro-1-hydroxy-1-trifluoromethyl-ethyl)-2,3,4,5-tetrahydro-1-benzazepine-1-carboxylic acid isopropyl ester;

7-(2,2,2-Trifluoro-1-hydroxy-1-trifluoromethyl-ethyl)-2,3,4,5-tetrahydro-1-benzazepine-1-carboxylic acid phenethyl-amide;

2-Phenyl-1-[2-(2,2,2-trifluoro-1-hydroxy-1-trifluoromethyl-ethyl)-6,7-dihydro-9H-8-thia-5-aza-benzocyclohepten-5-yl]-ethanone;

2-Methyl-1-[2-(2,2,2-trifluoro-1-hydroxy-1-trifluoromethyl-ethyl)-6,7-dihydro-9H-8-thia-5-aza-benzocyclohepten-5-yl]-propan-1-one;

2-Phenyl-1-[7-(2,2,2-trifluoro-1-hydroxy-1-trifluoromethyl-ethyl)-2,3-dihydro-5H-4,1-benzoxazepin-1-yl]-ethanone;

1-{7-[2-Chloro-1-(chloro-difluoro-methyl)-2,2-difluoro-1-hydroxy-ethyl]-2,3,4,5-tetrahydro-1-benzazepin-1-yl}-2-methyl-propan-1-one;

2-Methyl-1-[2-methyl-7-(2,2,2-trifluoro-1-hydroxy-1-trifluoromethyl-ethyl)-2,3,4,5-tetrahydro-1-benzazepin-1-yl]-propan-1-one;

1-[2-Isopropyl-7-(2,2,2-trifluoro-1-hydroxy-1-trifluoromethyl-ethyl)-2,3,4,5-tetrahydro-1-benzazepin-1-yl]-2-methyl-propan-1-one;

(S)-2-Phenyl-1-[2-phenyl-7-(2,2,2-trifluoro-1-hydroxy-1-trifluoromethyl-ethyl)-2,3,4,5-tetrahydro-1-benzazepin-1-yl]-propan-1-one;

(S)-1-[(S)-7-(3,5-Dimethyl-isoxazol-4-yl)-3-(3-methoxy-phenoxy)-2,3,4,5-tetrahydro-1-benzazepin-1-yl]-2-phenyl-propan-1-one;

(S)-1-[(R)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

2-Methyl-1-[3-phenoxy-7-(2,2,2-trifluoro-1-hydroxy-1-trifluoromethyl-ethyl)-2,3,4,5-tetrahydro-1-benzazepin-1-yl]-propan-1-one;

1-[3-(3-Methoxy-phenoxy)-7-(2,2,2-trifluoro-1-hydroxy-1-trifluoromethyl-ethyl)-2,3,4,5-tetrahydro-1-benzazepin-1-yl]-2-methyl-propan-1-one;

1-[3-(4-Methoxy-phenoxy)-7-(2,2,2-trifluoro-1-hydroxy-1-trifluoromethyl-ethyl)-2,3,4,5-tetrahydro-1-benzazepin-1-yl]-2-methyl-propan-1-one;

2-Methyl-1-[(S)-3-phenoxy-7-(2,2,2-trifluoro-1-hydroxy-1-trifluoromethyl-ethyl)-2,3,4,5-tetrahydro-1-benzazepin-1-yl]-propan-1-one;

(R)-1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid;

(S)-1-[(R)-3-Hydroxy-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(2,3-Dichloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(2,5-Dichloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(2,5-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(2,4-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

Toluene-4-sulfonic acid (S)-1-((S)-2-phenyl-propionyl)-7-(2,2,2-trifluoro-1-hydroxy-1-trifluoromethyl-ethyl)-2,3,4,5-tetrahydro-1H-1-benzazepin-3-yl ester;
Methane sulfonic acid (S)-1-((S)-2-phenyl-propionyl)-7-(2,2,2-trifluoro-1-hydroxy-1-trifluoromethyl-ethyl)-2,3,4,5-tetrahydro-1H-1-benzazepin-3-yl ester;
3-Pyridin-3-yl-1-[7-(2,2,2-trifluoro-1-hydroxy-1-trifluoromethyl-ethyl)-2,3,4,5-tetrahydro-1-benzazepin-1-yl]-propan-1-one;
2-Pyridin-3-yl-1-[7-(2,2,2-trifluoro-1-hydroxy-1-trifluoromethyl-ethyl)-2,3,4,5-tetrahydro-1-benzazepin-1-yl]-ethanone;
2-(5-Bromo-pyridin-3-yl)-1-[7-(2,2,2-trifluoro-1-hydroxy-1-trifluoromethyl-ethyl)-2,3,4,5-tetrahydro-1-benzazepin-1-yl]-ethanone;
2-(6-Chloro-pyridin-3-yl)-1-[7-(2,2,2-trifluoro-1-hydroxy-1-trifluoromethyl-ethyl)-2,3,4,5-tetrahydro-1-benzazepin-1-yl]-ethanone;
2-(Pyridin-4-ylsulfanyl)-1-[7-(2,2,2-trifluoro-1-hydroxy-1-trifluoromethyl-ethyl)-2,3,4,5-tetrahydro-1-benzazepin-1-yl]-ethanone;
1-[7-(2,2,2-Trifluoro-1-hydroxy-1-trifluoromethyl-ethyl)-2,3,4,5-tetrahydro-1-benzazepin-1-yl]-2-(4-trifluoromethyl-phenyl)-ethanone;
Acetic acid (S)-2-oxo-1-phenyl-2-[7-(2,2,2-trifluoro-1-hydroxy-1-trifluoromethyl-ethyl)-2,3,4,5-tetrahydro-1-benzazepin-1-yl]-ethyl ester;
1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-pyridin-4-yl-ethanone;
1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-pyridin-2-yl-ethanone;
1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-(pyridin-4-ylsulfanyl)-ethanone;
[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-pyridin-2-yl-methanone;
2-Methyl-1-[7-(2,2,2-trifluoro-1-hydroxy-1-trifluoromethyl-ethyl)-2,3-dihydro-1,4-benzothiazin-4-yl]-propan-1-one;
2-Phenyl-1-[7-(2,2,2-trifluoro-1-hydroxy-1-trifluoromethyl-ethyl)-2,3-dihydro-1,4-benzothiazin-4-yl]-ethanone;
3-Phenyl-1-[7-(2,2,2-trifluoro-1-hydroxy-1-trifluoromethyl-ethyl)-2,3-dihydro-1,4-benzothiazin-4-yl]-propan-1-one;
2-Methyl-1-[3-phenyl-7-(2,2,2-trifluoro-1-hydroxy-1-trifluoromethyl-ethyl)-2,3-dihydro-1,4-benzothiazin-4-yl]-propan-1-one;
2-Methyl-1-[3-phenyl-7-(2,2,2-trifluoro-1-hydroxy-1-trifluoromethyl-ethyl)-2,3-dihydro-1,4-benzothiazin-4-yl]-propan-1-one, Isomer B;
2-Phenyl-1-[3-phenyl-7-(2,2,2-trifluoro-1-hydroxy-1-trifluoromethyl-ethyl)-2,3-dihydro -1,4-benzothiazin-4-yl]-ethanone;
1-[3-(3-Methoxy-phenyl)-7-(2,2,2-trifluoro-1-hydroxy-1-trifluoromethyl-ethyl)-2,3-dihydro-1,4-benzothiazin-4-yl]-2-phenyl-ethanone;
1-[3-(3-Methoxy-phenyl)-7-(2,2,2-trifluoro-1-hydroxy-1-trifluoromethyl-ethyl)-2,3-dihydro-1,4-benzothiazin-4-yl]-2-methyl-propan-1-one;
1-[3-(3-Methoxy-phenyl)-7-(2,2,2-trifluoro-1-hydroxy-1-trifluoromethyl-ethyl)-2,3-dihydro-1,4-benzothiazin-4-yl]-2-methyl-propan-1-one, Isomer A;
1-[3-(4-Methoxy-phenyl)-7-(2,2,2-trifluoro-1-hydroxy-1-trifluoromethyl-ethyl)-2,3-dihydro-1,4-benzothiazin-4-yl]-2-phenyl-ethanone;
(+/−)-2-Methyl-1-[cis-(2-methyl-3-phenyl)-7-(2,2,2-trifluoro-1-hydroxy-1-trifluoromethyl-ethyl)-2,3-dihydro-1,4-benzothiazin-4-yl]-propan-1-one;
(+/−)-1-[cis-(2-Methyl-3-phenyl)-7-(2,2,2-trifluoro-1-hydroxy-1-trifluoromethyl-ethyl)-2,3-dihydro-1,4-benzothiazin-4-yl]-2-phenyl-ethanone;
1-[2-Methyl-3-phenyl-7-(2,2,2-trifluoro-1-hydroxy-1-trifluoromethyl-ethyl)-2,3-dihydro-1,4-benzothiazin-4-yl]-2-phenyl-ethanone, Cis Isomer A;
2-Methyl-1-[2-phenyl-7-(2,2,2-trifluoro-1-hydroxy-1-trifluoromethyl-ethyl)-2,3-dihydro-1,4-benzothiazin-4-yl]-propan-1-one;
2-Methyl-1-[2-methyl-7-(2,2,2-trifluoro-1-hydroxy-1-trifluoromethyl-ethyl)-2,3-dihydro-1,4-benzothiazin-4-yl]-propan-1-one;
1-[2-Methyl-7-(2,2,2-trifluoro-1-hydroxy-1-trifluoromethyl-ethyl)-2,3-dihydro-1,4-benzothiazin-4-yl]-2-phenyl-ethanone;
1-[2-Methyl-7-(2,2,2-trifluoro-1-hydroxy-1-trifluoromethyl-ethyl)-2,3-dihydro-1,4-benzothiazin-4-yl]-2-phenyl-ethanone, Isomer A;
1-[2-Methyl-7-(2,2,2-trifluoro-1-hydroxy-1-trifluoromethyl-ethyl)-2,3-dihydro-1,4-benzothiazin-4-yl]-2-phenyl-ethanone, Isomer B;
1-[(S)-2-Ethyl-7-(2,2,2-trifluoro-1-hydroxy-1-trifluoromethyl-ethyl)-2,3-dihydro-1,4-benzothiazin-4-yl]-2-methyl-propan-1-one;
1-[(S)-2-Ethyl-7-(2,2,2-trifluoro-1-hydroxy-1-trifluoromethyl-ethyl)-2,3-dihydro-1,4-benzothiazin-4-yl]-2-phenyl-ethanone;
1-[(S)-2-Ethyl-7-(2,2,2-trifluoro-1-hydroxy-1-trifluoromethyl-ethyl)-2,3-dihydro-1,4-benzothiazin-4-yl]-2-phenyl-ethane-1,2-dione;
1-[(S)-2-Ethyl-7-(2,2,2-trifluoro-1-hydroxy-1-trifluoromethyl-ethyl)-2,3-dihydro-1,4-benzothiazin-4-yl]-4-methyl-pentan-1-one;
4-[(S)-2-Ethyl-7-(2,2,2-trifluoro-1-hydroxy-1-trifluoromethyl-ethyl)-2,3-dihydro-1,4-benzothiazin-4-yl]-4-oxo-butyric acid methyl ester;
Cyclohexyl-[(S)-2-ethyl-7-(2,2,2-trifluoro-1-hydroxy-1-trifluoromethyl-ethyl)-2,3-dihydro-1,4-benzothiazin-4-yl]-methanone;
3-Cyclopentyl-1-[(S)-2-ethyl-7-(2,2,2-trifluoro-1-hydroxy-1-trifluoromethyl-ethyl)-2,3-dihydro-1,4-benzothiazin-4-yl]-propan-1-one;
3-Cyclohexyl-1-[(S)-2-ethyl-7-(2,2,2-trifluoro-1-hydroxy-1-trifluoromethyl-ethyl)-2,3-dihydro-1,4-benzothiazin-4-yl]-propan-1-one;
(2-Chloro-phenyl)-[(S)-2-ethyl-7-(2,2,2-trifluoro-1-hydroxy-1-trifluoromethyl-ethyl)-2,3-dihydro-1,4-benzothiazin-4-yl]-methanone;
[(S)-2-Ethyl-7-(2,2,2-trifluoro-1-hydroxy-1-trifluoromethyl-ethyl)-2,3-dihydro-1,4-benzothiazin-4-yl]-(4-methoxy-phenyl)-methanone;
1-[(S)-2-Ethyl-7-(2,2,2-trifluoro-1-hydroxy-1-trifluoromethyl-ethyl)-2,3-dihydro-1,4-benzothiazin-4-yl]-2-(4-methoxy-phenyl)-ethanone;
2-(4-Chloro-phenyl)-1-[(S)-2-ethyl-7-(2,2,2-trifluoro-1-hydroxy-1-trifluoromethyl-ethyl)-2,3-dihydro-1,4-benzothiazin-4-yl]-ethanone;
1-[(S)-2-Ethyl-7-(2,2,2-trifluoro-1-hydroxy-1-trifluoromethyl-ethyl)-2,3-dihydro-1,4-benzothiazin-4-yl]-3-phenyl-propan-1-one;

1-[(S)-2-Ethyl-7-(2,2,2-trifluoro-1-hydroxy-1-trifluoromethyl-ethyl)-2,3-dihydro-1,4-benzothiazin-4-yl]-2-phenoxy-ethanone;
2-(4-Chloro-phenoxy)-1-[(S)-2-ethyl-7-(2,2,2-trifluoro-1-hydroxy-1-trifluoromethyl-ethyl)-2,3-dihydro-1,4-benzothiazin-4-yl]-ethanone;
2-Benzyloxy-1-[(S)-2-ethyl-7-(2,2,2-trifluoro-1-hydroxy-1-trifluoromethyl-ethyl)-2,3-dihydro-1,4-benzothiazin-4-yl]-ethanone;
1-[(S)-2-Ethyl-7-(2,2,2-trifluoro-1-hydroxy-1-trifluoromethyl-ethyl)-2,3-dihydro-1,4-benzothiazin-4-yl]-4-phenoxy-butan-1-one;
1-[(S)-2-Ethyl-7-(2,2,2-trifluoro-1-hydroxy-1-trifluoromethyl-ethyl)-2,3-dihydro-1,4-benzothiazin-4-yl]-2-(3-methoxy-phenyl)-ethanone;
[(S)-2-Ethyl-7-(2,2,2-trifluoro-1-hydroxy-1-trifluoromethyl-ethyl)-2,3-dihydro-1,4-benzothiazin-4-yl]-furan-2-yl-methanone;
Benzo[b]thiophen-2-yl-[(S)-2-ethyl-7-(2,2,2-trifluoro-1-hydroxy-1-trifluoromethyl-ethyl)-2,3-dihydro-1,4-benzothiazin-4-yl]-methanone;
[(S)-2-Ethyl-7-(2,2,2-trifluoro-1-hydroxy-1-trifluoromethyl-ethyl)-2,3-dihydro-1,4-benzothiazin-4-yl]-(4-methyl-1,2,3-thiadiazol-5-yl)-methanone;
[(S)-2-Ethyl-7-(2,2,2-trifluoro-1-hydroxy-1-trifluoromethyl-ethyl)-2,3-dihydro-1,4-benzothiazin-4-yl]-pyridin-2-yl-methanone;
1-[(S)-2-Ethyl-7-(2,2,2-trifluoro-1-hydroxy-1-trifluoromethyl-ethyl)-2,3-dihydro-1,4-benzothiazin-4-yl]-2-thiophen-2-yl-ethanone;
1-[(S)-2-Ethyl-7-(2,2,2-trifluoro-1-hydroxy-1-trifluoromethyl-ethyl)-2,3-dihydro-1,4-benzothiazin-4-yl]-2,2-dimethyl-propan-1-one; (3-Chloro-phenyl)-[(S)-2-ethyl-7-(2,2,2-trifluoro-1-hydroxy-1-trifluoromethyl-ethyl)-2,3-dihydro-1,4-benzothiazin-4-yl]-methanone;
1,1,1,3,3,3-Hexafluoro-2-(1-phenethyl-2,3,4,5-tetrahydro-1H-1-benzazepin-7-yl)-propan-2-ol; and
2-{1-[2-(3-Chloro-2,6-difluoro-phenyl)-ethyl]-2,3,4,5-tetrahydro-1H-1-benzazepin-7-yl}-1,1,1,3,3,3-hexafluoro-propan-2-ol.

In another embodiment, compounds of the present invention are selected from the group consisting of:
2-Phenyl-1-[7-(2,2,2-trifluoro-1-hydroxy-1-trifluoromethyl-ethyl)-2,3,4,5-tetrahydro-1-benzazepin-1-yl]-ethanone;
(S)-2-Hydroxy-2-phenyl-1-[7-(2,2,2-trifluoro-1-hydroxy-1-trifluoromethyl-ethyl)-2,3,4,5-tetrahydro-1-benzazepin-1-yl]-ethanone;
(S)-2-Phenyl-1-[7-(2,2,2-trifluoro-1-hydroxy-1-trifluoromethyl-ethyl)-2,3,4,5-tetrahydro-1-benzazepin-1-yl]-butan-1-one;
2-Phenyl-1-[7-(2,2,2-trifluoro-1-hydroxy-1-trifluoromethyl-ethyl)-2,3,4,5-tetrahydro-1-benzazepin-1-yl]-propan-1-one;
(S)-2-Phenyl-1-[7-(2,2,2-trifluoro-1-hydroxy-1-trifluoromethyl-ethyl)-2,3,4,5-tetrahydro-1-benzazepin-1-yl]-propan-1-one;
2-p-Tolyl-1-[7-(2,2,2-trifluoro-1-hydroxy-1-trifluoromethyl-ethyl)-2,3,4,5-tetrahydro-1-benzazepin-1-yl]-ethanone;
2-Thiophen-3-yl-1-[7-(2,2,2-trifluoro-1-hydroxy-1-trifluoromethyl-ethyl)-2,3,4,5-tetrahydro-1-benzazepin-1-yl]-ethanone;
2-1,3-Benzodioxol-5-yl-1-[7-(2,2,2-trifluoro-1-hydroxy-1-trifluoromethyl-ethyl)-2,3,4,5-tetrahydro-1-benzazepin-1-yl]-ethanone;
2-(4-Dimethylamino-phenyl) 1-[7-(2,2,2-trifluoro-1-hydroxy-1-trifluoromethyl-ethyl)-2,3,4,5-tetrahydro-1-benzazepin-1-yl]-ethanone;
1-{7-[2-Chloro-1-(chloro-difluoro-methyl)-2,2-difluoro-1-hydroxy-ethyl]-2,3,4,5-tetrahydro-1-benzazepin-1-yl}-2-phenyl-ethanone;
(S)-1-[(S)-3-(4-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;
(S)-1-[(S)-3-Phenoxy-7-(2,2,2-trifluoro-1-hydroxy-1-trifluoromethyl-ethyl)-2,3,4,5-tetrahydro-1-benzazepin-1-yl]-2-phenyl-propan-1-one;
(S)-1-[(R)-3-Phenoxy-7-(2,2,2-trifluoro-1-hydroxy-1-trifluoromethyl-ethyl)-2,3,4,5-tetrahydro-1-benzazepin-1-yl]-2-phenyl-propan-1-one;
(S)-1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;
(S)-2-Hydroxy-1-[(S)-3-(4-methoxy-phenoxy)-7-(2,2,2-trifluoro-1-hydroxy-1-trifluoromethyl-ethyl)-2,3,4,5-tetrahydro-1-benzazepin-1-yl]-2-phenyl-ethanone;
(S)-2-Hydroxy-1-[(S)-3-phenoxy-7-(2,2,2-trifluoro-1-hydroxy-1-trifluoromethyl-ethyl)-2,3,4,5-tetrahydro-1-benzazepin-1-yl]-2-phenyl-ethanone;
(S)-2-Hydroxy-1-[(S)-3-(3-methoxy-phenoxy)-7-(2,2,2-trifluoro-1-hydroxy-1-trifluoromethyl-ethyl)-2,3,4,5-tetrahydro-1-benzazepin-1-yl]-2-phenyl-ethanone;
1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-methyl-propan-1-one;
(S)-1-[(S)-3-(3-Chloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;
(S)-1-[(S)-3-(2-Chloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;
(S)-2-Phenyl-1-[(S)-7-(2,2,2-trifluoro-1-hydroxy-1-trifluoromethyl-ethyl)-3-(2-trifluoromethyl-phenoxy)-2,3,4,5-tetrahydro-1-benzazepin-1-yl]-propan-1-one;
(S)-1-[(S)-3-(4-Chloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;
(S)-2-Phenyl-1-[(S)-7-(2,2,2-trifluoro-1-hydroxy-1-trifluoromethyl-ethyl)-3-(3-trifluoromethyl-phenoxy)-2,3,4,5-tetrahydro-1-benzazepin-1-yl]-propan-1-one;
(S)-2-Phenyl-1-[(S)-7-(2,2,2-trifluoro-1-hydroxy-1-trifluoromethyl-ethyl)-3-(4-trifluoromethyl-phenoxy)-2,3,4,5-tetrahydro-1-benzazepin-1-yl]-propan-1-one;
(S)-2-Phenyl-1-[(S)-7-(2,2,2-trifluoro-1-hydroxy-1-trifluoromethyl-ethyl)-3-(2-trifluoromethyl-pyrimidin-4-yloxy)-2,3,4,5-tetrahydro-1-benzazepin-1-yl]-propan-1-one;
(S)-2-Phenyl-1-[(S)-7-(2,2,2-trifluoro-1-hydroxy-1-trifluoromethyl-ethyl)-3-(6-trifluoromethyl-pyrimidin-4-yloxy)-2,3,4,5-tetrahydro-1-benzazepin-1-yl]-propan-1-one;
(S)-2-Amino-3-{4-[(S)-1-((S)-2-phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-propionic acid;
(R)-2-Amino-3-{4-[(S)-1-((S)-2-phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-propionic acid;
{3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-acetic acid methyl ester;

3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid ethyl ester;

3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid methyl ester;

4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid methyl ester;

4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid ethyl ester;

(S)-1-[(S)-3-[4-(2-Methoxy-acetyl)-phenoxy]-7-(2,2,2-trifluoro-1-hydroxy-1-trifluoromethyl-ethyl)-2,3,4,5-tetrahydro-1-benzazepin-1-yl]-2-phenyl-propan-1-one;

3-{4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-propionic acid methyl ester;

{4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-acetic acid;

3-{4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-propionic acid;

4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid;

(S)-1-[(S)-3-(4-Imidazol-1-yl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(2-Methyl-5-trifluoromethyl-2H-pyrazol-3-yloxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(3,5-Dimethoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(2-Chloro-5-methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-Hydroxy-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(3,5-Dichloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(2,4-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(3,4-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(3,5-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(3-Hydroxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

(S)-1-[(S)-3-(3,4-Dichloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one;

1-[7-(2,2,2-Trifluoro-1-hydroxy-1-trifluoromethyl-ethyl)-2,3,4,5-tetrahydro-1-benzazepin-1-yl]-2-(4-trifluoromethyl-phenyl)-ethanone;

2-(3-Chloro-phenyl)-1-[7-(2,2,2-trifluoro-1-hydroxy-1-trifluoromethyl-ethyl)-2,3,4,5-tetrahydro-1-benzazepin-1-yl]-ethanone;

1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-pyridin-3-yl-ethanone;

2-(5-Bromo-pyridin-3-yl)-1-[(S)-3-(3-methoxy-phenoxy)-7-(2,2,2-trifluoro-1-hydroxy-1-trifluoromethyl-ethyl)-2,3,4,5-tetrahydro-1-benzazepin-1-yl]-ethanone;

2-(6-Chloro-pyridin-3-yl)-1-[(S)-3-(3-methoxy-phenoxy)-7-(2,2,2-trifluoro-1-hydroxy-1-trifluoromethyl-ethyl)-2,3,4,5-tetrahydro-1-benzazepin-1-yl]-ethanone;

1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-(4-trifluoromethyl-phenyl)-ethanone;

2-(3-Chloro-phenyl)-1-[(S)-3-(3-methoxy-phenoxy)-7-(2,2,2-trifluoro-1-hydroxy-1-trifluoromethyl-ethyl)-2,3,4,5-tetrahydro-1-benzazepin-1-yl]-ethanone;

1-[(S)-2-Ethyl-7-(2,2,2-trifluoro-1-hydroxy-1-trifluoromethyl-ethyl)-2,3-dihydro-1,4-benzothiazin-4-yl]-3-methyl-butan-1-one;

[(S)-2-Ethyl-7-(2,2,2-trifluoro-1-hydroxy-1-trifluoromethyl-ethyl)-2,3-dihydro-1,4-benzothiazin-4-yl]-phenyl-methanone;

[(S)-2-Ethyl-7-(2,2,2-trifluoro-1-hydroxy-1-trifluoromethyl-ethyl)-2,3-dihydro-1,4-benzothiazin-4-yl]-o-tolyl-methanone;

[(S)-2-Ethyl-7-(2,2,2-trifluoro-1-hydroxy-1-trifluoromethyl-ethyl)-2,3-dihydro-1,4-benzothiazin-4-yl]-thiophen-2-yl-methanone;

{4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-acetic acid; and {3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-acetic acid.

SYNTHESIS

Generally, compounds of the present invention may be prepared by methods such as those illustrated in the following Schemes. Exemplary compounds of the present invention were prepared by the methods illustrated in the examples set forth below. Solvents, temperatures, pressures, and other reaction conditions may readily be selected by one of ordinary skill in the art. Starting materials are commercially available or readily prepared by one of ordinary skill in the art. Combinatorial techniques may be employed in the preparation of compounds, for example, where the intermediates possess groups suitable for these techniques.

SCHEME 1

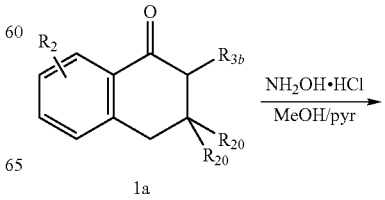

1a

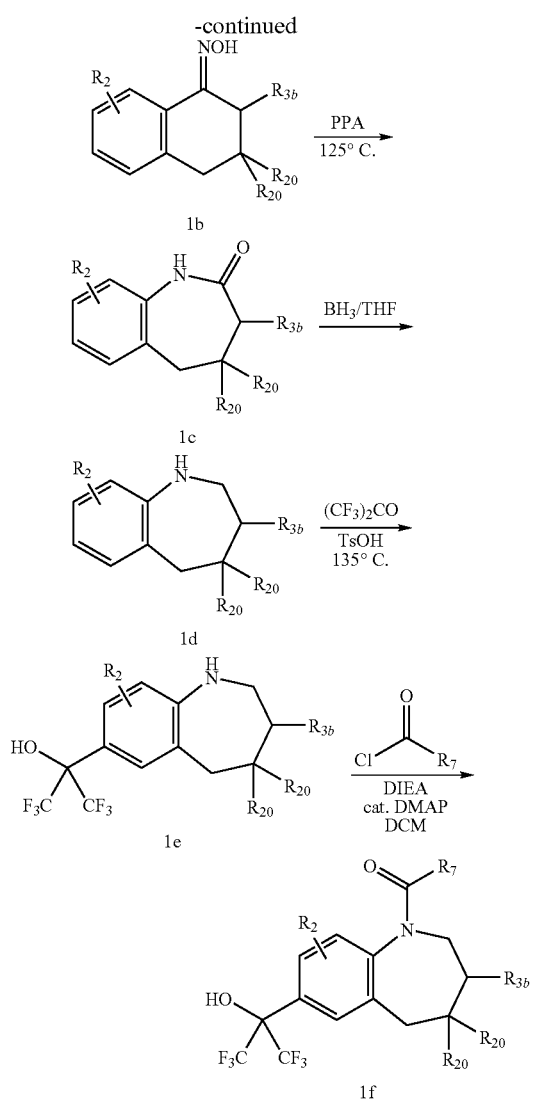

product 1f. Acid chlorides for use in this reaction may be synthesized by a number of standard methods known to one skilled in the art, such as treatment of a carboxylic acid with trichloroacetonitrile in the presence of PPh$_3$ in a solvent such as DCM. In cases when the diacylation product is obtained with acylation both on the amine and the alcohol, a subsequent ester hydrolysis with LiOH in THF or NaOH in MeOH will provide the desired product 1f. Purification to a single diastereomer or enantiomer may be performed on the final products or one of the intermediates as described in the examples or as known to one skilled in the art.

Alternatively, carbamate functionalities may be introduced in place of the amide group by reaction of amine 1e with chloroformate reagents in the presence of an appropriate base, such as DIEA, and in an appropriate solvent, such as DCM, as determined by one skilled in the art. Urea functionalities can be incorporated by treatment of amine 1e with isocyanate reagents. Urea groups could also be incorporated by a number of other reactions of amine 1e as known to one skilled in the art. Sulfonamide functionalities may be introduced by treating amine 1e with sulfonyl chloride reagents in the presence of an appropriate base, such as DIEA and in an appropriate solvent such as DCM as determined by one skilled in the art.

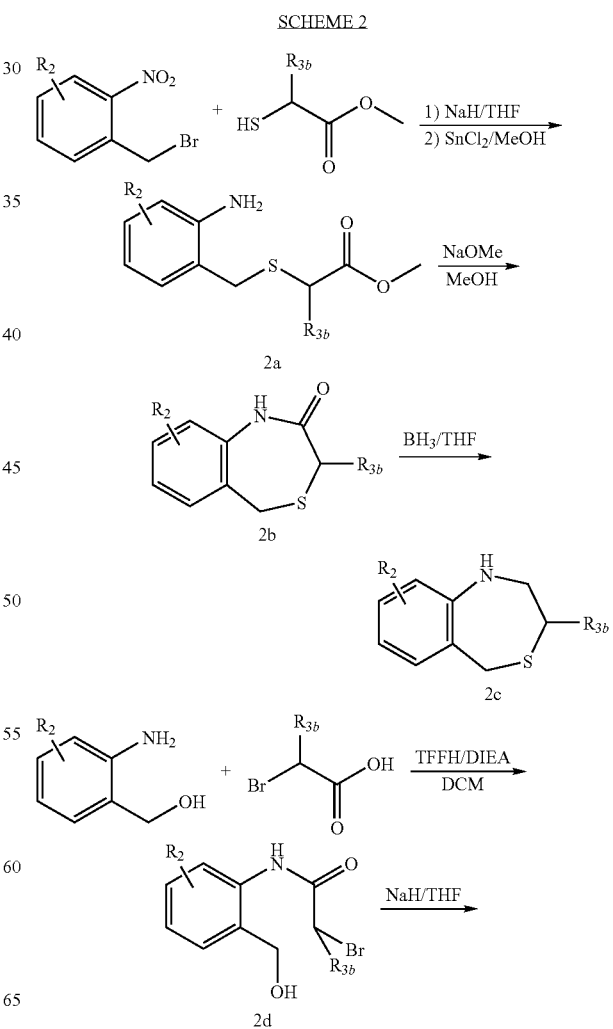

As illustrated in Scheme 1, the synthesis of 2,3,4,5-tetrahydrobenzazepine compounds of this invention where the nitrogen atom in the ring forms part of an amide substituent. These compounds can be prepared by treatment of an optionally substituted 3,4-dihydro-2H-naphthalen-1-one starting material 1a with hydroxylamine hydrochloride in MeOH/pyridine to provide the corresponding oxime 1b (see, e.g. Donaruma and Heldt, Org. Reactions (1960) 11: 1-156). Treatment of oxime 1b with PPA at elevated temperatures affords the 6,7-bicyclic amide product 1c, which can be reduced to the corresponding amine 1d by treatment with BH$_3$ in THF or other reductants known to one skilled in the art. Reaction of amine 1d with hexafluoroacetone in the presence of catalytic TsOH at elevated temperatures provides 1e. As shown in subsequent schemes, alternative methods can be used to install a variety of A groups. Acylation of amine 1e with an acid chloride in the presence of an appropriate base, such as N,N-diisopropylethylamine, and catalytic DMAP in an appropriate solvent such as DCM affords the desired final product 1f. Alternative acylation conditions known to one skilled in the art, such as reaction of amine 1e with an acid chloride in the presence of morpholinomethyl polystyrene resin in an organic solvent such as DCM, may also be applied to prepare the final amide

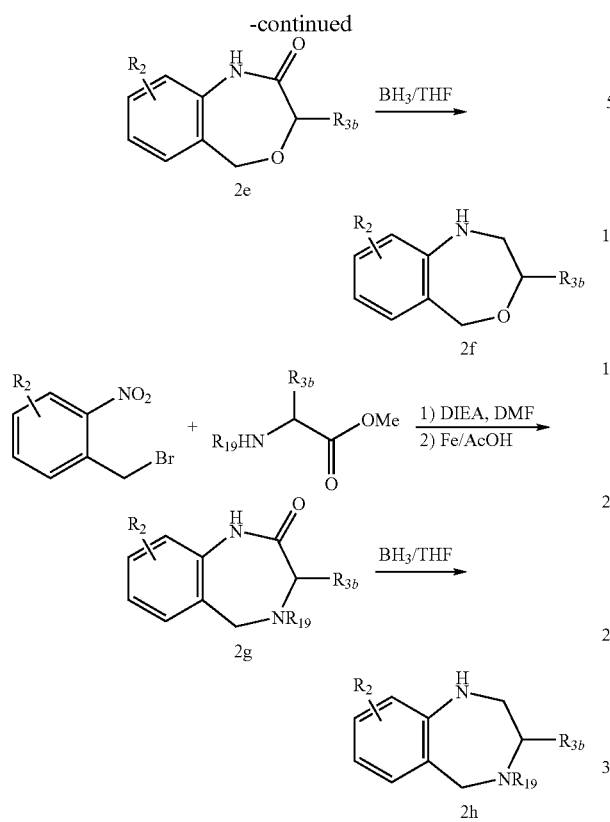

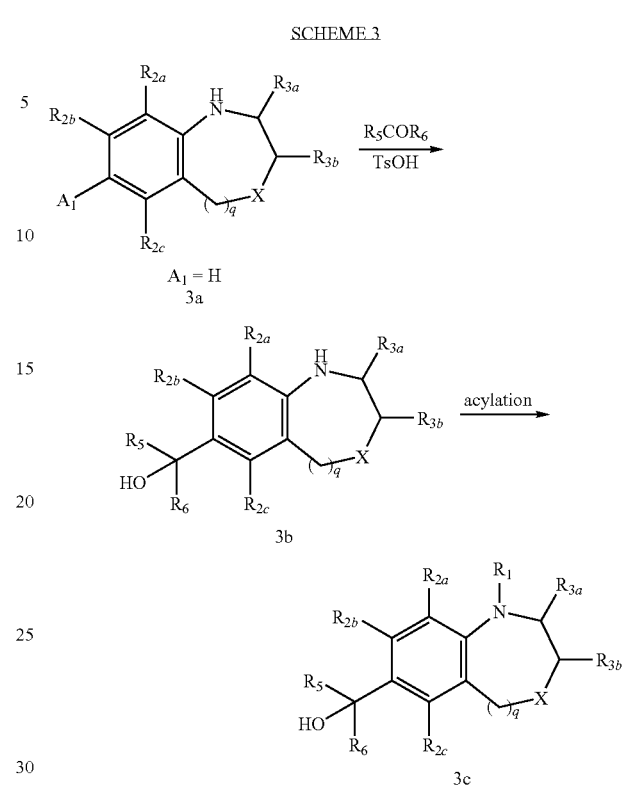

As illustrated in Scheme 2, three strategies for the synthesis of compounds of this invention where the X group is an S, O or $NR_{19}$ atom are depicted. In the first instance, reaction of 1-bromomethyl-2-nitrobenzene with mercapto-acetic acid methyl ester in the presence of NaH base in THF solvent provides (2-nitro-benzylsulfanyl)-acetic acid methyl ester, which can be reduced to the corresponding aniline (2a) by treatment with tin(II) chloride in MeOH or another appropriate reductant as determine by one skilled in the art. Treatment with a strong base, such as NaOMe in MeOH, provides the cyclic amide 2b. Reduction of the amide carbonyl with $BH_3$/THF, or another appropriate reductant, provides amine 2c. Alternatively, reaction of (2-amino-phenyl)-methanol with bromo-acetic acid in the presence of TFFH and a base such as DIEA in a solvent such as DCM affords acetamide 2d. Treatment of 2d with a base such as NaH affords the cyclic amide product 2e, which can again be reduced, for example with $BH_3$/THF, to provide amine 2f. The amine compounds ($X=NR_{19}$) can be prepared by alkylation of an α-amino ester with a 1-bromomethyl-2-nitrobenzene or other conditions known to one skilled in the art (see, e.g. Mishra and Panda, Synthesis (2005) 11:1881-1887). Nitro reduction and cyclization can be obtained in one step using Fe/AcOH conditions as reported by Mishra and Panda to afford 2g. The reduction and cyclization may be performed using other conditions known to one skilled in the art. Reduction of the amide carbonyl (2g) with $BH_3$/THF, or another appropriate reductant, provides amine 2h. The intermediates 2c, 2f and 2h can be further elaborated to introduce the A group as well as $R_1$ substitution of the ring nitrogen as described in Scheme 1,3, 5, 8, 9 and 10 to provide compounds of this invention.

Scheme 3 describes the preparation of polyhalogenated alkyl hydroxyl compounds ($A=C(OH)R_5R_6$) by reacting the derivatized amine 3a with a polyhalogenated alkyl ketone (e.g., $R_5,R_6=CF_3$, $CF_2Cl$) in the presence of a catalytic amount of TsOH at elevated temperatures for one or more hours to provide 3b (see, e.g. Gilbert, Everett E. et al. (1965) J Org. Chem. 30(4): 1001-3). The amine is then treated with an appropriate acylating reagent, such as an acid chloride, sulfonyl chloride, isocyanate, or chloroformate and an appropriate base such as DIEA, as known to one skilled in the art provides the product 3c. In cases when the diacylation product is obtained with acylation both on the amine and the alcohol, a subsequent ester hydrolysis with LiOH in THF or NaOH in MeOH will provide the desired product 3c. Purification to a single diastereomer or enantiomer may be performed on any one of these compounds as described in the examples or as known to one skilled in the art. The diacyl intermediate has been found to facilitate purification of a single pure diastereomer as described for several Examples.

SCHEME 4

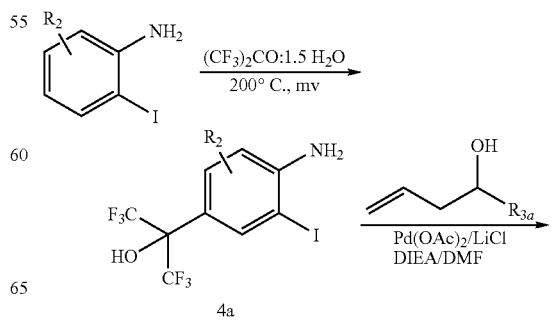

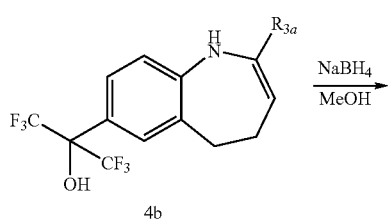

4b

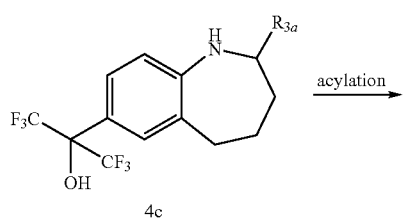

4c

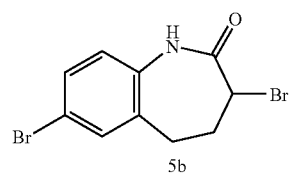

5b

Scheme 5 describes an example of bromination of a tetrahydrobenzazepine intermediate. Bromine can be added slowly to commercially available 3-bromo-1,3,4,5-tetrahydro-1-benzazepin-2-one in acetic acid with stirring at room temperature to provide the useful intermediate 3,7-dibromo-1,3,4,5-tetrahydro-1-benzazepin-2-one, which can be used in many transformations described herein. Bromination using similar conditions can be carried out on other amino aryl cores described herein to provide intermediates for transformation to the compounds of the invention described in Schemes 8, 9 and 10.

SCHEME 6

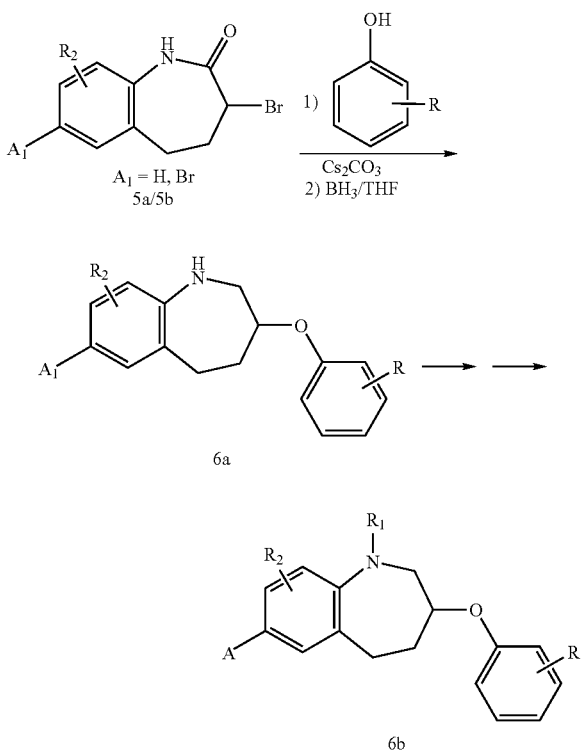

Scheme 4 describes one method for substitution at $R_{3a}$ via a Heck palladium coupling of an alkene (see, e.g. Dyker and Markwitz, Synthesis, (1998) 12: 1750-1754). Acylation of 2-iodoaniline with hexafluoroacetone at 200° C. in a microwave provides the tertiary alcohol 4a. Coupling of the aryl iodide with an appropriately substituted but-3-enol using a palladium reagent such as palladium acetate in the presence of lithium chloride, diisopropyl ethyl amine, and a solvent such as DMF and heating in a microwave reactor at temperatures from 80-140° C. provides the 4,5-dihydrobenzazepine 4b. Alternative coupling and cyclization conditions could be determined by one skilled in the art. Reduction to the tetrahydrobenzazepine (4c) can be carried out using NaBH$_4$ or other reducing agents known to one skilled in the art. Acylation with an appropriate reagent as described in Schemes 1 and 3 provides the amide, urea, sulfonamide, or carbamate products 4d. Compounds with alternative A substituents that are described below in Schemes 8, 9, and 10 are prepared from the aryl bromide. The aryl bromide can be prepared by performing the palladium coupling and cyclization on the unsubstituted 2-iodoaniline followed by NaBH$_4$ reduction as described above. Bromination can then be carried out as described in Scheme 5. The final products are then prepared as described in Schemes 8, 9, and 10.

Scheme 6 describes the phenol displacement of an alkyl bromide to provide phenyl ether compounds. A 3-bromo-1,3,4,5-tetrahydro-1-benzazepin-2-one (5a/5b) is treated with a substituted phenol or hydroxyl heteroaryl and Cs$_2$CO$_3$ in acetone or with other conditions as known to one skilled in the art. Reduction of the carbonyl is carried out by treatment with BH$_3$ in THF and heating at 60-80° C. to provide the amine 6a. Further elaboration of the A and $R_1$ substituents as described in Schemes 1, 3, 8, 9, and 10 provides aryl or heteroaryl ether compounds (6b) of this invention.

SCHEME 5

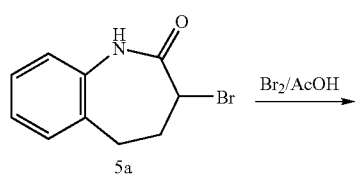

5a

SCHEME 7

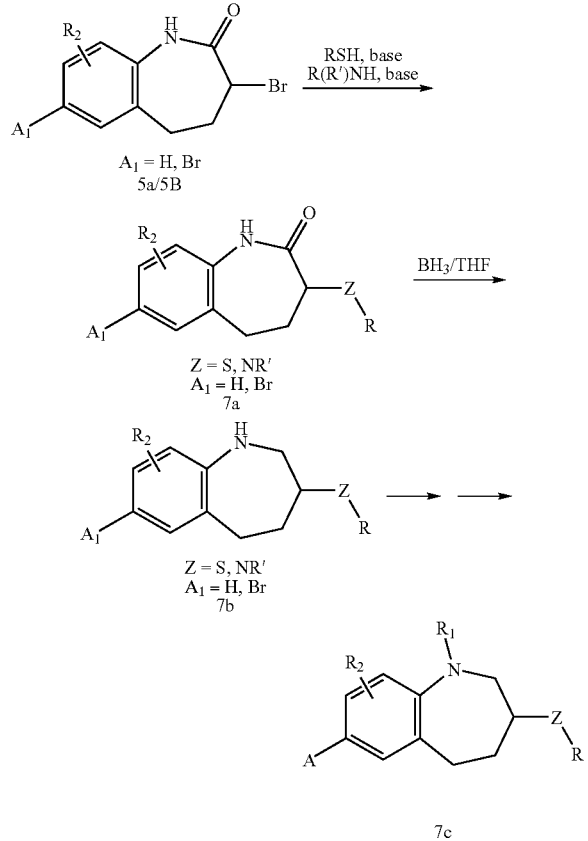

Scheme 7 describes nucleophilic displacement of an alpha bromo amide to obtain a thioether or amine substitution at $R_{3b}$. An alkyl bromide such as a 3-bromo-1,3,4,5-tetrahydro-1-benzazepin-2-one (5a/5b) can be reacted with a thiol reagent and an appropriate base such as $Cs_2CO_3$, or other reagents known to one skilled in the art, to provide thio ether analogs (7a; Z=S). An amine (7a, Z=NR') may be obtained by amine displacement of the bromide (5a/5b) using a primary or secondary amine in a solvent such as DMF at temperatures ranging from 20-100° C. The intermediate 7a is then treated with $BH_3$/THF with heating as described above to obtain the amine 7b. Secondary amines (7b) may be further reacted with a protecting group or acylation as known to one skilled in the art to provide compounds of this invention. Further elaboration of the A and $R_1$ substituents as described in Schemes 1, 3, 8, 9, and 10 provides compounds 7c of this invention.

SCHEME 8

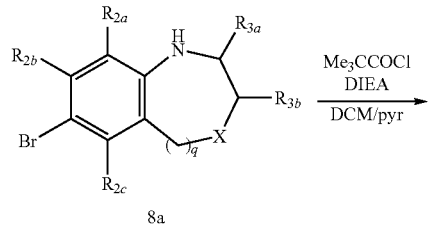

Scheme 8 describes the transformation of an aryl bromide to secondary or tertiary alcohols (A=C(OH)$R_5R_6$) when $R_5$ and $R_6$ may or may not be equivalent. Acylation of the bromo aniline 8a with an appropriate protecting group, such as pivaloyl chloride, yields the pivalamide 8b. The aryl bromide 8b can be treated with a lithiation reagent such as t-BuLi at −78° C. for 10 min to 1 h followed by addition of an acylpiperadine at low temperatures ranging from −78° C. to −20° C. to provide a ketone 8c. The ketone 8c can be treated with an alkyl or haloalkyl Grignard reagent ($R_6$=alkyl or haloalkyl) followed by hydrolysis of the amide to provide the tertiary alcohol 8d. Alternatively the ketone can be reduced to the secondary alcohol ($R_6$=H) with an appropriate reducing agent, such as sodium borohydride ($NaBH_4$) or other reducing agents known to one skilled in the art. The pivalamide is then removed by treatment with an HCl solution in a microwave reactor at temperatures ranging from 80-160° C. for 5-30 min to provide the amine 8d. Amine acylation to obtain compounds of this invention can be carried out as described in Schemes 1 and 3.

SCHEME 9

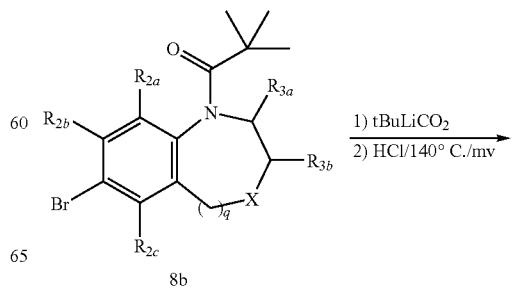

49

-continued

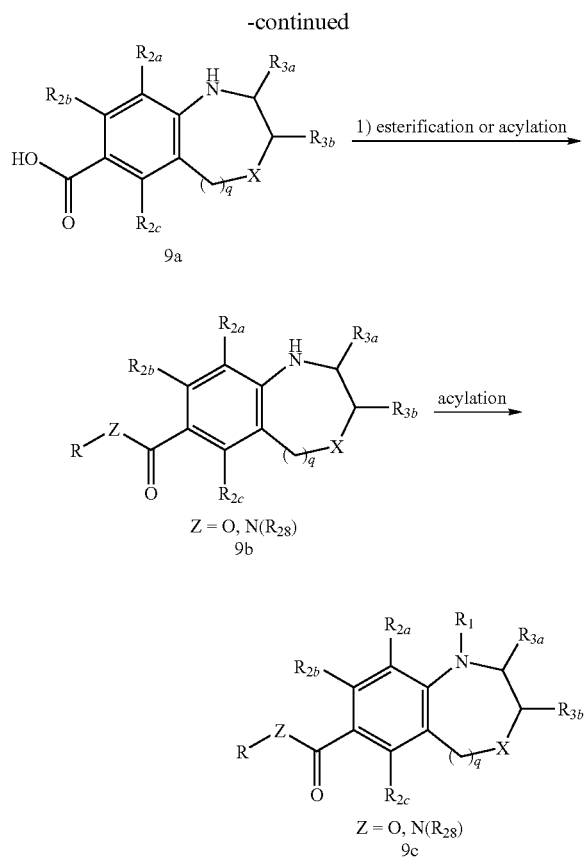

Scheme 9 describes the transformation from an aryl bromide to an ester or amide (A=—C(O)NR$_{28}$R$_{29}$, —CO$_2$(C$_1$-C$_6$)-alkyl). The aryl bromide 8b can be treated with a lithiation reagent such as t-BuLi at −78° C. for 10 min to 1 h, and then CO$_2$ gas is passed through the solution. The resulting mixture is stirred at room temperature for 1 to 8 h. The protecting group is then removed by treatment with an HCl solution in a microwave reactor at temperatures ranging from 80-160° C. for 5 min to 1 hr to provide 9a. The resulting carboxylic acid (9a) can be converted to the corresponding ester (9b; Z=O) under standard conditions known to one skilled in the art. Alternatively, the carboxylic acid (9a) can be converted to amides following the standard coupling protocols using coupling reagents such as EDC/HOBt or BOP with an appropriate amine to afford the amide 9b (Z=N(R$_{28}$)). Acylation of the aniline to obtain compounds (9c) of this invention can be carried out as described in Schemes 1 and 3.

SCHEME 10

50

-continued

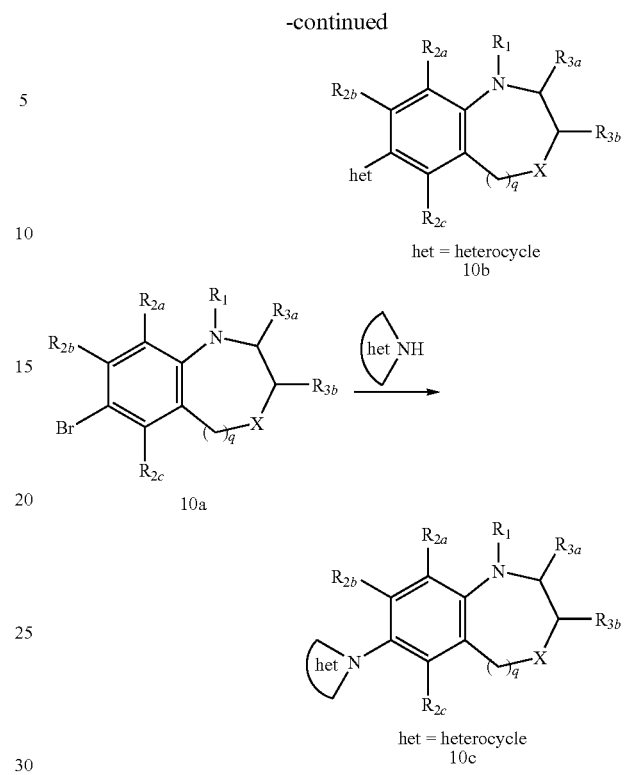

Scheme 10 describes the transformation from an aryl bromide to a heterocycle substituent (A=heterocycle). The aryl bromide (10a) can be coupled to the appropriate heteroaryl boronic acid or boronic ester using a palladium catalyst such as chloro(di-2-norbornylphosphino)(20-dimethylamino-1,10-biphenyl-2-yl)palladium in an appropriate solvent, such as 5:4:3 toluene/EtOH/2N Na$_2$CO$_3$, DME, or dioxane with heating to temperatures ranging from 60-120° C. to provide 10b. The coupling may be performed with other catalysts, solvents, or conditions as known to one skilled in the art. The boronic acid or boronic ester may be purchased from a vendor or prepared from a heteroaryl halide as known by one skilled in the art (see, e.g., Corbet and Mignani. (2006), Chemical Reviews 106(7): 2651-2710; Bellina, et. al. (2004) Synthesis (15): 2419-2440). Alternatively, coupling to the heterocycle can take place through a Buchwald-Hartwig amination of the aryl bromide (10a) using an appropriate palladium catalyst (see, e.g., Hartwig, J. F., Angewandte Chemie, Int. Ed., 1998, 37(15), 2046-2067) to provide 10c. The heteroaryl couplings described above can be performed earlier in the synthetic sequence as would be known to one skilled in the art to obtain compounds of this invention.

SCHEME 11

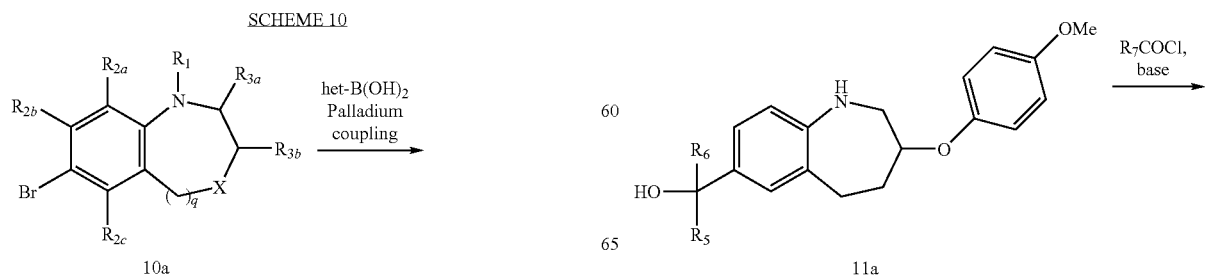

-continued

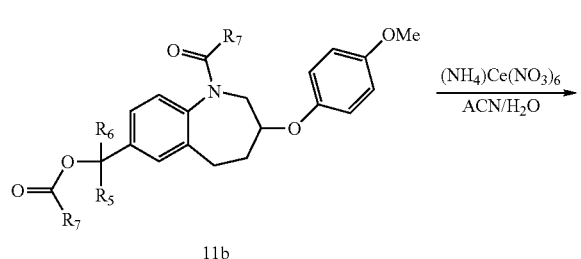
11b

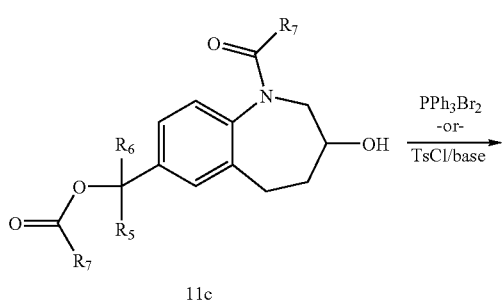
11c

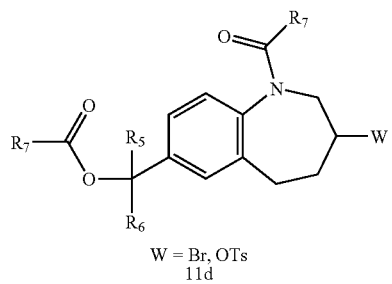
W = Br, OTs
11d

Scheme 11 describes the deprotection of 4-methoxy phenol to unmask a hydroxyl group that is a useful functional handle for further transformations. The 4-methoxy phenyl ether intermediate 11a is prepared using chemistry described in Scheme 6. The amine and tertiary alcohol are acylated using an acyl chloride with an appropriate base, such as diisopropylethyl amine, to provide the diacyl intermediate 11b. The 4-methoxy phenyl protecting group is removed using ammonium cerium nitrate to provide the alcohol 11c (see, e.g. Fukuyama, et. al, Tetrahedron Lett., (1985) 26: 6291; Petitou, et. al., Tetrahedron Lett., (1988) 29: 1398). The alcohol can be further functionalized by alkylation, acylation, or Mitsunobu displacement as known to one skilled in the art to provide compounds of the invention (e.g., Scheme 12). Alternatively the alcohol can be converted to an activated leaving group such as bromide or tosylate (11d) using $PPh_3Br_2$ or tosyl chloride and a base, respectively. Similar transformations can be carried out with alternative substitutions on the molecule as described herein (e.g. A=—C(O)$NR_{28}R_{29}$, —$CO_2(C_1$-$C_6)$-alkyl, or heterocyclyl) as known to one skilled in the art. These intermediates (11c and 11d) are useful for transformation to ether, thioether, amine and carbon substituted ($R_{3b}$) products as described in Scheme 6, 7, 12, 13, 14 and 15.

SCHEME 12

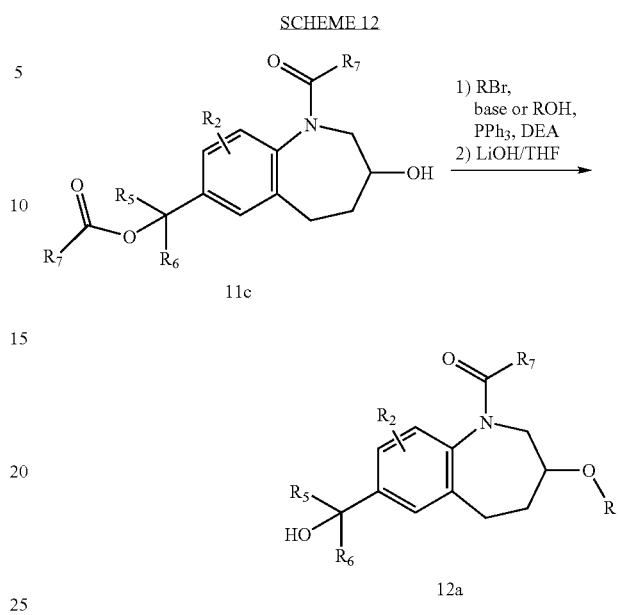

Scheme 12 describes functionalization of the secondary alcohol 11c to provide an ether (12a). Alkylation of the alcohol 11c using an alkylating agent (R-halide) with a base such as NaH can provide an ether. The ether can also be obtained via a Mitsunobu reaction with an alcohol, triphenylphosphine, and diethyl azodicarboxylate. Treatment with LiOH/THF to hydrolyze the ester yields the product 12a. Similar conditions could be used by one skilled in the art to obtain functionalized ethers with alternative A groups described for compounds of the invention.

SCHEME 13

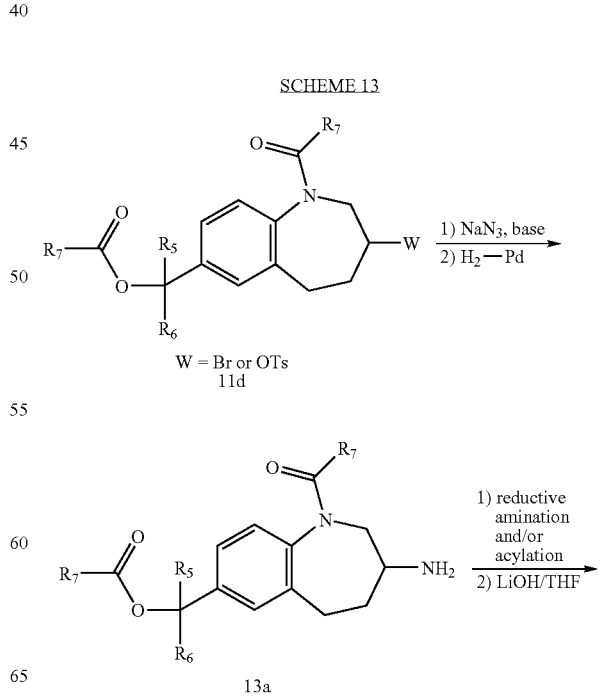

-continued

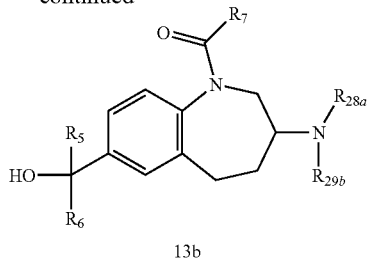

13b

Scheme 13 describes transformation of the bromo or tosylate intermediates (11d) to amine analogs. The activated intermediate (11d) is treated with sodium azide and a base such as diisopropylethyl amine to provide the azide intermediate that is reduced to the primary amine (13a) by palladium-catalyzed hydrogenation or other reducing conditions known to one skilled in the art. The primary amine can be acylated with an acyl chloride, activated ester, isocyanate, or other acylating reagent known to one skilled in the art to provide the amide, urea, carbamate or sulfonamide. Alternatively, reductive amination with the primary amine 13a, an appropriate aldehyde, and a reductant such as sodium cyanoborohydride can be carried out to provide the secondary amine, which may be acylated as described above to provide the derivatized amine product 13b.

SCHEME 14

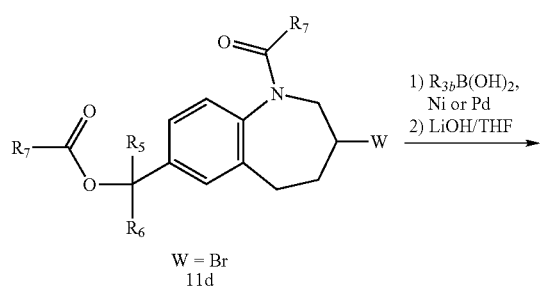

W = Br
11d

1) $R_{3b}B(OH)_2$, Ni or Pd
2) LiOH/THF

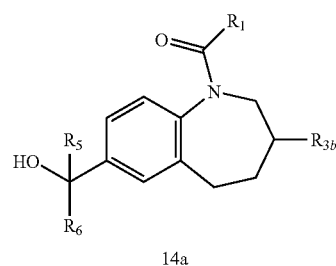

14a

Scheme 14 describes coupling of the alkyl bromide 11d with a boronic acid to provide heteroaryl, aryl, or alkenyl products. A heteroaryl, aryl, or alkenyl boronic acid may be coupled to the alkyl bromide using nickel bis(1,5-cyclooctadiene), bathophenathroline and potassium t-butoxide (see, e.g., Zhou and Fu, *J. Amer. Chem. Soc.*, 2004, 126(5), 1340-1341), or other conditions known to one skilled in the art. Subsequent hydrolysis with LiOH in THF provides the product 14a. Similar transformations as known to one skilled in the art can be carried out with alternative substitution on the tetrahydrobenzepine (e.g. A=heterocyclyl, —$CONR_{28}R_{29}$, —$CO_2(C_1-C_6)$alkyl) to provide the $R_{3b}$ aryl, heteroaryl, and alkenyl compounds of this invention as known to one skilled in the art.

SCHEME 15

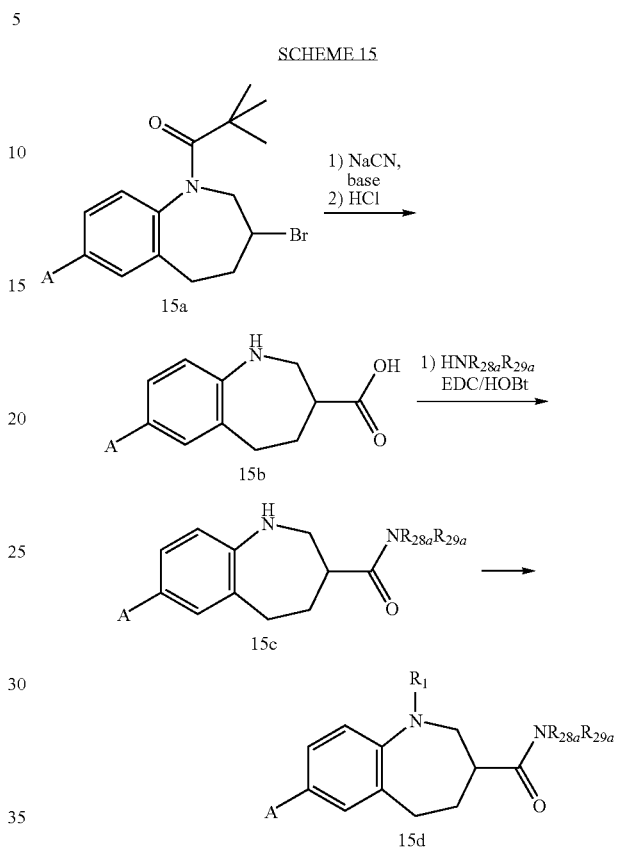

Scheme 15 describes the introduction of a carbonyl substituent at $R_{3b}$ to provide compounds of this invention. The alkyl bromide 15a, which can be prepared by chemistry described herein, is reacted with sodium cyanide and an appropriate base as known to one skilled in the art. The cyanide and pivalamide are hydrolyzed by treatment with an HCl solution in a microwave reactor at elevated temperatures to provide the acid (15b). The acid can be coupled with an amine using coupling reagents such as EDC-HCl and HOBt or other reagents known to one skilled in the art to provide the amide 15c. Alternatively the carboxylic acid could be transformed to a primary alcohol or aldehyde for further elaboration to compounds of this invention by methods known to one skilled in the art. Further elaboration of the $R_1$ substituents as described in Schemes 1 and 3 provides compounds 15d of this invention.

SCHEME 16

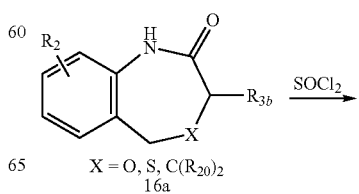

X = O, S, C($R_{20}$)$_2$
16a

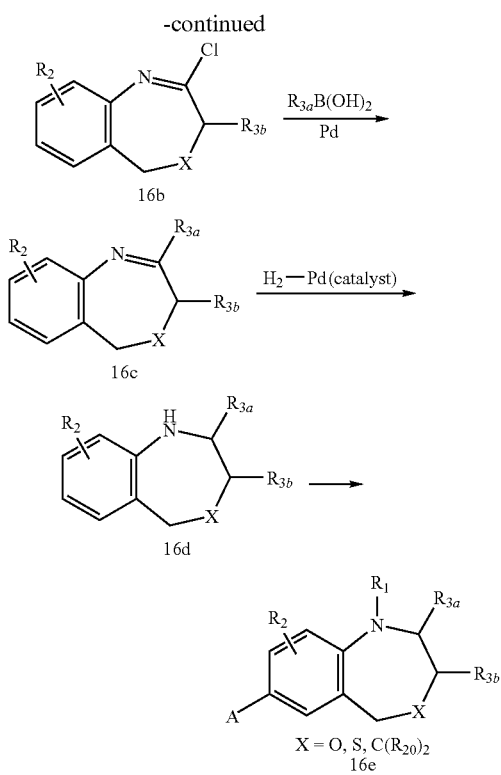

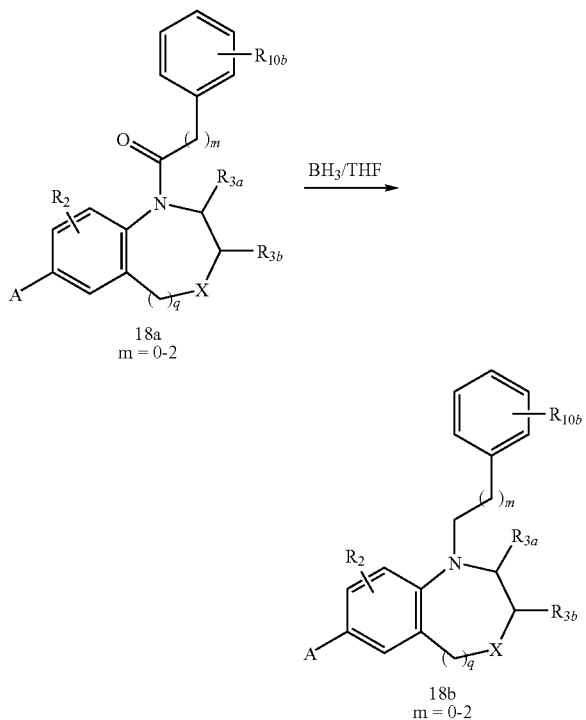

Scheme 17 describes the preparation of thiazine compounds of the invention. The 2-amino-benzenethiol and substituted α-bromo ketone are combined in DMF with AcOH, followed by addition of sodium cyanoborohydride or another reductant known to one skilled in the art, to provide thiazine 17a. For compounds with $R_{3a}$ equal to hydrogen, the 2-amino-benzenethiol is combined with a substituted α-bromo methyl ester in DMF followed $BH_3$/THF reduction to provide thiazine 17b. Further elaboration of thiazines 17a and 17b with the A and $R_1$ substituents as described in Schemes 1, 3, 8, 9, 10 provide thiazines 17c of this invention.

Scheme 16 describes chemistry to introduce aryl, heteroaryl or alkenyl functional groups to the $R_{3a}$ position. The amide (16a) is converted to the corresponding chloro imidate (16b) by refluxing in thionyl chloride for several hours (see, e.g. Org Reactions (1965), 14:1-15). The chloro imidate can be reacted with a boronic acid to introduce an aryl, heteroaryl or alkenyl $R_{3a}$ substituent to provide imine 16c (see, e.g., Corbet and Mignani. (2006), Chemical Reviews 106(7): 2651-2710; Bellina, et. al. (2004) Synthesis (15): 2419-2440). Reduction of the imine by palladium-catalyzed hydrogenation or another reductant known to one skilled in the art can be carried out to obtain the amine 16d. Further elaboration of the A and $R_1$ substituents as described in Schemes 1, 3, 8, 9, 10 provides compounds 16e of this invention.

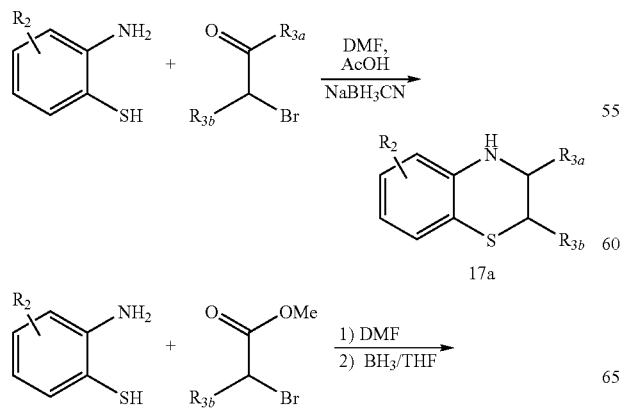

Scheme 18 describes the reduction of an alkylaryl amide (18a) to an alkylaryl amine (18b). The amide 18a is treated with a reducing agent such as $BH_3$ in THF, or other reducing agents known to one skilled in the art, to provide the alkylaryl amine 18b. The reduction can be carried out on a variety of alkyaryl amides and alkylheteroaryl amides to provide the corresponding alkylaryl amines and alkylheteroaryl amines.

As known to one skilled in the art, this reduction may be performed at an earlier step of the synthesis depending on the substituents present in the molecule.

The included schemes give an overview of several general processes for the synthesis of compounds of Formula I. Additional compounds of Formula I can readily be made by one of ordinary skill in the art by further modification of functional groups at positions A, X, q, $R_1$, $R_{2a}$, $R_{2b}$, $R_{2c}$, $R_{3a}$, and $R_{3b}$ of compounds of Formula I made by the processes illustrated in the included schemes.

UTILITY

Compounds within the scope of the present invention alter nuclear receptor activity, including LXR and/or orphan nuclear receptor activity, and as such are useful in the treatment, prevention, or amelioration of one or more symptoms of diseases or disorder that are modulated by nuclear receptor activity, including LXR and/or orphan nuclear receptor activity, or in which nuclear receptor activity, including LXR and/or orphan nuclear receptor activity, is implicated.

As described above, LXR is implicated in modulated cholesteral metabolism and catabolism. See, e.g., International Patent Application Publication No. 00/40965. As such, it is believed that the compounds within the scope of the present invention are useful in: (i) reducing cholesterol levels and of modulating cholesterol metabolism; (ii) the treatment, prevention, or amelioration of one or more symptoms of a disease or disorder which is affected by cholesterol, triglyceride, or bile acid levels; (iii) increasing cholesterol efflux from mammalian cells; (iv) increasing the expression of ATP-Binding Cassette (ABC1) in mammalian cells; and (v) selectively regulating LXR$\alpha$ or LXR$\beta$.

As described above, nuclear receptor activity has been implicated in a variety of diseases and disorders. As such, it is believed that the compounds of the present invention are useful in the treatment and/or prevention of various disorders, for example, arteriosclerosis, atherosclerosis, hypercholesterolemia, hyperlipoproteinemia, hypertriglyceridemia, lipodystrophy, hyperglycemia, cardiac arrhythmias, angina pectoris, gastrointestinal disorders, disorders of vascular and visceral smooth muscle, inflammatory and immunological diseases, cell proliferative disorders, disorders of the auditory system, disorders of the visual system, diabetes, muscle disease, cognitive disorders, migraine, memory loss, CNS mediated motor dysfunction, epilepsy, and the like.

As modulators of nuclear receptor activity, including LXR and/or orphan nuclear receptor activity, it is believed that the compounds of the present invention are useful to treat a variety of further disorders including resistance by transplantation of organs or tissue, graft-versus-host diseases brought about by medulla ossium transplantation, rheumatoid arthritis, systemic lupus erythematosus, hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenicmicroorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idopathic interstitial pneumonia, dermatomyositis, leukoderma vulgaris, ichthyosis vulgaris, photoallergic sensitivity, cutaneous T cell lymphoma, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The present invention thus provides methods for the prevention or treatment of one or more of the aforementioned disorders, comprising the step of administering to a subject in need thereof an effective amount of at least one compound of the formula I. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the formula I or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

LXR ASSAY

LXR modulation can be determined at a specific concentration of test compound in the assay described herein or other assays known to one of ordinary skill in the art. Potencies are more generally calculated by determining $EC_{50}$ values using this assay or others as known to one of ordinary skill in the art. Compounds of the present invention have been shown to have $EC_{50}$ values less than 10 μM, preferably with a potency less than 1 μM, more preferably with a potency less than 100 nM.

Compounds were assayed for agonist activity using stably transfected Human Embryonic Kidney 293 cells. The cells stably express a chimera consisting of a synthetic promoter with five tandem repeats of the yeast GAL4 binding site controlling the expression of the *Photinus pyralis* (American firefly) luciferase gene. The cells are subsequently transiently transfected with a plasmid (pcDNA3.1) consisting of a chimaeric construct of the yeast GAL4 DNA Binding Domain upstream from the human liver X-receptors α (amino acid 163-447) and β (amino acid 153-461). When challenged with LXR alpha or beta agonists, the cells will express the luciferase protein in a dose responsive manner. Luciferase activity is then determined by cell lysis and detection of luminescence, a by-product of the luciferase catalysis of luciferin substrate. Transiently transfected cells were challenged in the presence and absence of test compounds for a time period of 20 hr, at which point cells were lysed and assayed for the presence of luciferase enzyme activity.

Cells were maintained in DMEM at 37° C. and 5% $CO_2$ in T-225 flasks with 1% P/S 500 ug/ml Zeocin and 10% csFBS. Cells at ≈90% confluency were removed by trypsinization. Cells were gently dispersed and diluted in DMEM and centrifuged at 1000 rpm for 5 minutes. The cell pellet was resuspended in 3-5 ml of DMEM. Cells were counted and the cell stock is diluted to 3.07×10⁵ cell/ml. Cells were plated with a multidrop (in phenol red free DMEM with 10% csFBS, 1% P/S) into opaque, clear bottom plates 130 μl/well with a final cell count of 4×10⁴ cells/well.

Cells were transfected using Lipofectamine 2000 (Invitrogen, Carlsbad, Calif.) according to the instructions of the manufacturer. After addition of LXRα/Lipofectamine 2000 or LXRβ/Lipofectamine 2000 to each well of the cell plate the plates were placed in an incubator at 37° C. and 5% $CO_2$ for 4.5-5 hr. Compounds were dissolved in DMSO and added to the cells after dilution in DMEM w/o phenol red, but with 1% P/S and 10% csFCS (0.5% final concentration of DMSO). Compounds were characterized by incubation with cells for 20 hr across a range of concentrations. Cells were lysed using Promega Steady-Glo reagents as described in the manufacturer instructions, except the solution was diluted 1:1 in DMEM without phenol red. The conditioned media was aspirated from all wells and 100 μl of the 1:1 mix was added. The plates were sealed with Packard clear sealing tape (or equivalent) and allowed to sit at room temperature for 20 minutes before reading on Topcount (Perkin Elmer) at 5 sec/well.

Compounds to be tested were serially diluted 3 fold in neat DMSO (starting from 10 μM stock solution) for a total of 10 dilution points. All compounds were tested in 0.5% DMSO.

Compounds were tested in duplicate on the same plate and normalized by subtracting the vehicle background and then dividing by activity of a full pan agonist for the assay. The data is then reported as an $EC_{50}$ value calculated using the XLfit (ID Business Solutions, Ltd.) in Microsoft Excel (4 parameter fit 205 and floating all parameters).

LIST OF ABBREVIATIONS

| LIST OF ABBREVIATIONS | |
|---|---|
| LBD | Ligand Binding Domain |
| DBD | DNA binding domain |
| NHR | Nuclear Hormone Receptor |
| csFCS | Charcoal/Dextran treated Fetal Calf Serum |
| hr | Hour |
| ID | Identification |
| HEK | Human Embryonic Kidney |
| DMEM | Dulbecco's Modified Eagle's Medium |
| 5xG4RE | 5 repeats GAL4 Response Element |
| P/S | Penicillin/Streptomycin |
| rpm | Revolutions per minute |
| ml | Milliters |
| μl | Microliters |

Other assays to determine the degree of activity of a compound to modulate the activity of nuclear receptors, including the LXRs (LXRa and LXRb.) are well known in the art. They include, for example, biochemical assays such as binding assays, fluorescence polarization assays, FRET based coactivator recruitment assays (see Glickman et al., J. Biomolecular Screening, 7 No. 1 3-10 (2002)); as well as cell based transfection methods using LBD-GAL4 chimeras coupled to GAL4 promoter reporters, or endogenous LXR receptors coupled with ABCA1 or SREBP1c promoter reporters. Others include protein-protein interaction assays, and the cellular cholesterol efflux assay (see, generally Lehmann. et al., J. Biol Chem., 272(6) 3137-3140 (1997), Janwoski et al., Nature, (1996) 383(6602): 728-31; Costet et al., J Biol Chem. (2000); 275(36): 28240-5; Repa et al., Genes Dev. (2000); 14(22): 2819-30; Venkateswaran et al., Proc Natl Acad Sci USA. (2000); 97(22): 12097-102).

In addition, various animal models exist for a number of diseases of direct relevance to the claimed compounds, which can be used to further profile and characterize the claimed compounds. For example, model systems including diabetic dislipidemia using Zucker (fa/fa) rats or (db/db) mice, spontaneous hyperlipidemia using apolipoprotein E deficient mice (ApoE.sup.−/−), diet-induced hyperlipidemia, using low density lipoprotein receptor deficient mice (LDLR.sup.−/−) and atherosclerosis using both the Apo E(.sup.−/−) and LDLR (.sup.−/−) mice fed a western diet. (21% fat, 0.05% cholesterol) may be used. Additionally LXR or FXR animal models (e.g., knockout mice) can be used to further evaluate the present compounds and compositions in vivo (see, for example, Peet, et al., Cell, 93:693-704 (1998), Sinal, et al., Cell, 102: 731-744 (2000)).

The present invention also provides pharmaceutical compositions comprising at least one of the compounds of the present invention, their prodrugs and the salts of such compounds and prodrugs capable of preventing, treating, and/or slowing the progression of one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of present invention may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders.

For example, they may be used in combination with a HMG-CoA reductase inhibitor, a cholesterol synthesis inhibitor, a cholesterol absorption inhibitor, another LXR modulator, a MTP/Apo B secretion inhibitor, a PPAR modulator and other cholesterol lowering agents such as a fibrate, niacin, an ion-exchange resin, an antioxidant, an ACAT inhibitor, and a bile acid sequestrant. Other pharmaceutical agents would also include the following: a bile acid reuptake inhibitor, an ileal bile acid transporter inhibitor, an ACC inhibitor, an antihypertensive (such as NORVASC®), a selective estrogen receptor modulator, a selective androgen receptor modulator, an antibiotic, an antidiabetic (such as metformin, a PPARγ activator, a sulfonylurea, insulin, an aldose reductase inhibitor (ARI) and a sorbitol dehydrogenase inhibitor (SDI)), aspirin (acetylsalicylic acid) and niacin and combinations thereof.

Any HMG-CoA reductase inhibitor may be used in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. EnzymoL 1981; 71:455-509 and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus *Aspergillus*, such as Iovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP-491226A (the disclosure of which is incorporated by reference) discloses certain pyridyldihydroxyheptenoic acids, such as cerivastatin. In addition, U.S. Pat. No. 5,273,995 (the disclosure of which is incorporated by reference) discloses certain 6-[2-(substituted-pyrrol-1-yl)alkyl]pyran-2-ones such as atorvastatin and any pharmaceutically acceptable form thereof (i.e. LIPITOR®). Additional HMG-CoA reductase inhibitors include rosuvastatin and pitavastatin. Statins also include such compounds as rosuvastatin disclosed in U.S. Pat. No. RE 37,314 E, pitavastatin disclosed in EP 304063 B1 and U.S. Pat. No. 5,011,930; mevastatin, disclosed in U.S. Pat. No. 3,983,140; velostatin, disclosed in U.S. Pat. No. 4,448,784 and U.S. Pat. No. 4,450,171; compactin, disclosed in U.S. Pat. No. 4,804,770; dalvastatin, disclosed in European Patent Application Publication No. 738510 A2; fluindostatin, disclosed in European Patent Application Publication No. 363934 A1; and dihydrocompactin, disclosed in U.S. Pat. No. 4,450,171.

Any PPAR modulator may be used In the combination aspect of this invention. The term PPAR modulator refers to compounds which modulate peroxisome proliferator activator receptor (PPAR) activity in mammals, particularly humans. Such modulation is readily determined by those skilled in the art according to standard assays known in the literature. It is believed that such compounds, by modulating the PPAR receptor, regulate transcription of key genes involved in lipid and glucose metabolism such as those in fatty acid oxidation and also those involved in high density lipoprotein (HDL) assembly (for example, apolipoprotein AI gene transcription), accordingly reducing whole body fat and increasing HDL cholesterol. By virtue of their activity, these compounds also reduce plasma levels of triglyceddes, VLDL cholesterol, LDL cholesterol and their associated components such as apolipoprotein B in mammals, particularly humans, as welt as increasing HDL cholesterol and apolipoprotain AI. Hence, these compounds are useful for the treatment and correction of the various dyslipidemias observed to be associated with the development and incidence of atherosclerosis and cardiovascular disease, including hypoalphalipoproteinemia and hypertriglyceridemia. A variety of these compounds are described and referenced below, however, others will be known to those skilled in the art. International Publication Nos. WO 02/064549 and 02/064130, U.S. patent application Ser. No. 10/720,942, and U.S. patent application No. 60/552,114 disclose certain compounds which are PPARα activators.

Any other PPAR modulator may be used in the combination aspect of this invention. In particular, modulators of PPARβ and/or PPARγ may be useful in combination with compounds of the present invention. An example PPAR inhibitor is described in US 2003/0225158 as {5-Methoxy-2-methyl-4-[4-(4-trifluoromethyt-benzy]oxy)-benzylsulfanyl-phenoxy}-acetic acid.

Any MTP/Apo B (microsomal triglyceride transfer protein and or apolipoprotein B) secretion inhibitor may be used in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R. 1992; Science 258:999). A variety of these compounds are described and referenced below however other MTP/Apo B secretion inhibitors will be known to those skilled in the art, including implitapride (Bayer) and additional compounds such as those disclosed in WO 96/40640 and WO 98/23593, (two exemplary publications). For example, the following MTP/ApoB secretion inhibitors are particularly useful: 4'-trifluoromethyl-biphenyl-2-carboxylic acid [2-(1H-[1,2,4,]triazol-3-ylmethyl)-1,2,3,4-tetrahydro-isoquinolin-6-yl]-amide; 4'-trifluoromethyl-biphenyl-2-carboxylic acid [2-(2-acetylamino-ethyl)-1,2,3,4-tetrahydro-isoquinolin-6-yl]-amide; (2-{6-[(4'-trifluoromethyl-biphenyl-2-carbonyl)-amino]-3,4-dihydro-1H-isoquinolin-2-yl}-ethyl)-carbamic acid methyl ester; 4'-trifluoromethyl-biphenyl-2-carboxylic acid [2-(1H-imidazol-2-ylmethyl)-1,2,3,4-tetrahydro-isoquinolin-6-yl]-amide; 4'-trifluoromethyl-biphenyl-2-carboxylic acid [2-(2,2-diphenyl-ethyl)-1,2,3,4-tetrahydro-isoquinolin-6-yl]-amide; 4'-trifluoromethyl-biphenyl-2-carboxylic acid [2-(2-ethoxy-ethyl)-1,2,3,4-tetrahydro-isoquinolin-6-yl]-amide; (S)—N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide; (S)-2-[(4'-trifluoromethyl-biphenyl-2-carbonyl)-amino]-quinoline-6-carboxylic acid (pentylcarbamoyl-phenyl-methyl)-amide; 1H-indole-2-carboxamide,1-methyl-N-[(1S)-2-[methyl (phenylmethyl)amino]-2-oxo-1-phenylethyl]-5-[[[4'-(trifluoromethyl)[1,1'-biphenyl]-2-yl]carbonyl]amino]; and N-[(1S)-2-(benzylmethylamino)-2-oxo-1-phenylethyl]-1-methyl-5-[[[4'-(trifluoromethyl)[1,1'-biphenyl]-2-yl]carbonyl]amino]-1H-indole-2-carboxamide.

Any HMG-CoA synthase inhibitor may be used in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth Enzymol. 1975; 35:155-160: Meth. EnzymoL 1985; 110:19-26 and references cited therein). A variety of these compounds are described and referenced below, however other HMG-CoA synthase inhibitors will be known to those skilled in the art. U.S. Pat. No. 5,120,729 discloses certain beta-lactam derivatives. U.S. Pat. No. 5,064,856 discloses certain spiro-lactone derivatives prepared by culturing a microorganism (MF5253). U.S. Pat. No. 4,847,271 discloses certain oxetane compounds such as 11-(3-hydroxymethyl-4-oxo-2-oxetayl)-3,5,7-trimethyl-2,4-undecadienoic acid derivatives.

Any compound that decreases HMG-CoA reductase gene expression may be used in the combination aspect of this invention. These agents may be HMG-CoA reductase transcription inhibitors that block the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such compounds may cause this effect by decreasing levels of SREBP (sterol receptor binding protein) by inhibiting the activity of site-1 protease (SIP) or agonizing the oxysterol receptor or SCAP. Such regulation is readily determined by those skilled in the art according to standard assays (Meth. Enzymol. 1985; 110:9-19). Several compounds are described and referenced below, however other inhibitors of HMG-CoA reductase gene expression will be known to those skilled in the art. U.S. Pat. No. 5,041,432 discloses certain 15-substituted lanosterol derivatives. Other oxygenated sterols that suppress synthesis of HMG-CoA reductase are discussed by E. I. Mercer (Prog. Lip. Res. 1993; 32:357-416).

Any compound having activity as an LXR modulator can serve as the second compound in the combination therapy aspect of the present invention.

Any squalene synthetase inhibitor may be used in the combination aspect of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (Meth. Enzymol. 1969; 15: 393-454 and Meth. Enzymol. 1985; 110:359-373 and references contained therein). A variety of these compounds are described in and referenced below however other squalene synthetase inhibitors will be known to those skilled in the art. U.S. Pat. No. 5,026,554 discloses fermentation products of the microorganism MF5465 (ATCC 74011) including zaragozic acid. A summary of other patented squalene synthetase inhibitors has been compiled (Curr. Op. Ther. Patents (1993) 861-4).

Any squalene epoxidase inhibitor may be used in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794:466-471). A variety of these compounds are described and referenced below, however other squalene epoxidase inhibitors will be known to those skilled in the art. U.S. Pat. Nos. 5,011,859 and 5,064,864 disclose certain fluoro analogs of squalene. EP publication 395,768 A discloses certain substituted allylamine derivatives. PCT publication WO 9312069 A discloses certain amino alcohol derivatives. U.S. Pat. No. 5,051,534 discloses certain cyclopropyloxy-squalene derivatives.

Any squalene cyclase inhibitor may be used as the second component in the combination aspect of this invention. The term squalene cyclase inhibiter refers to compounds which inhibit the bioconversion of squalene-2,3-epoxide to lanosterol, catalyzed by the enzyme squalene cyclase. Such inhibition is readily determined by those skilled in the art according to standard assays (FEBS Lett. 1989; 244:347-350.). In addition, the compounds described and referenced below are squalene cyclase inhibitors, however other squalene cyclase inhibitors will also be known to those skilled in the art. PCT publication WO 94/10150 discloses certain 1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8(beta)-trimethyl-6(beta)-isoquinolineamine. French patent publication 2697250 discloses certain beta, beta-dimethyl-4-piperidine ethanol derivatives such as 1-(1,5,9-trimethyldecyl)-beta, beta-dimethyl-4-piperidine ethanol.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors, however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 disclose certain azadecalin derivatives. EP publication 468,434 discloses certain piperidyl ether and thioether derivatives such as 2-(1-piperidyl)pentyl isopentyl sulfoxide and 2-(1-piperidyl)ethyl ethyl sulfide. PCT publication WO 9401404 discloses certain acyl-piperidines such as 1-(1-oxopentyl-5-phenylthio)-4-(2-hydroxy-1-methyl)-ethyl)piperidine. U.S. Pat. No. 5,102,915 discloses certain cyclopropyloxy-squalene derivatives.

The compounds of the present invention may also be administered in combination with naturally occurring compounds that act to lower plasma cholesterol levels. These naturally occurring compounds are commonly called nutraceuticals and include, for example, garlic extract and niacin. A slow-release form of niacin is available and is known as Niaspan. Niacin may also be combined with other therapeutic agents such as iovastatin, or another is an HMG-CoA reductase inhibitor. This combination therapy with iovastatin is known as ADVICOR™ (Kos Pharmaceuticals Inc.).

Any cholesterol absorption inhibitor can be used as an additional component in the combination aspect of the present invention. The term cholesterol absorption inhibition refers to the ability of a compound to prevent cholesterol contained within the lumen of the intestine from entering into the intestinal cells and/or passing from within the intestinal cells into the lymph system and/or into the blood stream. Such cholesterol absorption inhibition activity is readily determined by those skilled in the art according to standard assays (e.g., J. Lipid Res. (1993) 34: 377-395). Cholesterol absorption inhibitors are known to those skilled in the art and are described, for example, in PCT WO 94/00480. An example of a recently approved cholesterol absorption inhibitor is ZETIA™ (ezetimibe) (Schering-Plough/Merck).

Any ACAT inhibitor may be used in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in Journal of Lipid Research., 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (Ell Lilly and Pierre Fabre).

A lipase inhibitor may be used in the combination therapy aspect of the present invention. A lipase inhibitor is a compound that inhibits the metabolic cleavage of dietary triglycerides or plasma phospholipids into free fatty acids and the corresponding glycerides (e.g. EL, HL, etc.). Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a glyceride and fatty acid. In the intestine, the resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Methods Enzymol. 286: 190-231). Pancreatic lipase mediates the metabolic cleavage of fatty acids from triglycerides at the 1- and 3-carbon positions. The primary site of the metabolism of ingested fats is in the duodenum and proximal jejunum by pancreatic tipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Methods Enzymol. 286: 190-231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., Gastroenterology, 92,125 (1987). Such gastric lipase inhibition activity is readily determined by those skilled in the art according to standard assays (e.g., Methods Enzymol. 286: 190-231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis (iminocarbonyl)dioximes related thereto may be prepared as described in Petersen et al., *Liebig's Annalen,* 562, 205-229 (1949).

A variety of pancreatic lipase inhibitors are described herein below. The pancreatic lipase inhibitors lipstatin, (2S, 3S,5S,7Z,10Z)-5-[(S)-2-formamido-4-methyl-valeryloxy]-2-hexyl-3-hydroxy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed In U.S. Pat. No. 4,598,089. For example, tetrahydrolipstatin is prepared as described in, e.g., U.S. Pat. Nos. 5,274,143; 5,420, 305; 5,540,917; and 5,643,874. The pancreatic lipase inhibitor, FL-386, 1-[4-(2-methylpropyl)cyclohexyl]-2-[(phenylsulfonyl)oxy]ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512, 565; 5,391,571 and 5,602,151. The pancreatic lipase inhibitor, valilactone, and a process for the preparation thereof by the microbial cultivation of *Actinomycetes* strain MG147-CF2, are disclosed in Kitahara, et al., *J. Antibiotics,* 40 (11), 1647-1650 (1987). The pancreatic lipase inhibitors, ebelactone A and ebelactone B, and a process for the preparation thereof by the microbial cultivation of *Actinomycetes* strain MG7-G1, are disclosed in Umezawa, et al., *J. Antibiotics,* 33, 1594-1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid®, Lopid® and Tricot®.

Diabetes can be treated by administering to a patient having diabetes (especially Type II), insulin resistance, impaired glucose tolerance, metabolic syndrome, or the like, or any of the diabetic complications such as neuropathy, nephropathy, retinopathy or cataracts, a therapeutically effective amount of a compound of the present invention in combination with other agents (e.g., insulin) that can be used to treat diabetes. This includes the classes of anti-diabetic agents (and specific agents) described herein.

Any glycogen phosphorylase inhibitor can be used as the second agent in combination with a compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem. 41 (1998) 2934-2938). A variety of glycogen phosphorylase inhibitors are known to those skilled in the art including those described in WO 96/39384 and WO 96/39385.

Any aldose reductase inhibitor can be used in combination with a compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, *Diabetes,* 29:861-864 (1980). "Red Celt Sorbitol, an Indicator of Diabetic Control"). A variety of aldose reductase inhibitors are known to those skilled in the art, such as those described in U.S. Pat. No. 6,579,879, which includes 6-(5-chloro-3-methylbenzofuran-2-sulfonyl)-2H-pyridazin-3-one.

Any sorbitol dehydrogenase inhibitor can be used in combination with a compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem (2000) 280: 329-331). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) 8: 4214). A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Methods Enzymol. (1955) 1: 149). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R,3R,4R,5S)-3,4,5-trihydroxy-2-(hydroxymethyl)piperidino]-(α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatln and the various pseudosaccharides related thereto, are disclosed in U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatln B and trestatin C and the various trehalose-containing aminosugars related thereto are disclosed in U.S. Pat. No. 4,273,765.

Additional anti-diabetic compounds, which can be used as the second agent in combination with a compound of the present invention, include, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1,6-BPase(Metabasis/Sankyo), GLP-1/analogs (AC 2993, also known as exendin-4), insulin and insulin mimetics (Merck natural products). Other examples would include PKC-β inhibitors and AGE breakers.

The compounds of the present invention can be used in combination with anti-obesity agents. Any anti-obesity agent can be used as the second agent in such combinations and examples are provided herein. Such anti-obesity activity is readily determined by those skilled in the art according to standard assays known in the art.

Suitable anti-obesity agents include phenylpropanolamine, ephedrine, pseudoephedrine, phentermine, β3 adrenergic receptor agonists, apolipoprotein-B secretion/microsomal triglyceride transfer protein (apo-B/MTP) inhibitors, MCR-4-agonists, cholecystokinin-A (CCK-A) agonists, monoamine reuptake inhibitors (e.g., sibutramine), sympathomimetic agents, serotoninergic agents, cannabinoid receptor (CB-1) antagonists (e.g., rimonabant described in U.S. Pat. No. 5,624,941 (SR-141,716A), purine compounds, such as those described in US Patent Publication No. 2004/0092520; pyrazolo[1,5-a][1,3,5]triazine compounds, such as those described in U.S. Non-Provisional patent application Ser. No. 10/763,105; and bicyclic pyrazolyl and imidazolyl compounds, such as those described in U.S. Provisional Application No. 60/518,280, dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-related proteins (AGRP), ghrelin receptor antagonists, histamine 3 receptor antagonists or inverse agonists, neuromedin U receptor agonists, and the like. Rimonabant (SR-141,716A also known under the tradename Acomplia™ available from Sanofi-Aventis) can be prepared as described in U.S. Pat. No. 5,624,941. Other suitable CB-1 antagonists include those described in U.S. Pat. Nos. 5,747,524, 6,432,984 and 6,518,264; U.S. Patent Publication Nos. US2004/0092520, US2004/0157839, US2004/0214855, and US2004/0214838; U.S. patent application Ser. No. 10/971,599; and PCT Patent Publication Nos. WO 02/076949, WO 03/1075660, WO 04/048317, WO 04/013120, and WO 04/012671.

Preferred apolipoprotein-B secretion/microsomal triglyceride transfer protein (apo-B/MTP) inhibitors for use as anti-obesity agents are gut-selective MTP inhibitors, such as dirlotapide described in U.S. Pat. No. 6,720,351; 4-(4-(4-(4-((2-((4-methyl-4H-1,2,4-triazol-3-ylthio)methyl)-2-(4-chlorophenyl)-1,3-dioxolan-4-yl)methoxy)phenyl) piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,431. As used herein, the term "gut-selective" means that the MTP Inhibitor has a higher exposure to the gastrointestinal tissues versus systemic exposure.

Any thyromimetic can be used as the second agent in combination with a compound of the present Invention. Such thyromimetic activity is readily determined by those skilled in the art according to standard assays (e.g., Atherosclerosis (1996) 126: 53-63). A variety of thyromimetic agents are known to those skilled in the art, for example those disclosed in U.S. Pat. Nos. 4,766,121; 4,826,876; 4,910,305; 5,061,798; 5,284,971; 5,401,772; 5,654,468; and 5,569,674. Other antiobesity agents include sibutramine which can be prepared as described in U.S. Pat. No. 4,929,629 and bromocriptine which can be prepared as described in U.S. Pat. Nos. 3,752,814 and 3,752,888.

The compounds of the present invention can also be used in combination with other antihypertensive agents. Any antihypertensive agent can be used as the second agent in such combinations and examples are provided herein. Such antihypertensive activity is readily determined by those skilled in the art according to standard assays (e.g., blood pressure measurements).

Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendile; angiotensin converting enzyme (ACE) inhibitors, such as Accupril®, Altace®, Captopril®, Lotensin®, Mavik®, Monopril®, Prinivil®, Univasc®, Vasotec® and Zestril®.

Amlodipine and related dihydropyridine compounds are disclosed in U.S. Pat. No. 4,572,909, as potent anti-ischemic and antihypertensive agents. U.S. Pat. No. 4,879,303 discloses amlodipine benzenesulfonate salt (also termed amlodipine besylate). Amlodipine and amlodipine besylate are potent and long lasting calcium channel blockers. As such, amlodipine, amlodipine besylate, amlodipine maleate and other pharmaceutically acceptable acid addition salts of amlodipine have utility as antihypertensive agents and as antiischemic agents. Amlodipine besylate is currently sold as Norvasc®.

Calcium channel blockers which are within the scope of this invention include, but are not limited to: bepridil, which may be prepared as disclosed in U.S. Pat. No. 3,962,238 or U.S. Pat. No. Re. 30,577; clentiazem, which may be prepared as disclosed in U.S. Pat. No. 4,567,175; diltiazem, fendiline, which may be prepared as disclosed in U.S. Pat. No. 3,262,977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No. 3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; aranipine, which may be prepared as disclosed in U.S. Pat. No. 4,572,909; barnidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485,847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No. 3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267,104; lomerizine, which may be prepared as disclosed in U.S. Pat. No. 4,663,325; bencyclane, which may be prepared as disclosed in Hungarian Patent No. 151,865; etafenone, which may be prepared as disclosed in German Patent No. 1,265,758; and perhexiline, which may be prepared as disclosed in British Patent No. 1,025,578.

Angiotensin Converting Enzyme Inhibitors (ACE-Inhibitors) which are within the scope of this invention include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046,889 and 4,105,776; ceronapril, which may be prepared as disclosed in U.S. Pat. No. 4,462,790; delapril, which may be prepared as disclosed in U.S. Pat. No. 4,385,051; enalapril, which may be prepared as disclosed in U.S. Pat. No. 4,374,829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470,972; temocapril, which may be prepared as disclosed in U.S. Pat. No. 4,699,905; and trandolapril, which may be prepared as disclosed in U.S. Pat. No. 4,933,361.

Angiotensin-II receptor antagonists (A-II antagonists) which are within the scope of this invention include, but are not limited to: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578.

Beta-adrenergic receptor blockers (beta- or β-blockers) which are within the scope of this invention include, but are not limited to: acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., Journal of Medicinal Chemistry, 1982, 25, 670; epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol, which may be prepared as disclosed in Seeman et al., Heir. Chim. Acta, 1971, 54, 241; metipranolol, which may be prepared as disclosed in Czechoslovakian Patent Application No. 128,471; metoprblol, which may be prepared as disclosed in U.S. Pat. No. 3,873,600; moprolol, which may be prepared as disclosed in U.S. Pat. No. 3,501,7691; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., Journal of Medicinal Chemistry, 1966, 9, 88; sufmalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824.

Alpha-adrenergic receptor blockers (alpha- or α-blockers) which are within the scope of this invention include, but are not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art.

The term "vasodilator," where used herein, is meant to include cerebral vasodilators, coronary vasodilators and peripheral vasodilators. Cerebral vasodilators within the scope of this invention include, but are not limited to: bencyclane; cinnarizine; citicoline, which may be isolated from natural sources as disclosed in Kennedy et al., Journal of the American Chemical Society, 1955, 77, 250 or synthesized as disclosed in Kennedy, Journal of Biological Chemistry, 1956, 222, 185; cyclandelate, which may be prepared as disclosed in U.S. Pat. No. 3,663,597; ciclonicate, which may be prepared as disclosed in German Patent No, 1,910,481; diisopropylamine dichloroacetate, which may be prepared as disclosed in British Patent No. 862,248; ebumamonine, which may be prepared as disclosed in Hermann et al., Journal of the American Chemical Society, 1979, 101, 1540; fasudil, which may be prepared as disclosed in U.S. Pat. No. 4,678,783; fenoxedil, which may be prepared as disclosed in U.S. Pat. No. 3,818,021; flunarizine, which may be prepared as disclosed in U.S. Pat. No. 3,773,939; ibudilast, which may be prepared as disclosed in U.S. Pat. No. 3,850,941; ifenprodil, which may be prepared as disclosed in U.S. Pat. No. 3,509,164; Iomerizine, which may be prepared as disclosed in U.S. Pat. No. 4,663,325; nafronyl, which may be prepared as disclosed in U.S. Pat. No. 3,334,096; nicametate, which may be prepared as disclosed in Blicke et al., Journal of the American Chemical Society, 1942, 64, 1722; nicergoline, which may be prepared as disclosed above; nimodipine, which may be prepared as disclosed in U.S. Pat. No. 3,799,934; papaverine, which may be prepared as reviewed in Goldberg, Chem. Prod. Chem. News, 1954, 17, 371; pentifylline, which may be prepared as disclosed in German Patent No. 860,217; tinofedrine, which may be prepared as disclosed in U.S. Pat. No. 3,563,997; vincamine, which may be prepared as disclosed in U.S. Pat. No. 3,770,724; vinpocetine, which may be prepared as disclosed in U.S. Pat. No. 4,035,750; and viquidil, which may be prepared as disclosed in U.S. Pat. No. 2,500,444.

Coronary vasodilators within the scope of this invention include, but are not limited to: amotriphene, which may be prepared as disclosed in U.S. Pat. No. 3,010,965; bendazol, which may be prepared as disclosed in J. Chem. Soc. 1958, 2426; benfurodil hemisuccinate, which may be prepared as disclosed in U.S. Pat. No. 3,355,463; benziodarone, which may be prepared as disclosed in U.S. Pat. No. 3,012,042; chloracizine, which may be prepared as disclosed in British Patent No. 740,932; chromonar, which may be prepared as disclosed in U.S. Pat. No. 3,282,938; clobenfural, which may be prepared as disclosed in British Patent No. 1,160,925; clonitrate, which may be prepared from propanediol according to methods well known to those skilled in the art, e.g., see Annalen, 1870, 155, 165; cloricromen, which may be prepared as disclosed in U.S. Pat. No. 4,452,811; dilazep, which may be prepared as disclosed in U.S. Pat. No. 3,532,685; dipyridamole, which may be prepared as disclosed in British Patent No. 807,826; droprenilamine, which may be prepared as disclosed in German Patent No. 2,521,113; efloxate, which may be prepared as disclosed in British Patent Nos. 803,372 and 824,547; erythrityl tetranitrate, which may be prepared by nitration of erythritol according to methods well-known to those skilled in the art; etafenone, which may be prepared as disclosed in German Patent No. 1,265,758; fendiline, which may be prepared as disclosed in U.S. Pat. No. 3,262,977; floredil, which may be prepared as disclosed in German Patent No. 2,020,464; ganglefene, which may be prepared as disclosed in U.S.S.R. Patent No. 115,905; hexestrol, which may be prepared as disclosed in U.S. Pat. No. 2,357,985; hexobendine, which may be prepared as disclosed in U.S. Pat. No. 3,267,103; itramin tosylate, which may be prepared as disclosed in Swedish Patent No. 168,308; khellin, which may be prepared as disclosed in Baxter et al., Journal of the Chemical Society, 1949, S 30; lidoflazine, which may be prepared as disclosed in U.S. Pat. No. 3,267,104; mannitol hexanitrate, which may be prepared by the nitration of mannitol according to methods well-known to those skilled in the art; medibazine, which may be prepared as disclosed in U.S. Pat. No. 3,119,826; nitroglycerin; pentaerythritol tetranitrate, which may be prepared by the nitration of pentaerythritol according to methods well-known to those skilled in the art; pentrinitrol, which may be prepared as disclosed in German Patent No. 638,422-3; perhexilline, which may be prepared as disclosed above; pimefylline, which may be prepared as disclosed in U.S. Pat. No. 3,350,400; prenylamine, which may be prepared as disclosed in U.S. Pat. No. 3,152,173; propatyl nitrate, which may be prepared as disclosed in French Patent No. 1,103,113; trapidil, which may be prepared as disclosed in East German Patent No. 55,956; tricromyl, which may be prepared as disclosed in U.S. Pat. No. 2,769,015; trimetazidine, which may be prepared as disclosed in U.S. Pat. No. 3,262,852; trolnitrate phosphate, which may be prepared by nitration of triethanolamine followed by precipitation with phosphoric acid according to methods well-known to those skilled in the art; visnadine, which may be prepared as disclosed in U.S. Pat. Nos. 2,816,118 and 2,980,699.

Peripheral vasodilators within the scope of this invention include, but are not limited to: aluminum nicotinate, which may be prepared as disclosed in U.S. Pat. No. 2,970,082; bamethan, which may be prepared as disclosed in Corrigan et al., Journal of the American Chemical Society, 1945, 67, 1894; bencyclane, which may be prepared as disclosed above; betahistine, which may be prepared as disclosed in Walter et al.; Journal of the American Chemical Society, 1941, 63, 2771; bradykinin, which may be prepared as disclosed in Hamburg et al., Arch. Biochem. Biophys., 1958, 76, 252; brovincamine, which may be prepared as disclosed in U.S. Pat. No. 4,146,643; bufeniode, which may be prepared as disclosed in U.S. Pat. No. 3,542,870; buflomedil, which may be prepared as disclosed in U.S. Pat. No. 3,895,030; butalamine, which may be prepared as disclosed in U.S. Pat. No. 3,338,899; cetiedil, which may be prepared as disclosed in French Patent No. 1,460,571; ciclonicate, which may be prepared as disclosed in German Patent No, 1,910,481; cinepazide, which may be prepared as disclosed in Belgian Patent No. 730,345; cinnarizine, which may be prepared as disclosed above; cyclandelate, which may be prepared as disclosed above; diisopropylamine dichloroacetate, which may be prepared as disclosed above; eledoisin, which may be prepared as disclosed in British Patent No. 984,810; fenoxedil, which may be prepared as disclosed above; flunarizine, which may be prepared as disclosed above; heproni-cate, which may be prepared as disclosed in U.S. Pat. No. 3,384,642; ifenprodil, which may be prepared as disclosed above; iloprost, which may be prepared as disclosed in U.S. Pat. No. 4,692,464; inositol niacinate, which may be prepared as disclosed in Badgett et al., Journal of the American Chemical Society, 1947, 69, 2907; isoxsuprine, which may be prepared as disclosed in U.S. Pat. No. 3,056,836; kallidin, which may be prepared as disclosed in Biacham. Biophys. Res. Commun., 1961, 6, 210; kallikrein, which may be prepared as disclosed in German Patent No. 1,102,973; moxisylyte, which may be prepared as disclosed in German Patent No. 905,738; nafronyl, which may be prepared as disclosed above; nicametate, which may be prepared as disclosed above; nicergoline, which may be prepared as disclosed above; nicofuranose, which may be prepared as disclosed in Swiss Patent No. 366,523; nylidrin, which may be prepared as disclosed in U.S. Pat. Nos. 2,661,372 and 2,661,373; pentifylline, which may be prepared as disclosed above; pentoxifylline, which may be prepared as disclosed in U.S. Pat. No. 3,422,107; piribedil, which may be prepared as disclosed in U.S. Pat. No. 3,299,067; prostaglandin $E_1$, which may be prepared by any of the methods referenced in the Merck Index, Twelfth Edition, Budaveri, Ed., New Jersey, 1996, p. 1353; suloctidil, which may be prepared as disclosed in German Patent No. 2,334,404; tolazoline, which may be prepared as disclosed in U.S. Pat. No. 2,161,938; and xanthinol niacinate, which may be prepared as disclosed in German Patent No. 1,102,750.

The term "diuretic," within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, which may be prepared as disclosed in Austrian Patent No. 168,063; amiloride, which may be prepared as disclosed in Belgian Patent No. 639,386; arbutin, which may be prepared as disclosed in Tschitschibabin, Annalen, 1930, 479, 303; chlorazanil, which may be prepared as disclosed in Austrian Patent No. 168,063; ethacrynic acid, which may be prepared as disclosed in U.S. Pat. No. 3,255,241; etozolin, which may be prepared as disclosed in U.S. Pat. No. 3,072,653; hydracarbazine, which may be prepared as disclosed in British Patent No. 856,409; isosorbide, which may be prepared as disclosed in U.S. Pat. No. 3,160,641; mannitol; metochalcone, which may be prepared as disclosed in Freudenberg et al., Ber., 1957, 90, 957; muzolimine, which may be prepared as disclosed in U.S. Pat. No. 4,018,890; perhexiline, which may be prepared as disclosed above; ticrynafen, which may be prepared as disclosed in U.S. Pat. No. 3,758,506; triamterene which may be prepared as disclosed in U.S. Pat. No. 3,051,230; and urea.

Diuretic benzothiadiazine derivatives within the scope of this invention include, but are not limited to: althiazide, which may be prepared as disclosed in British Patent No. 902,658; bendroflumethiazide, which may be prepared as disclosed in U.S. Pat. No. 3,265,573; benzthiazide, McManus et al., 136th Am. Soc. Meeting (Atlantic City, September 1959), Abstract of papers, pp 13-O; benzylhydrochlorothiazide, which may be prepared as disclosed in U.S. Pat. No. 3,108,097; buthiazide, which may be prepared as disclosed in British Patent Nos. 861,367 and 885,078; chlorothiazide, which may be prepared as disclosed in U.S. Pat. Nos. 2,809,194 and 2,937,169; chlorthalidone, which may be prepared as disclosed in U.S. Pat. No. 3,055,904; cyclopenthiazide, which may be prepared as disclosed in Belgian Patent No. 587,225; cyclothiazide, which may be prepared as disclosed in Whitehead et al., Journal of Organic Chemistry, 1961, 26, 2814; epithiazide, which may be prepared as disclosed in U.S. Pat. No. 3,009,911; ethiazide, which may be prepared as disclosed in British Patent No. 861,367; fenquizone, which may be prepared as disclosed in U.S. Pat. No. 3,870,720; indapamide, which may be prepared as disclosed in U.S. Pat. No. 3,565,911; hydrochlorothiazide, which may be prepared as disclosed in U.S. Pat. No. 3,164,588; hydroflumethiazide, which may be prepared as disclosed in U.S. Pat. No. 3,254,076; methyclothiazide, which may be prepared as disclosed in Close et al, Journal of the American Chemical Society, 1960, 82, 1132; meticrane, which may be prepared as disclosed in French Patent Nos. M2790 and 1,365,504; metolazone, which may be prepared as disclosed in U.S. Pat. No. 3,360,518; paraflutizide, which may be prepared as disclosed in Belgian Patent No. 620,829; polythiazide, which may be prepared as disclosed in U.S. Pat. No. 3,009,911; quinethazone, which may be prepared as disclosed in U.S. Pat. No. 2,976,289; teclothiazide, which may be prepared as disclosed in Close et al., Journal of the American Chemical Society, 1960, 82, 1132; and trichlormethiazide, which may be prepared as dislcosed in deStevens et al., Experientia, 1960, 16, 113.

Diuretic sulfonamide derivatives within the scope of this invention include, but are not limited to: acetazolamide, which may be prepared as disclosed in U.S. Pat. No. 2,980,679; ambuside, which may be prepared as disclosed in U.S. Pat. No. 3,188,329; azosemide, which may be prepared as disclosed in U.S. Pat. No. 3,665,002; bumetanide, which may be prepared as disclosed in U.S. Pat. No. 3,634,583; butazolamide, which may be prepared as disclosed in British Patent No. 769,757; chloraminophenamide, which may be prepared as disclosed in U.S. Pat. Nos. 2,809,194, 2,965,655 and 2,965,656; clofenamide, which may be prepared as disclosed in Olivier, Rec. Trav, Chim., 1918, 37, 307; clopamide, which may be prepared as disclosed in U.S. Pat. No. 3,459,756; clorexolone, which may be prepared as disclosed in U.S. Pat. No. 3,183,243; disulfamide, which may be prepared as disclosed in British Patent No. 851,287; ethoxolamide, which may be prepared as disclosed in British Patent No. 795,174; furosemide, which may be prepared as disclosed in U.S. Pat. No. 3,058,882; mefruside, which may be prepared as disclosed in U.S. Pat. No. 3,356,692; methazolamide, which may be prepared as disclosed in U.S. Pat. No. 2,783,241; piretanide, which may be prepared as disclosed in U.S. Pat. No. 4,010,273; torasemide, which may be prepared as disclosed in U.S. Pat. No. 4,018,929; tripamide, which may be prepared as disclosed in Japanese Patent No. 73 05,585; and xipamide, which may be prepared as disclosed in U.S. Pat. No. 3,567,777.

Osteoporosis is a systemic skeletal disease, characterized by low bone mass and deterioration of bone tissue, with a consequent increase in bone fragility and susceptibility to fracture, in the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly within the aging of the population. Worldwide fracture incidence is forecasted to increase three-fold over the next 60 years, and one study has estimated that there will be 4.5 million hip fractures worldwide in 2050. Women are at greater risk of osteoporosis than men. Women experience a sharp acceleration of bone loss during the five years following menopause. Other factors that increase the risk include smoking, alcohol abuse, a sedentary lifestyle and low calcium intake.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenproprionate, progesterone, quingestanol acetate, quingestrone, and tigestol. Preferred progestins are medroxyprogestrone, norethindrone and norethynedrel.

Exemplary bone resorption inhibiting polyphosphonates include polyphosphenates of the type disclosed in U.S. Pat. No. 3,683,080. Preferred polyphosphonates are geminal diphosphonates (also referred to as bis-phosphonates). Tiludronate disodium is an especially preferred polyphosphonata. Ibandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N-(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used in the combination aspect of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods (Eriksen E. F. et al., Bone Histomorphometry, Raven Press, New York, 1994, pages 1-74; Grier S. J. et. A1., The Use of Dual-Energy X-Ray Absorptiometry In Animals, Inv. Radiol., 1996, 31(1): 50-62; Wahner H. W. and Fogelman I., The Evaluation of Osteoporosis: Dual Energy X-Ray Absorptiometry in Clinical Practice., Martin Dunitz Ltd., London 1994, pages 1-296). A variety of these compounds are described and referenced below. Another preferred estrogen agonist/antagonist is 3-(4-{1,2-diphenyl-but-1-enyl)-phenyl)-acrylic acid, which is disclosed in Willson et aL, Endocrinology, 1997, 138, 3901-3911. Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516. Another related compound is 4-hydroxy tamoxifen, which is disclosed in U.S. Pat. No. 4,623, 660. A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol, which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxyphenyl)-benzo[b]thiophen-3-yl)-methanone which is disclosed, along with methods of preparation, in PCT Publication No. WO 95/10513. Other preferred estrogen agonist/antagonists include the compounds, TSE-424 (Wyeth-Ayerst Laboratories) and arazoxifene.

Other preferred estrogen agonist/antagonists include compounds as described in U.S. Pat. No. 5,552,412. Especially preferred compounds described therein are: cis-6-(4-fluoro-phenyl)-5-(4-(2-piperidin-1-yl-ethoxy)-phenyl)-5,6,7,8-tetrahydronaphthalene-2-ol; (−)-cis-6-phenyl-5-(4-(2-pyrrolidin-1-yl-ethoxy)-phenyl)-5,6,7,8-tetrahydronaphthalene-2-ol (also known as lasofoxifene); cis-6-phenyl-5-(4-(2-pyrrolidin-1-yl-ethoxy)-phenyl)-5,6,7,8-tetrahydronaphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydronaphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814, which discloses derivatives of 2-phenyl-3-aroyl-benzothiophene and 2-phenyl-3-aroylbenzothiophene-1-oxide.

Other anti-osteoporosis agents, which can be used as the second agent in combination with a compound of the present invention, include, for example, the following: parathyroid hormone (PTH) (a bone anabolic agent); parathyroid hormone (PTH) secretagogues (see, e.g., U.S. Pat. No. 6,132, 774), particularly calcium receptor antagonists; calcitonin; vitamin D and vitamin D analogs.

Any selective androgen receptor modulator (SARM) can be used in combination with a compound of the present invention. A selective androgen receptor modulator (SARM) is a compound that possesses androgenic activity and which exerts tissue-selective effects. SARM compounds can function as androgen receptor agonists, partial agonists, partial antagonists or antagonists. Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino [3,2-g]quinoline derivatives, 1,2-dihydropyridino [5,6-g] quinoline derivatives and piperidino[3,2-g]quinolinone derivatives.

Cypterone, also known as (1b,2b)-6-chloro-1,2-dihydro-17-hydroxy-3'H-cyclopropa[1,2]pregna-1,4,6-triene-3,20-dione is disclosed in U.S. Pat. No. 3,234,093. Chlormadinone, also known as 17-(acetyloxy)-6-chloropregna-4-,6-diene-3,20-dione, in its acetate form, acts as an anti-androgen and is disclosed in U.S. Pat. No. 3,485,852. Nilutamide, also known as 5,5-dimethyl-3-[4-nito-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl)phenyl]propanamide and the trade name Eulexin® is disclosed in U.S. Pat. No. 3,847,988. Bicalutamide, also known as 4'-cyano-a',a',a'-trifluoro-3-(4-fluorophenylsulfonyl)-2-hydroxy-2-methylpropiono-m-toluidide and the trade name Casodex® is disclosed in EP-100172. The enantiomers of biclutamide are discussed by Tucker and Chesterton, *J. Med. Chem.* 1988, 31, 885-887. Hydroxyflutamide, a known androgen receptor antagonist in most tissues, has been suggested to function as a SARM for effects on IL-6 production by osteoblasts as disclosed in Hofbauer et al., *J. Bone Miner. Res.* 1999, 14, 1330-1337. Additional SARMs have been disclosed in U.S. Pat. No. 6,017,924; WO 01/16108, WO 01/16133, WO 01/16139, WO 02/00617, WO 02/16310, U.S. Patent Application Publication No, US 2002/0099096, U.S. Patent Application Publication No. US 2003/0022868, WO 03/011302 and WO 03/011824.

All of the above referenced patents and patent applications are hereby incorporated by reference herein.

The combinations can be co-formulated or in the form of kits packaged to provide appropriate dosages for co-administration.

The above other therapeutic agents, when employed in combination with the compounds of the present invention, may be used, for example, in those amounts indicated in the Physicians' Desk Reference (PDR) or as otherwise determined by one of ordinary skill in the art.

The following examples further illustrate the present invention, but of course, should not be construed as in any way limiting its scope.

Solution ratio expresses a volume relationship, unless stated otherwise. NMR chemical shifts (δ) are reported in parts per million relative to TMS as an internal standard. Compounds were named using the CAS ring naming convention in MDL CrossFire Commander v. 7.0 SP2 (© 1995-2005 MDL Information Systems GmbH). Microwave-assisted reactions were performed using a Biotage Optimizer microwave reactor.

Purification of intermediates and final products was carried out via either normal or reverse phase chromatography. Normal phase flash chromatography was either carried out on silica gel according to Still's method (Still, W. C. et al. *J. Org. Chem.* 1978, 43, 2923), or on a Jones Chromatography Flash Master Personal™ pump or an ICSO CombiFlash™ 16x system using prepacked silica gel cartridges and eluted with gradients of hexanes and ethyl acetate or methylene chloride and methanol. Reverse phase preparative HPLC was carried out using a Shimadzu Preparative HPLC system running DiscoveryVP software using a Phenomenex Luna 5 μm C18 21.20×100 mm column with a 10 min gradient at 20 mL/min from 100% A to 100% B (A: 10% acetonitrile, 89.9% water, 0.1% TFA; B: 10% water, 89.9% acetonitrile, 0.1% TFA, UV 220 nm), or using similar columns and methods.

Products were analyzed by reverse phase analytical HPLC carried out on a Shimadzu Analytical HPLC system running DiscoveryVP software using Method A: Phenomenex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm), Method B: Phenomenex Luna C18 column (4.6×50 mm) eluted at 4 mL/min with a 4 min gradient from 100% A to 100% B (A: 10% MeOH, 89.9% water, 0.1% NH$_4$OAc; B: 10% water, 89.9% MeOH, 0.1% MH$_4$OAc, UV 220 nm), Method C: Phenomenex Luna C18 column (4.6×50 mm) eluted at 4 mL/min with a 4 min gradient from 100% A to 100% B (A: 10% MeOH, 89.8% water, 0.2% H$_3$PO$_4$; B: 10% water, 89.8% MeOH, 0.2% H$_3$PO$_4$, UV 220 nm), or Method D: Phenomenex Luna C18 column (4.6×50 mm) eluted at 4 mL/min with a 4 min gradient from 100% A to 100% B (A: 10% MeOH, 89.9% water, 0.1% TFA; B: 10% water, 89.9% MeOH, 0.1% TFA, UV 220 nm).

Chiral products were purified by chiral normal phase preparative HPLC carried out on a Septech Analytical HPLC system running LC Responder software using Method A: Chiralcel OD-H column (20×250 mm, 10 μm) eluted at 6 mL/min with an isocratic run of 15% 1:1 MeOH/EtOH in heptane (UV 220 nm); Method B: Chiralcel OD column (4.6×250 mm, 10 μm) eluted at 1 mL/min with an isocratic run of 15% 1:1 MeOH/EtOH in heptane (UV 220 nm); Method C: Chiralcel OJ column (5×50 mm, 20 μm) eluted at 50 mL/min with an isocratic run of 20% 1:1 MeOH/EtOH in heptane (UV 220 nM); Method D: Chiralcel OJ column (5×50 mm, 5 μm) eluted at 50 mL/min with an isocratic run of 8% 1:1 MeOH/EtOH in heptane (UV 220 nM); Method E: Chiralcel OJ column (20×250 mm, 20 μm) eluted at 50 mL/min with an isocratic run of 15% 1:1 MeOH/EtOH in heptane (UV 220 nM); Method F: Chiralcel OD column (4.6×250 mm, 10 μm) eluted at 12 mL/min with an isocratic run of 8% 1:1 MeOH/EtOH in heptane (UV 220 nm); or Method G: Chiralcel OD-H column (20×250 mm, 10 μm) eluted at 14 mL/min with an isocratic run of 10% 1:1 MeOH/EtOH in heptane (UV 220 nm).

ABBREVIATIONS

As used throughout the specification, the following abbreviations apply:
ACN=acetonitrile
HOAc or AcOH=acetic acid
BH$_3$.THF=borane-tetrahydrofuran complex
Bn=benzyl
Br$_2$=bromine
Bu=butyl
t-Bu=tertiary butyl
t-BuCOCl=pivalyl chloride
t-BuLi=tertiary butyl lithium
t-BuOH=tertiary butyl alcohol
Boc=tert-butyloxycarbonyl
BOP reagent=Benzotriazole-1-yl-oxy-tris-(dimethylamino)-phosphoniumhexafluorophosphate
Cat.=catalytic
(CF$_3$)$_2$CO=hexafluoroacetone
CH$_2$Cl$_2$=dichloromethane
CH$_3$CN=acetonitrile
Conc.=concentrated
Cs$_2$CO$_3$=cesium carbonate
DCE=1,2-dichloroethane
DCM=dichloromethane
DEA=diethyl azodicarboxylate
DIEA=N,N-diisopropylethylamine
DMAP=4-dimethylaminopyridine
DMF=dimethylformamide
DMSO=dimethyl sulfoxide
EDC-HCl=ethyl-3(3-dimethylamino)propyl carbodiimide, hydrochloride salt
Et=ethyl
EtOH=ethanol
EtOAc=ethyl acetate
HOAt=1-hydroxy-7-azabenzotriazole
HCl=hydrochloric acid
Hunig's base=diisopropyl ethylamine
LiCl=lithium chloride
LiOH=lithium hydroxide
MgSO$_4$=magnesium sulfate
Me=methyl
MeMgBr=methylmagnesium bromide
MeNH$_2$.HCl=methylamine hydrochloride
MeOH=methanol
NaBH$_3$CN=sodium cyanoborohydride
NaBH$_4$=sodium borohydride
NaH=sodium hydride
NaHCO$_3$=sodium bicarbonate
NaOAc=sodium actetate
NaOH=sodium hydroxide
NaOMe=sodium methoxide
Na$_2$SO$_4$=sodium sulfate
NH$_2$Me.HCl=methylamine hydrochloride
(NH$_4$)Ce(NO$_3$)$_6$=ammonium cerium(IV) nitrate
NH$_4$Cl=ammonium chloride
NH$_2$OH.HCl=hydroxylamine hydrochloride
NMM=N-methylmorpholine
OAc=acetate
Pd(OAc)$_2$=palladium(II) acetate
Ph=phenyl
PL-MPH=polymer-supported morpholine resin
PPA=polyphosphoric acid
PPh$_3$=triphenyl phosphine
Pr=propyl
i-Pr=isopropyl
i-PrOH=isopropanol
PS=polystyrene
Pyr=pyridine
SnCl$_2$.H$_2$O=tin(II) chloride monohydrate
TEA=triethylamine
TFA=trifluoroacetic acid
TFFH=tetramethylfluoroformamidinium hexafluorophosphate
THF=tetrahydrofuran
TsOH=p-toluenesulfonic acid
H$_2$O=water
° C.=degrees Celsius
atm=atmosphere
cat.=catalytic
conc.=concentrated
d=days
eq=equivalent(s)
h or hr=hour(s)
g=gram(s)
mg=milligram(s)
mL=milliliter(s)
μl=microliter(s)
mmol=millimolar
M=molar
meq=milliequivalent(s)
min=minute(s)

MW=molecular weight
mp=melting point
N=normal
rt or RT=room temperature
Rt=retention time
s=seconds
sat or sat'd=saturated
ESI=electrospray ionization mass spectroscopy
HPLC=high performance liquid chromatography
HRMS=high resolution mass spectroscopy
MS=mass spectrometry
LC/MS=liquid chromatography mass spectrometry
NMR=nuclear magnetic resonance spectroscopy
TLC=thin layer chromatography

EXAMPLES

The following Examples have been prepared, isolated and characterized using the methods disclosed herein. The following Examples demonstrate a partial scope of the invention and are not meant to be limiting of the scope of the invention.

Example 1

3-Phenyl-1-[7-(2,2,2-trifluoro-1-hydroxy-1-trifluoromethyl-ethyl)-2,3,4,5-tetrahydro-1-benzazepin-1-yl]-propan-1-one

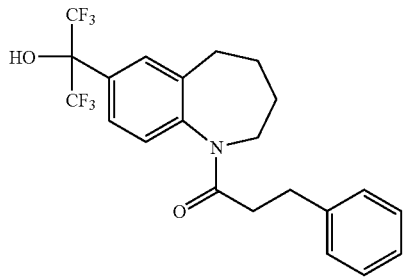

1A. 3,4-Dihydro-2H-naphthalen-1-one oxime: To a solution of 3,4-dihydro-2H-naphthalen-1-one (30 g, 20.5 mmol) in 1:1 MeOH/pyridine (100 mL) was added hydroxylamine hydrochloride (1.88 g, 31 mmol) and the resulting mixture was heated at reflux for 16 h. The solvent was evaporated to give a brown solid that was dissolved in $CH_2Cl_2$ and washed with 0.5 N HCl. After trituation from EtOAc, 1A was obtained as a brown solid (24.8 g, 75%). LC/MS m/z 162.0 $(M+H)^+$.

1B. 1,3,4,5-Tetrahydro-1-benzazepin-2-one: To polyphosphoric acid (30 g) heated to 125° C. was added 1A (21.6 g, 13.4 mmol) and the resulting mixture was stirred with a mechanical stirrer for 10 min. After the reaction was cooled and ice was added, the mixture was extracted with $CH_2Cl_2$. The organic layer was washed with $NaHCO_3$ and the solvent was evaporated to give a brown solid that was recrystallized from $MeOH/H_2O$ to give 1B as a white solid (13.3 g, 62%). LC/MS m/z 162.0 $(M+H)^+$.

1C. 2,3,4,5-Tetrahydro-1H-1-benzazepine: To amide 1B (4.15 g, 21.7 mmol) in anhydrous THF (80 mL) was added dropwise 1M $BH_3$.THF (64 mL). After stirring the reaction at rt for 60 h, the solvent was evaporated and the resulting residue was dissolved in EtOAc. The organic layer was washed with 1N NaOH and brine, then dried over $MgSO_4$ and evaporated. The resulting residue was purified by flash chromatography to give 1C as a white solid (3.18 g, 80%). LC/MS m/z 148.0 $(M+H)^+$.

1D. 1,1,1,3,3,3-Hexafluoro-2-(2,3,4,5-tetrahydro-1H-1-benzazepin-7-yl)-propan-2-ol: A mixture of 1C (3.14 g, 21 mmol), hexafluoroacetone hydrate (4.8 g, 25 mmol), and TsOH (40 mg) was heated at 90° C. for 15 min, then at 135° C. for 14 h. The reaction mixture was cooled to rt and dissolved in EtOAc. The EtOAc solution was washed with saturated $NaHCO_3$ and brine. Drying over $MgSO_4$ and removal of solvent afforded a crude product that was purified by flash chromatography to give 1D as white solid (3.5 g, 53%). LC/MS m/z 314.1 $(M+H)^+$.

Example 1: A solution of 1D (32 mg, 0.1 mmol), 3-phenylpropanoyl chloride (18.5 mg, 0.11 mmol), DIEA (13 mg, 0.1 mmol), and cat. DMAP in anhydrous $CH_2Cl_2$ (2 mL) was stirred at rt for 16 h. The reaction mixture was evaporated and the residue was dissolved in MeOH and purified by prep-HPLC to give the desired product as a white solid (22.4 mg, 50%). LC/MS m/z 446.24=$(M+H)^+$. $^1$H NMR (500 MHz, DMSO-$d_6$) δ ppm 1.30-1.39 (m, 1H) 1.75-1.80 (m, 1H) 1.82-1.86 (m, 1H) 1.88-1.95 (m, 1H) 2.25-2.32 (m, 1H) 2.41-2.50 (m, 2H) 2.56-2.66 (m, 2H) 2.83-2.93 (m, 2H) 4.71 (d, 1H) 7.02 (t, 4H) 7.14-7.23 (m, 4H) 7.54-7.61 (m, 2H).

Examples 2 to 5

Examples 2 to 5 in Table 1 were prepared in a similar manner as described in Example 1.

TABLE 1

| Ex. # | Name | Structure | MS $(M + H)^+$ |
|---|---|---|---|
| 2 | 2-Phenyl-1-[7-(2,2,2-trifluoro-1-hydroxy-1-trifluoromethyl-ethyl)-2,3,4,5-tetrahydro-1-benzazepin-1-yl]-ethanone | 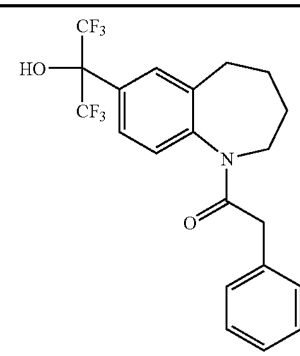 | 432.2 |

TABLE 1-continued

| Ex. # | Name | Structure | MS (M + H)+ |
|---|---|---|---|
| 3 | (3,4-Dimethoxy-phenyl)-[7-(2,2,2-trifluoro-1-hydroxy-1-trifluoromethyl-ethyl)-2,3,4,5-tetrahydro-1-benzazepin-1-yl]-methanone | 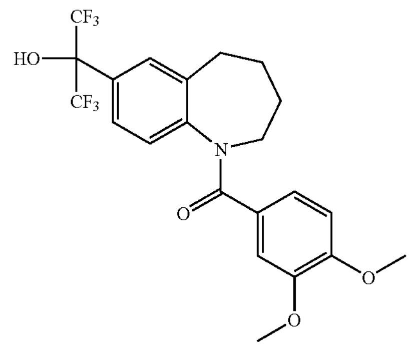 | 478.3 |
| 4 | (2,6-Dichloro-phenyl)-[7-(2,2,2-trifluoro-1-hydroxy-1-trifluoromethyl-ethyl)-2,3,4,5-tetrahydro-1-benzazepin-1-yl]-methanone | 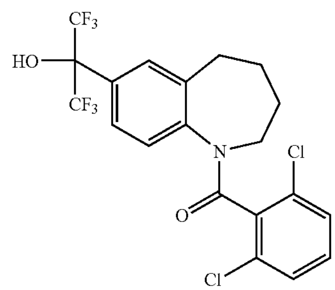 | 486.0 |
| 5 | 2-Cyclopentyl-1-[7-(2,2,2-trifluoro-1-hydroxy-1-trifluoromethyl-ethyl)-2,3,4,5-tetrahydro-1-benzazepin-1-yl]-ethanone | 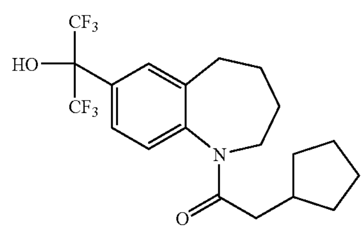 | 424.23 |

Example 6

(S)-2-Hydroxy-2-phenyl-1-[7-(2,2,2-trifluoro-1-hydroxy-1-trifluoromethyl-ethyl)-2,3,4,5-tetrahydro-1-benzazepin-1-yl]-ethanone

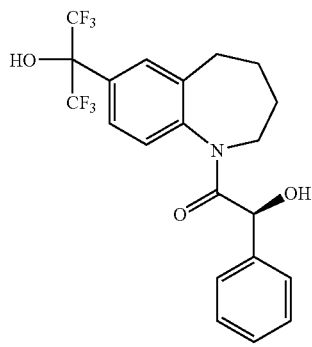

6A. Acetic acid (S)-2-oxo-1-phenyl-2-[7-(2,2,2-trifluoro-1-hydroxy-1-trifluoromethyl-ethyl)-2,3,4,5-tetrahydro-1-benzazepin-1-yl]-ethyl ester: To a suspension of triphenylphosphine polystyrene resin (370 mg, 0.55 mmol) in anhydrous $CH_2Cl_2$ (1 mL) were added a solution of (S)-acetoxy-phenyl-acetic acid (17 mg, 0.18 mmol) in anhydrous $CH_2Cl_2$ (3 mL) and trichloroacetonitrile (22 µL, 0.22 mmol). The mixture was stirred at rt for 3 h. The acid chloride solution was then transferred via pipette to a vial that contained 1D (56 mg, 0.18 mmol). The triphenylphosphine polystyrene resin was rinsed with anhydrous $CH_2Cl_2$ (1 mL) and the rinse solution was transferred to the same vial. To the solution was added morpholinomethyl polystyrene resin (170 mg, 0.55 mmol). The mixture was stirred at rt overnight. The resin was removed by filtration. The solution was dried in vacuo and the product was purified by prep-HPLC to yield 6A.

Example 6: To 6A dissolved in THF (0.5 mL), 2N LiOH solution (0.08 mL) was added. After the mixture was stirred at rt for 2 h, another 0.08 mL of 2N LiOH solution was added followed by stirring for an additional 2 h. The mixture was diluted with EtOAc and neutralized with 1N HCl. The organic layer was washed with brine and dried over anhydrous Na$_2$SO$_4$. The solvent was removed in vacuo to yield Example 6 (13.8 mg, 17%). HRMS m/z 448.1343 (M+H)$^+$. $^1$H NMR (500 MHz, Acetone-D$_6$) δ 7.78 (d, 1H), 7.63 (d, 1H), 7.39 (s, 1H), 7.12 (m, 1H), 7.03 (t, 2H), 6.55 (d, 2H), 5.18 (s, 1H), 4.66 (d, 1H), 2.62 (t, 1H), 2.14 (dd, 1H), 1.71 (m, 2H), 1.58 (m, 1H), 1.29 (t, 1H), 1.18 (m, 1H).

Examples 7 to 12

In Table 2, Examples 7 to 10 were prepared in a similar manner as described in Example 6. Examples 11 and 12 were prepared in a similar manner as described in Example 6 except 50 μl of triethylamine was used rather than morpholinomethyl polystyrene resin.

TABLE 2

| Ex. # | Name | Structure | MS (M + H)$^+$ |
|---|---|---|---|
| 7 | (R)-2-Hydroxy-2-phenyl-1-[7-(2,2,2-trifluoro-1-hydroxy-1-trifluoromethyl-ethyl)-2,3,4,5-tetrahydro-1-benzazepin-1-yl]-ethanone | 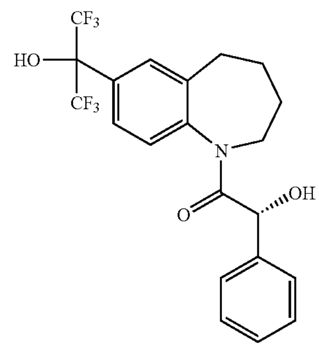 | 448.1 |
| 8 | Phenyl-[7-(2,2,2-trifluoro-1-hydroxy-1-trifluoromethyl-ethyl)-2,3,4,5-tetrahydro-1-benzazepin-1-yl]-methanone | 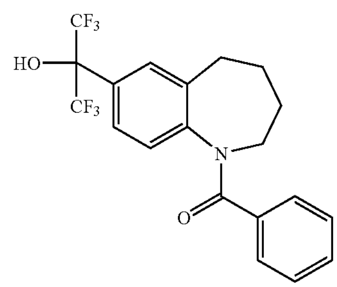 | 418.1 |
| 9 | (R)-2-Phenyl-1-[7-(2,2,2-trifluoro-1-hydroxy-1-trifluoromethyl-ethyl)-2,3,4,5-tetrahydro-1-benzazepin-1-yl]-butan-1-one | 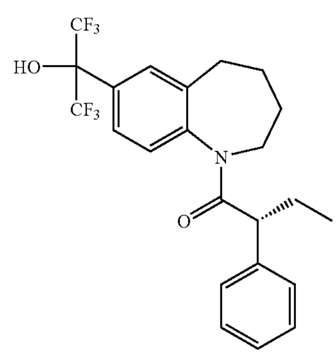 | 460.4 |
| 10 | (S)-2-Phenyl-1-[7-(2,2,2-trifluoro-1-hydroxy-1-trifluoromethyl-ethyl)-2,3,4,5-tetrahydro-1-benzazepin-1-yl]-butan-1-one | 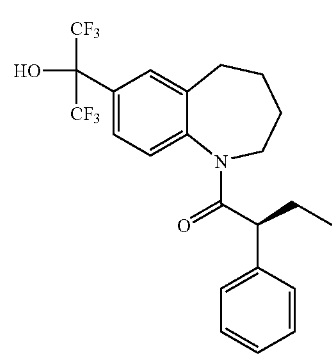 | 460.2 |

TABLE 2-continued

| Ex. # | Name | Structure | MS (M + H)+ |
|---|---|---|---|
| 11 | 2-Phenyl-1-[7-(2,2,2-trifluoro-1-hydroxy-1-trifluoromethyl-ethyl)-2,3,4,5-tetrahydro-1-benzazepin-1-yl]-propan-1-one | 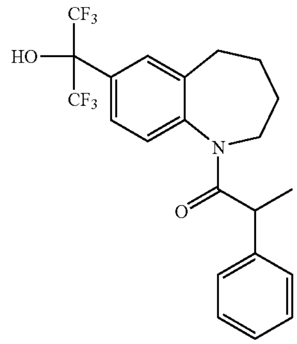 | 446.3 |
| 12 | (S)-2-Phenyl-1-[7-(2,2,2-trifluoro-1-hydroxy-1-trifluoromethyl-ethyl)-2,3,4,5-tetrahydro-1-benzazepin-1-yl]-propan-1-one | 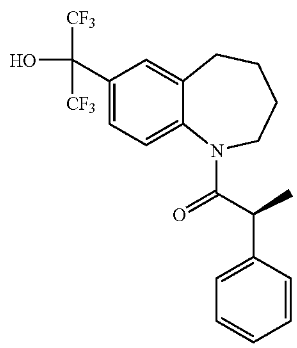 | 446.2 |

Examples 13 to 48

Examples 13 to 48 in Table 3 were prepared in a parallel library fashion. To 1D (0.04 mmol), NMM (0.06 mmol), trichloroacetonitrile (0.05 mmol), and PS-triphenylphosphine resin (0.120 mmol) in DCE (~0.8 mL) was added the appropriate carboxylic acid (0.042 mmol) and the reaction was agitated at rt overnight. Workup and purification as described in the previous examples afforded the target compounds.

TABLE 3

| Ex. # | Name | Structure | MS (M + H)+ |
|---|---|---|---|
| 13 | m-Tolyl-[7-(2,2,2-trifluoro-1-hydroxy-1-trifluoromethyl-ethyl)-2,3,4,5-tetrahydro-1-benzazepin-1-yl]-methanone | 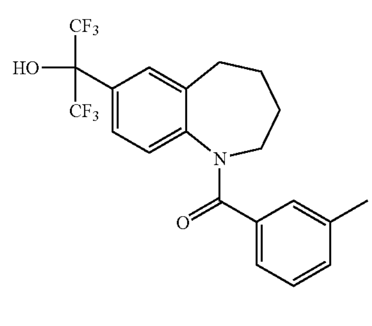 | 432.0 |

TABLE 3-continued

| Ex. # | Name | Structure | MS (M + H)+ |
|---|---|---|---|
| 14 | 2-Thiophen-2-yl-1-[7-(2,2,2-trifluoro-1-hydroxy-1-trifluoromethyl-ethyl)-2,3,4,5-tetrahydro-1-benzazepin-1-yl]-ethanone | 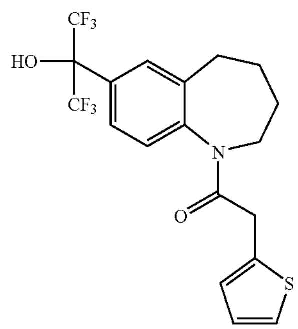 | 438.0 |
| 15 | Furan-2-yl-[7-(2,2,2-trifluoro-1-hydroxy-1-trifluoromethyl-ethyl)-2,3,4,5-tetrahydro-1-benzazepin-1-yl]-methanone | 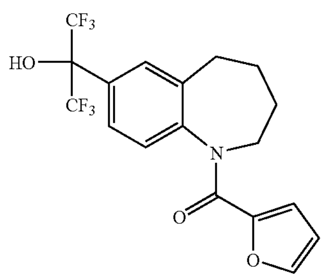 | 408.0 |
| 16 | 2-Phenoxy-1-[7-(2,2,2-trifluoro-1-hydroxy-1-trifluoromethyl-ethyl)-2,3,4,5-tetrahydro-1-benzazepin-1-yl]-ethanone | 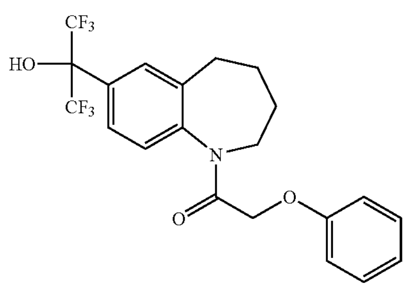 | 448.0 |
| 17 | (2-Methoxy-phenyl)-[7-(2,2,2-trifluoro-1-hydroxy-1-trifluoromethyl-ethyl)-2,3,4,5-tetrahydro-1-benzazepin-1-yl]-methanone | 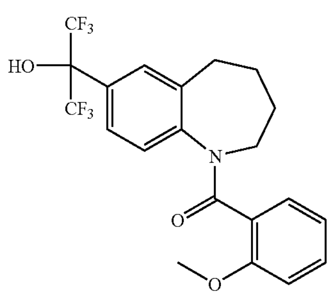 | 448.0 |
| 18 | 3-Cyclopentyl-1-[7-(2,2,2-trifluoro-1-hydroxy-1-trifluoromethyl-ethyl)-2,3,4,5-tetrahydro-1-benzazepin-1-yl]-propan-1-one | 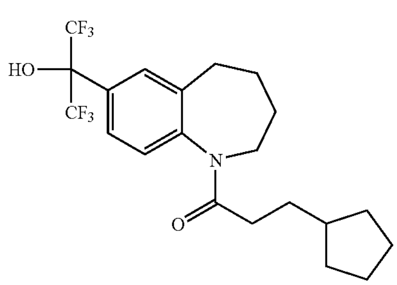 | 438.0 |

TABLE 3-continued

| Ex. # | Name | Structure | MS (M + H)+ |
|---|---|---|---|
| 19 | Thiophen-2-yl-[7-(2,2,2-trifluoro-1-hydroxy-1-trifluoromethyl-ethyl)-2,3,4,5-tetrahydro-1-benzazepin-1-yl]-methanone | 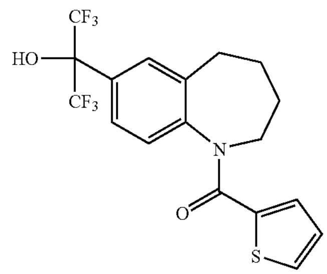 | 423.9 |
| 20 | 2-(3-Methoxy-phenyl)-1-[7-(2,2,2-trifluoro-1-hydroxy-1-trifluoromethyl-ethyl)-2,3,4,5-tetrahydro-1-benzazepin-1-yl]-ethanone | 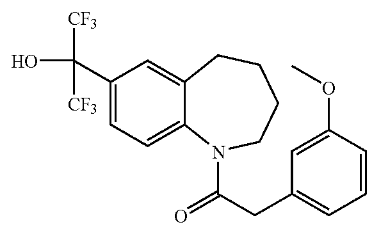 | 462.0 |
| 21 | 2-(4-Methoxy-phenyl)-1-[7-(2,2,2-trifluoro-1-hydroxy-1-trifluoromethyl-ethyl)-2,3,4,5-tetrahydro-1-benzazepin-1-yl]-ethanone | 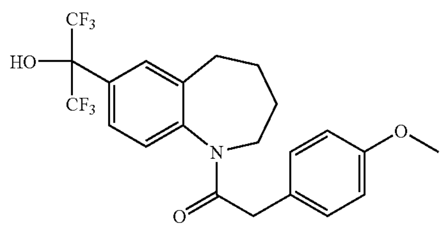 | 462.0 |
| 22 | 2-Phenylsulfanyl-1-[7-(2,2,2-trifluoro-1-hydroxy-1-trifluoromethyl-ethyl)-2,3,4,5-tetrahydro-1-benzazepin-1-yl]-ethanone | 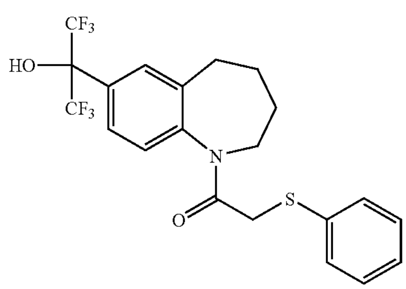 | 464.0 |
| 23 | 2-(4-Fluoro-phenyl)-1-[7-(2,2,2-trifluoro-1-hydroxy-1-trifluoromethyl-ethyl)-2,3,4,5-tetrahydro-1-benzazepin-1-yl]-ethanone | 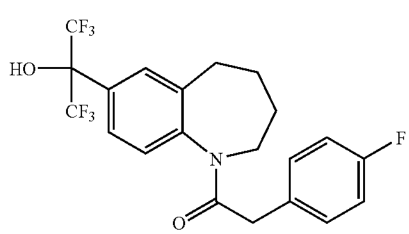 | 450.0 |
| 24 | 2-(4-Chloro-phenyl)-1-[7-(2,2,2-trifluoro-1-hydroxy-1-trifluoromethyl-ethyl)-2,3,4,5-tetrahydro-1-benzazepin-1-yl]-ethanone | 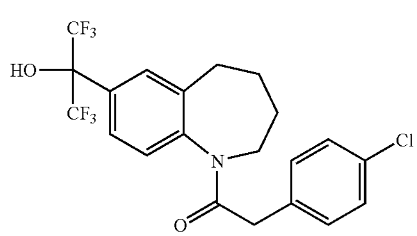 | 466.0 |

TABLE 3-continued

| Ex. # | Name | Structure | MS (M + H)+ |
|---|---|---|---|
| 25 | 2-(2-Bromo-phenyl)-1-[7-(2,2,2-trifluoro-1-hydroxy-1-trifluoromethyl-ethyl)-2,3,4,5-tetrahydro-1-benzazepin-1-yl]-ethanone | 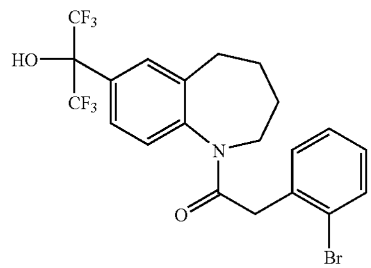 | 509.9 |
| 26 | 2-(3,5-Difluoro-phenyl)-1-[7-(2,2,2-trifluoro-1-hydroxy-1-trifluoromethyl-ethyl)-2,3,4,5-tetrahydro-1-benzazepin-1-yl]-ethanone | 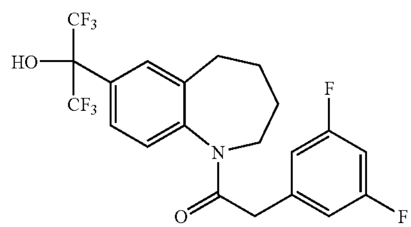 | 468.0 |
| 27 | Furan-3-yl-[7-(2,2,2-trifluoro-1-hydroxy-1-trifluoromethyl-ethyl)-2,3,4,5-tetrahydro-1-benzazepin-1-yl]-methanone | 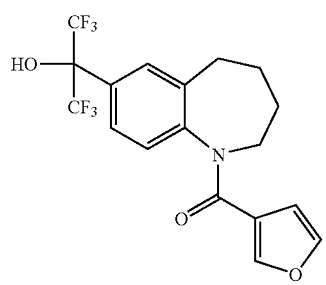 | 408.0 |
| 28 | 2-(2,4-Dichloro-phenyl)-1-[7-(2,2,2-trifluoro-1-hydroxy-1-trifluoromethyl-ethyl)-2,3,4,5-tetrahydro-1-benzazepin-1-yl]-ethanone | 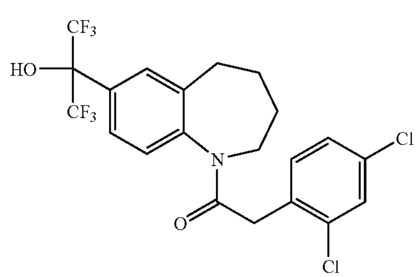 | 500.1 |
| 29 | Bicyclo[4.2.0]octa-1(6),2,4-trien-7-yl-[7-(2,2,2-trifluoro-1-hydroxy-1-trifluoromethyl-ethyl)-2,3,4,5-tetrahydro-1-benzazepin-1-yl]-methanone | 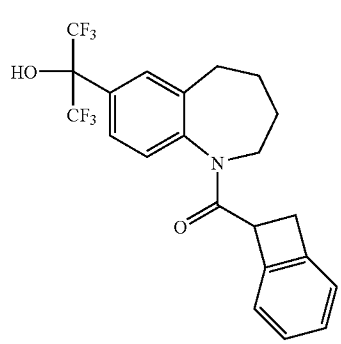 | 444.2 |

TABLE 3-continued

| Ex. # | Name | Structure | MS (M + H)+ |
|---|---|---|---|
| 30 | 2-Cyclohexyl-1-[7-(2,2,2-trifluoro-1-hydroxy-1-trifluoromethyl-ethyl)-2,3,4,5-tetrahydro-1-benzazepin-1-yl]-ethanone | 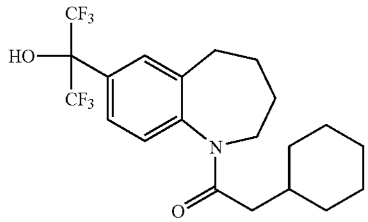 | 438.3 |
| 31 | (2,6-Difluoro-phenyl)-[7-(2,2,2-trifluoro-1-hydroxy-1-trifluoromethyl-ethyl)-2,3,4,5-tetrahydro-1-benzazepin-1-yl]-methanone | 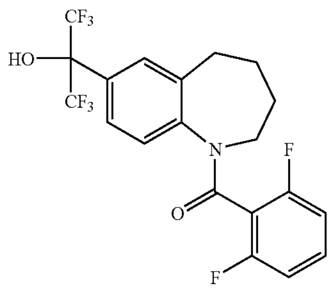 | 454.2 |
| 32 | (R)-2-Methoxy-2-phenyl-1-[7-(2,2,2-trifluoro-1-hydroxy-1-trifluoromethyl-ethyl)-2,3,4,5-tetrahydro-1-benzazepin-1-yl]-ethanone | 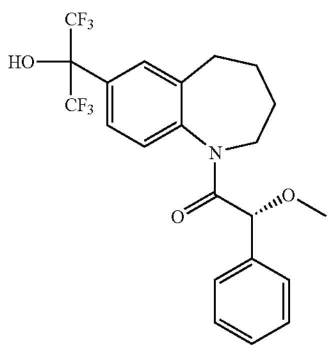 | 462.2 |
| 33 | 2-(2,6-Dichloro-phenyl)-1-[7-(2,2,2-trifluoro-1-hydroxy-1-trifluoromethyl-ethyl)-2,3,4,5-tetrahydro-1-benzazepin-1-yl]-ethanone | 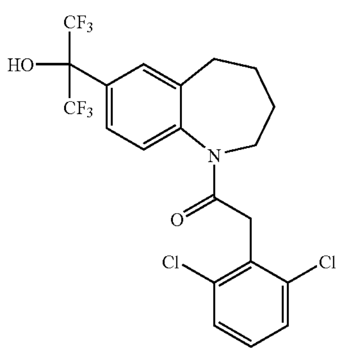 | 500.1 |
| 34 | 2-(2-Methoxy-phenyl)-1-[7-(2,2,2-trifluoro-1-hydroxy-1-trifluoromethyl-ethyl)-2,3,4,5-tetrahydro-1-benzazepin-1-yl]-ethanone | 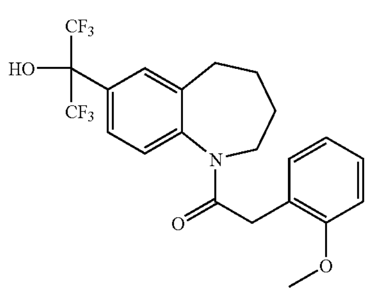 | 462.2 |

TABLE 3-continued

| Ex. # | Name | Structure | MS (M + H)+ |
|---|---|---|---|
| 35 | 2-o-Tolyl-1-[7-(2,2,2-trifluoro-1-hydroxy-1-trifluoromethyl-ethyl)-2,3,4,5-tetrahydro-1-benzazepin-1-yl]-ethanone | 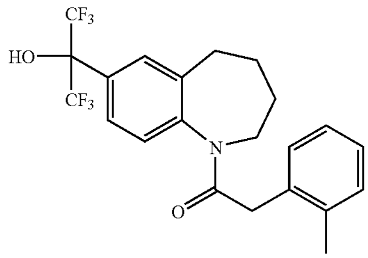 | 446.2 |
| 36 | 2-m-Tolyl-1-[7-(2,2,2-trifluoro-1-hydroxy-1-trifluoromethyl-ethyl)-2,3,4,5-tetrahydro-1-benzazepin-1-yl]-ethanone | 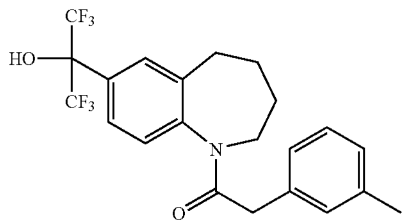 | 446.2 |
| 37 | 2-(4-Ethoxy-phenyl)-1-[7-(2,2,2-trifluoro-1-hydroxy-1-trifluoromethyl-ethyl)-2,3,4,5-tetrahydro-1-benzazepin-1-yl]-ethanone | 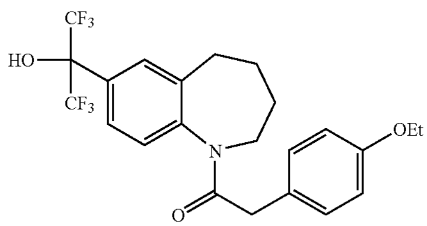 | 476.2 |
| 38 | 2-p-Tolyl-1-[7-(2,2,2-trifluoro-1-hydroxy-1-trifluoromethyl-ethyl)-2,3,4,5-tetrahydro-1-benzazepin-1-yl]-ethanone | 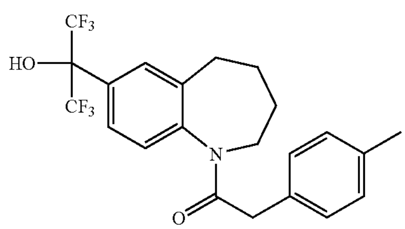 | 446.2 |
| 39 | 2-Thiophen-3-yl-1-[7-(2,2,2-trifluoro-1-hydroxy-1-trifluoromethyl-ethyl)-2,3,4,5-tetrahydro-1-benzazepin-1-yl]-ethanone | 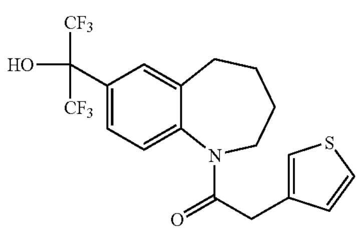 | 438.2 |
| 40 | 2-Methyl-2-phenyl-1-[7-(2,2,2-trifluoro-1-hydroxy-1-trifluoromethyl-ethyl)-2,3,4,5-tetrahydro-1-benzazepin-1-yl]-propan-1-one | 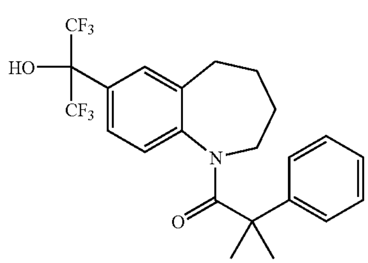 | 460.2 |

TABLE 3-continued

| Ex. # | Name | Structure | MS (M + H)+ |
|---|---|---|---|
| 41 | 2-1,3-Benzodioxol-5-yl-1-[7-(2,2,2-trifluoro-1-hydroxy-1-trifluoromethyl-ethyl)-2,3,4,5-tetrahydro-1-benzazepin-1-yl]-ethanone | 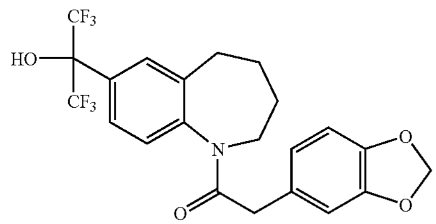 | 476.2 |
| 42 | 2-(3,5-Dimethoxy-phenyl)-1-[7-(2,2,2-trifluoro-1-hydroxy-1-trifluoromethyl-ethyl)-2,3,4,5-tetrahydro-1-benzazepin-1-yl]-ethanone | 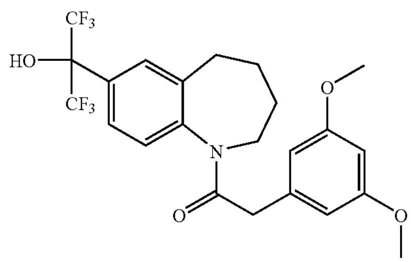 | 492.2 |
| 43 | 2-(4-Isopropyl-phenyl)-1-[7-(2,2,2-trifluoro-1-hydroxy-1-trifluoromethyl-ethyl)-2,3,4,5-tetrahydro-1-benzazepin-1-yl]-ethanone | 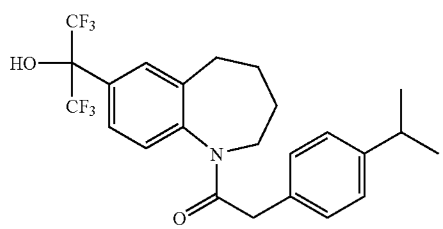 | 474.3 |
| 44 | 2-(2,3-Dimethoxy-phenyl)-1-[7-(2,2,2-trifluoro-1-hydroxy-1-trifluoromethyl-ethyl)-2,3,4,5-tetrahydro-1-benzazepin-1-yl]-ethanone | 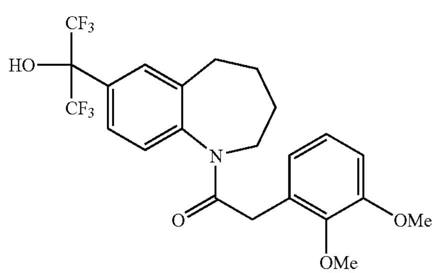 | 492.2 |
| 45 | (R)-2-Phenyl-1-[7-(2,2,2-trifluoro-1-hydroxy-1-trifluoromethyl-ethyl)-2,3,4,5-tetrahydro-1-benzazepin-1-yl]-propan-1-one | 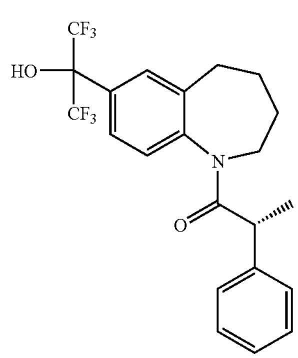 | 446.2 |

TABLE 3-continued

| Ex. # | Name | Structure | MS (M + H)+ |
|---|---|---|---|
| 46 | (S)-2-Methoxy-2-phenyl-1-[7-(2,2,2-trifluoro-1-hydroxy-1-trifluoromethyl-ethyl)-2,3,4,5-tetrahydro-1-benzazepin-1-yl]-ethanone | 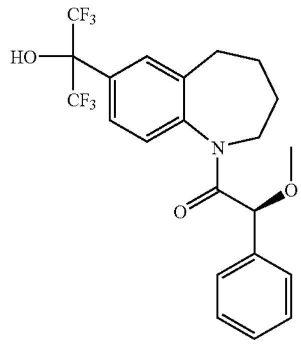 | 462.2 |
| 47 | 4,4,4-Trifluoro-1-[7-(2,2,2-trifluoro-1-hydroxy-1-trifluoromethyl-ethyl)-2,3,4,5-tetrahydro-1-benzazepin-1-yl]-butan-1-one | 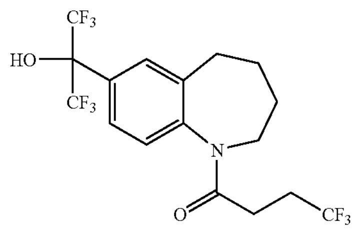 | 438.2 |
| 48 | 2-(1R,4S)-Bicyclo[2.2.1]hept-2-yl-1-[7-(2,2,2-trifluoro-1-hydroxy-1-trifluoromethyl-ethyl)-2,3,4,5-tetrahydro-1-benzazepin-1-yl]-ethanone | 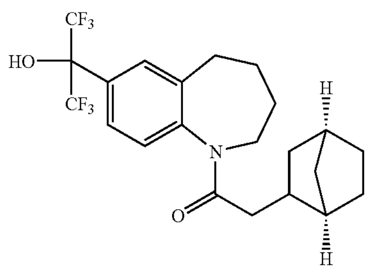 | 450.3 |

Example 49

2-(4-Dimethylamino-phenyl)-1-[7-(2,2,2-trifluoro-1-hydroxy-1-trifluoromethyl-ethyl)-2,3,4,5-tetrahydro-1-benzazepin-1-yl]-ethanone

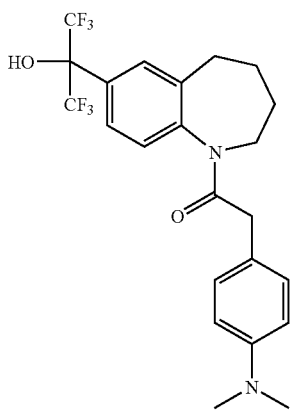

To a solution of 2-(4-(dimethylamino)phenyl)acetic acid (36 mg, 0.2 mmol) in anhydrous $CH_2Cl_2$ (1 mL) were added HOAt (27.0 mg, 0.2 mmol) and EDC-HCl (40 mg, 0.21 mmol). The mixture was stirred until a clear solution was observed, and then 1D (31 mg, 0.1 mmol) was added and the mixture was stirred at 60° C. overnight. The solvent was removed in vacuo and the product was purified by prep-HPLC to yield Example 49 (14.5 mg, 30%). HRMS m/z 475.1819 (M+H)+. $^1$H NMR (500 MHz, Acetone-$D_6$) δ 7.71 (d, 1H), 7.59 (s, 1H), 7.51 (d, 1H), 7.22 (d, 2H), 6.92 (d, 2H), 4.62 (dd, 1H), 3.57 (d, 1H), 3.50 (d, 1H), 3.13 (s, 6H), 2.54 (m, 2H), 2.20 (t, 1H), 1.84 (m, 1H), 1.72 (m, 2H), 1.28 (m, 1H).

Examples 50 to 52

In Table 4, Example 50 was prepared in a similar manner as described in Example 49. Examples 51 and 52 were prepared in a similar manner except the crude products were treated with 3N NaOH solution in methanol to hydrolyze the esters before purifying by prep-HPLC.

TABLE 4

| Ex. # | Name | Structure | MS (M + H)+ |
|---|---|---|---|
| 50 | 2-(4-Methanesulfonyl-phenyl)-1-[7-(2,2,2-trifluoro-1-hydroxy-1-trifluoromethyl-ethyl)-2,3,4,5-tetrahydro-1-benzazepin-1-yl]-ethanone | 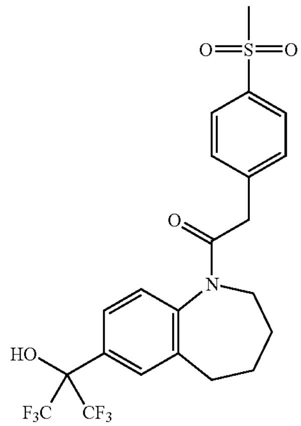 | 510.1 |
| 51 | 2-(4-Hydroxymethyl-phenyl)-1-[7-(2,2,2-trifluoro-1-hydroxy-1-trifluoromethyl-ethyl)-2,3,4,5-tetrahydro-1-benzazepin-1-yl]-ethanone | 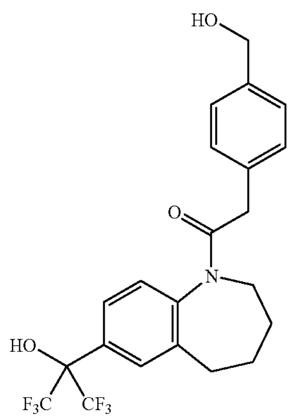 | 462.1 |
| 52 | 2-(3-Hydroxy-phenyl)-1-[7-(2,2,2-trifluoro-1-hydroxy-1-trifluoromethyl-ethyl)-2,3,4,5-tetrahydro-1-benzazepin-1-yl]-ethanone | 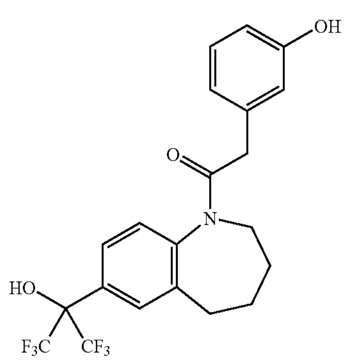 | 448.1 |

Example 53

7-(2,2,2-Trifluoro-1-hydroxy-1-trifluoromethyl-ethyl)-2,3,4,5-tetrahydro-1-benzazepine-1-carboxylic acid benzyl ester

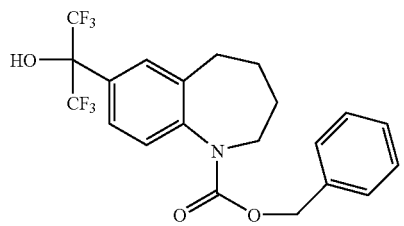

To a suspension of 1D (31.5 mg, 0.1 mmol) and DIEA (28 mg, 0.215 mmol) in anhydrous $CH_2Cl_2$ (0.4 mL) at 0° C. was added a solution of benzylchloroformate (19 mg, 0.11 mmol) in anhydrous $CH_2Cl_2$ (0.3 mL), and the mixture was stirred at rt overnight. The solvent was removed under vacuum and the product was purified by prep-HPLC to yield Example 53 (19.2 mg, 43%). LC/MS m/z 448.1 (M+H)$^+$. $^1$H NMR (500 MHz, DMSO-D$_6$, 75° C.) δ 8.49 (s, 1H), 7.56 (s, 1H), 7.48 (d, 1H), 7.28 (m, 5H), 5.11 (s, 2H), 3.13 (s, 2H), 2.74 (s, 2H), 1.76 (s, 2H), 1.63 (s, 2H).

Example 54

7-(2,2,2-Trifluoro-1-hydroxy-1-trifluoromethyl-ethyl)-2,3,4,5-tetrahydro-1-benzazepine-1-carboxylic acid isopropyl ester

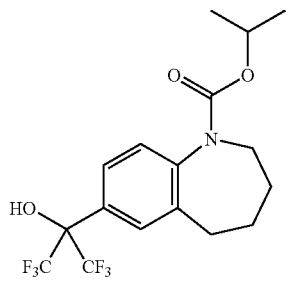

Example 54 was prepared in a similar manner as described in Example 53. LC/MS m/z 400.1 (M+H)$^+$.

Example 55

7-(2,2,2-Trifluoro-1-hydroxy-1-trifluoromethyl-ethyl)-2,3,4,5-tetrahydro-1-benzazepine-1-carboxylic acid phenylamide

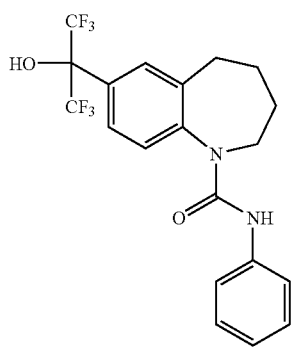

To a solution of 1D (32 mg, 0.1 mmol) in THF (0.25 mL) was added phenylisocyanate (12 mg, 0.1 mmol). The mixture was stirred at 75° C. for 3 h, then the solvent was removed under vacuum. The product was purified by prep-HPLC to yield Example 55 (12 mg, 28%). LC/MS m/z 433.1 (M+H)$^+$. $^1$H NMR (500 MHz, DMSO-D$_6$, 75° C.) δ 8.48 (s, 1H), 7.88 (s, 1H), 7.60 (s, 1H), 7.50 (d, 1H), 7.38 (m, 2H), 7.31 (d, 1H), 7.21 (m, 2H), 6.94 (m, 1H), 3.14 (s, 2H), 2.83 (m, 2H), 1.75 (m, 2H), 1.64 (s, 2H).

Examples 56 to 58

Examples 56 to 58 in Table 5 were prepared via a similar manner as described in Example 55.

TABLE 5

| Ex. # | Name | Structure | MS (M + H)$^+$ |
|---|---|---|---|
| 56 | 7-(2,2,2-Trifluoro-1-hydroxy-1-trifluoromethyl-ethyl)-2,3,4,5-tetrahydro-1-benzazepine-1-carboxylic acid benzylamide | 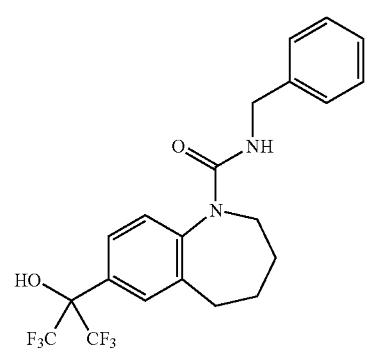 | 447.3 |

TABLE 5-continued

| Ex. # | Name | Structure | MS (M + H)+ |
|---|---|---|---|
| 57 | 7-(2,2,2-Trifluoro-1-hydroxy-1-trifluoromethyl-ethyl)-2,3,4,5-tetrahydro-1-benzazepine-1-carboxylic acid phenethyl-amide | 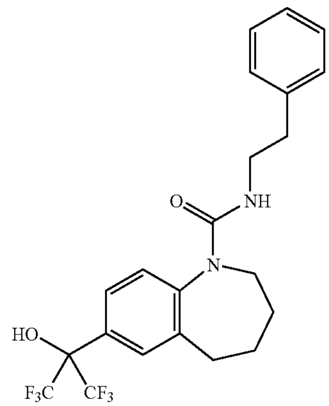 | 447.3 |
| 58 | 7-(2,2,2-Trifluoro-1-hydroxy-1-trifluoromethyl-ethyl)-2,3,4,5-tetrahydro-1-benzazepine-1-carboxylic acid isopropylamide | 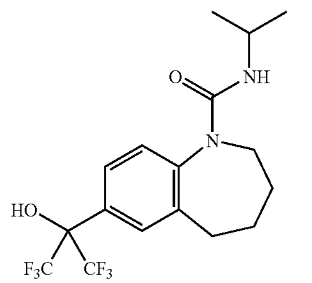 | 399.1 |

Example 59

2-Phenyl-1-[2-(2,2,2-trifluoro-1-hydroxy-1-trifluoromethyl-ethyl)-6,7-dihydro-9H-8-thia-5-aza-benzocyclohepten-5-yl]-ethanone

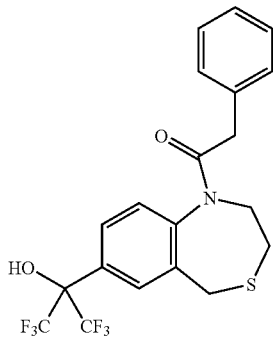

59A. (2-Nitro-benzylsulfanyl)-acetic acid methyl ester: To a solution of o-nitrobenzylbromide (1.08 g, 5.05 mmol) and methyl 2-mercaptoacetate (530 mg, 5 mmol) in anhydrous THF (25 mL) was added NaH (220 mg, 5.5 mmol) and the reaction was stirred at rt for 2 h. The solvent was evaporated and the resulting residue was dissolved in EtOAc and washed with brine. The crude product was purified by flash chromatography to give 59A as a white solid (1.2 g, 99%). LC/MS m/z 242 (M+H)+.

59B. (2-Amino-benzylsulfanyl)-acetic acid methyl ester: A solution of 59A (2.41 g, 10 mmol) and SnCl$_2$.H$_2$O (30 mmol) in MeOH (30 mL) was refluxed for 16 h. The solvent was evaporated and the resulting residue was dissolved in EtOAc and washed with 1N NaOH and brine. The resulting mixture was dried over MgSO$_4$ and the solvent was removed to provide 59B as a yellow oil (2.07 g, ~90% pure by HPLC) that was used directly for the subsequent reaction without further purification.

59C. 5,9-Dihydro-8-thia-5-aza-benzocyclohepten-6-one: 59B (1.9 g) was heated at 160° C. in a sealed tube in an oil bath for 16 h. The crude product was purified by flash chromatography to afford 59C as an off-white solid (890 mg, 55%). LC/MS m/z 180 (M+H)+.

59D. 5,6,7,9-Tetrahydro-8-thia-5-aza-benzocycloheptene: A mixture of 59C (890 mg, 4.97 mmol) and BH$_3$.THF (1M, 10 mL) in anhydrous THF (10 mL) was heated at 50° C. for 14 h. The solvent was evaporated and the resulting residue was dissolved in EtOAc and washed with 1N NaOH and brine. Drying over MgSO$_4$ and removal of solvent gave 59D as a white solid (790 mg, 96%). LC/MS m/z 166 (M+H)+.

59E. 1,1,1,3,3,3-Hexafluoro-2-(5,6,7,9-tetrahydro-8-thia-5-aza-benzocyclohepten-2-yl)-propan-2-ol: 59E was prepared from 59D in a similar manner as described for the preparation of 1D. LC/MS m/z 332 (M+H)+.

Example 59: Example 59 was prepared from 59E in a similar manner as described in Example 1. The title compound was purified by prep-HPLC and isolated as a white solid (38 mg, 50%). LC/MS m/z 450.1 (M+H)+. $^1$H NMR (500 MHz, MeOH-d$_4$) δ ppm 2.59-2.64 (m, 1H) 2.88 (t, 1H) 3.05-3.12 (m, 3H) 3.30-3.32 (m, 3H) 3.49 (d, 1H) 3.60 (d, 1H) 4.86-4.91 (m, 1H) 6.74 (dd, 2H) 7.11-7.19 (m, 3H) 7.50 (dd, 2H) 7.73-7.76 (m, 2H).

Example 60

2-Methyl-1-[2-(2,2,2-trifluoro-1-hydroxy-1-trifluoromethyl-ethyl)-6,7-dihydro-9H-8-thia-5-aza-benzocyclohepten-5-yl]-propan-1-one

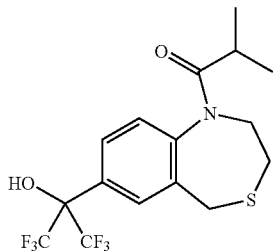

Example 60 was prepared in a similar manner as described in Example 59. LC/MS m/z 402.1 (M+H)+. 1H NMR (500 MHz, MeOH-d4) δ ppm 0.96 (d, 3H) 1.10 (d, 3H) 2.44 (q, 1H) 2.69 (d, 1H) 2.91 (t, 1H) 3.20 (t, 1H) 3.65 (d, 1H) 4.03 (d, 1H) 7.40-7.19 (d, 1H) 7.70 (d, 1H) 7.73-7.76 (s, 1H).

Example 61

2-Phenyl-1-[7-(2,2,2-trifluoro-1-hydroxy-1-trifluoromethyl-ethyl)-2,3-dihydro-5H-4,1-benzoxazepin-1-yl]-ethanone

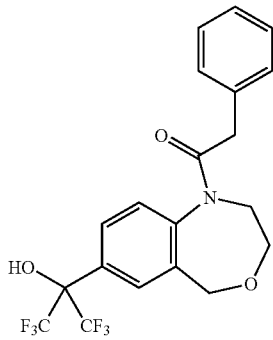

61A. 2-Bromo-N-(2-hydroxymethyl-phenyl)-acetamide: To a suspension of bromoacetic acid (6.95 g, 50 mmol) and TFFH (13.2 g, 50 mmol) in CH2Cl2 (80 mL) was added DIEA in CH2Cl2 (20 mL) dropwise. The resulting reaction mixture was stirred for 10 min, and to this mixture was added (2-aminophenyl)methanol (6.2 g, 50.2 mmol) in CH2Cl2 (100 mL). The resulting solution was stirred at rt for 2 h, then washed with 0.5 N HCl and brine. After drying over MgSO4 and removal of solvent under vacuum, the resulting residue was purified by flash chromatography to give 61A as white solid (5.3 g, 43%). LC/MS m/z 243 (M+H)+.

61B. 1,5-Dihydro-4,1-benzoxazepin-2-one: To a suspension of NaH (400 g, 10 mol) in anhydrous THF was added dropwise 61A (1.22 g, 5 mmol) in THF (30 mL). After stirring at rt for 2 h, the solvent was removed under vacuum and the resulting residue was dissolved in EtOAc and washed with 0.5 N HCl and brine. The resulting mixture was dried over MgSO4 and the solvent was removed to provide 61B as a white solid (740 mg, ~80% pure). LC/MS m/z 164.1 (M+H)+.

61C. 1,2,3,5-Tetrahydro-4,1-benzoxazepine: To a solution of 61B (740 mg) in anhydrous THF (10 mL) was added BH3.THF (1M, 7.5 mL) and the mixture was heated at 60° C. for 6 h. After removal of solvent, the resulting residue was dissolved in EtOAc and washed with 1 N NaOH and brine. Removal of solvent under vacuum afforded 61C as a white solid (670 mg, purity~81%). LC/MS m/z 150.2 (M+H)+.

61D. 1,1,1,3,3,3-Hexafluoro-2-(1,2,3,5-tetrahydro-4,1-benzoxazepin-7-yl)-propan-2-ol: 61D was prepared in a similar manner as described in 1D and isolated as a white solid. LC/MS m/z 316.2 (M+H)+.

Example 9: Example 9 was prepared from 61D in a similar manner as described in Example 1. LC/MS m/z 432.1 (M+H)+. 1H NMR (500 MHz, MeOH-d4) δ ppm 2.86-2.92 (m, 1H) 3.56-3.63 (m, 2H) 3.65 (d, 1H) 3.81 (d, 1H) 3.93 (d, 1H) 4.25 (d, 2H) 4.67 (d, 2H) 6.72 (d, 2H) 7.07-7.15 (m, 3H) 7.52 (s, 1H) 7.60 (d, 1H) 7.82-7.84 (m, 1H).

Example 62

2-Cyclopentyl-1-[7-(2,2,2-trifluoro-1-hydroxy-1-trifluoromethyl-ethyl)-2,3-dihydro-5H-4,1-benzoxazepin-1-yl]-ethanone

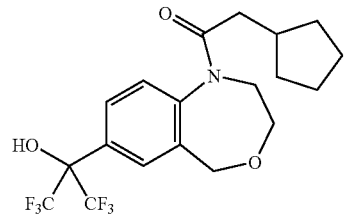

The title compound was prepared by a similar procedure to Example 61. LC/MS m/z 425.2 (M+H)+. 1H NMR (500 MHz, MeOH-d4) δ ppm 0.88-0.96 (m, 1H) 1.07-1.14 (m, 1H) 1.47-1.56 (m, 4H) 1.69-1.75 (m, 1H) 1.77-1.83 (m, 1H), 2.13-2.20 (m, 2H) 2.38 (q, 1H) 2.90 (t, 1H) 3.76 (t, 1H) 4.02 (d, 1H) 4.58 (d, 1H), 4.71 (d, 2H) 7.46 (d, 1H) 7.77 (s, 2H).

Example 63

2-Methyl-1-[7-(2,2,2-trifluoro-1-hydroxy-1-trifluoromethyl-ethyl)-2,3-dihydro-5H-4,1-benzoxazepin-1-yl]-propan-1-one

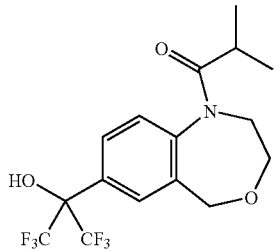

The title compound was prepared by a similar procedure to Example 61. LC/MS m/z 386.2 (M+H)+. 1H NMR (500 MHz, MeOH-d4) δ ppm 0.96 (dd, 3H) 1.19 (dd, 3H) 2.67-2.74 (m, 1H) 2.92 (t, 1H) 3.80 (t, 1H) 4.05 (d, 1H) 4.55 (d, 1H) 4.71 (d, 1H) 4.77 (d, 1H) 7.32 (d, 1H) 7.73 (s, 2H).

Example 64

2-Phenyl-1-[7-(2,2,2-trifluoro-1-hydroxy-1-methyl-ethyl)-2,3,4,5-tetrahydro-1-benzazepin-1-yl]-ethanone

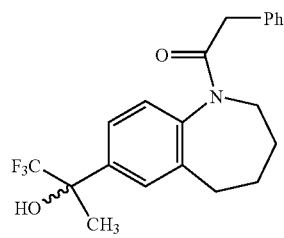

64A. 7-Bromo-1,3,4,5-tetrahydro-1-benzazepin-2-one: To a solution of 1B (4.89 g, 30 mmol) in acetic acid (90 mL) was added dropwise a solution of bromine (9.6 g, 60 mmol) in acetic acid (20 mL) over 15 min. The mixture was stirred at rt for 6 h, and the resulting precipitate was collected and washed with additional HOAc. The desired product was recrystalized from MeOH/H$_2$O as an off-white solid (4.78 g, 66%). LC/MS m/z 240 (M+H)$^+$.

64B. 7-Bromo-2,3,4,5-tetrahydro-1H-1-benzazepine: 64B was prepared from 64A in a similar procedure as described for 1C (2.7 g, 80%). LC/MS m/z 225 (M+H)$^+$.

64C. 1-(7-Bromo-2,3,4,5-tetrahydro-1-benzazepin-1-yl)-2,2-dimethyl-propan-1-one: A mixture of 64B (720 mg, 3 mmol), pivalyl chloride (720 mg, 6 mmol), and DIEA (387 mg, 3 mmol) in 9:1 CH$_2$Cl$_2$/pyridine (15 mL) was stirred at rt for 14 h. The solvent was removed under vacuum and the resulting residue was purified by flash chromatography to give 64C as a white solid (820 mg, 85%). LC/MS m/z 309.1 (M+H)$^+$.

64D. 2,2-Dimethyl-1-[7-(2,2,2-trifluoro-acetyl)-2,3,4,5-tetrahydro-1-benzazepin-1-yl]-propan-1-one: To a solution of 64C (980 mg, 3.17 mmol) in anhydrous THF (15 mL) at −78° C. was added t-BuLi (1.7 M, 2.66 mL, 7.92 mmol). The resulting mixture was stirred at −78° C. for an additional 15 min, then 2,2,2-trifluoro-1-(piperidin-1-yl)ethanone (573 mg, 3.17 mmol) in THF (2 mL) was added. The resulting mixture was stirred at −78° C. for 10 min, then warmed to rt and stirred for 1 h and quenched with saturated NH$_4$Cl. The aqueous solution was extracted with EtOAc, and the combined organic layers were evaporated to dryness. The resulting residue was purified by flash chromatography to give 64D as a yellow oil (620 mg, 60%). LC/MS m/z 346 (M+H$_2$O)+; 360 (M+MeOH)$^+$.

64E. 1,1,1-Trifluoro-2-(2,3,4,5-tetrahydro-1H-1-benzazepin-7-yl)-propan-2-ol: To 64D (155 mg, 0.48 mmol) in THF (5 mL) was added MeMgBr (1M, 0.9 mL). The resulting mixture was stirred at 0° C. for 1 h and quenched with saturated NH$_4$Cl. The aqueous solution was extracted with EtOAc and the combined organic layers were evaporated to dryness. The resulting yellow solid was dissolved in conc. HCl/dioxane solution (1:1, 1.4 mL) and heated at 170° C. in a microwave reactor for 10 min. After removal of solvent, the crude product was purified by prep-HPLC to give a TFA salt that was neutralized with saturated NaHCO$_3$ to give 64E (32 mg, 26%). LC/MS m/z 260.1 (M+H)$^+$.

Example 64: To a solution of 64E (19.4 mg, 0.075 mmol) in toluene (1 mL) was added phenylacetyl chloride (15.4 mg, 0.1 mmol) and the resulting solution was heated at 90° C. for 90 min. Solvent was removed under vacuum and the resulting residue was purified by flash chromatography to give Example 64 as a colorless oil (8.7 mg, 30%). LC/MS m/z 378.1 (M+H)$^+$. $^1$H NMR (500 MHz, MeOH-d$_4$) δ ppm 1.25-1.33 (m, 1H) 1.71-1.79 (m, 4H) 1.80-1.86 (m, 1H) 2.01 (t, 1H) 2.40 (dd, 1H) 2.62 (t, 1H) 3.45 (d, 1H) 3.64 (d, 1H) 4.61 (d, 1H) 6.77 (d, 2H) 7.10-7.16 (m, 3H) 7.28 (d, 1H) 7.39 (d, 1H) 7.57 (dd, 1H).

Example 65

(S)-2-Phenyl-1-[7-(2,2,2-trifluoro-1-hydroxy-1-methyl-ethyl)-2,3,4,5-tetrahydro-1-benzazepin-1-yl]-propan-1-one

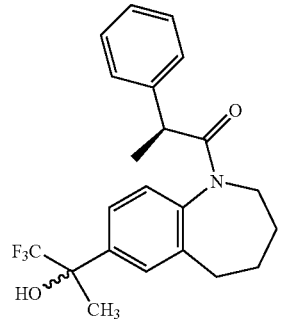

Example 65 was prepared in a similar manner as described for Example 64. LC/MS m/z 392.0 (M+H)$^+$.

Example 66

1-{7-[2-Chloro-1-(chloro-difluoro-methyl)-2,2-difluoro-1-hydroxy-ethyl]-2,3,4,5-tetrahydro-1-benzazepin-1-yl}-2-methyl-propan-1-one

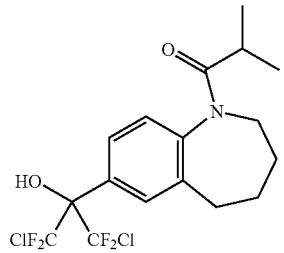

Example 66 was prepared by a similar procedure to Example 1 using 1,3-dichloro-tetrafluoroacetone instead of hexafluoroacetone. LC/MS m/z 416.1 (M+H)$^+$.

Example 67

1-{7-[2-Chloro-1-(chloro-difluoro-methyl)-2,2-difluoro-1-hydroxy-ethyl]-2,3,4,5-tetrahydro-1-benzazepin-1-yl}-2-phenyl-ethanone

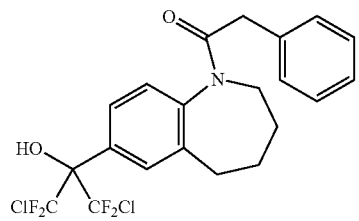

Example 67 was prepared by a similar procedure to Example 1. LC/MS m/z 464.1 (M+H)$^+$.

Example 68

2-Methyl-1-[2-methyl-7-(2,2,2-trifluoro-1-hydroxy-1-trifluoromethyl-ethyl)-2,3,4,5-tetrahydro-1-benzazepin-1-yl]-propan-1-one

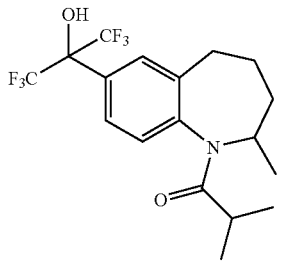

68A. 2-(4-Amino-3-iodo-phenyl)-1,1,1,3,3,3-hexafluoropropan-2-ol: Hexafluoroacetone sesquihydrate (1.93 g, 10 mmol) and 2-iodoaniline (1.75 g, 8 mmol) were heated at 200° C. for 1000 s in a sealed reaction vessel in a microwave reactor. Volatiles were removed under vacuum and the resulting residue was dissolved in ethyl acetate and dried over anhydrous $Na_2SO_4$, filtered, and evaporated. The resulting residue was purified by flash chromatography to give 68A as a pink solid (450 mg, 15%). LC/MS m/z 383.9 (M−H)−. $^1$H NMR (500 MHz, Acetone-$D_6$) δ 7.96 (s, 1H), 7.44 (d, 1H), 7.29 (s, 1H), 6.9 (d, 1H), 5.3 (bs, 2H).

68B. 1,1,1,3,3,3-Hexafluoro-2-(2-methyl-4,5-dihydro-1H-1-benzazepin-7-yl)-propan-2-ol: A mixture of 68A (101 mg, 0.26 mmol), pent-4-en-2-ol (23 mg, 0.26 mmol), palladium acetate (2.5 mg), lithium chloride (33 mg, 0.78 mmol), and DIEA (270 mg, 2.1 mmol) in DMF (2.6 mL) was heated at 120° C. in a microwave reactor for 700 s. The DMF was removed under vacuum and the resulting residue was dissolved in ethyl acetate, washed with water, dried over anhydrous $Na_2SO_4$ and filtered. The ethyl acetate was removed in vacuo to give 68B. LC/MS m/z 326.1 (M+H)+.

68C. 1,1,1,3,3,3-Hexafluoro-2-(2-methyl-2,3,4,5-tetrahydro-1H-1-benzazepin-7-yl)-propan-2-ol: To a solution of 68B in dry MeOH (0.5 mL) at 0° C. were added sodium borohydride pellets (40 mg, 1.1 mmol) in portions. The mixture was stirred at 0° C. until bubbling stopped and then stirred at rt for 10 min. The MeOH was removed in vacuo and the mixture was quenched with HCl/ice. The solution was neutralized with 1N NaOH to pH~8 and the product was extracted with ethyl acetate. The combined organic layers were washed with brine, dried over anhydrous $Na_2SO_4$, filtered, and evaporated. The product was purified by prep-HPLC to give 68C (17.5 mg, 20%). LC/MS m/z 328.3 (M−H)−. $^1$H-NMR (500 MHz, Methanol-$D_3$) δ 7.75 (s, 1H), 7.73 (d, 1H), 7.52 (d, 1H), 3.66 (m, 1H), 3.04 (m, 2H), 2.20 (m, 1H), 1.98 (m, 2H), 1.68 (m, 1H), 1.36 (d, 3H).

Example 68: Example 68 was prepared by a similar procedure to 68C. LC/MS m/z 398.2 (M+H)+.

Example 69

1-[2-Phenyl-7-(2,2,2-trifluoro-1-hydroxy-1-trifluoromethyl-ethyl)-2,3,4,5-tetrahydro-1-benzazepin-1-yl]-ethanone

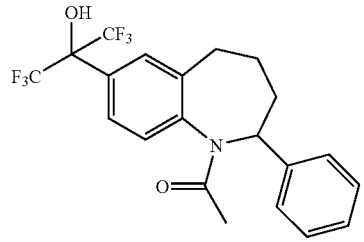

69A. 1,1,1,3,3,3-Hexafluoro-2-(2-phenyl-4,5-dihydro-1H-1-benzazepin-7-yl)-propan-2-ol: The title compound was prepared from 68A by a procedure similar to that described for 68B.

69B. 1,1,1,3,3,3-Hexafluoro-2-(2-phenyl-2,3,4,5-tetrahydro-1H-1-benzazepin-7-yl)-propan-2-ol: The title compound was prepared by a procedure similar to that described for 68C.

Example 69: To a solution of 69B (35 mg, 0.09 mmol) in $CH_2Cl_2$ (0.5 mL) were added acetyl chloride (0.04 mL, 0.45 mmol) and DIEA (58 mg, 0.45 mmol) and the mixture was stirred at rt for 2 h. The reaction mixture was diluted with $CH_2Cl_2$ and washed with water, sat'd $NaHCO_3$, and brine, then dried over anhydrous $Na_2SO_4$ and filtered. Solvent was removed in vacuo and the resulting mixture was re-dissolved in THF (0.8 mL) and stirred with 2N LiOH (0.2 mL) at rt for 3 h. The mixture was diluted with EtOAc, washed with water and brine, and dried over anhydrous $Na_2SO_4$. The solvent was removed in vacuo to yield Example 69 as an off-white solid (32 mg, 82%). LC/MS m/z 432.1 (M+H)+. $^1$H-NMR (500 MHz, Methanol-$D_3$) δ 7.62 (m, 2H), 7.26 (d, 1H), 7.18 (m, 4H), 7.10 (m, 1H), 5.37 (dd, 1H), 2.86 (m, 1H), 2.71 (m, 1H), 1.90 (m, 1H), 1.74 (m, 2H), 1.70 (s, 3H), 1.42 (m, 1H).

Examples 70 and 71

Examples 70 and 71 in Table 6 were prepared by a similar procedure to Example 69.

TABLE 6

| Ex. # | Name | Structure | MS (M + H)+ |
|---|---|---|---|
| 70 | 1-[2-Isopropyl-7-(2,2,2-trifluoro-1-hydroxy-1-trifluoromethyl-ethyl)-2,3,4,5-tetrahydro-1-benzazepin-1-yl]-2-methyl-propan-1-one | 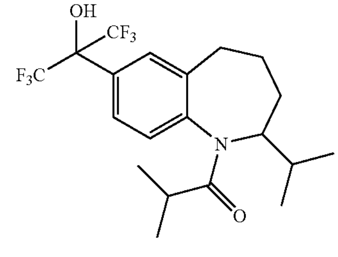 | 426.2 |

TABLE 6-continued

| Ex. # | Name | Structure | MS (M + H)+ |
|---|---|---|---|
| 71 | (S)-2-Phenyl-1-[2-phenyl-7-(2,2,2-trifluoro-1-hydroxy-1-trifluoromethyl-ethyl)-2,3,4,5-tetrahydro-1-benzazepin-1-yl]-propan-1-one | 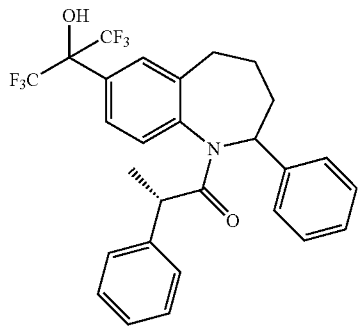 | 522.4 |

Example 72

(S)-3-(3-Methoxy-phenoxy)-1-((S)-2-phenyl-propionyl)-2,3,4,5-tetrahydro-1H-1-benzazepine-7-carboxylic acid methylamide

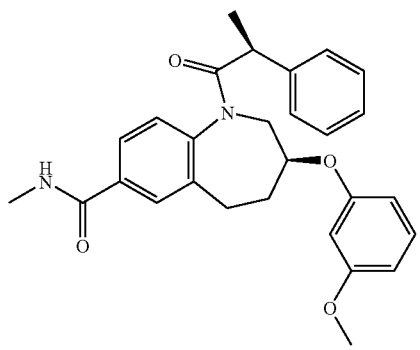

72A. 3,7-Dibromo-1,3,4,5-tetrahydro-1-benzazepin-2-one: To a suspension of 3-bromo-1,3,4,5-tetrahydro-1-benzazepin-2-one (9.56 g, 40 mmol) in acetic acid (40 mL) was added bromine (12.8 g, 80 mmol) dropwise. The resulting mixture was stirred at rt for 14 h. The resulting precipitate was collected by filtration, washed with HOAc, and dried to give 72A as a white solid (11.54 g, 91%). LC/MS m/z 317 (M+H)+.

72B. 7-Bromo-3-(3-methoxy-phenoxy)-1,3,4,5-tetrahydro-1-benzazepin-2-one: To a suspension of 3-methoxy-phenol (3.72 g, 30 mmol) and $Cs_2CO_3$ (19.5 g, 60 mmol) in acetone (80 mL) was added 72A (6.34 g, 20 mmol). The resulting mixture was stirred at rt for 16 h, then the insoluble material was removed by filtration. After removal of solvent, the residue was purified by flash chromatography to give 72B (3.6 g, 50%). LC/MS m/z 362 (M+H)+.

72C. 7-Bromo-3-(3-methoxy-phenoxy)-2,3,4,5-tetrahydro-1H-1-benzazepine: To a solution of 72B (361 mg, 1 mmol) in anhydrous THF (2 mL) was added 1M $BH_3$.THF solution (2 mL). The resulting mixture was stirred at 60° C. for 24 h. Removal of solvent gave a residue that was dissolved in EtOAc and washed with 1N NaOH and brine. Drying over $MgSO_4$ and removal of solvent gave a residue that was purified by flash chromatography to yield 72C as an oil (200 mg, 57%). LC/MS m/z 348 (M+H)+.

72D. 1-[7-Bromo-3-(3-methoxy-phenoxy)-2,3,4,5-tetrahydro-1-benzazepin-1-yl]-2,2-dimethyl-propan-1-one: To a mixture of 72C (200 mg, 0.57 mmol) and TEA (101 mg, 1 mmol) in $CH_2Cl_2$ (3 mL) were added pivalyl chloride (120 mg, 1 mmol) and cat. DMAP. The resulting mixture was stirred at rt for 24 h, then the solvent was evaporated and the residue was purified by flash chromatography to give 72D (230 mg, 93%). LC/MS m/z 432 (M+H)+.

72E. 1-(2,2-Dimethyl-propionyl)-3-(3-methoxy-phenoxy)-2,3,4,5-tetrahydro-1H-1-benzazepine-7-carboxylic acid: To 72D (370 mg, 0.86 mmol) in anhydrous THF (5 mL) at −78° C. was added t-BuLi (1.5 M, 2.2 mL) via a dropping funnel. The resulting mixture was stirred at −78° C. for 10 min as $CO_2$ gas was passed through the solution. The reaction mixture was allowed to warm to rt over a period of 2 h. The solvent was removed and the resulting residue was acidified with 1N HCl. This aqueous solution was extracted with EtOAc and the combined organic layers were washed with brine. The solvent was removed and the resulting residue was triturated with MeOH to give 72E as a white solid (80 mg, 53%). LC/MS m/z 398 (M+H)+.

72F. 3-(3-Methoxy-phenoxy)-2,3,4,5-tetrahydro-1H-1-benzazepine-7-carboxylic acid: 72E (552 mg, 1.4 mmol) dissolved in a 1:1 mixture of conc. HCl/dioxane (15 mL) was heated at 140° C. for 15 min in a sealed tube in a microwave reactor. After removal of the solvent, the resulting residue was purified by prep-HPLC to give 72F as a white solid (200 mg, 45%). LC/MS m/z 314 (M+H)+.

Example 72: Acid 72F (32 mg, 0.1 mmol) was treated with $NH_2Me.HCl$ (13.4 mg, 0.2 mmol), BOP reagent (45 mg, 0.1 mmol), and TEA (33 mg, 0.3 mmol) in acetonitrile (1 mL). The resulting mixture was stirred at rt for 3 h, then the solvent was removed and the resulting residue was dissolved in EtOAc. The organic phase was washed with $NaHCO_3$ and brine, dried over $MgSO_4$, and evaporated to provide 3-(3-methoxy-phenoxy)-2,3,4,5-tetrahydro-1H-1-benzazepine-7-carboxylic acid methylamide. To this intermediate in anhydrous 1,2-dichloroethane (1 mL) were added freshly prepared (S)-2-phenyl-propionyl chloride (43 mg, 0.25 mol) and TEA (25 mg, 0.25 mmol). The resulting mixture was stirred at rt for 16 h, then the solvent was removed and the residue was purified and the diastereomers were separated by prep-HPLC. The desired slow eluting diastereomer, Example 72, was isolated (8.2 mg, 21%). LC/MS m/z 459.2 (M+H)+.

Example 73

(S)-3-(3-Methoxy-phenoxy)-1-((S)-2-phenyl-propionyl)-2,3,4,5-tetrahydro-1H-1-benzazepine-7-carboxylic acid dimethylamide

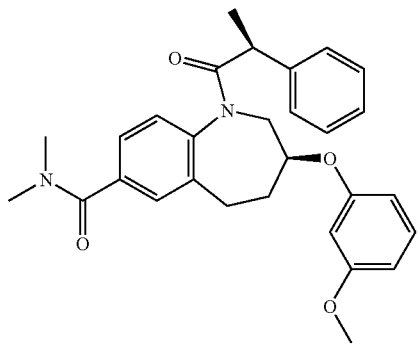

The title compound was prepared by a procedure similar to that described for Example 72. LC/MS m/a 473 (M+H)+.

Example 74

(S)-3-(3-Methoxy-phenoxy)-1-((S)-2-phenyl-propionyl)-2,3,4,5-tetrahydro-1H-1-benzazepine-7-carboxylic acid

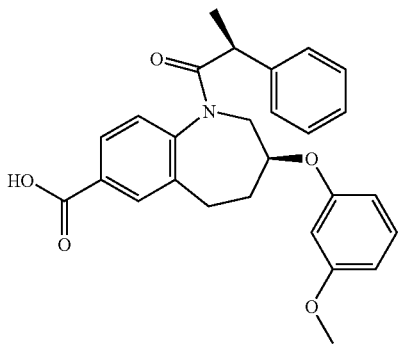

The title compound was prepared from 72F by acylation with (S)-2-phenyl-propionyl chloride by a procedure similar to that described for 72G. LC/MS m/z 446 (M+H)+.

Example 75

(S)-3-(3-Methoxy-phenoxy)-1-((S)-2-phenyl-propionyl)-2,3,4,5-tetrahydro-1H-1-benzazepine-7-carboxylic acid methyl ester

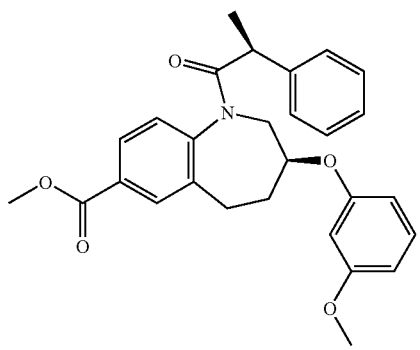

The carboxylic acid intermediate 72F (100 mg, 0.23 mmol) was refluxed in MeOH (4 mL) containing 2M HCl/ether (1 mL) for 3 h. The resulting methyl ester was isolated and subsequently acylated according to the procedure described for 72G. The crude product was purified and the diastereomeric mixture was separated by prep-HPLC and the desired diastereomer was isolated as Example 75. LC/MS m/z 460.2 (M+H)+.

Example 76

3-(3-Methoxy-phenoxy)-1-((S)-2-phenyl-propionyl)-2,3,4,5-tetrahydro-1H-1-benzazepine-7-carboxylic acid tert-butyl ester

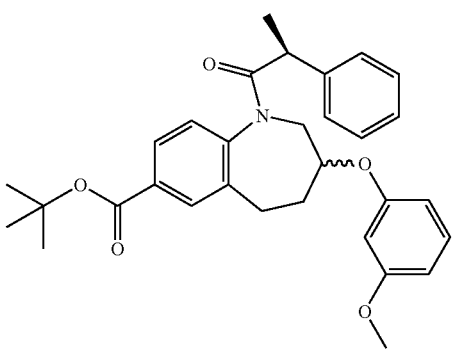

A mixture of acid 72F (60 mg, 0.13 mmol), Boc-anhydride (57 mg, 0.26 mmol) and DMAP (5 mg, 0.04 mmol) in t-BuOH (1 mL) was stirred at rt for 16 h. The product was acylated according to the procedure described for 72G, and Example 76 was purified by prep-HPLC and isolated as a mixture of diastereomers (14.4 mg, 22%). LC/MS m/z 502.14 (M+H)+.

Example 77

(S)-1-[(S)-7-(3,5-Dimethyl-isoxazol-4-yl)-3-(3-methoxy-phenoxy)-2,3,4,5-tetrahydro-1-benzazepin-1-yl]-2-phenyl-propan-1-one

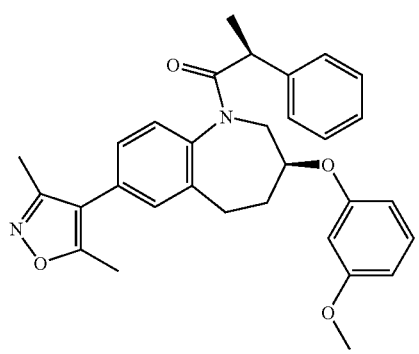

To 72C (1.74 g, 5 mmol) and DIEA (1.62 g 12.5 mmol) in DCE (10 mL) was added dropwise freshly prepared (S)-2-phenyl-propionyl chloride (2.1 g 16.5 mmol) in DCE (10 mL). The resulting mixture was stirred at rt for 16 h, then the solvent was evaporated and the crude product was purified by flash chromatography to give (S)-1-[7-bromo-3-(3-methoxy-phenoxy)-2,3,4,5-tetrahydro-1-benzazepin-1-yl]-2-phenylpropan-1-one as a foamy solid (1.8 g, 72%). LC/MS m/z 498 (M+H)⁺. To this intermediate (96 mg, 0.2 mmol) were added 3,5-dimethyl-4-(4,4,5,5-tetramethyl-1,3,2-dioxoborolane-2-yl)isoxazole (90 mg, 0.4 mmol) and chloro(di-2-nor-bornylphosphino)(20-dimethylamino-1,10-biphenyl-2-yl) palladium (10 mg) in 5:4:3 toluene/EtOH/2N Na$_2$CO$_3$ (2.4 mL). The resulting mixture was heated at 80° C. under an argon atmosphere for 16 h. Aqueous work-up and removal of solvent, followed by purification by prep-HPLC, gave Example 77 as an oil (22.7 mg, 23%). LC/MS m/z 497.26 (M+H)⁺.

Example 78

(S)-1-[(R)-3-(3-Methoxy-phenoxy)-7-(2,2,2-trifluoro-1-hydroxy-1-methyl-ethyl)-2,3,4,5-tetrahydro-1-benzazepin-1-yl]-2-phenyl-propan-1-one

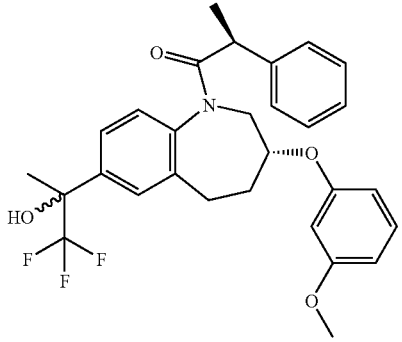

78A. 1-[3-(3-Methoxy-phenoxy)-7-(2,2,2-trifluoro-acetyl)-2,3,4,5-tetrahydro-1-benzazepin-1-yl]-2,2-dimethyl-propan-1-one: To 72D (360 mg, 0.8 mmol) in anhydrous THF (6 mL) at −78° C. was added t-BuLi (1.5 M, 1.2 mL) and the resulting solution was stirred at −78° C. for 10 min. To this solution was added 2,2,2-trifluoro-1-(piperidin-1-yl)ethanone (250 mg, 1.4 mmol) in THF (1 mL) slowly via a syringe and the resulting mixture was stirred at −78° C. for 30 min, then warmed to 0° C. and stirred for an additional 1 h. The reaction was quenched with sat'd NH$_4$Cl. After aqueous work-up, the crude product was purified by flash chromatography to give 78A as a white solid (270 mg, 75%). LC/MS m/z 467 (M+H$_2$O)⁺.

Example 78: To 78A (63 mg, 0.14 mmol) in anhydrous THF (1 mL) was added 3M MeMgBr (0.2 mL) and the resulting mixture was stirred at 0° C. for 1 h. The reaction was quenched with sat'd NH$_4$Cl. Aqueous workup gave 1-[3-(3-methoxy-phenoxy)-7-(2,2,2-trifluoro-1-hydroxy-1-methyl-ethyl)-2,3,4,5-tetrahydro-1-benzazepin-1-yl]-2,2-dimethyl-propan-1-one (60 mg). This intermediate in 1:1 HCl/dioxane solution (2 mL) was heated at 150° C. for 15 min in a microwave reactor. The solvent was evaporated and the resulting residue was dissolved in EtOAc and washed with NaHCO$_3$. To the free amine, 1,1,1-trifluoro-2-[3-(3-methoxy-phenoxy)-2,3,4,5-tetrahydro-1H-1-benzazepin-7-yl]-propan-2-ol, in DCE (2 mL) with DIEA (30 mg, 0.23 mmol) was added (S)-2-phenyl-propionyl chloride (30 mg, 0.2 mmol) and the mixture was stirred at rt for 16 h. Evaporation of solvent and purification by prep-HPLC gave the fast eluting diastereomer Example 78. LC/MS m/z 514.1 (M+H)⁺. ¹H NMR (500 MHz, CDCl$_3$) δ ppm 1.39 (s, 3H) 1.80 (s, 3H) 2.43 (s, 1H) 2.51 (s, 2H) 2.81 (s, 1H) 3.82 (s, 3H) 6.52 (s, 1H) 6.72 (s, 1H) 7.15 (s, 1H) 7.23 (s, 5H), 7.31 (s, 2H).

Example 79

(S)-1-[(S)-3-(3-Methoxy-phenoxy)-7-(2,2,2-trifluoro-1-hydroxy-1-methyl-ethyl)-2,3,4,5-tetrahydro-1-benzazepin-1-yl]-2-phenyl-propan-1-one

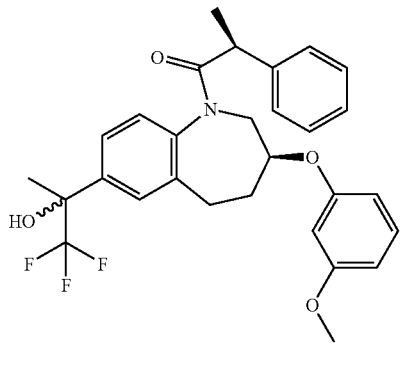

Example 79 (slow eluting diastereomer) was prepared by a similar procedure to Example 78. LC/MS m/z 514.1 (M+H)⁺. ¹H NMR (500 MHz, CDCl$_3$) δ ppm 1.41 (s, 4H) 1.83 (s, 3H) 2.10 (s, 1H) 2.54 (s, 2H) 3.85 (s, 4H) 4.25 (m, 1H), 5.01 (d, 1H) 6.53 (s, 1H) 6.66 (s, 3H) 7.06 (s, 2H) 7.11 (s, 1H) 7.25 (s, 2H) 7.32 (s, 1H) 7.45-7.60 (dd, 1H).

Example 80

1,1,1,3,3,3-Hexafluoro-2-[3-(4-methoxy-phenoxy)-2,3,4,5-tetrahydro-1H-1-benzazepin-7-yl]-propan-2-ol

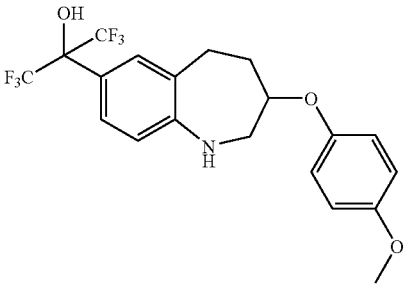

80A. 3-(4-Methoxy-phenoxy)-1,3,4,5-tetrahydro-1-benzazepin-2-one: To a solution of commercially available 3-bromo-1,3,4,5-tetrahydro-1-benzazepin-2-one (7.2 g, 30 mmol) in acetone (35 mL) were added 4-methoxyphenol (3.72 g, 30 mmol) and cesium carbonate (20.0 g, 61 mmol) and the mixture was stirred at rt overnight. The mixture was diluted with acetone (50 mL) and filtered to remove the cesium carbonate. The cesium carbonate was dissolved in water (50 mL) and washed with EtOAc (2×30 mL). The acetone and EtOAc solutions were combined and the solvent was removed in vacuo. The crude product was redissolved in EtOAc and washed with water, 1N NaOH, and brine, and then dried over anhydrous $Na_2SO_4$. The solvent was removed in vacuo to give 80A (7.78 g). LC/MS m/z 284.1 (M+H)+.

80B. 3-(4-Methoxy-phenoxy)-2,3,4,5-tetrahydro-1H-1-benzazepine: To a solution of 80A (4.93 g, 17.4 mmol) in anhydrous THF (10 mL) was added 1M $BH_3$.THF solution in THF (38 mL). After the bubbling stopped, the mixture was refluxed at 78° C. for 3 h. The mixture was cooled to rt, concentrated in vacuo, then dissolved in EtOAc and washed with 1N NaOH solution and brine, and dried over anhydrous $Na_2SO_4$. The solvent was removed in vacuo and the product was purified by flash chromatography to yield 80B as a white solid (3.86 g, 82%). LC/MS m/z 270.3 (M+H)+. $^1$H NMR (500 MHz, Methanol-$D_3$) δ 7.09 (d, 1H), 7.00 (t, 1H), 6.91 (m, 2H), 6.83 (m, 4H), 4.39 (m, 1H), 3.71 (s, 3H), 3.35 (dd, 1H), 2.93 (m, 2H), 2.66 (m, 1H), 2.11 (m, 1H), 1.74 (m, 1H).

Example 80: To a solution of 80B (2.56 g, 9.5 mmol) in $CH_2Cl_2$ (10 mL), hexafluoroacetone sesquihydrate (2.5 g, 19 mmol) and p-toluenesulfonic acid monohydrate (50 mg) were added and the reaction was heated at 138° C. in a sealed tube for 2.5 h in microwave reactor. The mixture was diluted with $CH_2Cl_2$ and a small amount of EtOAc, washed with water and brine, and dried over anhydrous $Na_2SO_4$. The solvent was removed in vacuo and the product was purified by flash chromatography to yield Example 80 (2.55 g, 62%). LC/MS m/z 433.9 (M−H)−. $^1$H NMR (500 MHz, Methanol-$D_3$) δ 7.39 (s, 1H), 7.30 (d, 1H), 6.90 (d, 2H), 6.83 (m, 3H), 4.43 (m, 1H), 3.74 (s, 3H), 3.40 (dd, 1H), 3.02 (m, 2H), 2.70 (m, 1H) 2.18 (m, 1H), 1.82 (m, 1H).

Examples 81 and 82

Example 81

(S)-1-[(S)-3-(4-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one

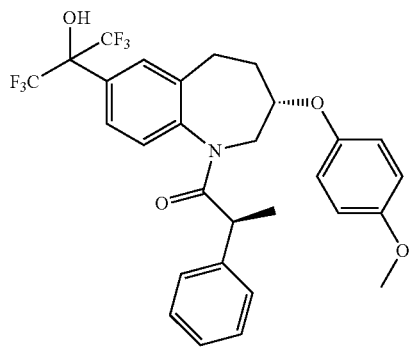

Example 82

(S)-1-[(R)-3-(4-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one

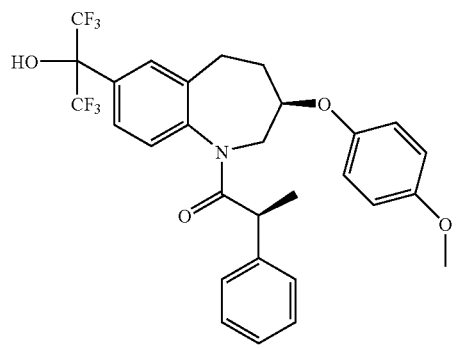

81A and 82A. (S)-2-Phenyl-propionic acid 2,2,2-trifluoro-1-[(S)-3-(4-methoxy-phenoxy)-1-((S)-2-phenyl-propionyl)-2,3,4,5-tetrahydro-1H-1-benzazepin-7-yl]-1-trifluoromethyl-ethyl ester and (S)-2-Phenyl-propionic acid 2,2,2-trifluoro-1-[(R)-3-(4-methoxy-phenoxy)-1-((S)-2-phenyl-propionyl)-2,3,4,5-tetrahydro-1H-1-benzazepin-7-yl]-1-trifluoromethyl-ethyl ester, respectively: To a solution of Example 80 (2.55 g, 5.86 mmol) were added freshly prepared (S)-2-phenylpropanoyl chloride (4.0 g, 24 mmol) in anhydrous $CH_2Cl_2$ (48 mL) and DIEA (3.09 g, 24 mmol), and the mixture was stirred in a capped vial at 40° C. overnight. The mixture was cooled to rt and washed with water, saturated sodium bicarbonate solution, and brine, then dried over anhydrous $Na_2SO_4$. The solvent was removed in vacuo, and the products were separated and purified by flash chromatography (hexanes/EtOAc) to yield 81A (1.47 g) and 82A (1.65 g). LC/MS m/z 700.1 (M+H)+.

Example 81: A solution of 81A (66 mg, 0.094 mmol) in THF (0.8 mL) was stirred with 1N LiOH solution (0.2 mL, 0.2 mmol) at rt overnight. The mixture was diluted with EtOAc and washed with water, saturated $NaHCO_3$, and brine, then dried over anhydrous $Na_2SO_4$. The solvent was evaporated to yield Example 81 (39 mg, 73%). HRMS m/z 568.1904 (M+H)+. $^1$H NMR (500 MHz, Chloroform-D) δ 7.72 (d, 1H), 7.39 (m, 2H), 7.06 (m, 5H), 6.87 (d, 2H), 6.59 (d, 2H), 4.98 (d, 1H), 4.18 (m, 1H), 3.85 (m, 1H), 3.77 (s, 3H), 2.50 (t, 1H), 2.05 (m, 2H), 1.43 (d, 3H), 1.30 (m, 2H).

Example 82: Example 82 was prepared from 82A by a similar procedure to Example 81. LC/MS m/z 568.2 (M+H)+.

Examples 83 to 100

Examples 83 to 100 in Table 7 were prepared by procedures similar to that described for Examples 81 and 82. Example 87 was prepared similarly from a chiral analogue of 80B that was separated by chiral prep-HPLC using Method C described above.

TABLE 7

| Ex. # | Name | Structure | MS (M + H)+ |
|---|---|---|---|
| 83 | (S)-1-[(S)-3-Phenoxy-7-(2,2,2-trifluoro-1-hydroxy-1-trifluoromethyl-ethyl)-2,3,4,5-tetrahydro-1-benzazepin-1-yl]-2-phenyl-propan-1-one | 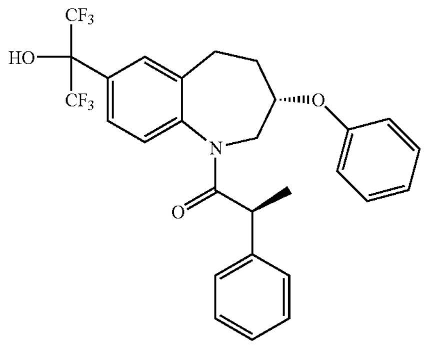 | 538.3 |
| 84 | (S)-1-[(R)-3-Phenoxy-7-(2,2,2-trifluoro-1-hydroxy-1-trifluoromethyl-ethyl)-2,3,4,5-tetrahydro-1-benzazepin-1-yl]-2-phenyl-propan-1-one | 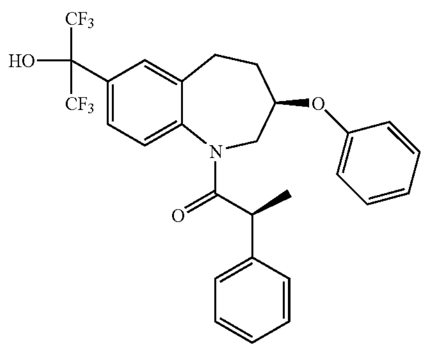 | 538.2 |
| 85 | (S)-1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 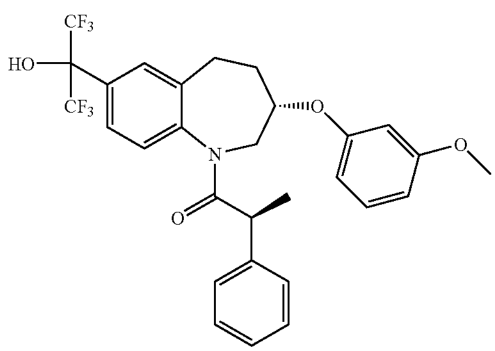 | 568.4 |
| 86 | (S)-1-[(R)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 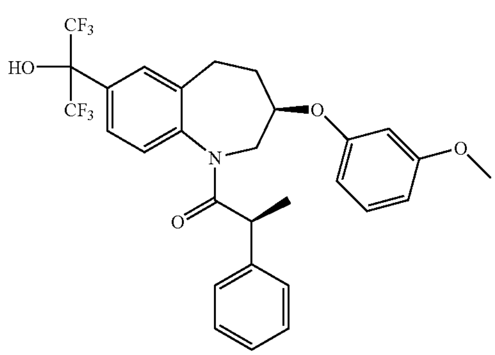 | 568.2 |

TABLE 7-continued

| Ex. # | Name | Structure | MS (M + H)+ |
|---|---|---|---|
| 87 | (S)-2-Hydroxy-1-[(S)-3-(4-methoxy-phenoxy)-7-(2,2,2-trifluoro-1-hydroxy-1-trifluoromethyl-ethyl)-2,3,4,5-tetrahydro-1-benzazepin-1-yl]-2-phenyl-ethanone | 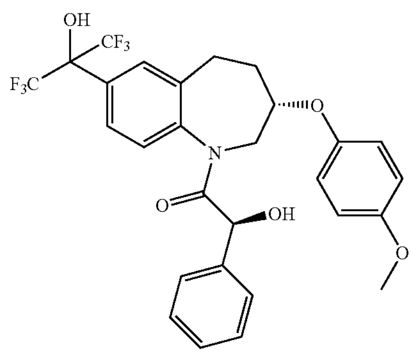 | 570.1 |
| 88 | (S)-2-Hydroxy-1-[(S)-3-phenoxy-7-(2,2,2-trifluoro-1-hydroxy-1-trifluoromethyl-ethyl)-2,3,4,5-tetrahydro-1-benzazepin-1-yl]-2-phenyl-ethanone | 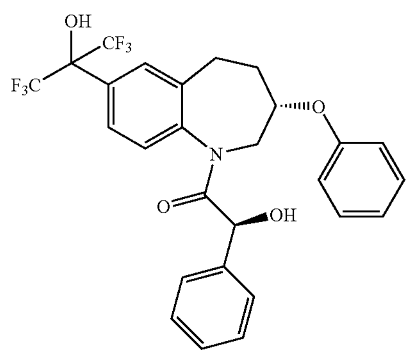 | 540.1 |
| 89 | (S)-2-Hydroxy-1-[(S)-3-(3-methoxy-phenoxy)-7-(2,2,2-trifluoro-1-hydroxy-1-trifluoromethyl-ethyl)-2,3,4,5-tetrahydro-1-benzazepin-1-yl]-2-phenyl-ethanone | 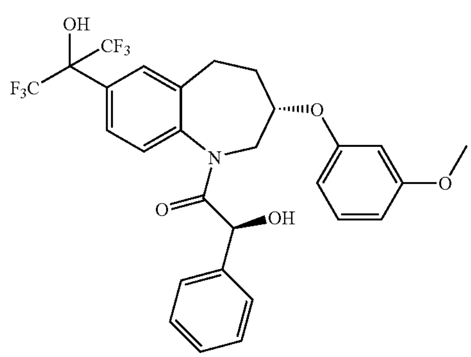 | 570.1 |
| 90 | 2-Methyl-1-[3-phenoxy-7-(2,2,2-trifluoro-1-hydroxy-1-trifluoromethyl-ethyl)-2,3,4,5-tetrahydro-1-benzazepin-1-yl]-propan-1-one | 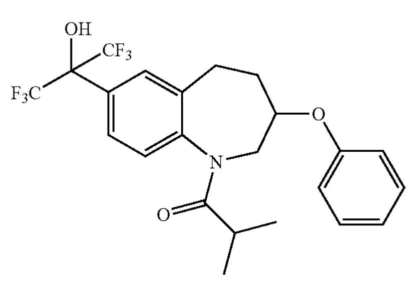 | 476.17 |

TABLE 7-continued

| Ex. # | Name | Structure | MS (M + H)+ |
|---|---|---|---|
| 91 | 1-[3-(3-Methoxy-phenoxy)-7-(2,2,2-trifluoro-1-hydroxy-1-trifluoromethyl-ethyl)-2,3,4,5-tetrahydro-1-benzazepin-1-yl]-2-methyl-propan-1-one | 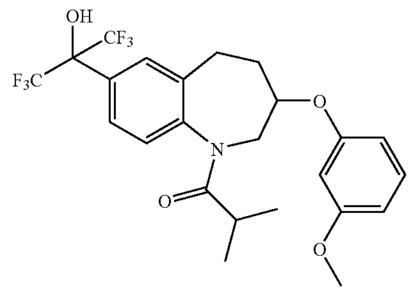 | 506.2 |
| 92 | 1-[3-(4-Methoxy-phenoxy)-7-(2,2,2-trifluoro-1-hydroxy-1-trifluoromethyl-ethyl)-2,3,4,5-tetrahydro-1-benzazepin-1-yl]-2-methyl-propan-1-one | 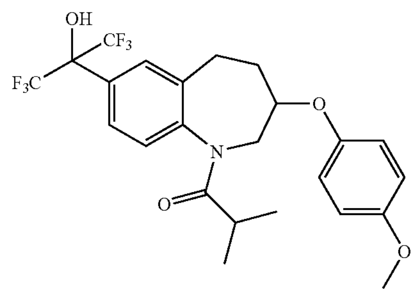 | 506.2 |
| 93 | 2-Methyl-1-[(R)-3-phenoxy-7-(2,2,2-trifluoro-1-hydroxy-1-trifluoromethyl-ethyl)-2,3,4,5-tetrahydro-1-benzazepin-1-yl]-propan-1-one | 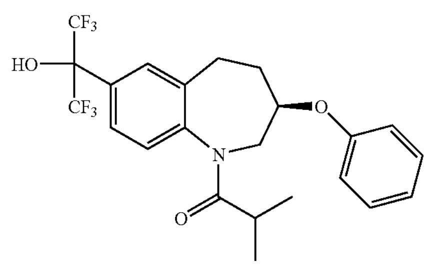 | 476.0 |
| 94 | 2-Methyl-1-[(S)-3-phenoxy-7-(2,2,2-trifluoro-1-hydroxy-1-trifluoromethyl-ethyl)-2,3,4,5-tetrahydro-1-benzazepin-1-yl]-propan-1-one | 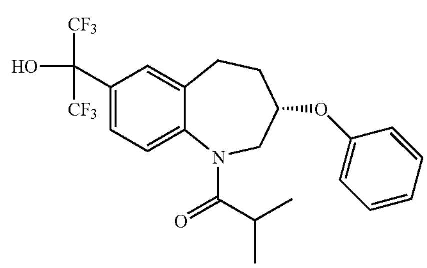 | 476.0 |
| 95 | 1-[(R)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-methyl-propan-1-one | 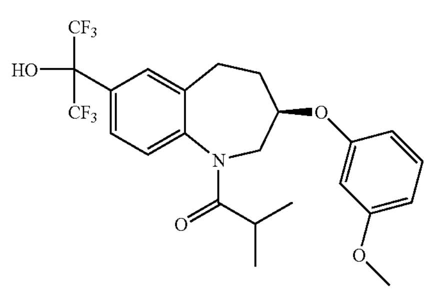 | 506.1 |

TABLE 7-continued

| Ex. # | Name | Structure | MS (M + H)+ |
|---|---|---|---|
| 96 | 1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-methyl-propan-1-one | 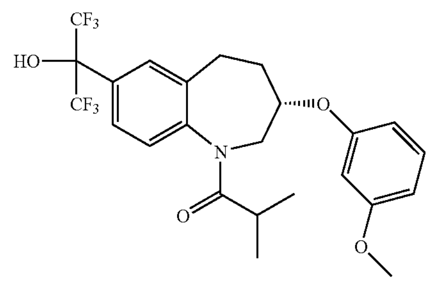 | 506.1 |
| 97 | (R)-1-[(R)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 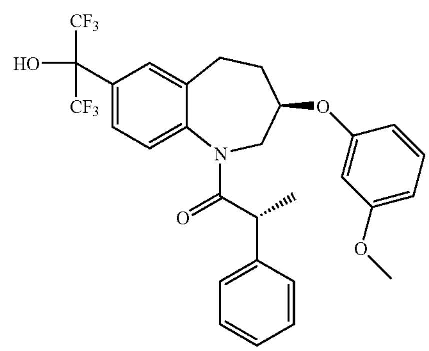 | 568.2 |
| 98 | (R)-1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 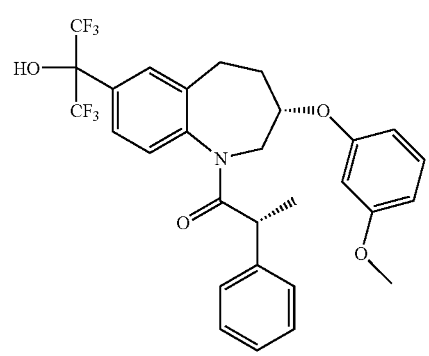 | 568.2 |
| 99 | (R)-1-[(R)-3-Phenoxy-7-(2,2,2-trifluoro-1-hydroxy-1-trifluoromethyl-ethyl)-2,3,4,5-tetrahydro-1-benzazepin-1-yl]-2-phenyl-propan-1-one | 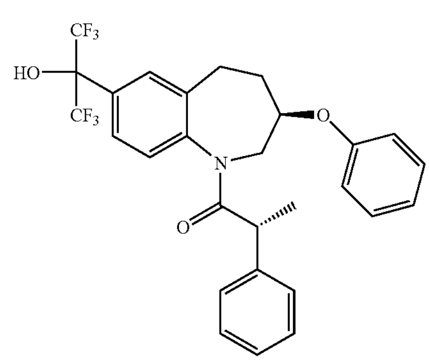 | 538.2 |

TABLE 7-continued

| Ex. # | Name | Structure | MS (M + H)+ |
|---|---|---|---|
| 100 | (R)-1-[(S)-3-Phenoxy-7-(2,2,2-trifluoro-1-hydroxy-1-trifluoromethyl-ethyl)-2,3,4,5-tetrahydro-1-benzazepin-1-yl]-2-phenyl-propan-1-one | 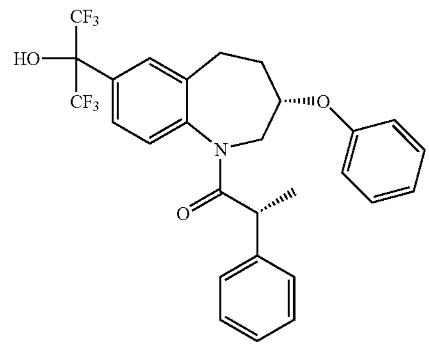 | 538.2 |

Example 101

(S)-1-[(S)-3-(3-Chloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one

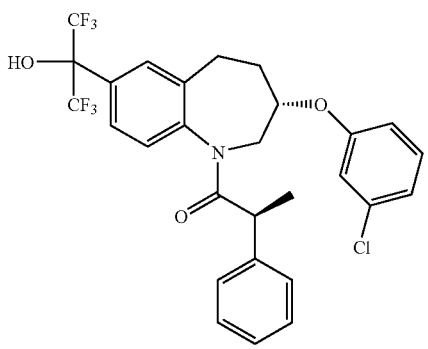

101A. (S)-2-Phenyl-propionic acid 2,2,2-trifluoro-1-[(R)-3-hydroxy-1-((S)-2-phenyl-propionyl)-2,3,4,5-tetrahydro-1H-1-benzazepin-7-yl]-1-trifluoromethyl-ethyl ester: To a solution of 82A (850 mg, 1.22 mmol) in 4:1 acetonitrile/water (15 mL) was added ammonium cerium(IV) nitrate (1.9 g, 3.46 mmol) in portions. The mixture was stirred at 0° C. for 20 min, then concentrated in vacuo. The mixture was dissolved in EtOAc and washed with water and brine, then dried over anhydrous $Na_2SO_4$. The solvent was removed in vacuo and the desired product was purified by flash chromatography to yield 101A (600 mg, 83%) as a brown oil. LC/MS m/z 594.0 (M+H)+.

Example 101: To a solution of 101A (40 mg, 0.067 mmol) and 3-chlorophenol (17.5 mg, 0.135 mmol) in anhydrous $CH_2Cl_2$ (0.5 mL) at 0° C. was added a solution of triphenylphosphine (35 mg, 0.133 mmol) in anhydrous $CH_2Cl_2$ (0.5 mL) dropwise under an argon atmosphere. To the mixture was added 40% diethyl azodicarboxylate solution in toluene (31 µL, 0.067 mmol) dropwise. The mixture was stirred at rt for 2 h, then additional 40% diethyl azodicarboxylate solution in toluene (15 uL, 0.033 mmol) was added dropwise and the mixture was stirred at rt overnight. The solvent was removed under vacuum and the product was purified by prep-HPLC to yield (S)-2-phenyl-propionic acid 1-[(S)-3-(3-chloro-phenoxy)-1-((S)-2-phenyl-propionyl)-2,3,4,5-tetrahydro-1H-1-benzazepin-7-yl]-2,2,2-trifluoro-1-trifluoromethyl-ethyl ester. This intermediate was dissolved in THF (0.5 mL) and stirred with 2N LiOH solution (0.5 mL) at rt for 2 h. The solvent was removed under vacuum. The residue was dissolved in EtOAc and washed water, saturated sodium bicarbonate, and brine, then dried over anhydrous $Na_2SO_4$. The solvent was removed under vacuum to yield Example 101 (4.5 mg, 12%) as a white solid. HRMS m/z 572.1431 (M+H)+. $^1$H NMR (500 MHz, Chloroform-D) δ 7.64 (d, 1H), 7.34 (d, 1H), 7.30 (s, 1H), 7.20 (m, 1H), 7.11 (dd, 1H), 7.03 (m, 1H), 6.98 (m, 3H), 6.89 (d, 1H), 6.54 (d, 2H), 4.88 (d, 1H), 4.21 (m, 1H), 3.78 (m, 1H), 2.45 (t, 1H), 2.05 (m, 1H), 1.98 (m, 1H), 1.39 (d, 3H), 1.30 (m, 2H).

Examples 102 to 106

Examples 102 to 106 in Table 8 were prepared by procedures similar to that described for Example 101.

TABLE 8

| Ex. # | Name | Structure | MS (M + H)+ |
|---|---|---|---|
| 102 | (S)-1-[(S)-3-(2-Chloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 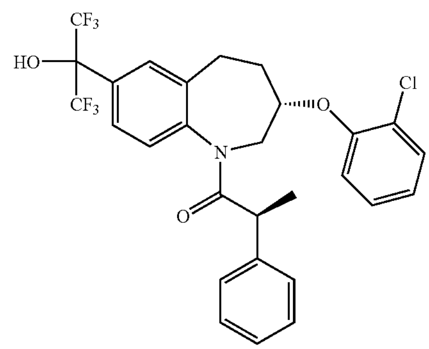 | 572.1 |
| 103 | (S)-2-Phenyl-1-[(S)-7-(2,2,2-trifluoro-1-hydroxy-1-trifluoromethyl-ethyl)-3-(2-trifluoromethyl-phenoxy)-2,3,4,5-tetrahydro-1-benzazepin-1-yl]-propan-1-one | 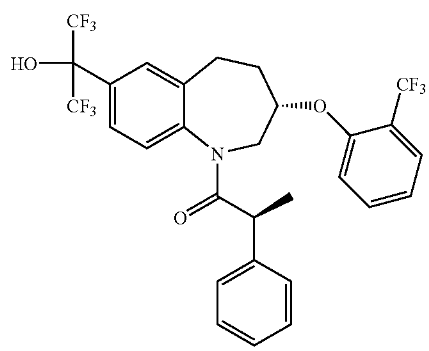 | 606.2 |
| 104 | (S)-1-[(S)-3-(4-Chloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 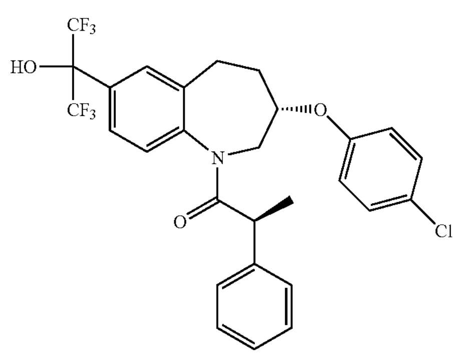 | 572.1 |
| 105 | (S)-2-Phenyl-1-[(S)-7-(2,2,2-trifluoro-1-hydroxy-1-trifluoromethyl-ethyl)-3-(3-trifluoromethyl-phenoxy)-2,3,4,5-tetrahydro-1-benzazepin-1-yl]-propan-1-one | 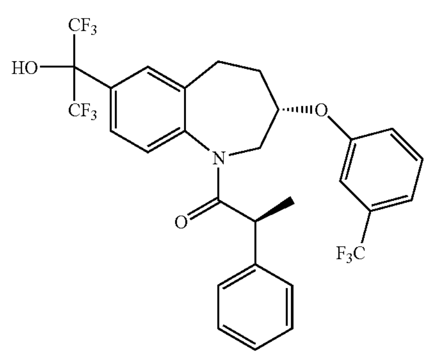 | 606.2 |

TABLE 8-continued

| Ex. # | Name | Structure | MS (M + H)+ |
|---|---|---|---|
| 106 | (S)-2-Phenyl-1-[(S)-7-(2,2,2-trifluoro-1-hydroxy-1-trifluoromethyl-ethyl)-3-(4-trifluoromethyl-phenoxy)-2,3,4,5-tetrahydro-1-benzazepin-1-yl]-propan-1-one | 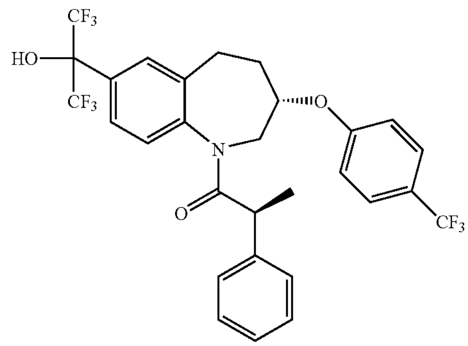 | 606.2 |

Examples 107 to 110

Examples 107 and 108 in Table 9 were prepared by procedures similar to that described for Example 101, with the final hydrolysis step carried out using NaOH/MeOH instead of LiOH/THF. Examples 109 and 110 in Table 9 were prepared procedures similar to that described for Example 107 except the products were treated with 30% TFA in dichloromethane for 0.5 h to obtain the title compounds.

TABLE 9

| Ex. # | Name | Structure | MS (M + H)+ |
|---|---|---|---|
| 107 | (S)-2-Phenyl-1-[(S)-7-(2,2,2-trifluoro-1-hydroxy-1-trifluoromethyl-ethyl)-3-(2-trifluoromethyl-pyrimidin-4-yloxy)-2,3,4,5-tetrahydro-1-benzazepin-1-yl]-propan-1-one | 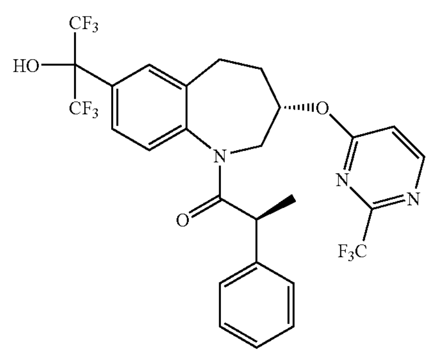 | 605.9 (M − H)− |
| 108 | (S)-2-Phenyl-1-[(S)-7-(2,2,2-trifluoro-1-hydroxy-1-trifluoromethyl-ethyl)-3-(6-trifluoromethyl-pyrimidin-4-yloxy)-2,3,4,5-tetrahydro-1-benzazepin-1-yl]-propan-1-one | 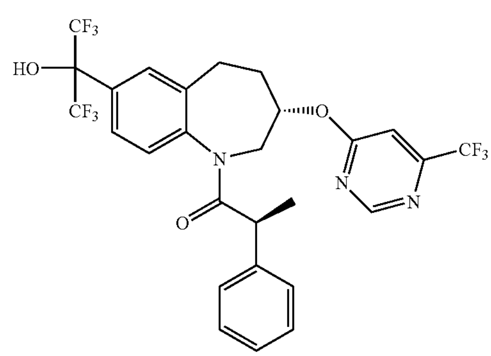 | 606.0 (M − H)− |

TABLE 9-continued

| Ex. # | Name | Structure | MS (M + H)+ |
|---|---|---|---|
| 109 | (S)-2-Amino-3-{4-[(S)-1-((S)-2-phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-propionic acid | 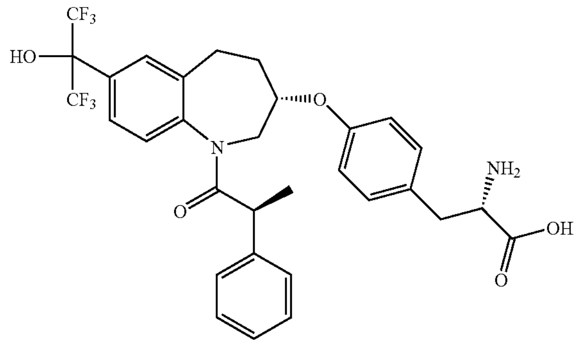 | 625.0 |
| 110 | (R)-2-Amino-3-{4-[(S)-1-((S)-2-phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-propionic acid | 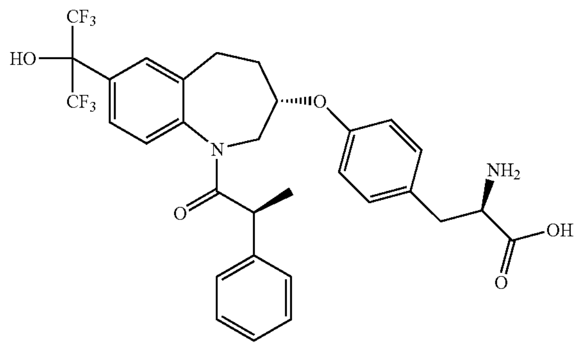 | 625.0 |

Example 111

{3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-acetic acid methyl ester

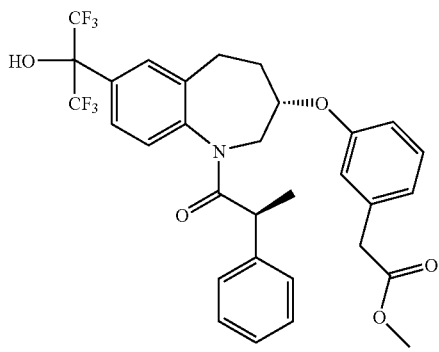

111A. {3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-acetic acid: To a solution of 101A (50 mg, 0.084 mmol) and methyl-3-hydroxyphenylacetate (21 mg, 0.126 mmol) in anhydrous toluene (0.4 mL) at 0° C. was added a solution of triphenylphosphine (33 mg, 0.126 mmol) in anhydrous toluene (0.85 mL) under argon atmosphere. To this mixture was added 40% diethyl azodicarboxylate solution in toluene (45 µL, 0.1 mmol) dropwise and the mixture was stirred at rt overnight. Additional 40% diethyl azodicarboxylate solution in toluene (15 µL, 0.033 mmol) was added dropwise and the reaction was stirred at rt for 2.5 h. The solvent was removed under vacuum and the product was purified by prep-HPLC to yield (S)-2-phenyl-propionic acid 2,2,2-trifluoro-1-[(S)-3-(3-methoxycarbonyl-methyl-phenoxy)-1-((S)-2-phenyl-propionyl)-2,3,4,5-tetrahydro-1H-1-benzazepin-7-yl]-1-trifluoromethyl-ethyl ester (23 mg, 37%). To a solution of this intermediate (23 mg, 0.03 mmol) in THF (0.8 mL) was added 1N LiOH solution (0.2 mL). The mixture was stirred at rt overnight, then diluted with EtOAc, washed with water, and dried over anhydrous Na$_2$SO$_4$. The solvent was removed in vacuo to yield 111A (5.4 mg, 30%). LC/MS m/z 596.17 (M+H)+. $^1$H NMR (500 MHz, Acetonitrile-D$_3$) δ 7.68 (d, 1H), 7.53 (d, 1H), 7.34 (s, 1H), 7.28 (t, 1H), 7.15 (m, 1H), 7.09 (d, 1H), 7.04 (t, 2H), 6.93 (s, 1H), 6.88 (d, 1H), 6.60 (d, 2H), 4.83 (dd, 1H), 4.26 (m, 1H), 3.90 (m, 1H), 3.58 (s, 2H), 2.48 (t, 1H), 2.19 (m, 1H), 2.02 (m, 1H), 1.35 (d, 3H), 1.30 (m, 2H).

Example 111: The aqueous layer of the above reaction that contained 111A was dried in a SpeedVac. The resulting residue was dissolved in MeOH (1.0 mL) and insoluble material was removed by filtration. To the methanol solution was added 2N HCl in ether (0.6 mL, 1.2 mmol) and the reaction was stirred at rt for 2.5 h. The solvent was evaporated and Example 111 was purified by prep-HPLC (2.6 mg). LC/MS m/z 610.19 (M+H)+. $^1$H NMR (500 MHz, Chloroform-D) δ 7.69 (d, 1H), 7.39 (d, 1H), 7.35 (s, 1H), 7.30 (t, 1H), 7.17 (dd, 1H),7.09 (d, 1H), 7.03 (t, 2H), 6.91 (s, 1H), 6.86 (d, 1H), 6.59 (d, 2H), 4.96 (dd, 1H), 4.26 (m, 1H), 3.83 (m, 1H), 3.69 (s, 3H), 3.61 (s, 2H), 2.50 (t, 1H), 2.12 (m, 1H), 2.09 (m, 1H), 1.42 (d, 3H), 1.31 (m, 2H).

Example 112

3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid ethyl ester

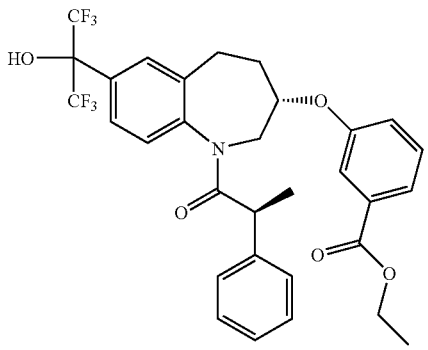

To a solution of 3-{(S)-1-((S)-2-phenyl-propionyl)-7-[2,2,2-trifluoro-1-((S)-2-phenyl-propionyloxy)-1-trifluoromethyl-ethyl]-2,3,4,5-tetrahydro-1H-1-benzazepin-3-yloxy}-benzoic acid ethyl ester (30 mg, 0.04 mmol), which was prepared by a similar procedure as that used to prepare (S)-2-phenyl-propionic acid 2,2,2-trifluoro-1-[(S)-3-(3-methoxycarbonylmethyl-phenoxy)-1-((S)-2-phenyl-propionyl)-2,3,4,5-tetrahydro-1H-1-benzazepin-7-yl]-1-trifluoromethyl-ethyl ester (intermediate in preparation of 101A), in MeOH (1 mL) was added 1N NaOH solution (0.05 mL) and the mixture was stirred at rt for 2.5 h. Another 0.05 mL of 1N NaOH was added and the reaction was stirred for 4 h. The mixture was neutralized with 1N HCl and the solvent was evaporated. The product was purified by prep-HPLC to yield Example 112 (16 mg, 66%) as well as Example 113 as a by-product (see Table 10 below). Example 112: LC/MS m/z 610.2 (M+H)$^+$. $^1$H NMR (500 MHz, Chloroform-D) δ 7.70 (d, 1H), 7.69 (s, 1H), 7.62 (d, 1H), 7.39 (m, 3H), 7.36 (s, 1H), 7.09 (m, 1H), 7.03 (t, 2H), 6.59 (d, 2H), 4.96 (dd, 1H), 4.36 (m, 3H), 3.84 (m, 1H), 2.53 (t, 1H), 2.12 (m, 1H), 2.09 (m, 1H), 1.42 (m, 6H), 1.31 (m, 2H).

Examples 114 to 125

Examples 114 to 125 in Table 10 were prepared by procedures similar to that described for Example 112.

TABLE 10

| Ex. # | Name | Structure | MS (M + H)$^+$ |
|---|---|---|---|
| 113 | 3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid methyl ester | 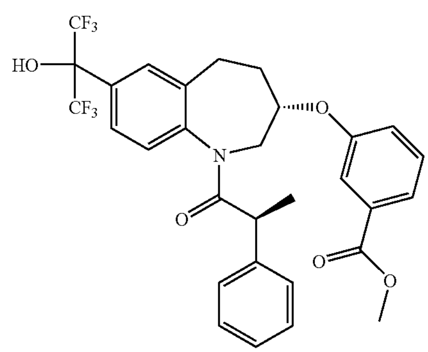 | 596.0 |
| 114 | 4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid methyl ester | 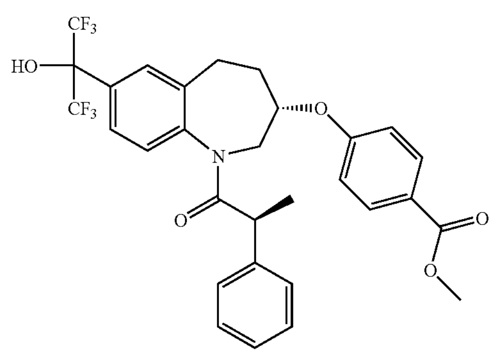 | 596.0 |

TABLE 10-continued

| Ex. # | Name | Structure | MS (M + H)+ |
|---|---|---|---|
| 115 | 4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid ethyl ester | 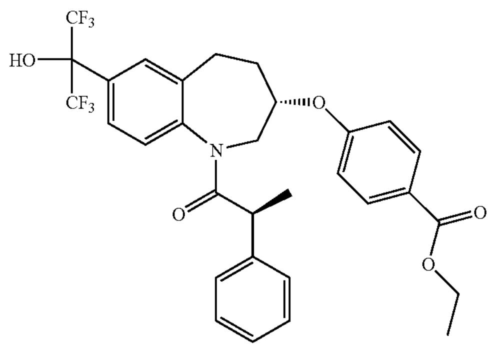 | 610.0 |
| 116 | (S)-1-[(S)-3-[4-(2-Methoxy-acetyl)-phenoxy]-7-(2,2,2-trifluoro-1-hydroxy-1-trifluoromethyl-ethyl)-2,3,4,5-tetrahydro-1-benzazepin-1-yl]-2-phenyl-propan-1-one | 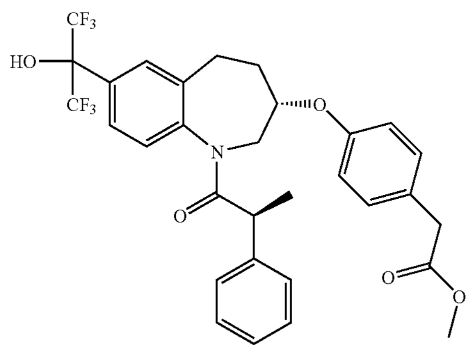 | 610.0 |
| 117 | 3-{4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-propionic acid methyl ester | 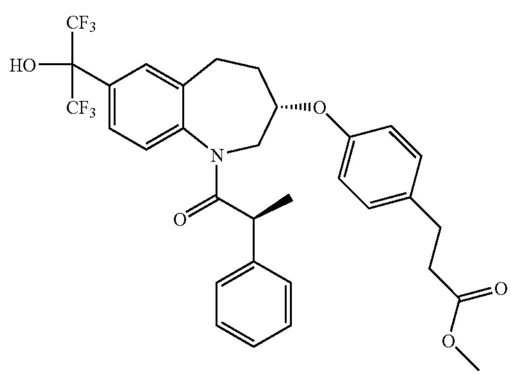 | 624.0 |
| 118 | {4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-acetic acid | 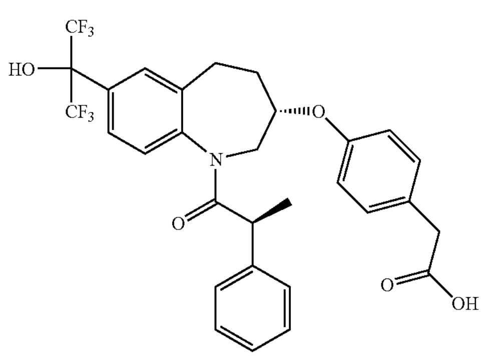 | 596.2 |

TABLE 10-continued

| Ex. # | Name | Structure | MS (M + H)+ |
|---|---|---|---|
| 119 | 3-{4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-propionic acid | 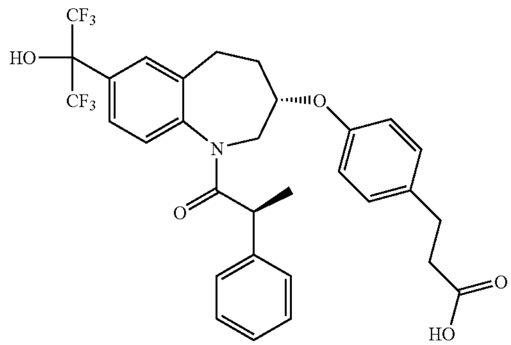 | 610.2 |
| 120 | 4-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid | 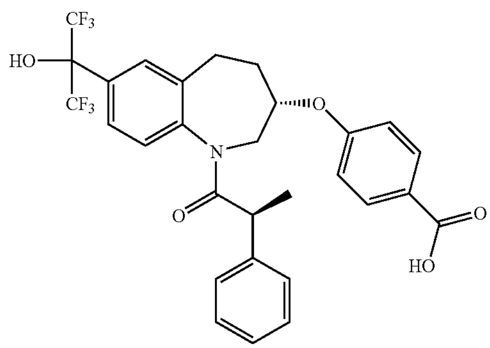 | 582.0 |
| 121 | 3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-benzoic acid | 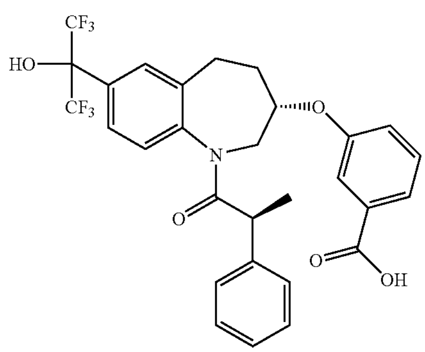 | 582.0 |
| 122 | (S)-1-[(S)-3-(4-Imidazol-1-yl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 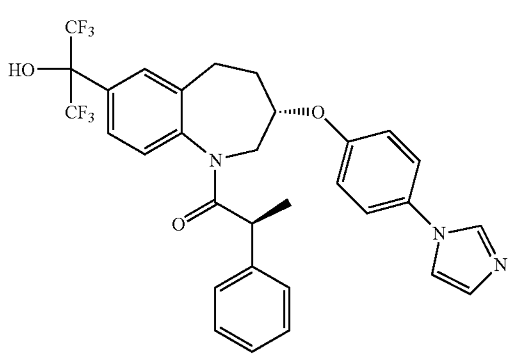 | 604.1 |

TABLE 10-continued

| Ex. # | Name | Structure | MS (M + H)+ |
|---|---|---|---|
| 123 | (S)-1-[(S)-3-(2-Methyl-5-trifluoromethyl-2H-pyrazol-3-yloxy)-7-(2,2,2-trifluoro-1-hydroxy-1-trifluoromethyl-ethyl)-2,3,4,5-tetrahydro-1-benzazepin-1-yl]-2-phenyl-propan-1-one | 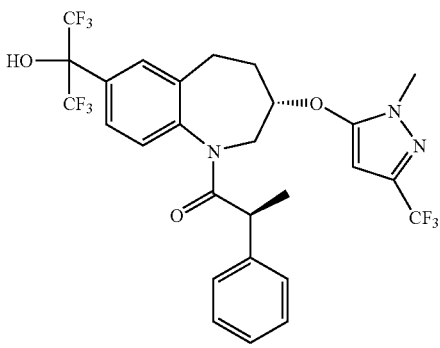 | 610.0 |
| 124 | (S)-1-[(S)-3-(3,5-Dimethoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 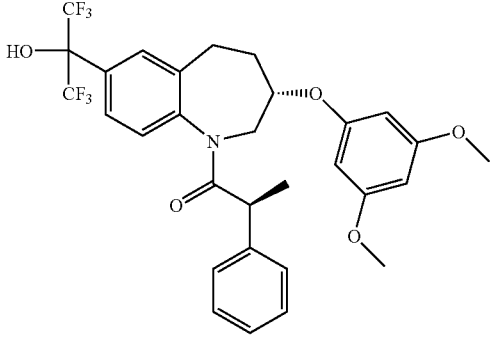 | 598.0 |
| 125 | (S)-1-[(S)-3-(2-Chloro-5-methoxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 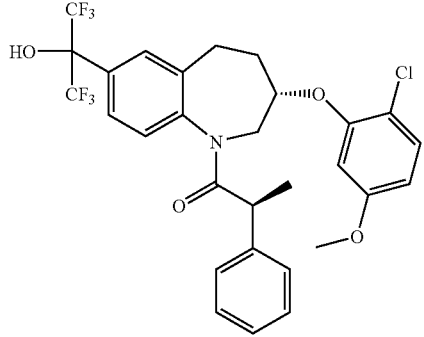 | 602.0 |

Example 126

(S)-1-[(S)-3-Hydroxy-7-(2,2,2-trifluoro-1-hydroxy-1-trifluoromethyl-ethyl)-2,3,4,5-tetrahydro-1-benzazepin-1-yl]-2-phenyl-propan-1-one

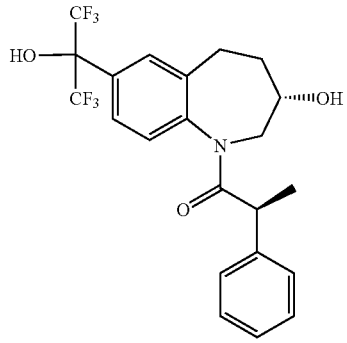

To a solution of (S)-2-phenyl-propionic acid 2,2,2-trifluoro-1-[(S)-3-hydroxy-1-((S)-2-phenyl-propionyl)-2,3,4,5-tetrahydro-1H-1-benzazepin-7-yl]-1-trifluoromethyl-ethyl ester (15.0 mg, 0.025 mmol), which was prepared from Example 81 by a similar procedure as that used to prepare 101A, in MeOH (0.5 mL) was added 1N NaOH (0.05 mL, 0.05 mmol) and the mixture was stirred at rt for 5 h. The solvent was removed in vacuo and the residue was dissolved in THF and neutralized with 1N HCl. Volatiles were removed under vacuum and the product was purified by prep-HPLC. The fraction containing the title compound was neutralized with 1N NaOH and evaporated. The residue was dissolved in EtOAc, washed with water, and dried over anhydrous Na$_2$SO$_4$. The solvent was removed under vacuum to give Example 126. LC/MS m/z 462.2 (M+H)$^+$. $^1$H NMR (500 MHz, Methanol) δ 7.74 (d, 1H), 7.49 (d, 1H), 7.38 (s, 1H), 7.10 (m, 1H), 7.03 (m, 2H), 6.55 (d, 2H), 4.70 (dd, 1H), 3.91 (m, 1H), 3.59 (m, 1H), 2.36 (t, 1H), 2.07 (m, 1H), 1.89 (m, 1H), 1.35 (d, 3H), 1.31 (m, 1H), 1.12 (m, 1H).

Example 127

(S)-1-[(R)-3-Hydroxy-7-(2,2,2-trifluoro-1-hydroxy-1-trifluoromethyl-ethyl)-2,3,4,5-tetrahydro-1-benzazepin-1-yl]-2-phenyl-propan-1-one

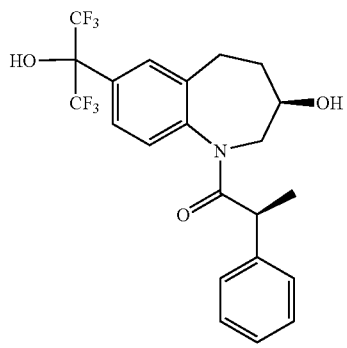

127A. 4-Nitro-benzoic acid (R)-1-((S)-2-phenyl-propionyl)-7-[2,2,2-trifluoro-1-((S)-2-phenyl-propionyloxy)-1-trifluoromethyl-ethyl]-2,3,4,5-tetrahydro-1H-1-benzazepin-3-yl ester: To a solution of (S)-2-phenyl-propionic acid 2,2,2-trifluoro-1-[(S)-3-hydroxy-1-((S)-2-phenyl-propionyl)-2,3,4,5-tetrahydro-1H-1-benzazepin-7-yl]-1-trifluoromethyl-ethyl ester (15.0 mg, 0.025 mmol), which was prepared from Example 81 by a similar procedure as that used to prepare 101A, (1.64 g, 2.76 mmol) and 4-nitrobenzoic acid (693 mg, 4.1 mmol) in anhydrous toluene (25 mL) at 0° C. was added a solution of triphenylphosphine (1.07 g, 4.1 mmol) in anhydrous toluene (25 mL) under an argon atmosphere. To this mixture was added 40% diethyl azodicarboxylate solution in toluene (1.9 mL, 4.1 mmol) dropwise and the mixture was stirred at rt overnight. The solvent was removed in vacuo and the product was purified by flash chromatography to yield 127A as a white solid (1.55 g, 75%).

Example 127: To a solution of 127A (1.47 g, 1.98 mmol) in MeOH (46 mL) was added 1N NaOH (4.6 mL, 4.6 mmol) and the mixture was stirred at rt for 1.5 h. The solvent was removed in vacuo. The mixture was dissolved in EtOAc and washed with water and brine, then dried over anhydrous Na$_2$SO$_4$. The solvent was removed in vacuo and the residue was purified by flash chromatography to yield Example 127 as a clear oil (0.72 g, 78%). LC/MS m/z 462.2 (M+H)$^+$. $^1$H NMR (500 MHz, Chloroform) δ 7.68 (d, 1H), 7.36 (d, 1H), 7.33 (s, 1H), 7.07 (m, 1H), 7.03 (t, 2H), 6.61 (d, 2H), 4.94 (d, 1H), 4.19 (m, 1H), 4.12 (m, 1H), 3.89 (m, 1H), 2.82 (d, 1H), 2.18 (t, 1H), 1.83 (m, 2H), 1.40 (d, 3H).

Example 128

(S)-1-[(S)-3-(3,5-Dichloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one

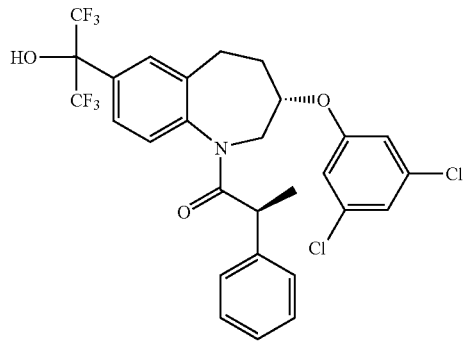

To a solution of Example 127 (36 mg, 0.078 mmol) and 3,5-dichlorophenol (18.5 mg, 0.114 mmol) in anhydrous toluene (0.4 mL) at 0° C. was added a solution of triphenylphosphine (30 mg, 0.114 mmol) in anhydrous toluene (0.35 mL) under an argon atmosphere. To this mixture was added 40% diethyl azodicarboxylate solution in toluene (41 uL, 0.09 mmol) and the mixture was stirred at 0° C. for 15 min, then at rt for 3 h. Another 10 μL (0.02 mmol) of 40% diethyl azodicarboxylate solution in toluene was added and the mixture was stirred at rt for 2 d. The solvent was removed in vacuo and the crude product was purified by prep-HPLC to yield Example 128 (13.8 mg, 29%). LC/MS m/z 606.2 (M+H)$^+$. $^1$H NMR (500 MHz, Methanol) δ 7.77 (d, 1H), 7.55 (d, 1H), 7.42 (s, 1H), 7.16 (s, 2H), 7.12 (m, 1H), 7.05 (t, 2H), 7.02 (s, 1H), 6.62 (d, 2H), 4.85 (d, 1H), 4.27 (m, 1H), 3.96 (m, 1H), 2.57 (t, 1H), 2.19 (m, 1H), 2.08 (m, 1H), 1.41 (m, 2H), 1.40 (d, 3H).

Examples 129 to 140

Examples 129 to 140 in Table 11 were prepared by procedures similar to that described for Example 128.

TABLE 11

| Ex. # | Name | Structure | MS (M + H)+ |
|---|---|---|---|
| 129 | (S)-1-[(S)-3-(2,3-Dichlorophenoxy)-7-(2,2,2-trifluoro-1-hydroxy-1-trifluoromethylethyl)-2,3,4,5-tetrahydro-1-benzazepin-1-yl]-2-phenyl-propan-1-one | 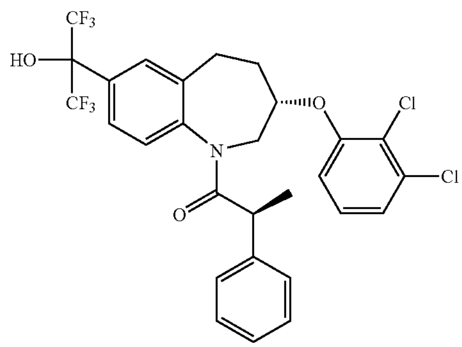 | 606.1 |
| 130 | (S)-1-[(S)-3-(2,4-Dichlorophenoxy)-7-(2,2,2-trifluoro-1-hydroxy-1-trifluoromethylethyl)-2,3,4,5-tetrahydro-1-benzazepin-1-yl]-2-phenyl-propan-1-one | 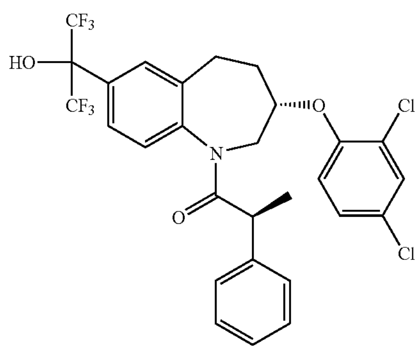 | 606.2 |
| 131 | (S)-1-[(S)-3-(2,5-Dichlorophenoxy)-7-(2,2,2-trifluoro-1-hydroxy-1-trifluoromethylethyl)-2,3,4,5-tetrahydro-1-benzazepin-1-yl]-2-phenyl-propan-1-one | 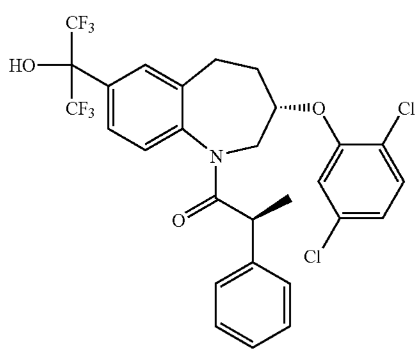 | 606.1 |
| 132 | (S)-1-[(S)-3-(2,6-Dichlorophenoxy)-7-(2,2,2-trifluoro-1-hydroxy-1-trifluoromethylethyl)-2,3,4,5-tetrahydro-1-benzazepin-1-yl]-2-phenyl-propan-1-one | 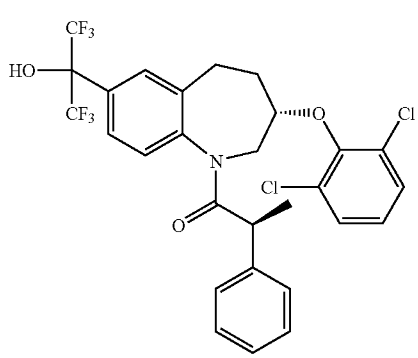 | 606.1 |

TABLE 11-continued

| Ex. # | Name | Structure | MS (M + H)+ |
|---|---|---|---|
| 133 | (S)-1-[(S)-3-(2,4-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 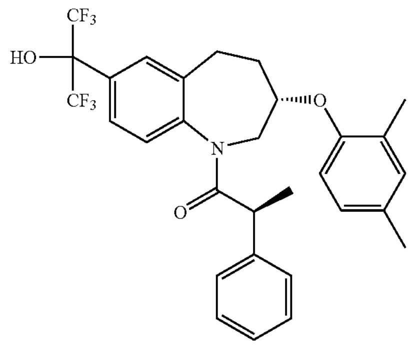 | 566.2 |
| 134 | (S)-1-[(S)-3-(2,5-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 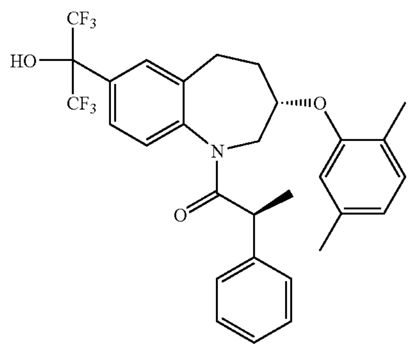 | 566.2 |
| 135 | (S)-1-[(S)-3-(2,4-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 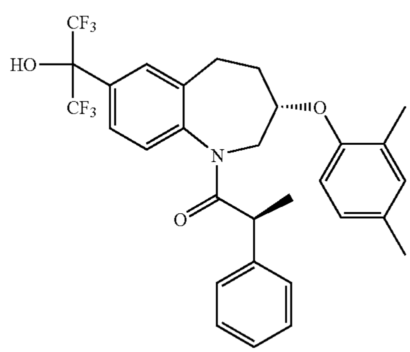 | 566.2 |
| 136 | (S)-1-[(S)-3-(3,4-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 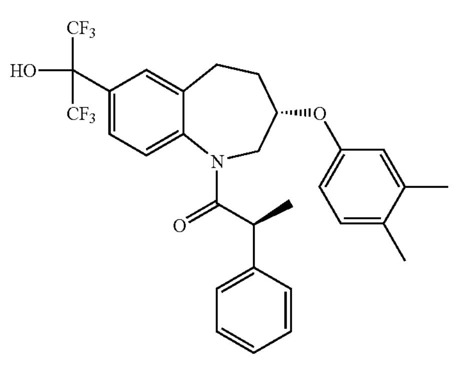 | 566.2 |

TABLE 11-continued

| Ex. # | Name | Structure | MS (M + H)+ |
|---|---|---|---|
| 137 | (S)-1-[(S)-3-(3,5-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 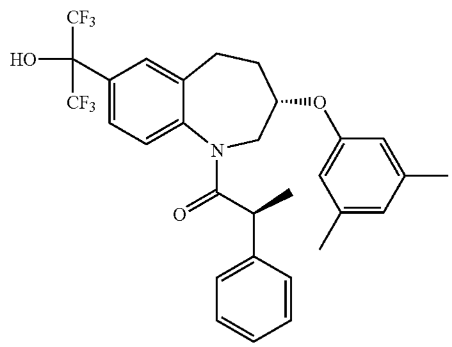 | 566.2 |
| 138 | (S)-1-[(S)-3-(3-Hydroxy-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 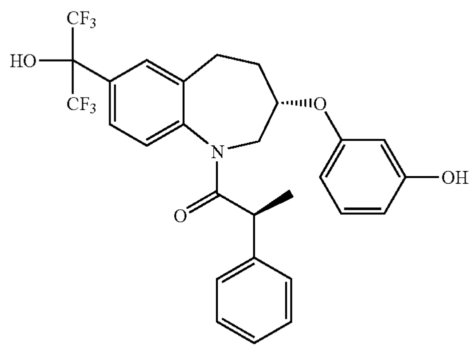 | 554.2 |
| 139 | (S)-1-[(S)-3-(2,6-Dimethyl-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 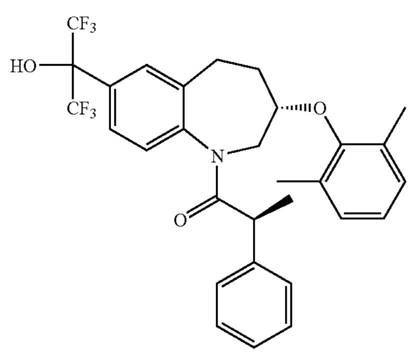 | 566.3 |
| 140 | (S)-1-[(S)-3-(3,4-Dichloro-phenoxy)-7-(2,2,2-trifluoro-1-hydroxy-1-trifluoromethyl-ethyl)-2,3,4,5-tetrahydro-1-benzazepin-1-yl]-2-phenyl-propan-1-one | 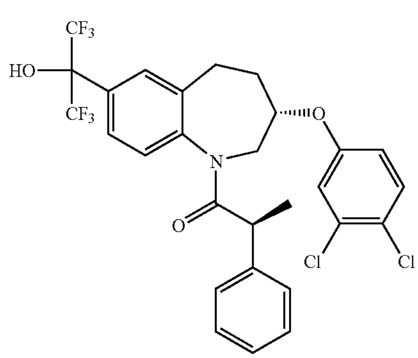 | 606.2 |

Example 141

Toluene-4-sulfonic acid (S)-1-((S)-2-phenyl-propionyl)-7-(2,2,2-trifluoro-1-hydroxy-1-trifluoromethyl-ethyl)-2,3,4,5-tetrahydro-1H-1-benzazepin-3-yl ester

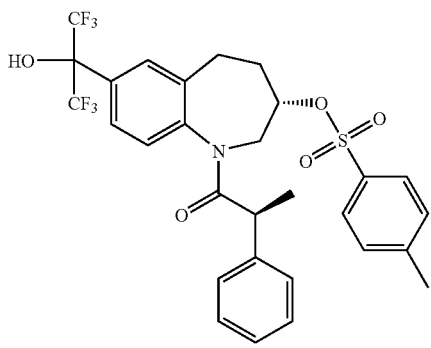

To a solution of (S)-2-phenyl-propionic acid 2,2,2-trifluoro-1-[(S)-3-hydroxy-1-((S)-2-phenyl-propionyl)-2,3,4,5-tetrahydro-1H-1-benzazepin-7-yl]-1-trifluoromethyl-ethyl ester (100 mg, 0.168 mmol), which was prepared from Example 81 by a similar procedure as that used to prepare 101A, in anhydrous DCM (0.6 mL) were added 4-methylphenylsulfonyl chloride (64 mg, 0.336 mmol) and TEA (34 mg, 0.336 mmol) and the mixture was stirred at rt overnight. Another 64 mg (0.336 mmol) of 4-methylphenylsulfonyl chloride and 50 µL of TEA were added and the mixture was stirred at 40° C. overnight. The mixture was diluted with DCM and washed with water, saturated sodium bicarbonate, and brine, then dried over anhydrous $Na_2SO_4$. The solvent was removed in vacuo and the product was purified by flash chromatography to give Example 141 as brown oil (99 mg, 79%). LC/MS m/z 748.4 $(M+H)^+$.

Example 142

Methanesulfonic acid (S)-1-((S)-2-phenyl-propionyl)-7-(2,2,2-trifluoro-1-hydroxy-1-trifluoromethyl-ethyl)-2,3,4,5-tetrahydro-1H-1-benzazepin-3-yl ester

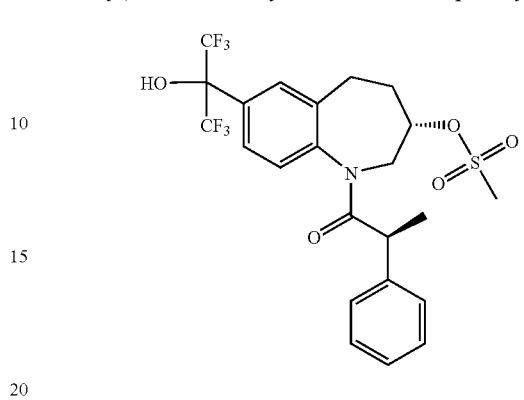

Example 142 was prepared by a procedure similar to that described for Example 141. LC/MS m/z 539.9 $(M+H)^+$.

Examples 143 to 172

Examples 143 to 172 in Table 12 were generated via a 2×22 library format: A 2 dram vial containing the corresponding carboxylic acid (0.28 mmol) was charged with a solution of diisopropylcarbodiimide (0.14 mmol) in toluene (0.5 mL). The vial was capped and allowed to stir at ambient temperature. After 30 minutes the first 22 reactions were charged with 1D (0.7 mmol) and the second 22 reactions were charged with (S)-1,1,1,3,3,3-hexafluoro-2-(3-(3-methoxyphenoxy)-2,3,4,5-tetrahydro-1H-benzo[b]azepin-7-yl)propan-2-ol (0.7 mmol) (isolated by chiral separation of 1,1,1,3,3,3-hexafluoro-2-(3-(3-methoxyphenoxy)-2,3,4,5-tetrahydro-1H-benzo[b]azepin-7-yl)propan-2-ol, which was prepared similar to Example 80). The reactions were placed in a heating block at 100° C. with stirring. After stirring for 21 h, the reactions were allowed to cool to ambient temperature and then concentrated under reduced pressure. Purification was performed via preparatory HPLC on a Shim pack ODS 20×50 mm column in 30-100% B, where B was a mixture of 90% methanol and 10% water with 0.1% TFA and A was a mixture of 10% methanol and 90% water with 0.1% TFA. The desired fractions were concentrated under reduced pressure and purity was determined by LC/MS spectroscopy.

TABLE 12

| Ex. # | Name | Structure | MS $(M+H)^+$ |
|---|---|---|---|
| 143 | 2-Pyridin-4-yl-1-[7-(2,2,2-trifluoro-1-hydroxy-1-trifluoromethyl-ethyl)-2,3,4,5-tetrahydro-1-benzazepin-1-yl]-ethanone | 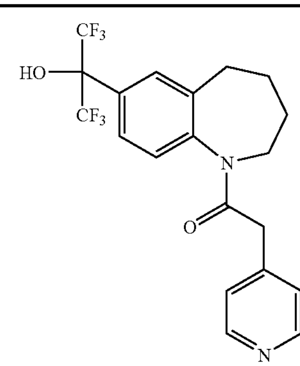 | 433.3 |

TABLE 12-continued

| Ex. # | Name | Structure | MS (M + H)+ |
|---|---|---|---|
| 144 | 2-Pyridin-2-yl-1-[7-(2,2,2-trifluoro-1-hydroxy-1-trifluoromethyl-ethyl)-2,3,4,5-tetrahydro-1-benzazepin-1-yl]-ethanone | 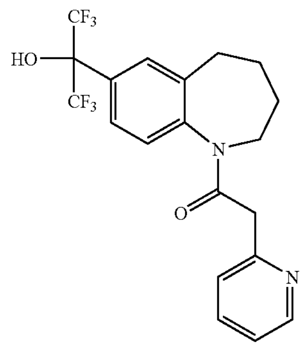 | 433.2 |
| 145 | 2-(1-Methyl-1H-imidazol-4-yl)-1-[7-(2,2,2-trifluoro-1-hydroxy-1-trifluoromethyl-ethyl)-2,3,4,5-tetrahydro-1-benzazepin-1-yl]-ethanone | 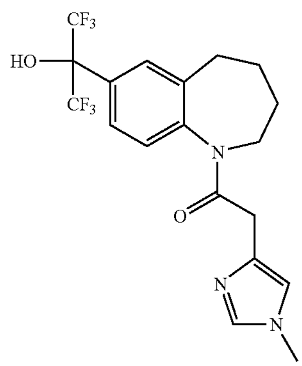 | 436.3 |
| 146 | 3-Pyridin-3-yl-1-[7-(2,2,2-trifluoro-1-hydroxy-1-trifluoromethyl-ethyl)-2,3,4,5-tetrahydro-1-benzazepin-1-yl]-propan-1-one | 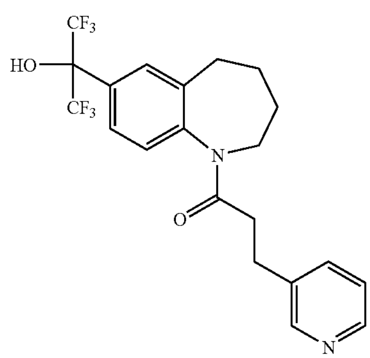 | 447.3 |
| 147 | 2-Pyridin-3-yl-1-[7-(2,2,2-trifluoro-1-hydroxy-1-trifluoromethyl-ethyl)-2,3,4,5-tetrahydro-1-benzazepin-1-yl]-ethanone | 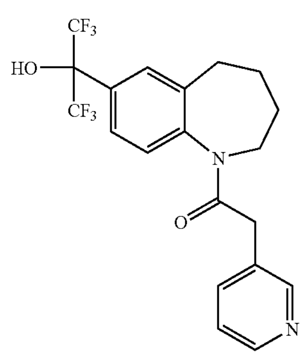 | 433.3 |

TABLE 12-continued

| Ex. # | Name | Structure | MS (M + H)+ |
|---|---|---|---|
| 148 | 2-(5-Bromo-pyridin-3-yl)-1-[7-(2,2,2-trifluoro-1-hydroxy-1-trifluoromethyl-ethyl)-2,3,4,5-tetrahydro-1-benzazepin-1-yl]-ethanone | 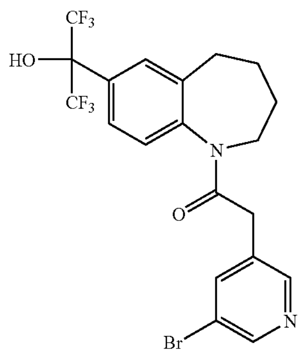 | 511.1 |
| 149 | 2-(6-Chloro-pyridin-3-yl)-1-[7-(2,2,2-trifluoro-1-hydroxy-1-trifluoromethyl-ethyl)-2,3,4,5-tetrahydro-1-benzazepin-1-yl]-ethanone | 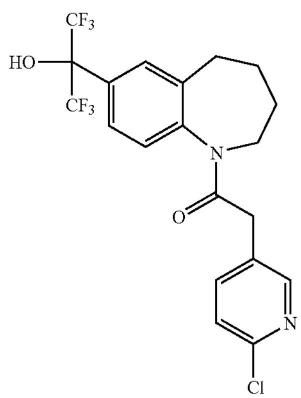 | 467.2 |
| 150 | 2-(Pyridin-4-ylsulfanyl)-1-[7-(2,2,2-trifluoro-1-hydroxy-1-trifluoromethyl-ethyl)-2,3,4,5-tetrahydro-1-benzazepin-1-yl]-ethanone | 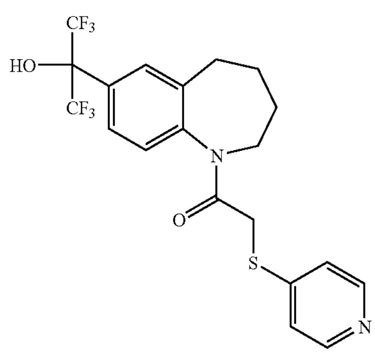 | 465.2 |
| 151 | Pyridin-3-yl-[7-(2,2,2-trifluoro-1-hydroxy-1-trifluoromethyl-ethyl)-2,3,4,5-tetrahydro-1-benzazepin-1-yl]-methanone | 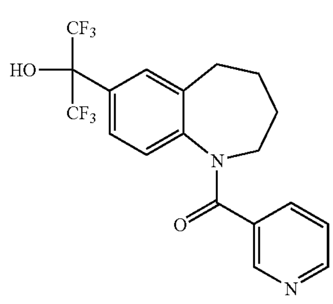 | 419.3 |

TABLE 12-continued

| Ex. # | Name | Structure | MS (M + H)⁺ |
|---|---|---|---|
| 152 | Pyridin-4-yl-[7-(2,2,2-trifluoro-1-hydroxy-1-trifluoromethyl-ethyl)-2,3,4,5-tetrahydro-1-benzazepin-1-yl]-methanone | 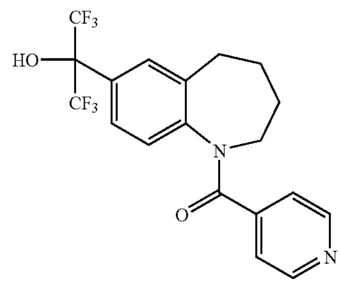 | 419.3 |
| 153 | (2-Chloro-pyridin-3-yl)-[7-(2,2,2-trifluoro-1-hydroxy-1-trifluoromethyl-ethyl)-2,3,4,5-tetrahydro-1-benzazepin-1-yl]-methanone | 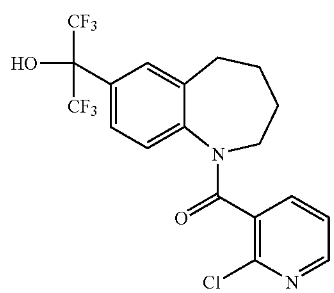 | 453.2 |
| 154 | 1-[7-(2,2,2-Trifluoro-1-hydroxy-1-trifluoromethyl-ethyl)-2,3,4,5-tetrahydro-1-benzazepin-1-yl]-2-(4-trifluoromethyl-phenyl)-ethanone | 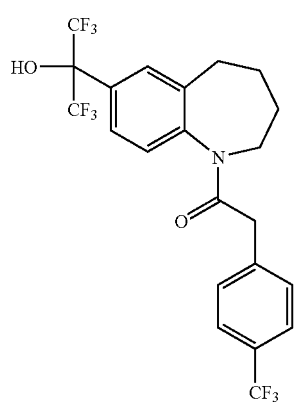 | 500.3 |
| 155 | 2-(3-Chloro-phenyl)-1-[7-(2,2,2-trifluoro-1-hydroxy-1-trifluoromethyl-ethyl)-2,3,4,5-tetrahydro-1-benzazepin-1-yl]-ethanone | 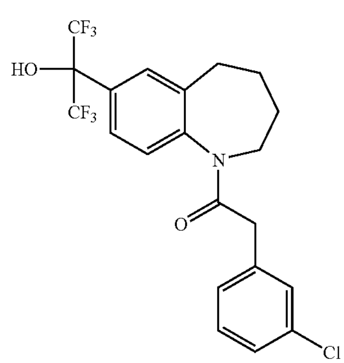 | 466.2 |

TABLE 12-continued

| Ex. # | Name | Structure | MS (M + H)+ |
|---|---|---|---|
| 156 | (3-Chloro-2,6-difluoro-phenyl)-[7-(2,2,2-trifluoro-1-hydroxy-1-trifluoromethyl-ethyl)-2,3,4,5-tetrahydro-1-benzazepin-1-yl]-methanone | 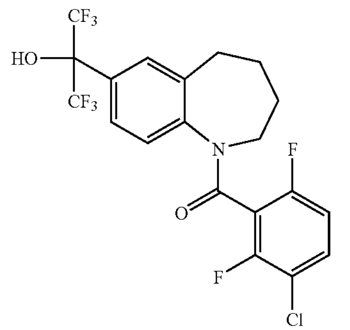 | 488.2 |
| 157 | 3-Imidazol-1-yl-1-[7-(2,2,2-trifluoro-1-hydroxy-1-trifluoromethyl-ethyl)-2,3,4,5-tetrahydro-1-benzazepin-1-yl]-propan-1-one | 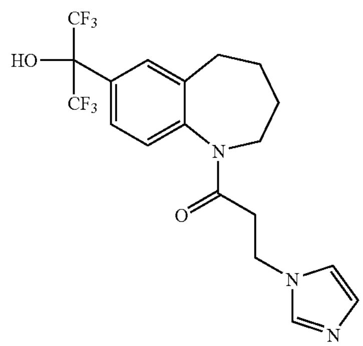 | 436.3 |
| 158 | Acetic acid (S)-2-oxo-1-phenyl-2-[7-(2,2,2-trifluoro-1-hydroxy-1-trifluoromethyl-ethyl)-2,3,4,5-tetrahydro-1-benzazepin-1-yl]-ethyl ester | 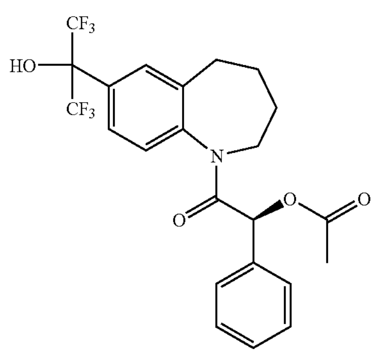 | 490.3 |
| 159 | 1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-pyridin-4-yl-ethanone | 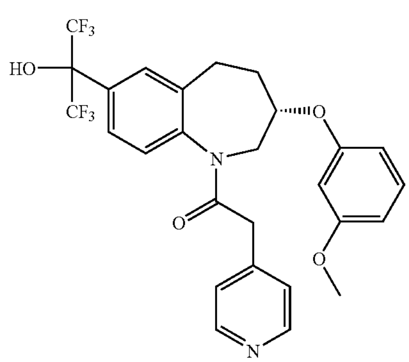 | 555.2 |

TABLE 12-continued

| Ex. # | Name | Structure | MS (M + H)+ |
|---|---|---|---|
| 160 | 1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-pyridin-2-yl-ethanone | 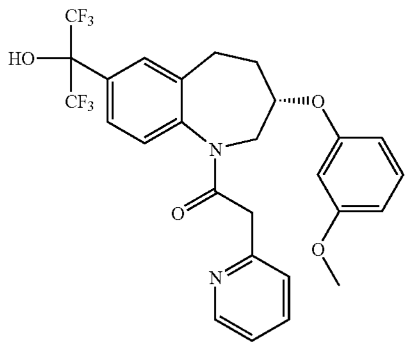 | 555.1 |
| 161 | 1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-(1-methyl-1H-imidazol-4-yl)-ethanone | 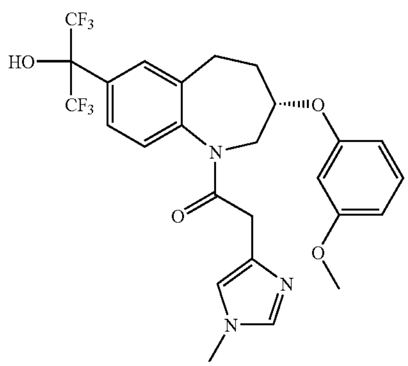 | 558.2 |
| 162 | 1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-3-pyridin-3-yl-propan-1-one | 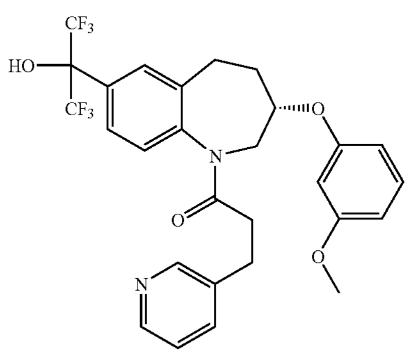 | 569.2 |
| 163 | 1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-pyridin-3-yl-ethanone | 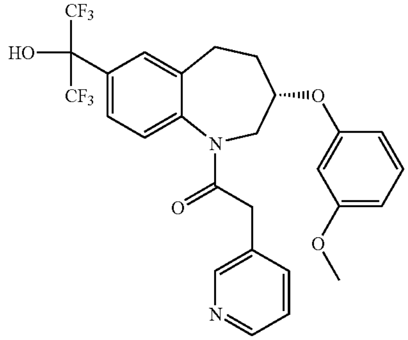 | 555.1 |

TABLE 12-continued

| Ex. # | Name | Structure | MS (M + H)+ |
|---|---|---|---|
| 164 | 2-(5-Bromo-pyridin-3-yl)-1-[(S)-3-(3-methoxy-phenoxy)-7-(2,2,2-trifluoro-1-hydroxy-1-trifluoromethyl-ethyl)-2,3,4,5-tetrahydro-1-benzazepin-1-yl]-ethanone | 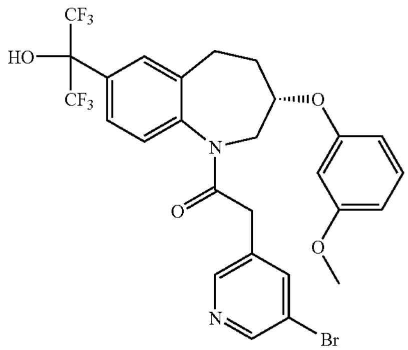 | 633.0 |
| 165 | 2-(6-Chloro-pyridin-3-yl)-1-[(S)-3-(3-methoxy-phenoxy)-7-(2,2,2-trifluoro-1-hydroxy-1-trifluoromethyl-ethyl)-2,3,4,5-tetrahydro-1-benzazepin-1-yl]-ethanone | 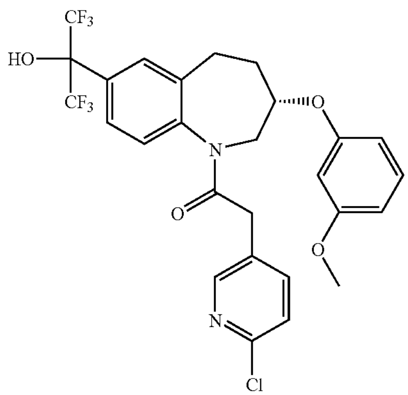 | 589.1 |
| 166 | [(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-(5-methyl-pyrazin-2-yl)-methanone | 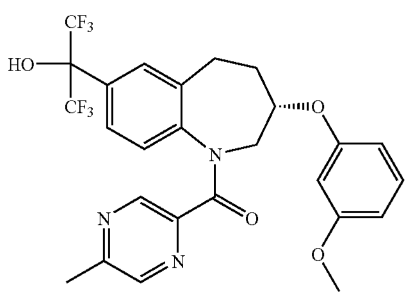 | 556.2 |
| 167 | 1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-(pyridin-4-ylsulfanyl)-ethanone | 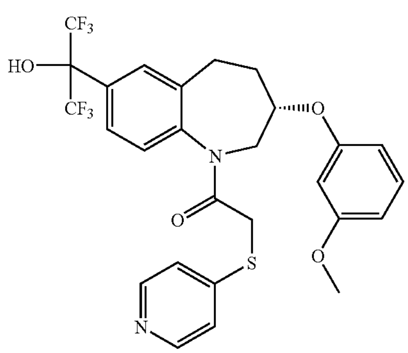 | 587.1 |

TABLE 12-continued

| Ex. # | Name | Structure | MS (M + H)+ |
|---|---|---|---|
| 168 | [(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-pyridin-2-yl-methanone | 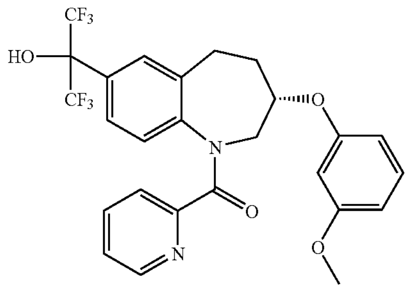 | 541.1 |
| 169 | [(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-pyridin-3-yl-methanone | 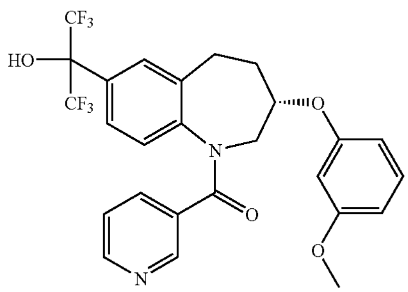 | 541.1 |
| 170 | 1-[(S)-3-(3-Methoxy-phenoxy)-7-(2,2,2-trifluoro-1-hydroxy-1-trifluoromethyl-ethyl)-2,3,4,5-tetrahydro-1-benzazepin-1-yl]-2-(4-trifluoromethyl-phenyl)-ethanone | 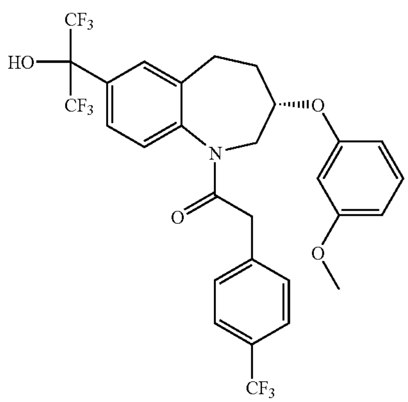 | 622.1 |
| 171 | 2-(3-Chloro-phenyl)-1-[(S)-3-(3-methoxy-phenoxy)-7-(2,2,2-trifluoro-1-hydroxy-1-trifluoromethyl-ethyl)-2,3,4,5-tetrahydro-1-benzazepin-1-yl]-ethanone | 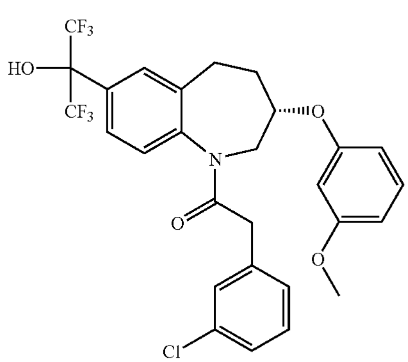 | 588.1 |

TABLE 12-continued

| Ex. # | Name | Structure | MS (M + H)+ |
|---|---|---|---|
| 172 | 3-Imidazol-1-yl-1-[(S)-3-(3-methoxy-phenoxy)-7-(2,2,2-trifluoro-1-hydroxy-1-trifluoromethyl-ethyl)-2,3,4,5-tetrahydro-1-benzazepin-1-yl]-propan-1-one | 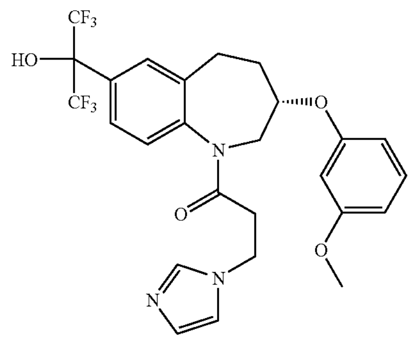 | 558.2 |

Example 173

2-Methyl-1-[7-(2,2,2-trifluoro-1-hydroxy-1-trifluoromethyl-ethyl)-2,3-dihydro-1,4-benzothiazin-4-yl]-propan-1-one

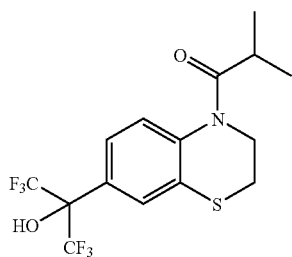

173A. 2-(3,4-Dihydro-2H-1,4-benzothiazin-7-yl)-1,1,1,3,3,3-hexafluoro-propan-2-ol: 173A was prepared by a procedure similar to that described for 178B. LC/MS m/z 318.1 (M+H)+.

Example 173: 173A (80 mg, 0.252 mmol) was dissolved in DCM (0.5 mL) and TEA (43 µL, 0.303 mmol) and isobutyryl chloride (29 µL, 0.277 mmol) were added. The reaction was stirred at rt overnight. The reaction mixture was loaded onto a silica gel column and Example 173 was purified by flash chromatography. LC/MS m/z 388.14 (M+H)+. 1H NMR (400 MHz, CHLOROFORM-d) δ ppm 1.09 (br. s., 6H), 3.05 (m, 1H), 3.22 (s, 2H), 3.96 (br. s, 2H), 5.19 (brs., 1H), 7.18 (m, 1H), 7.47 (m, 1H), 7.68 (s, 1H).

Examples 174 to 176

Examples 174 to 176 in Table 13 were prepared by procedures similar to that described for Example 173.

TABLE 13

| Ex. Name | Structure | MS (M + H)+ |
|---|---|---|
| 174 Cyclobutyl-[7-(2,2,2-trifluoro-1-hydroxy-1-trifluoromethyl-ethyl)-2,3-dihydro-1,4-benzothiazin-4-yl]-methanone | | 400.15 |
| 175 2-Phenyl-1-[7-(2,2,2-trifluoro-1-hydroxy-1-trifluoromethyl-ethyl)-2,3-dihydro-1,4-benzothiazin-4-yl]-ethanone | | 436.10 |

TABLE 13-continued

| Ex. Name | Structure | MS (M + H)+ |
|---|---|---|
| 176 3-Phenyl-1-[7-(2,2,2-trifluoro-1-hydroxy-1-trifluoromethyl-ethyl)-2,3-dihydro-1,4-benzothiazin-4-yl]-propan-1-one | | 450.10 |

Example 177

2-Phenyl-1-[7-(2,2,2-trifluoro-1-hydroxy-1-trifluoromethyl-ethyl)-2,3-dihydro-1,4-benzoxazin-4-yl]-ethanone

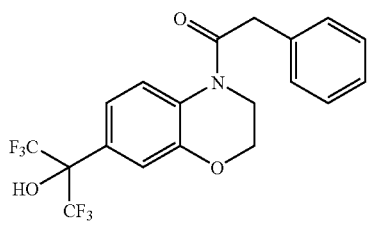

177A. 2-(3,4-Dihydro-2H-1,4-benzoxazin-7-yl)-1,1,1,3,3,3-hexafluoro-propan-2-ol: To 3,4-dihydro-2H-1,4-benzoxazine (963 mg, 7.12 mmol) were added cat. TsOH and hexafluoroacetone (1.51 g, 7.84 mmol) and the reaction was stirred at rt for 30 min, then at 65° C. overnight and at rt for an additional 2 d. The temperature was raised to 100° C. and the reaction was stirred for 1 h. After cooling to rt, the reaction was diluted with EtOAc, washed with sat'd NaHCO$_3$ and brine, dried, and concentrated to a dark oil. The title compound was separated from its regioisomer and purified by flash chromatography. LC/MS m/z 302.1 (M+H)+.

Example 177: Example 177 was synthesized from 177A and phenylacetyl chloride by a procedure similar to that described for Example 173. LC/MS m/z 420.22 (M+H)+. 1H NMR (DMSO, 400 MHz) δ ppm 3.87-3.93 (m, 2H), 3.97 (s, 2H), 4.19-4.27 (m, 2H), 7.10-7.35 (m, 7H), 8.00 (bs, 1H), 8.66 (s, 1H).

Example 178

2-Methyl-1-[3-phenyl-7-(2,2,2-trifluoro-1-hydroxy-1-trifluoromethyl-ethyl)-2,3-dihydro-1,4-benzothiazin-4-yl]-propan-1-one

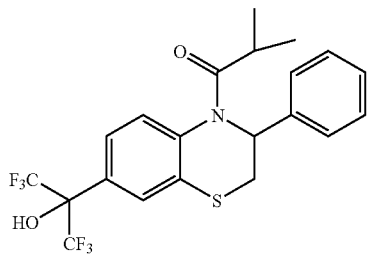

178A. 3-Phenyl-3,4-dihydro-2H-1,4-benzothiazine: To 2-amino-benzenethiol (535 mL, 5 mmol) in 99:1 DMF/AcOH (15 mL) was added α-bromoacetophenone (995 mg, 5 mmol) and the mixture was stirred for 5 min. NaBH$_3$CN (314 mg, 5 mmol) was added and the reaction was stirred for 2 h. The reaction was dilute with EtOAc and washed with dilute HCl, NaHCO$_3$, and brine, then dried over MgSO$_4$ and concentrated. The residue was purified by flash chromatography to give 178A as a yellow oil (1 g).

178B. 1,1,1,3,3,3-Hexafluoro-2-(3-phenyl-3,4-dihydro-2H-1,4-benzothiazin-7-yl)-propan-2-ol: To 178A (221 mg, 0.965 mmol) was added cat. TsOH and hexafluoroacetone monohydrate (186 mg, 0.965 mmol) and the mixture was heated at 95° C. overnight. The reaction mixture was loaded on a silica gel column and purified by flash chromatography to give 178B as a yellow oil (192 mg). LC/MS m/z 394.17 (M+H)+.

Example 178: Example 178 was synthesized from 178B by an acylation with isobutyryl chloride similar to the procedure described for Example 173. The crude product was dissolved in MeOH, then treated with excess LiOH.H$_2$O in enough H$_2$O and THF solvent to create a homogeneous solution and stirred for 3 h. Volatiles were removed in vacuo and the title compound was purified by flash chromatography. LC/MS m/z 463.82 (M+H)+. 1H NMR (400 MHz, CDCl$_3$) δ ppm 0.91 (d, J=8 Hz, 3H) 1.19 (d, J=8 Hz, 3H), 2.85-2.94 (m, 1H), 3.14-3.22 (m, 1H), 3.51-3.59 (m, 1H), 6.13-6.22 (m, 1H), 7.13-7.29 (m, 6H), 7.46-7.53 (m, 1H), 7.73 (s, 1H.

Examples 179 to 184

Examples 179 to 184 in Table 14 were prepared by procedures similar to that described for Example 178. Chiral compounds were purified by chiral prep-HPLC using Method D described above.

TABLE 14

| Ex. # | Name | Structure | MS (M + H)+ |
|---|---|---|---|
| 179 | Isomer B, fast eluting | 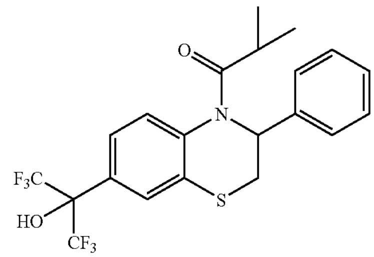 | 463.82 |
| 180 | Isomer A, slow eluting | 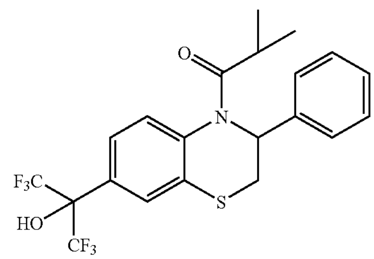 | 463.82 |
| 181 | 2-Phenyl-1-[3-phenyl-7-(2,2,2-trifluoro-1-hydroxy-1-trifluoromethyl-ethyl)-2,3-dihydro-1,4-benzothiazin-4-yl]-ethanone | 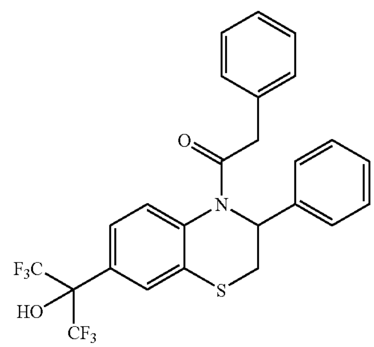 | 511.78 |
| 182 | Isomer A, fast eluting | 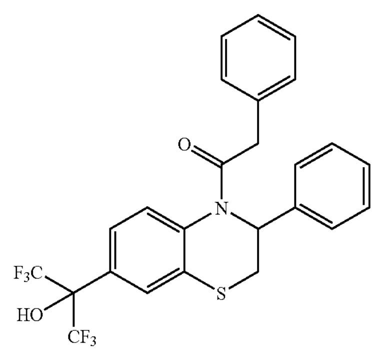 | 511.78 |
| 183 | Isomer B, slow eluting | 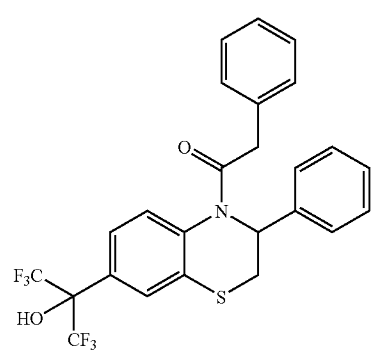 | 511.78 |

TABLE 14-continued

| Ex. # | Name | Structure | MS (M + H)+ |
|---|---|---|---|
| 184 | (R)-2-Phenyl-1-[3-phenyl-7-(2,2,2-trifluoro-1-hydroxy-1-trifluoromethyl-ethyl)-2,3-dihydro-1,4-benzothiazin-4-yl]-propan-1-one | 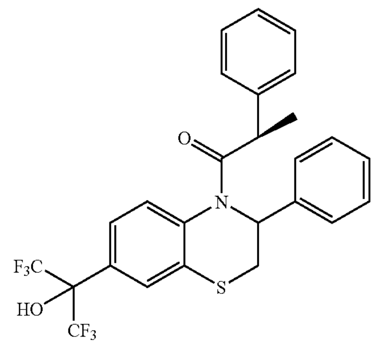 | 525.97 |

Example 185

1-[3-(3-Methoxy-phenyl)-7-(2,2,2-trifluoro-1-hydroxy-1-trifluoromethyl-ethyl)-2,3-dihydro-1,4-benzothiazin-4-yl]-2-phenyl-ethanone

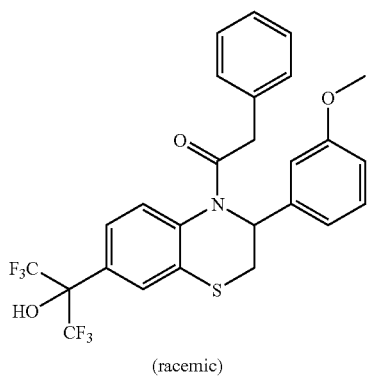

(racemic)

185A. 3-(3-Methoxy-phenyl)-3,4-dihydro-2H-1,4-benzothiazine: 185A was prepared from 2-amino-benzenethiol and α-bromo-3-methoxyacetophenone by a procedure similar to that described for 178A. LC/MS m/z 258.22 (M+H)+.

185B. 1,1,1,3,3,3-Hexafluoro-2-[3-(3-methoxy-phenyl)-3,4-dihydro-2H-1,4-benzothiazin-7-yl]-propan-2-ol: 185B was prepared from 185A by a procedure similar to that described for 178B. $^1$H NMR (CDCl$_3$, 400 MHz) δ ppm 2.95-3.03 (m, 1H), 3.04-3.14 (m, 1H), 3.79 (s, 3H), 3.88 (s, 1H), 4.37 (s, 1H) 4.66 (dd, J=8.68, 2.81 Hz, 1H), 6.53 (d, J=8.56 Hz, 1H), 6.85-6.95 (m, 3H), 7.19-7.24 (m, 1H), 7.29 (td, J=7.40, 1.35 Hz, 1H), 7.40 (d, J=1.96 Hz, 1H).

Example 185: Example 185 was prepared by a procedure similar to that described for Example 178. LC/MS m/z 542.30 (M+H)+. $^1$H NMR (CDCl$_3$, 400 MHz) δ ppm 0.92 (d, J=6.85 Hz, 3H), 1.20 (d, J=6.60 Hz, 3H), 2.84-2.95 (m, 1H), 3.15 (dd, J=13.08, 7.70 Hz, 1H), 3.51-3.57 (m, 1H), 3.71 (s, 3H), 6.13 (s, 1H), 6.71-6.77 (m, 2H), 6.82 (d, J=7.58 Hz, 1H), 7.16 (t, J=7.95 Hz, 1H), 7.20-7.26 (m, 1H), 7.51 (d, J=8.31 Hz, 1H), 7.74 (s, 1H).

Examples 186 to 190

Examples 186 to 190 in Table 15 were prepared by procedures similar to that described for Example 185. Chiral compounds were purified by chiral prep-HPLC using Method D described above.

TABLE 15

| Ex. # | Name | Structure | MS (M + H)+ |
|---|---|---|---|
| 186 | Isomer A, fast eluting | 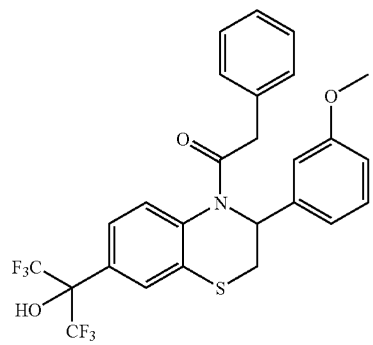 | 542.3 |

TABLE 15-continued
| Ex. # | Name | Structure | MS (M + H)+ |
|---|---|---|---|
| 187 | Isomer B, slow eluting | 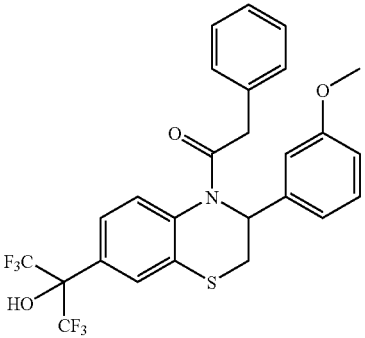 | 542.3 |
| 188 | 1-[3-(3-Methoxy-phenyl)-7-(2,2,2-trifluoro-1-hydroxy-1-trifluoromethyl-ethyl)-2,3-dihydro-1,4-benzothiazin-4-yl]-2-methyl-propan-1-one | 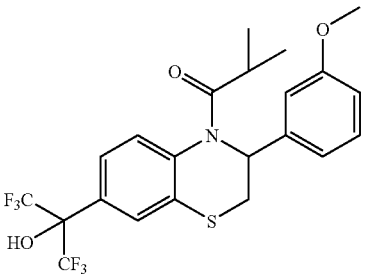 | 494.3 |
| 189 | Isomer A, fast eluting | 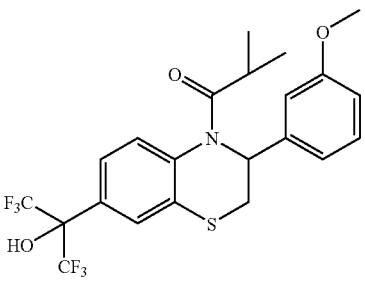 | 494.3 |
| 190 | Isomer B, slow eluting | 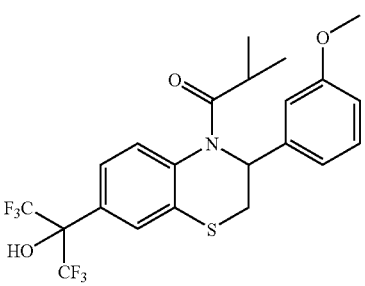 | 494.3 |

Example 191

(+/−)-1,1,1,3,3,3-Hexafluoro-2-(cis-(2-methyl-3-phenyl)-3,4-dihydro-2H-1,4-benzothiazin-7-yl)-propan-2-ol

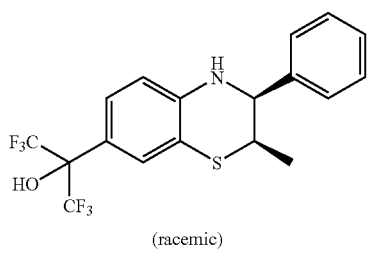

(racemic)

191A. 2-{4-Amino-3-[2-amino-5-(2,2,2-trifluoro-1-hydroxy-1-trifluoromethyl-ethyl)-phenyldisulfanyl]-phenyl}-1,1,1,3,3,3-hexafluoro-propan-2-ol: A mixture of 2-aminobenzenethiol (2.5 g, 20 mmol) and hexafluoroacetone (8.8 g, 40 mmol) was heated at 100° C. for 72 h. The reaction was cooled to rt and poured into cold water (100 mL). The product was extracted with EtOAc and the combined organic layers were dried over MgSO$_4$ and concentrated. The residue was purified by flash chromatography to give 191A (1.65 g). LC/MS m/z 359.3 (M+H)$^+$.

Example 191: To 191A (514 mg, 0.89 mmol) in DMF (1 mL) was added HOAc (0.6 mL, 10 mmol) and zinc powder (650 mg, 10 mmol) and the mixture was stirred at rt overnight. To the mixture was added 2-bromo-1-phenyl-propan-1-one (213 mg) and the reaction was stirred for 10 min before NaBH$_3$CN (63 mg, 1 mmol) was added. The reaction was stirred overnight; another portion of NaBH$_3$CN (50 mg) was added and the reaction was stirred at rt for 4 h. The reaction was quenched with 1N HCl, then neutralized to pH 8 with concentrated NaHCO$_3$. The product was extracted with EtOAc, dried over MgSO$_4$, concentrated, and purified by flash chromatography to give Example 191 as a colorless oil (385 mg). LC/MS m/z 407.93 (M+H)$^+$.

Example 192

1-[3-(4-Methoxy-phenyl)-7-(2,2,2-trifluoro-1-hydroxy-1-trifluoromethyl-ethyl)-2,3-dihydro-1,4-benzothiazin-4-yl]-2-phenyl-ethanone

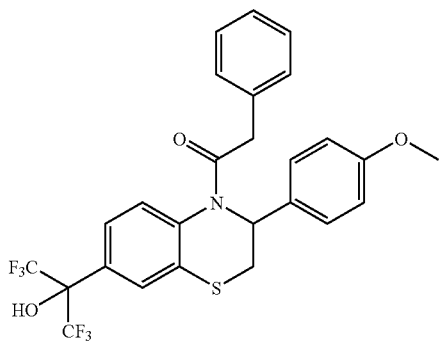

192A. 1,1,1,3,3,3-Hexafluoro-2-[3-(4-methoxy-phenyl)-3,4-dihydro-2H-1,4-benzothiazin-7-yl]-propan-2-ol: 192A was synthesized from 191A by a procedure similar to that described for Example 191. LC/MS m/z 424.2 (M+H)$^+$.

Example 192: To 192A (50 mg, 0.12 mmol) in DCE (1 mL) were added PL-MPH resin (185 mg, 0.6 mmol), phenylacetyl chloride (33 mL, 0.25 mmol), and cat. DMAP and the reaction was heated at 64° C. for overnight. The reaction was filtered to remove the resin. To the reaction mixture was added 0.5 mL of 3.25 M NaOH and the reaction was stirred at rt for 1 h. The crude product was purified by pre-HPLC to give Example 192 (31 mg). LC/MS m/z 542.31 (M+H)$^+$. $^1$H NMR (400 MHz, CDCl$_3$) δ ppm 2.99-3.04 (dd, J$_1$=8, J$_2$=8, 1H) 3.34-3.39 (dd, J$_1$=8, J$_2$=8, 1H) 3.60-3.63 (d, J=12, 1H) 3.67 (s, 3H) 3.71-3.74 (d, J=12, 1H) 5.96-6.12 (b, 1H) 6.70-6.72 (d, J=8, 2H) 6.81-6.93 (m, 2H) 7.04-7.15 (m, 5H) 7.19-7.26 (m, 1H) 7.42-7.44 (d, J=8, 1H) 7.54 (s, 1H).

Example 193

1-[3-(3,4-Dimethoxy-phenyl)-7-(2,2,2-trifluoro-1-hydroxy-1-trifluoromethyl-ethyl)-2,3-dihydro-1,4-benzothiazin-4-yl]-2-methyl-propan-1-one

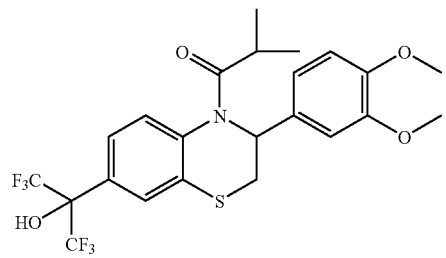

Example 193 was prepared by a procedure similar to that described for Example 192. LC/MS m/z 524.29 (M+H)$^+$.

Example 194

(+/−)-2-Methyl-1-[cis-(2-methyl-3-phenyl)-7-(2,2,2-trifluoro-1-hydroxy-1-trifluoromethyl-ethyl)-2,3-dihydro-1,4-benzothiazin-4-yl]-propan-1-one

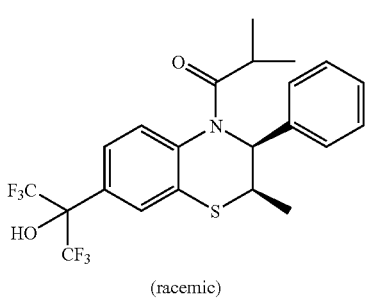

(racemic)

Example 194 was synthesized from Example 191 by using acylation with isobutyryl chloride by a procedure similar to that described for 192B. LC/MS m/z 478.25 (M+H)⁺. ¹H NMR (400 MHz, CDCl₃) δ ppm 0.90-0.92 (d, J=8, 3H) 1.14-1.17 (m, 6H) 2.90-2.97 (m, 1H) 3.97-4.00 (m, 1H) 6.18-6.20 (d, J=8, 1H) 6.86-6.88 (d, J=8, 1H) 7.08-7.10 (m, 3H) 7.15-7.24 (m, 3H) 7.59 (s, 1H).

Examples 195 and 196

Examples 195 and 196 in Table 16 were prepared by procedures similar to that described for Example 194.

Examples 197, 198, and 199

197A. 1-[2-Methyl-3-phenyl-7-(2,2,2-trifluoro-1-hydroxy-1-trifluoromethyl-ethyl)-2,3-dihydro-1,4-benzothiazin-4-yl]-2-phenyl-ethanone: 197A was prepared from Example 191 by a procedure similar to that described for 192B. LC/MS m/z 526 (M+H)⁺.

Examples 197, 198, and 199, as set forth in Table 17 below, were obtained by the chiral separation of 197A using Method F described above.

TABLE 16

| Ex. # | Name | Structure | MS (M + H)⁺ |
|---|---|---|---|
| 195 | (+/−)-1-[cis-(2-Methyl-3-phenyl)-7-(2,2,2-trifluoro-1-hydroxy-1-trifluoromethyl-ethyl)-2,3-dihydro-1,4-benzothiazin-4-yl]-2-phenyl-ethanone | racemic | 526.26 |
| 196 | (S)-1-[(2R,3S)-2-Methyl-3-phenyl-7-(2,2,2-trifluoro-1-hydroxy-1-trifluoromethyl-ethyl)-2,3-dihydro-1,4-benzothiazin-4-yl]-2-phenyl-propan-1-one and (S)-1-[(2S,3R)-2-Methyl-3-phenyl-7-(2,2,2-trifluoro-1-hydroxy-1-trifluoromethyl-ethyl)-2,3-dihydro-1,4-benzothiazin-4-yl]-2-phenyl-propan-1-one | | 540.03 |

TABLE 17

| Ex. # | Name | Structure | MS (M + H)+ |
|---|---|---|---|
| 197 | Cis Isomer A Rt 11.99 min | 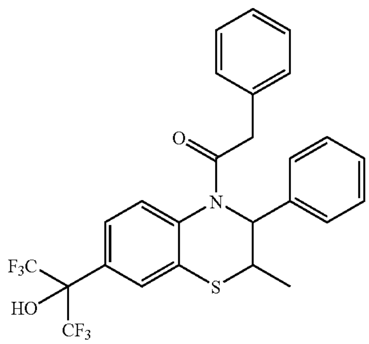 | 525.94 |
| 198 | Cis Isomer B Rt 16.03 min? | 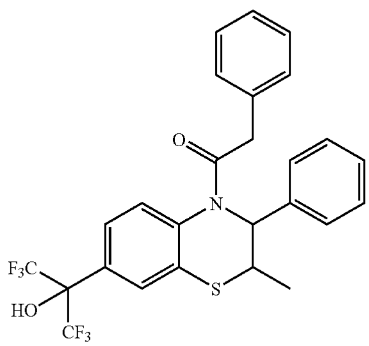 | 525.94 |
| 199 | Trans Isomer A Rt 13.60 min | 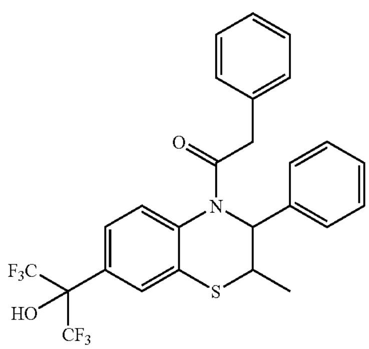 | 525.94 |

Example 200

1-[3-(2-Chloro-phenyl)-7-(2,2,2-trifluoro-1-hydroxy-1-trifluoromethyl-ethyl)-2,3-dihydro-1,4-benzothiazin-4-yl]-2-phenyl-ethanone

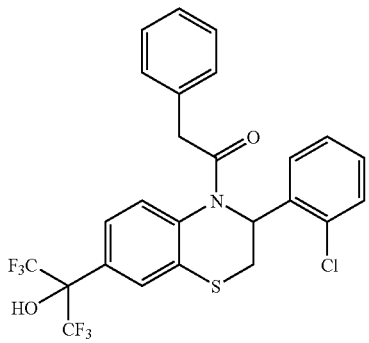

200A. 2-[3-(2-Chloro-phenyl)-3,4-dihydro-2H-1,4-benzothiazin-7-yl]-1,1,1,3,3,3-hexafluoro-propan-2-ol: To 2-amino-benzenethiol (1.07 mL, 10 mmol) in DMF (10 mL) under an argon atmosphere was added o-bromo-2-chloroacetophenone (1.5 mL, 9.8 mmol) at 0° C. and the reaction was warmed to rt. After 10 min, NaBH$_3$CN (1.5 g, 71 mmol) was added portion-wise over 5 min and the reaction was stirred for 16 h. The reaction was quenched with 1N HCl, then neutralized to pH 8 with conc. NaHCO$_3$. The product was extracted with ether, washed with water, dried over MgSO$_4$, and concentrated. The resulting residue was purified by flash chromatography to give 3-(2-chloro-phenyl)-3,4-dihydro-2H-1,4-benzothiazine (1.7 g). A mixture of this intermediate (420 mg, 1.6 mmol) and hexafluoroacetone: 1.5 H$_2$O (620 mg, 3.2 mmol) in DCM (1 mL) was heated in a sealed tube in a microwave reactor at 160° C. for 80 min. The resulting mixture was purified by flash chromatography to give 200A (260 mg). LC/MS m/z 427.87 (M+H)+. $^1$H NMR (400 MHz, CDCl$_3$) δ ppm 3.03-3.15 (m, 2H) 5.26 (m, 1H) 6.58 (d, J=8, 1H) 7.24-7.28 (m, 2H) 7.37-7.43 (m, 2H).

Example 200: Example 200 was prepared from 200A by a procedure similar to that described for 192B. LC/MS m/z 545.88 (M+H)+.

Example 201

2-Methyl-1-[2-phenyl-7-(2,2,2-trifluoro-1-hydroxy-1-trifluoromethyl-ethyl)-2,3-dihydro-1,4-benzothiazin-4-yl]-propan-1-one

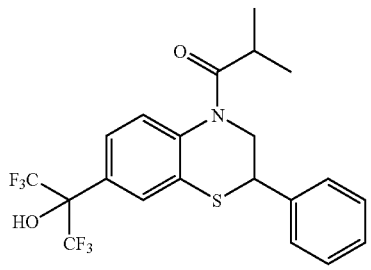

201A. 2-Phenyl-3,4-dihydro-2H-1,4-benzothiazine: To bromo-phenyl-acetic acid methyl ester (4.88 g, 21 mmol) in DMF (15 mL) under an argon atmosphere was added 2-amino-benzenethiol (2.3 mL, 21 mmol) and the reaction was stirred at rt overnight. The reaction mixture was diluted with EtOAc (5 mL) and water (50 mL) and the crude product was collected by filtration, washed with warm EtOAc, and dried to give 2-phenyl-4H-1,4-benzothiazin-3-one as a white solid (3.49 g). LC/MS m/z 242 (M+H)+. To this intermediate (3.48 g, 14.4 mmol) in THF (50 mL) under an argon atmosphere was added 1M $BH_3$.THF (50 mL, 50 mmol) and the reaction was stirred at rt overnight. The reaction was quenched with 1N HCl and extracted with ether. The combined organic fractions were dried over $MgSO_4$ and concentrated. 201A was purified by recrystallization from hot EtOAc/hexanes to yield pale pink crystals (1.5 g). LC/MS m/z 228.2 (M+H)+.

201B. 1,1,1,3,3,3-Hexafluoro-2-(2-phenyl-3,4-dihydro-2H-1,4-benzothiazin-7-yl)-propan-2-ol: A mixture of 201A (520 mg, 2.3 mmol) and hexafluoroacetone: 1.5 $H_2O$ (890 mg, 4.6 mmol) was heated at 160° C. in a sealed tube in a microwave reactor for 1000 s. The reaction mixture was cooled to rt and diluted with equal portions of water and DCM. The pH was adjusted to 8 with sat'd $NaHCO_3$ and the organic layer was separated, dried over $MgSO_4$, and concentrated. The resulting residue was purified by flash chromatography to give 201B (327 mg). LC/MS m/z 394 (M+H)+.

Example 201: Example 201 was prepared from 201B by a procedure similar to that described for Example 173. LC/MS m/z 464.26 (M+H)+. $^1$H NMR (400 MHz, $CDCl_3$) δ ppm 1.01-1.03 (d, J=8, 3H) 1.07-1.09 (d, J=8, 3H) 3.47-3.49 (m, 1H) 4.11-4.18 (m, 2H) 4.70-4.75 (m, 1H) 7.29-7.38 (m, 4H) 7.43-7.46 (m, 3H) 7.69 (s, 1H).

Example 202

2-Methyl-1-[2-methyl-7-(2,2,2-trifluoro-1-hydroxy-1-trifluoromethyl-ethyl)-2,3-dihydro-1,4-benzothiazin-4-yl]-propan-1-one

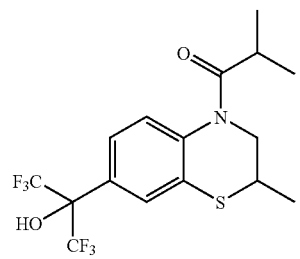

202A. 2-Methyl-7-(2,2,2-trifluoro-1-hydroxy-1-trifluoromethyl-ethyl)-4H-1,4-benzothiazin-3-one: 202A was prepared from 191A and 2-bromo-propionic acid methyl ester by a procedure similar to that described for 191A. LC/MS m/z 346.2 (M+H)+.

202B. 1,1,1,3,3,3-Hexafluoro-2-(2-methyl-3,4-dihydro-2H-1,4-benzothiazin-7-yl)-propan-2-ol: To 202A (303 mg, 0.88 mmol) in THF (5 mL) was added dropwise 1M $BH_3$.THF (2 mL, 2 mmol) at 0° C. The reaction was stirred at rt for 1 h, then heated at 50° C. for 1 h. The reaction was diluted with MeOH (5 mL) and stirred at rt overnight. The reaction mixture was concentrated and purified by flash chromatography to give 202B (237 mg, 80%). LC/MS m/z 332.4 (M+H)+.

Example 202: Example 202 was prepared from 202B by a procedure similar to that described for 192B. LC/MS m/z 402.41 (M+H)+. $^1$H NMR (400 MHz, $CDCl_3$) δ ppm 1.03-1.05 (d, J=8, 3H) 1.19-1.21 (d, J=8, 3H) 1.38-1.40 (d, J=8, 3H) 3.04-3.11 (m, 2H) 3.36-3.70 (m, 1H) 3.68 (m, 1H) 4.48 (m, 1H) 7.17-7.19 (d, J=8, 1H) 7.40-7.42 (d, J=8, 1H) 7.59 (s, 1H).

Examples 203 to 207

Examples 203 to 207 in Table 18 were prepared by procedures similar to that described for Example 202. Chiral compounds were purified by chiral prep-HPLC using Method G described above.

TABLE 18

| Ex. # | Name | Structure | MS (M + H)+ |
|---|---|---|---|
| 203 | Isomer A, fast eluting | 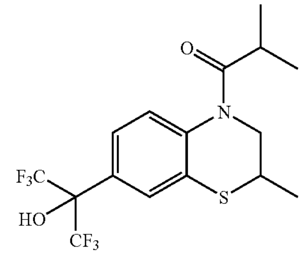 | 402.41 |

TABLE 18-continued

| Ex. # | Name | Structure | MS (M + H)+ |
|---|---|---|---|
| 204 | Isomer B, slow eluting | 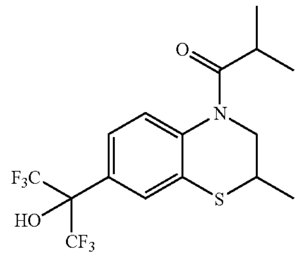 | 402.41 |
| 205 | 1-[2-Methyl-7-(2,2,2-trifluoro-1-hydroxy-1-trifluoromethyl-ethyl)-2,3-dihydro-1,4-benzothiazin-4-yl]-2-phenyl-ethanone | 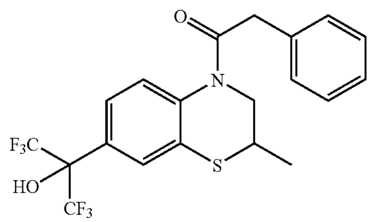 | 450.26 |
| 206 | Isomer A, fast eluting | 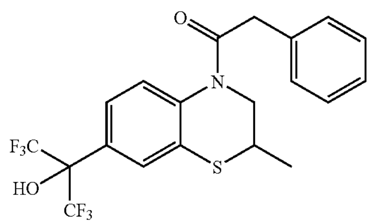 | 450.26 |
| 207 | Isomer B, slow eluting | 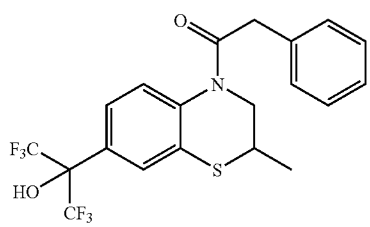 | 450.26 |

Examples 208 to 210

Examples 208 to 210 in Table 19 were prepared from 2-((S)-2-ethyl-3,4-dihydro-2H-1,4-benzothiazin-7-yl)-1,1,1,3,3,3-hexafluoro-propan-2-ol, which may be prepared by a procedure similar to that described for 201B, by procedures similar to that described for Example 173.

TABLE 19

| Ex. # | Name | Structure | MS (M + H)+ |
|---|---|---|---|
| 208 | 1-[(S)-2-Ethyl-7-(2,2,2-trifluoro-1-hydroxy-1-trifluoromethyl-ethyl)-2,3-dihydro-1,4-benzothiazin-4-yl]-2-methyl-propan-1-one | 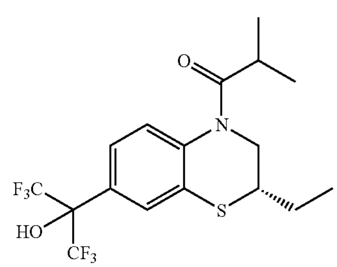 | 416.11 |

TABLE 19-continued

| Ex. # | Name | Structure | MS (M + H)+ |
|---|---|---|---|
| 209 | 1-[(S)-2-Ethyl-7-(2,2,2-trifluoro-1-hydroxy-1-trifluoromethyl-ethyl)-2,3-dihydro-1,4-benzothiazin-4-yl]-2-phenyl-ethanone | 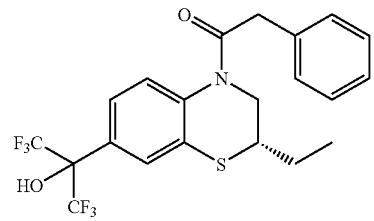 | 463.68 |
| 210 | 1-[(S)-2-Ethyl-7-(2,2,2-trifluoro-1-hydroxy-1-trifluoromethyl-ethyl)-2,3-dihydro-1,4-benzothiazin-4-yl]-2-phenyl-ethane-1,2-dione | 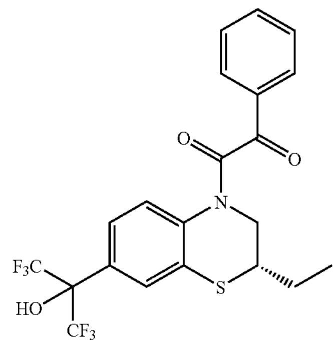 | 499.85 (M + Na)+ |

Examples 211 to 244

Examples 211 to 244 in Table 20 were prepared in a parallel library fashion from 2-((S)-2-ethyl-3,4-dihydro-2H-1,4-benzothiazin-7-yl)-1,1,1,3,3,3-hexafluoro-propan-2-ol (0.05 mmol) and the appropriate acid chloride (2 equivalents) in DCE (~0.5 mL) and pyridine (5 equivalents). The reactions were stirred at rt overnight. Workup and purification as described in the previous examples afforded the target compounds.

TABLE 20

| Ex. # | Name | Structure | MS (M + H)+ |
|---|---|---|---|
| 211 | 1-[(S)-2-Ethyl-7-(2,2,2-trifluoro-1-hydroxy-1-trifluoromethyl-ethyl)-2,3-dihydro-1,4-benzothiazin-4-yl]-propan-1-one | 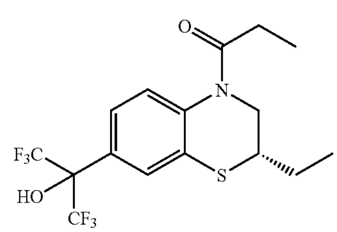 | 402.18 |
| 212 | 1-[(S)-2-Ethyl-7-(2,2,2-trifluoro-1-hydroxy-1-trifluoromethyl-ethyl)-2,3-dihydro-1,4-benzothiazin-4-yl]-3-methyl-butan-1-one | 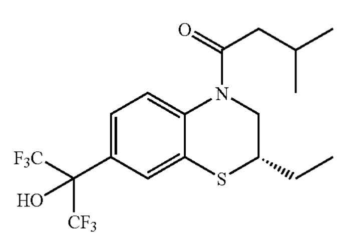 | 430.20 |

TABLE 20-continued

| Ex. # | Name | Structure | MS (M + H)+ |
|---|---|---|---|
| 213 | 1-[(S)-2-Ethyl-7-(2,2,2-trifluoro-1-hydroxy-1-trifluoromethyl-ethyl)-2,3-dihydro-1,4-benzothiazin-4-yl]-4-methyl-pentan-1-one | 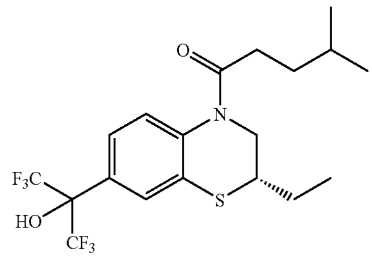 | 444.23 |
| 214 | 2-Dimethylamino-1-[(S)-2-ethyl-7-(2,2,2-trifluoro-1-hydroxy-1-trifluoromethyl-ethyl)-2,3-dihydro-1,4-benzothiazin-4-yl]-ethanone | 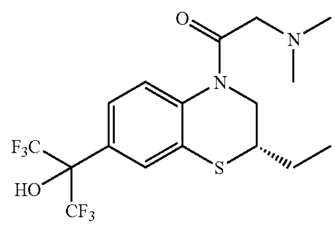 | 431.22 |
| 215 | Acetic acid 2-[(S)-2-ethyl-7-(2,2,2-trifluoro-1-hydroxy-1-trifluoromethyl-ethyl)-2,3-dihydro-1,4-benzothiazin-4-yl]-2-oxo-ethyl ester | 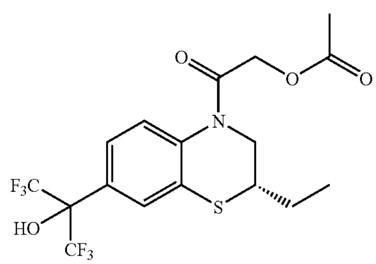 | 446.17 |
| 216 | 4-[(S)-2-Ethyl-7-(2,2,2-trifluoro-1-hydroxy-1-trifluoromethyl-ethyl)-2,3-dihydro-1,4-benzothiazin-4-yl]-4-oxo-butyric acid methyl ester | 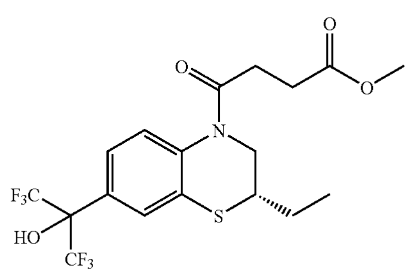 | 460.20 |
| 217 | Cyclohexyl-[(S)-2-ethyl-7-(2,2,2-trifluoro-1-hydroxy-1-trifluoromethyl-ethyl)-2,3-dihydro-1,4-benzothiazin-4-yl]-methanone | 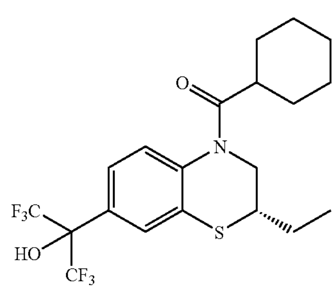 | 456.23 |

TABLE 20-continued

| Ex. # | Name | Structure | MS (M + H)+ |
|---|---|---|---|
| 218 | 3-Cyclopentyl-1-[(S)-2-ethyl-7-(2,2,2-trifluoro-1-hydroxy-1-trifluoromethyl-ethyl)-2,3-dihydro-1,4-benzothiazin-4-yl]-propan-1-one | 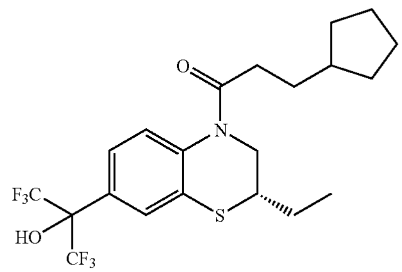 | 470.24 |
| 219 | 3-Cyclohexyl-1-[(S)-2-ethyl-7-(2,2,2-trifluoro-1-hydroxy-1-trifluoromethyl-ethyl)-2,3-dihydro-1,4-benzothiazin-4-yl]-propan-1-one | 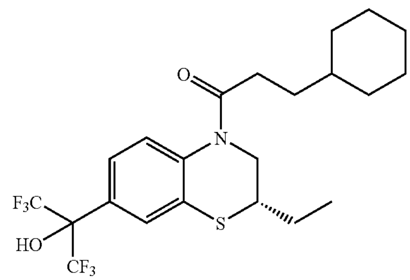 | 484.26 |
| 220 | [(S)-2-Ethyl-7-(2,2,2-trifluoro-1-hydroxy-1-trifluoromethyl-ethyl)-2,3-dihydro-1,4-benzothiazin-4-yl]-phenyl-methanone | 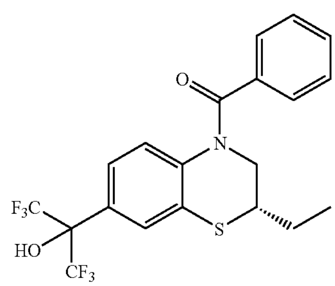 | 450.19 |
| 221 | [(S)-2-Ethyl-7-(2,2,2-trifluoro-1-hydroxy-1-trifluoromethyl-ethyl)-2,3-dihydro-1,4-benzothiazin-4-yl]-o-tolyl-methanone | 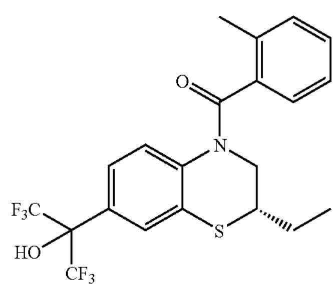 | 464.20 |
| 222 | (2-Chloro-phenyl)-[(S)-2-ethyl-7-(2,2,2-trifluoro-1-hydroxy-1-trifluoromethyl-ethyl)-2,3-dihydro-1,4-benzothiazin-4-yl]-methanone | 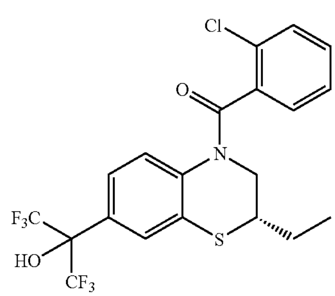 | 484.15 |

TABLE 20-continued

| Ex. # | Name | Structure | MS (M + H)+ |
|---|---|---|---|
| 223 | [(S)-2-Ethyl-7-(2,2,2-trifluoro-1-hydroxy-1-trifluoromethyl-ethyl)-2,3-dihydro-1,4-benzothiazin-4-yl]-(4-methoxy-phenyl)-methanone | 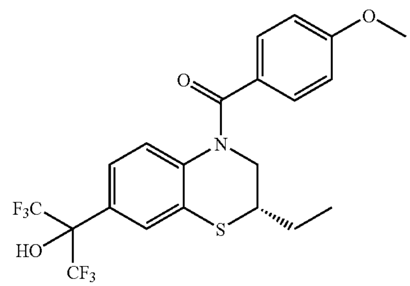 | 480.20 |
| 224 | 1-[(S)-2-Ethyl-7-(2,2,2-trifluoro-1-hydroxy-1-trifluoromethyl-ethyl)-2,3-dihydro-1,4-benzothiazin-4-yl]-2-(4-methoxy-phenyl)-ethanone | 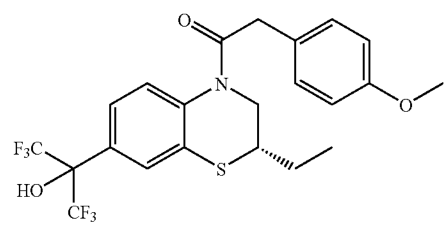 | 494.22 |
| 225 | 2-(4-Chloro-phenyl)-1-[(S)-2-ethyl-7-(2,2,2-trifluoro-1-hydroxy-1-trifluoromethyl-ethyl)-2,3-dihydro-1,4-benzothiazin-4-yl]-ethanone | 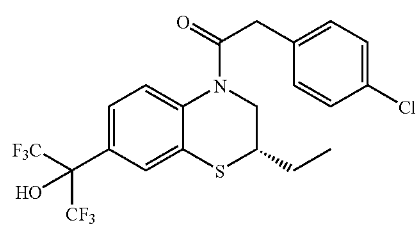 | 498.15 |
| 226 | 1-[(S)-2-Ethyl-7-(2,2,2-trifluoro-1-hydroxy-1-trifluoromethyl-ethyl)-2,3-dihydro-1,4-benzothiazin-4-yl]-3-phenyl-propan-1-one | 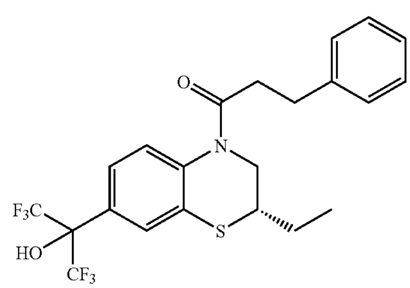 | 478.21 |
| 227 | 1-[(S)-2-Ethyl-7-(2,2,2-trifluoro-1-hydroxy-1-trifluoromethyl-ethyl)-2,3-dihydro-1,4-benzothiazin-4-yl]-2-phenoxy-ethanone | 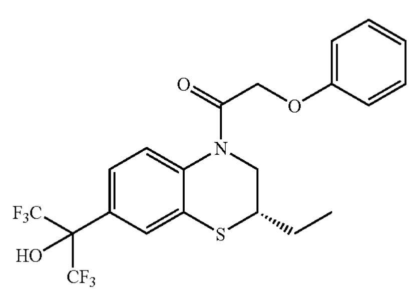 | 480.20 |

TABLE 20-continued

| Ex. # | Name | Structure | MS (M + H)+ |
|---|---|---|---|
| 228 | 2-(4-Chloro-phenoxy)-1-[(S)-2-ethyl-7-(2,2,2-trifluoro-1-hydroxy-1-trifluoromethyl-ethyl)-2,3-dihydro-1,4-benzothiazin-4-yl]-ethanone | 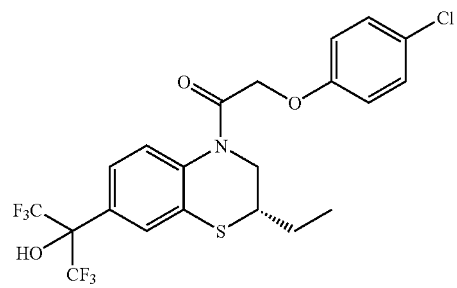 | 514.16 |
| 229 | 2-Benzyloxy-1-[(S)-2-ethyl-7-(2,2,2-trifluoro-1-hydroxy-1-trifluoromethyl-ethyl)-2,3-dihydro-1,4-benzothiazin-4-yl]-ethanone | 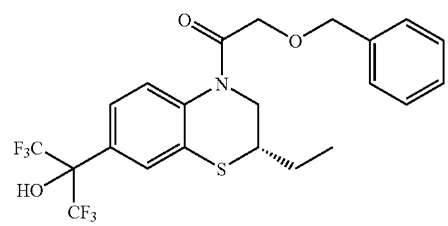 | 494.23 |
| 230 | 1-[(S)-2-Ethyl-7-(2,2,2-trifluoro-1-hydroxy-1-trifluoromethyl-ethyl)-2,3-dihydro-1,4-benzothiazin-4-yl]-4-phenoxy-butan-1-one | 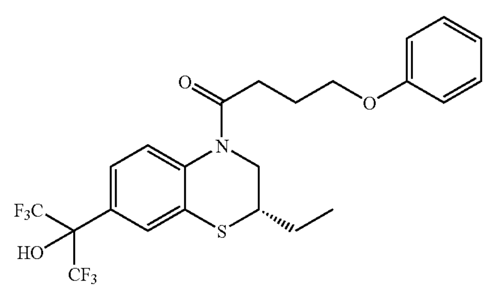 | 508.22 |
| 231 | 2-(4-Benzyloxy-phenyl)-1-[(S)-2-ethyl-7-(2,2,2-trifluoro-1-hydroxy-1-trifluoromethyl-ethyl)-2,3-dihydro-1,4-benzothiazin-4-yl]-ethanone | 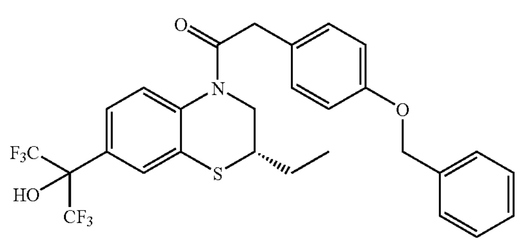 | 570.21 |
| 232 | 1-[(S)-2-Ethyl-7-(2,2,2-trifluoro-1-hydroxy-1-trifluoromethyl-ethyl)-2,3-dihydro-1,4-benzothiazin-4-yl]-2-(3-methoxy-phenyl)-ethanone | 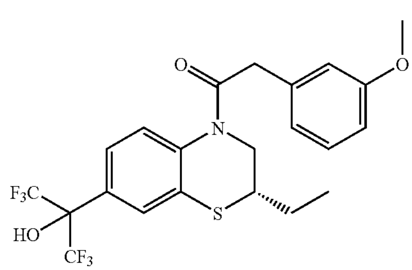 | 494.21 |

TABLE 20-continued

| Ex. # | Name | Structure | MS (M + H)+ |
|---|---|---|---|
| 233 | 1-{4-[(S)-2-Ethyl-7-(2,2,2-trifluoro-1-hydroxy-1-trifluoromethyl-ethyl)-2,3-dihydro-1,4-benzothiazine-4-carbonyl]-pipendin-1-yl}-ethanone | 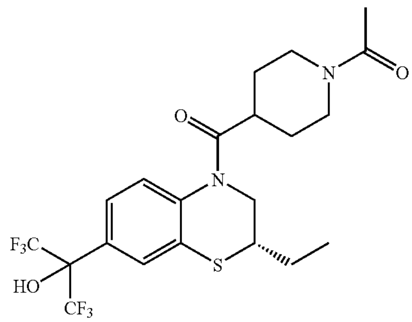 | 499.23 |
| 234 | [(S)-2-Ethyl-7-(2,2,2-trifluoro-1-hydroxy-1-trifluoromethyl-ethyl)-2,3-dihydro-1,4-benzothiazin-4-yl]-furan-2-yl-methanone | 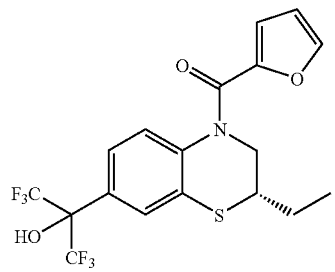 | 440.17 |
| 235 | [(S)-2-Ethyl-7-(2,2,2-trifluoro-1-hydroxy-1-trifluoromethyl-ethyl)-2,3-dihydro-1,4-benzothiazin-4-yl]-thiophen-2-yl-methanone | 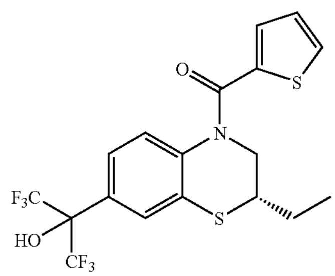 | 456.14 |
| 236 | Benzo[b]thiophen-2-yl-[(S)-2-ethyl-7-(2,2,2-trifluoro-1-hydroxy-1-trifluoromethyl-ethyl)-2,3-dihydro-1,4-benzothiazin-4-yl]-methanone | 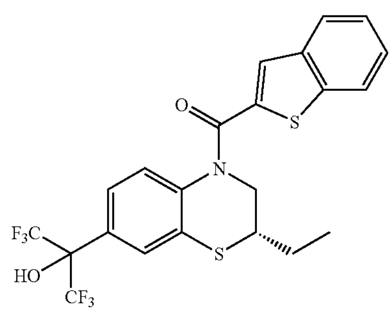 | 506.15 |
| 237 | [(S)-2-Ethyl-7-(2,2,2-trifluoro-1-hydroxy-1-trifluoromethyl-ethyl)-2,3-dihydro-1,4-benzothiazin-4-yl]-(4-methyl-1,2,3-thiadiazol-5-yl)-methanone | 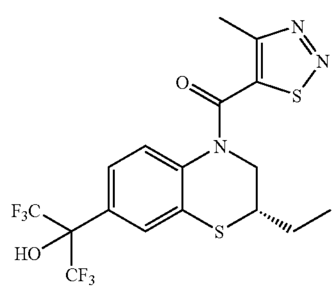 | 472.15 |

TABLE 20-continued

| Ex. # | Name | Structure | MS (M + H)+ |
|---|---|---|---|
| 238 | [(S)-2-Ethyl-7-(2,2,2-trifluoro-1-hydroxy-1-trifluoromethyl-ethyl)-2,3-dihydro-1,4-benzothiazin-4-yl]-(4-methyl-3,4-dihydro-2H-1,4-benzoxazin-7-yl)-methanone | 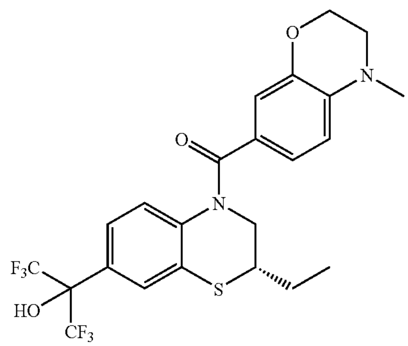 | 521.21 |
| 239 | [(S)-2-Ethyl-7-(2,2,2-trifluoro-1-hydroxy-1-trifluoromethyl-ethyl)-2,3-dihydro-1,4-benzothiazin-4-yl]-pyridin-2-yl-methanone | 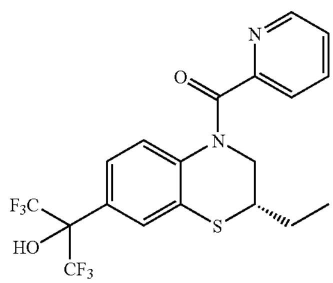 | 451.18 |
| 240 | 1-[(S)-2-Ethyl-7-(2,2,2-trifluoro-1-hydroxy-1-trifluoromethyl-ethyl)-2,3-dihydro-1,4-benzothiazin-4-yl]-2-thiophen-2-yl-ethanone | 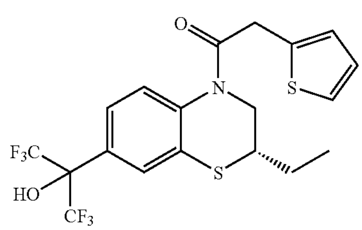 | 470.16 |
| 241 | 1-[(S)-2-Ethyl-7-(2,2,2-trifluoro-1-hydroxy-1-trifluoromethyl-ethyl)-2,3-dihydro-1,4-benzothiazin-4-yl]-ethanone | 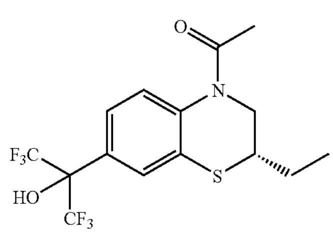 | 388.17 |
| 242 | 1-[(S)-2-Ethyl-7-(2,2,2-trifluoro-1-hydroxy-1-trifluoromethyl-ethyl)-2,3-dihydro-1,4-benzothiazin-4-yl]-2-methoxy-ethanone | 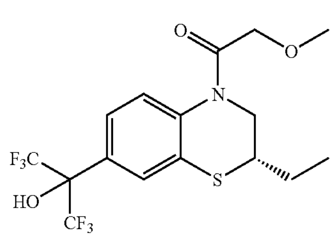 | 418.18 |

TABLE 20-continued

| Ex. # | Name | Structure | MS (M + H)+ |
|---|---|---|---|
| 243 | 1-[(S)-2-Ethyl-7-(2,2,2-trifluoro-1-hydroxy-1-trifluoromethyl-ethyl)-2,3-dihydro-1,4-benzothiazin-4-yl]-2,2-dimethyl-propan-1-one | 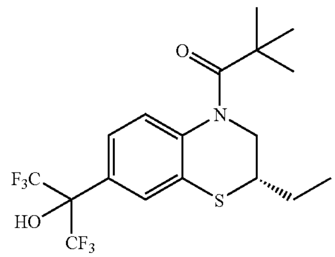 | 430.22 |
| 244 | (3-Chloro-phenyl)-[(S)-2-ethyl-7-(2,2,2-trifluoro-1-hydroxy-1-trifluoromethyl-ethyl)-2,3-dihydro-1,4-benzothiazin-4-yl]-methanone | 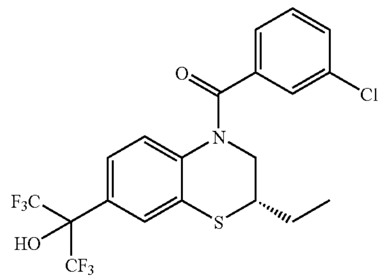 | 484.15 |

Example 245

1-[2-Benzyl-7-(2,2,2-trifluoro-1-hydroxy-1-trifluoromethyl-ethyl)-2,3-dihydro-1,4-benzothiazin-4-yl]-2-methyl-propan-1-one

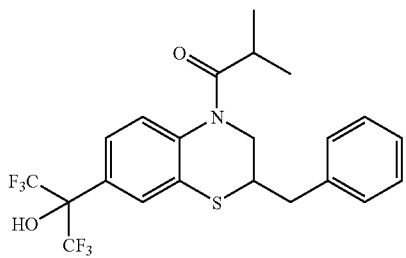

245A. 2-(2-amino-phenylsulfanyl)-3-phenyl-propionic acid methyl ester: A mixture of 2-bromo-3-phenyl-propionic acid methyl ester (2.6 g, 10.7 mmol), DIEA (8.7 mL, 50.3 mmol), and 2-amino-benzenethiol (1.14 mL, 10.7 mmol) in DMF (10 mL) was stirred at rt overnight under an argon atmosphere. The reaction mixture was partitioned between ether and water and the combined organic extracts were washed with water, dried over MgSO$_4$, and concentrated. The resulting residue was purified by flash chromatography to give 245A (1.5 g). LC/MS m/z 288 (M+H)$^+$.

245B. 2-benzyl-4H-1,4-benzothiazin-3-one: To 245A (1.5 g, 5.2 mmol) in DCM (10 mL) was added TFA (2 mL, 11.9 mmol) and the mixture was stirred at rt overnight. The mixture was concentrated and dried under vacuum to yield 245B (1.3 g, 100%). LC/MS m/z 256 (M+H)$^+$.

245C. 2-Benzyl-3,4-dihydro-2H-1,4-benzothiazine: To 245B (1.3 g, 5.2 mmol) in THF (25 mL) at 0° C. was added 1M BH$_3$.THF (15 mL, 15 mmol) and the reaction was stirred at rt for 2 h. The reaction was quenched with 1N HCl at 0° C., then stirred for 1 h before concentrated NaHCO$_3$ was added to adjust the mixture to pH 8. The crude product was extracted with ether and the combined organic extracts were dried over MgSO$_4$ and concentrated. The resulting residue was purified by flash chromatography to give 245C (870 mg). LC/MS m/z 242 (M+H)$^+$.

245D. 2-(2-Benzyl-3,4-dihydro-2H-1,4-benzothiazin-7-yl)-1,1,1,3,3,3-hexafluoro-propan-2-ol: 245D was prepared from 245C by a procedure similar to that described for 201B. LC/MS m/z 408 (M+H)$^+$.

Example 245: Example 245 was prepared from 245D by a procedure similar to that described for Example 173. LC/MS m/z 478.25 (M+H)$^+$.

Example 246

1-[2-Benzyl-7-(2,2,2-trifluoro-1-hydroxy-1-trifluoromethyl-ethyl)-2,3-dihydro-1,4-benzothiazin-4-yl]-2-phenyl-ethanone

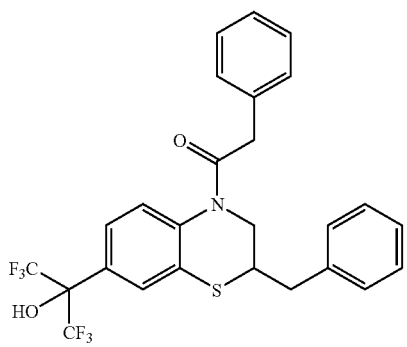

Example 246 was prepared by a procedure similar to that described for Example 245. LC/MS m/z 526.13 (M+H)$^+$.

Example 247

{3-[(S)-1-((S)-2-Phenyl-propionyl)-7-(2,2,2-trifluoro-1-hydroxy-1-trifluoromethyl-ethyl)-2,3,4,5-tetrahydro-1H-1-benzazepin-3-yloxy]-phenyl}-acetic acid

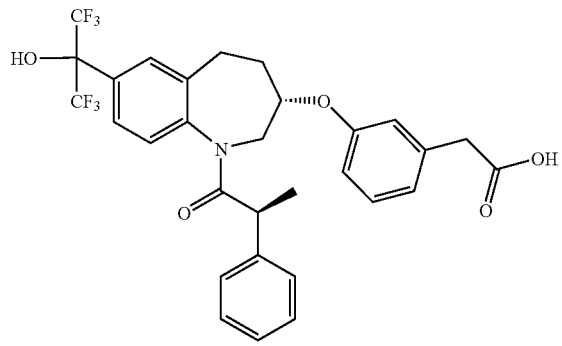

Example 247 was prepared by a procedure similar to that described for Example 112. LC/MS m/z 596.2 (M+H)$^+$.

Example 248

1,1,1,3,3,3-Hexafluoro-2-(1-phenethyl-2,3,4,5-tetrahydro-1H-1-benzazepin-7-yl)-propan-2-ol

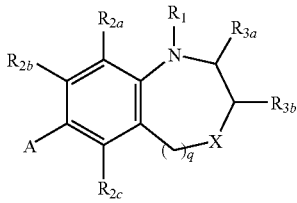

Example 248 was prepared from Example 2 by BH$_3$/THF reduction of the amide carbonyl as described in 80B. LC/MS m/z 418.4 (M+H)$^+$. $^1$H NMR (500 MHz, Acetone-D$_6$) δ 7.53 (m, 2H), 7.27 (m, 5H), 7.17 (m, 1H), 3.54 (m, 2H), 3.24 (m, 2H), 2.93 (m, 2H), 2.84 (m, 2H), 1.84 (m, 2H), 1.66 (m, 2H).

Example 249

2-{1-[2-(3-Chloro-2,6-difluoro-phenyl)-ethyl]-2,3,4,5-tetrahydro-1H-1-benzazepin-7-yl}-1,1,1,3,3,3-hexafluoro-propan-2-ol

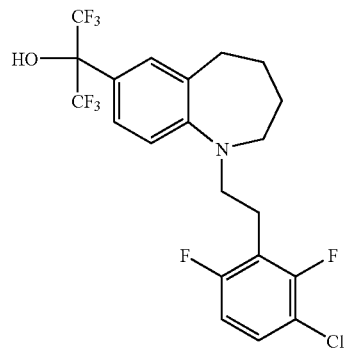

Example 249 was prepared by a procedure similar to that described for Example 248. LC/MS m/z 488.1 (M+H)$^+$.

What is claimed is:

1. A compound of formula I:

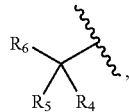

or stereoisomers or pharmaceutically acceptable salts or N-oxides thereof, wherein:

A is

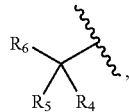

C(O)NR$_{28}$R$_{29}$, —CO$_2$(C$_1$-C$_6$)-alkyl, or heterocyclyl, wherein the alkyl and heterocyclyl may be optionally substituted with one or more R$_{10a}$'s;

X is CR$_{20}$R$_{20}$;

R$_1$ is —C(O)R$_7$, —C(O)OR$_7$, —S(O)R$_7$, —C(O)NR$_{28}$R$_{29}$, (C$_1$-C$_3$)alkylaryl or (C$_1$-C$_3$)alkylheteroaryl, wherein the alkylaryl and alkylheteroaryl may be optionally substituted with one or more R$_{10b}$'s;

R$_{2a}$, R$_{2b}$ and R$_{2c}$ are independently hydrogen, halo, —OH, —(C$_1$-C$_6$)-alkyl, —O(C$_1$-C$_6$)-alkyl, halo(C$_1$-C$_6$)-alkyl-, halo(C$_1$-C$_6$)-alkyloxy- or cyano;

R$_{3a}$ is hydrogen, (C$_1$-C$_8$)alkyl, aryl or heteroaryl, wherein the alkyl, aryl and heteroaryl may be optionally substituted with one or more R$_{10b}$'s;

R$_{3b}$ is (a) hydrogen, (b) —OH, (c) R$_{46}$—S(O)$_n$—, (d) cyano, (e) aryl-(C$_1$-C$_6$)alkyloxy-, which may optionally be substituted with one or more substituents selected from the group consisting of: halo, —OH, (C$_1$-C$_6$)- alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —O(C=O)—($C_1$-$C_6$)-alkyl, —O($C_1$-$C_6$)-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (f) heteroaryl-($C_1$-$C_6$)alkyloxy-, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —O(C=O)—($C_1$-$C_6$)-alkyl, —O($C_1$-$C_6$)-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (g) aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —O(C=O)—($C_1$-$C_6$)-alkyl, —O($C_1$-$C_6$)-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (h) heteroaryl optionally substituted with one or more substituents selected from the group consisting of: halo, —OH, ($C_1$-$C_6$)-alkyl, halo($C_1$-$C_6$)alkyl, halo($C_1$-$C_6$) alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —O(C=O)—($C_1$-$C_6$)-alkyl, —O($C_1$-$C_6$)-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (i) —($C_1$-$C_8$)-alkyl, which may optionally be substituted with one or more substituents selected from the group consisting of: halo, —OH, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, cyano, ($C_3$-$C_6$)-cycloalkyl, —COOH, —($C_1$-$C_6$)-alkyl-COOH, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —O(C=O)—($C_1$-$C_6$)-alkyl, —O($C_1$-$C_6$)-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (j) —O[(C=O)]$_s$aryl, which may optionally be substituted with one or more substituents selected from the group consisting of: halo, —OH, ($C_1$-$C_6$)-alkyl, halo ($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —O(C=O)—($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (k) —O[(C=O)]$_s$ heteroaryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl(NH$_2$)COOH, —CO($C_1$-$C_6$)-alkyl, —($C_1$-$C_6$)-alkyl-CO$_2$($C_1$-$C_6$)-alkyl, —CO$_2$($C_1$-$C_6$)-alkyl, —O(C=O)—($C_1$-$C_6$)-alkyl, —O($C_1$-$C_6$)-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (l) $R_{46}$—S(O)$_n$—O—;

$R_4$, $R_5$ and $R_6$ are independently hydroxy or halo($C_1$-$C_4$)-alkyl; provided that (i) only one of $R_4$, $R_5$ or $R_6$ is hydroxy and (ii) $R_5$ and $R_6$ are halo($C_1$-$C_4$)-alkyl when $R_{3a}$ and $R_{3b}$ are hydrogen and $R_4$ is hydroxy;

$R_7$ is alkyl, cycloalkyl, alkenyl, aryl or heterocyclyl, wherein the alkyl, cycloalkyl, aryl, or heterocyclyl may be optionally substituted with one or more $R_{10b}$'s;

$R_{10a}$ is halo, —OH, —O[(C=O)]$_s$($C_1$-$C_6$)-alkyl, —O[(C=O)]$_s$($C_2$-$C_6$)-alkenyl, cyano, nitro, —NR$_{28b}$R$_{29b}$, —COOH, —CO($C_1$-$C_6$)-alkyl, —CO$_2$($C_1$-$C_6$)-alkyl, —($C_1$-$C_6$)-haloalkyl, —($C_3$-$C_6$)-cycloalkyl or —($C_1$-$C_6$)-alkyl;

$R_{10b}$ is (a) halo; (b) —OH; (c) —O[(C=O)]$_s$($C_1$-$C_6$)-alkyl; (d) —O[(C=O)]$_s$($C_1$-$C_6$)-alkylaryl; (e) $R_{46}$—S(O)$_n$—; (f) cyano; (g) nitro; (h) —NR$_{28b}$R$_{29b}$; (i) —CO($C_1$-$C_6$)-alkyl; (j) —CO$_2$($C_1$-$C_6$)-alkyl; (k) aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, ($C_1$-$C_6$)-alkyl-S(O)$_n$—, cyano, nitro, —CO($C_1$-$C_6$)-alkyl, —($C_1$-$C_3$)-alkyl-CO$_2$ ($C_1$-$C_6$)-alkyl, —CO$_2$ ($C_1$-$C_6$)-alkyl, —NR$_{28b}$R$_{29b}$, —O(C=O)—($C_1$-$C_6$)-alkyl, —O($C_1$-$C_6$)-alkylaryl, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (l) heteroaryl optionally substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, cyano, nitro, —CO($C_1$-$C_6$)-alkyl, —($C_1$-$C_3$)-alkyl-CO$_2$($C_1$-$C_6$)-alkyl, —CO$_2$($C_1$-$C_6$)-alkyl, —O(C=O)—($C_1$-$C_6$)-alkyl, —O($C_1$-$C_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (m) heterocyclo, other than heteroaryl, which is optionally substituted with one or more substituents selected from the group consisting of: halo, —OH, $(C_1\text{-}C_6)$-alkyl, halo$(C_1\text{-}C_6)$alkyl, halo$(C_1\text{-}C_6)$alkyloxy, $(C_2\text{-}C_6)$-alkenyl, $(C_2\text{-}C_6)$-alkynyl, $(C_1\text{-}C_6)$-alkyloxy, (OH)—$(C_1\text{-}C_6)$-alkyl-, cyano, nitro, —CO$(C_1\text{-}C_6)$-alkyl, —$(C_1\text{-}C_3)$-alkyl-CO$_2(C_1\text{-}C_6)$-alkyl, —CO$_2(C_1\text{-}C_6)$-alkyl, —O(C=O)—$(C_1\text{-}C_6)$-alkyl, —O$(C_1\text{-}C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (n) —$(C_1\text{-}C_6)$-alkyl, which may optionally be substituted with one or more substituents selected from the group consisting of: halo, —OH, halo$(C_1\text{-}C_6)$alkyloxy, $(C_1\text{-}C_6)$-alkyloxy, cyano, —CO$(C_1\text{-}C_6)$-alkyl, —CO$_2(C_1\text{-}C_6)$-alkyl, —O(C=O)—$(C_1\text{-}C_6)$-alkyl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (o) =O, (p) —$(C_3\text{-}C_8)$-cycloalkyl, which may optionally be substituted with one or more substituents selected from the group consisting of: halo, —OH, $(C_1\text{-}C_6)$-alkyl, halo$(C_1\text{-}C_6)$alkyl, halo$(C_1\text{-}C_6)$alkyloxy, $(C_1\text{-}C_6)$-alkyloxy, (OH)—$(C_1\text{-}C_6)$-alkyl-, cyano, nitro, —CO$(C_1\text{-}C_6)$-alkyl, —$(C_1\text{-}C_6)$-alkyl-CO$_2(C_1\text{-}C_6)$-alkyl, —CO$_2(C_1\text{-}C_6)$-alkyl, —O(C=O)—$(C_1\text{-}C_6)$-alkyl, —O$(C_1\text{-}C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (q) —O[(C=O)]$_s$aryl, which may optionally be substituted with one or more substituents selected from the group consisting of: halo, —OH, $(C_1\text{-}C_6)$-alkyl, halo$(C_1\text{-}C_6)$alkyl, halo$(C_1\text{-}C_6)$alkyloxy, $(C_2\text{-}C_6)$-alkenyl, $(C_2\text{-}C_6)$-alkynyl, $(C_1\text{-}C_6)$-alkyloxy, (OH)—$(C_1\text{-}C_6)$-alkyl-, cyano, nitro, —CO$(C_1\text{-}C_6)$-alkyl, —$(C_1\text{-}C_6)$-alkyl-CO$_2(C_1\text{-}C_6)$-alkyl, —CO$_2(C_1\text{-}C_6)$-alkyl, and —O(C=O)—$(C_1\text{-}C_6)$-alkyl; or (r) halo$(C_1\text{-}C_6)$alkyloxy;

$R_{20}$ is hydrogen, or $(C_1\text{-}C_4)$-alkyl; or the two $R_{20}$'s are taken together with the carbon atom to which they are attached to form a 3- to 6-membered ring;

$R_{28}$ and $R_{29}$ are independently hydrogen, aryl, $(C_1\text{-}C_6)$ alkyl, halo$(C_1\text{-}C_6)$alkyl, aryl$(C_1\text{-}C_3)$alkyl or heterocyclyl, wherein the aryl, alkyl, arylalkyl and heterocyclyl may be optionally substituted with one or more $R_{50a}$'s;

or $R_{28}$ and $R_{29}$ are taken together with the nitrogen to which both are attached to form a 3- to 8-membered ring, which may optionally contain 1-4 heteroatoms selected from N, O, and S and be optionally substituted with one or more $R_{50a}$'s;

$R_{28a}$ and $R_{29a}$ are independently hydrogen, —[(C=O)O$_r$]$_s$aryl, —[(C=O)O$_r$]$_s$heteroaryl, —[(C=O)O$_r$]$_s(C_2\text{-}C_8)$-alkenyl, —[(C=O)O$_r$]$_s(C_1\text{-}C_8)$alkyl, —S(O)$_p(C_1\text{-}C_8)$alkyl, —S(O)$_p$aryl, —S(O)$_p$heteroaryl or heterocyclyl, wherein the aryl, heteroaryl, alkenyl, alkyl and heterocyclyl may be optionally substituted with one or more $R_{50}$'s;

or $R_{28a}$ and $R_{29a}$ are taken together with the nitrogen to which both are attached to form a 3- to 8-membered ring, which may optionally contain 1-4 heteroatoms selected from N, O, and S and be optionally substituted with one or more $R_{50}$'s;

$R_{28b}$ and $R_{29b}$ are independently hydrogen, alkyl or haloalkyl;

$R_{46}$ is (a) aryl, which may optionally be substituted with one or more substituents selected from the group consisting of: halo, —OH, $(C_1\text{-}C_6)$-alkyl, halo$(C_1\text{-}C_6)$alkyl, halo$(C_1\text{-}C_6)$alkyloxy, $(C_2\text{-}C_6)$-alkenyl, $(C_2\text{-}C_6)$-alkynyl, $(C_1\text{-}C_6)$-alkyloxy, (OH)—$(C_1\text{-}C_6)$-alkyl-, cyano, nitro, —COOH, —$(C_1\text{-}C_6)$-alkylCOOH, —$(C_1\text{-}C_6)$-alkyl(NH$_2$)COOH, —CO$(C_1\text{-}C_6)$-alkyl, —$(C_1\text{-}C_6)$-alkyl-CO$_2(C_1\text{-}C_6)$-alkyl, —CO$_2(C_1\text{-}C_6)$-alkyl, —O(C=O)—$(C_1\text{-}C_6)$-alkyl, —O$(C_1\text{-}C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (b) heteroaryl optionally substituted with one or more substituents selected from the group consisting of: halo, —OH, $(C_1\text{-}C_6)$-alkyl, halo$(C_1\text{-}C_6)$alkyl, halo$(C_1\text{-}C_6)$alkyloxy, $(C_2\text{-}C_6)$-alkenyl, $(C_2\text{-}C_6)$-alkynyl, $(C_1\text{-}C_6)$-alkyloxy, (OH)—$(C_1\text{-}C_6)$-alkyl-, cyano, nitro, —COOH, —$(C_1\text{-}C_6)$-alkylCOOH, —$(C_1\text{-}C_6)$-alkyl(NH$_2$)COOH, —CO$(C_1\text{-}C_6)$-alkyl, —$(C_1\text{-}C_6)$-alkyl-CO$_2(C_1\text{-}C_6)$-alkyl, —CO$_2(C_1\text{-}C_6)$-alkyl, —O(C=O)—$(C_1\text{-}C_6)$-alkyl, —O$(C_1\text{-}C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (c) heterocyclo, other than heteroaryl, which is optionally substituted with one or more substituents selected from the group consisting of: halo, —OH, $(C_1\text{-}C_6)$-alkyl, halo$(C_1\text{-}C_6)$ alkyl, halo$(C_1\text{-}C_6)$alkyloxy, $(C_2\text{-}C_6)$-alkenyl, $(C_2\text{-}C_6)$-alkynyl, $(C_1\text{-}C_6)$-alkyloxy, (OH)—$(C_1\text{-}C_6)$-alkyl-, cyano, nitro, —COOH, —$(C_1\text{-}C_6)$-alkylCOOH, —$(C_1\text{-}C_6)$-alkyl(NH$_2$)COOH, —CO$(C_1\text{-}C_6)$-alkyl, —$(C_1\text{-}C_6)$-alkyl-CO$_2(C_1\text{-}C_6)$-alkyl, —CO$_2(C_1\text{-}C_6)$-alkyl, —O(C=O)—$(C_1\text{-}C_6)$-alkyl, —O$(C_1\text{-}C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (d) —$(C_1\text{-}C_{10})$-alkyl, which may optionally be substituted with one or more substituents selected from the group consisting of: halo, —OH, $(C_1\text{-}C_6)$-alkyl, halo$(C_1\text{-}C_6)$alkyl, halo$(C_1\text{-}C_6)$alkyloxy, $(C_1\text{-}C_6)$-alkyloxy, (OH)—$(C_1\text{-}C_6)$-alkyl-, cyano, nitro, —COOH, —$(C_1\text{-}C_6)$-alkylCOOH, —$(C_1\text{-}C_6)$-alkyl(NH$_2$)COOH, —CO$(C_1\text{-}C_6)$-alkyl, —$(C_1\text{-}C_6)$-alkyl-CO$_2(C_1\text{-}C_6)$-alkyl, —CO$_2(C_1\text{-}C_6)$-alkyl, —O(C=O)—$(C_1\text{-}C_6)$-alkyl, —O$(C_1\text{-}C_6)$-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_{50}$ is (a) hydrogen, (b) halo, (c) —OH, (d) $(C_1\text{-}C_6)$-alkyl, (e) halo$(C_1\text{-}C_6)$-alkyl, (f) halo$(C_1\text{-}C_6)$-alkyloxy, (g) —O[(C=O)]$_s(C_1\text{-}C_6)$-alkyl, (h) cyano, (i) nitro, (j) —COOH, (k) —CO$(C_1\text{-}C_6)$-alkyl, (l) —CO$_2(C_1\text{-}C_6)$-alkyl, (m) (OH)—$(C_1\text{-}C_6)$-alkyl-, (n)-$(C_1\text{-}C_6)$-alkyl- COOH, (o) —($C_1$-$C_6$)-alkyl-heteroaryl, (p) —($C_1$-$C_6$)-alkyl-heterocyclyl, (q) —($C_1$-$C_6$)-alkyl($NH_2$)COOH, (r) —($C_1$-$C_6$)-alkyl-$CO_2$($C_1$-$C_6$)-alkyl, or (s) —($C_3$-$C_6$)-cycloalkyl;

$R_{50a}$ is halo, —OH, —O[(C=O)]$_s$($C_1$-$C_6$)-alkyl, cyano, nitro, —$NR_{51}R_{52}$, —COOH, —CO($C_1$-$C_6$)-alkyl, —$CO_2$($C_1$-$C_6$)-alkyl, —($C_1$-$C_6$)-haloalkyl, —($C_3$-$C_6$)-cycloalkyl or —($C_1$-$C_6$)-alkyl;

$R_{51}$ and $R_{52}$, at each occurrence, are independently hydrogen, —($C_1$-$C_6$)-alkyl, —($C_3$-$C_8$)-cycloalkyl, or -halo($C_1$-$C_6$)-alkyl;

n is 0 to 2;
p is 1 or 2;
q is 1;
r is 0 or 1; and
s is 0 or 1;
with the following provisos:
a) excluding compounds wherein:
A is

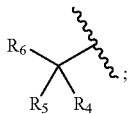

X is $CH_2$; $R_1$ is —C(O)$R_7$; $R_{2a}$ is hydrogen, methyl or ethyl; $R_{2b}$, $R_{2c}$, $R_{3a}$ and $R_{3b}$ are hydrogen; $R_4$ and $R_6$ are —$CF_3$; $R_5$ is hydroxy; and $R_7$ is $C_{1-5}$ alkyl, propenyl or cycloalkyl; and b) excluding compounds wherein:
A is

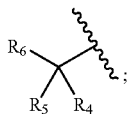

X is $CH_2$; $R_1$ is —S(O)$R_7$; $R_{2a}$, $R_{2b}$, $R_{2c}$, $R_{3a}$ and $R_{3b}$ are hydrogen; $R_5$ is hydroxy; $R_4$ and $R_6$ are —$CF_3$; $R_7$ is phenyl optionally substituted with cyano; and n is 2.

2. The compound of claim 1, wherein:
A is

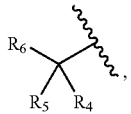

$CO_2$($C_1$-$C_6$)-alkyl, or heterocyclyl, wherein the alkyl and heterocyclyl may be optionally substituted with one or more $R_{10a}$'s;

X is $CR_{20}R_{20}$;

$R_1$ is —C(O)$R_7$, —C(O)O$R_7$, —S(O)$_n R_7$, —C(O)$NR_{28}R_{29}$, or ($C_1$-$C_3$)alkylaryl, wherein the alkylaryl may be optionally substituted with one or more $R_{10b}$'s;

$R_{2a}$, $R_{2b}$ and $R_{2c}$ are independently hydrogen, halo, —($C_1$-$C_6$)-alkyl, —O($C_1$-$C_6$)-alkyl, halo($C_1$-$C_6$)-alkyl- or halo($C_1$-$C_6$)-alkyloxy-;

$R_{3a}$ is hydrogen, ($C_1$-$C_8$)alkyl, aryl or heteroaryl, wherein the alkyl, aryl and heteroaryl may be optionally substituted with one or more $R_{10b}$'s;

$R_{3b}$ is (a) hydrogen, (b) —OH, (c) $R_{46}$—S(O)$_n$—, (d) aryl-($C_1$-$C_6$)alkyloxy-, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkyl($NH_2$)COOH, —CO($C_1$-$C_6$)-alkyl, —($C_1$-$C_6$)-alkyl-$CO_2$($C_1$-$C_6$)-alkyl, —$CO_2$($C_1$-$C_6$)-alkyl, —O(C=O)—($C_1$-$C_6$)-alkyl, —O($C_1$-$C_6$)-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (e) heteroaryl-($C_1$-$C_6$)alkyloxy-, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_2$-$C_6$)-alkenyl, ($C_2$-$C_6$)-alkynyl, ($C_1$-$C_6$)-alkyloxy, (OH)—($C_1$-$C_6$)-alkyl-, $R_{46}$—S(O)$_n$—, cyano, nitro, —COOH, —($C_1$-$C_6$)-alkylCOOH, —($C_1$-$C_6$)-alkyl($NH_2$)COOH, —CO($C_1$-$C_6$)-alkyl, —($C_1$-$C_6$)-alkyl-$CO_2$($C_1$-$C_6$)-alkyl, —$CO_2$($C_1$-$C_6$)-alkyl, —O(C=O)—($C_1$-$C_6$)-alkyl, —O($C_1$-$C_6$)-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (f) aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl($NH_2$)COOH, —CO($C_1$-$C_6$)-alkyl, —$CO_2$($C_1$-$C_6$)-alkyl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (g) heteroaryl optionally substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl($NH_2$)COOH, —CO($C_1$-$C_6$)-alkyl, —$CO_2$($C_1$-$C_6$)-alkyl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (h) —($C_1$-$C_8$)-alkyl, which may optionally be substituted with one or more substituents selected from the group consisting of: halo, —OH, halo($C_1$-$C_6$)alkyloxy, ($C_1$-$C_6$)-alkyloxy, (OH)—($C_1$-$C_6$)-alkyl-, cyano, ($C_3$-$C_6$)-cycloalkyl, —COOH, —($C_1$-$C_6$)-alkylCOOH, —($C_1$-$C_6$)-alkyl($NH_2$)COOH, —CO($C_1$-$C_6$)-alkyl, —$CO_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (i) —O[(C=O)]$_s$aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl($NH_2$)COOH, —($C_1$-$C_6$)-alkyl-$CO_2$($C_1$-$C_6$)-alkyl, —$CO_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (j) —O[(C=O)]$_s$heteroaryl, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, —COOH, —$(C_1$-$C_6)$-alkylCOOH, —$(C_1$-$C_6)$-alkyl$(NH_2)$COOH, —$(C_1$-$C_6)$-alkyl-$CO_2(C_1$-$C_6)$-alkyl, —$CO_2(C_1$-$C_6)$-alkyl, aryl, which may be optionally substituted with one or more $R_{50}$s, heteroaryl, which may be optionally substituted with one or more $R_{50}$'s, and heterocyclo, which may be optionally substituted with one or more $R_{50}$s;

$R_4$, $R_5$ and $R_6$ are independently hydroxy or halo$(C_1$-$C_4)$-alkyl; provided that (i) only one of $R_4$, $R_5$ or $R_6$ is hydroxy and (ii) $R_5$ and $R_6$ are halo$(C_1$-$C_4)$-alkyl when $R_{3a}$ and $R_{3b}$ are hydrogen and $R_4$ is hydroxy;

$R_7$ is alkyl, cycloalkyl, alkenyl, aryl or heterocyclyl, wherein the alkyl, cycloalkyl, aryl, or heterocyclyl may be optionally substituted with one or more $R_{10b}$'s;

$R_{10a}$ is halo, —OH, —O[(C=O)]$_s(C_1$-$C_6)$-alkyl, —O[(C=O)]$_s(C_2$-$C_6)$-alkenyl, cyano, nitro, —COOH, —$CO_2(C_1$-$C_6)$-alkyl, —$(C_3$-$C_6)$-cycloalkyl or —$(C_1$-$C_6)$-alkyl;

$R_{10b}$ is (a) halo; (b) —OH; (c) —O[(C=O)]$_s(C_1$-$C_6)$-alkyl; (d) —O[(C=O)]$_s(C_1$-$C_6)$-alkylaryl; (e) $R_{46}$—S(O)$_n$—; (f) cyano; (g) nitro; (h) —$NR_{28b}R_{29b}$; (i) —CO$(C_1$-$C_6)$-alkyl; (j) —$CO_2(C_1$-$C_6)$-alkyl; (k) aryl, which may optionally be substituted with one or more substituents selected from the group consisting of: halo, —OH, halo$(C_1$-$C_6)$alkyl, halo$(C_1$-$C_6)$alkyloxy, $(C_1$-$C_6)$-alkyloxy, (OH)—$(C_1$-$C_6)$-alkyl-, $(C_1$-$C_6)$-alkyl-S(O)$_n$—, cyano, nitro, —$NR_{28b}R_{29b}$, —O$(C_1$-$C_6)$-alkylaryl, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (l) heteroaryl optionally substituted with one or more substituents selected from the group consisting of: halo, —OH, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, —O$(C_1$-$C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (m) heterocyclo, other than heteroaryl, which is optionally substituted with one or more substituents selected from the group consisting of: halo, —OH, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, —CO$(C_1$-$C_6)$-alkyl, —O$(C_1$-$C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (n) —$(C_1$-$C_6)$-alkyl, which may be optionally substituted with one or more substituents selected from the group consisting of: halo, —OH, halo$(C_1$-$C_6)$alkyloxy, $(C_1$-$C_6)$-alkyloxy, cyano, —$CO_2(C_1$-$C_6)$-alkyl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (o) —$(C_3$-$C_8)$-cycloalkyl, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, —$CO_2(C_1$-$C_6)$-alkyl, —O$(C_1$-$C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (p) —O[(C=O)]$_s$aryl, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, and —$CO_2(C_1$-$C_6)$-alkyl; or (q) halo$(C_1$-$C_6)$alkyloxy;

$R_{20}$ is hydrogen, or $(C_1$-$C_4)$-alkyl; or the two $R_{20}$'s are taken together with the carbon atom to which they are attached to form a 3- to 6-membered ring;

$R_{28}$ and $R_{29}$ are independently hydrogen, aryl, $(C_1$-$C_6)$ alkyl, halo$(C_1$-$C_6)$alkyl, aryl$(C_1$-$C_3)$alkyl or heterocyclyl, wherein the aryl, alkyl, arylalkyl and heterocyclyl may be optionally substituted with one or more $R_{50a}$'s;

or $R_{28}$ and $R_{29}$ are taken together with the nitrogen to which both are attached to form a 3- to 8-membered ring, which may optionally contain 1-4 heteroatoms selected from N, O, and S and be optionally substituted with one or more $R_{50a}$'s;

$R_{28a}$ and $R_{29a}$ are independently hydrogen, —[(C=O)O$_r$]$_s$ aryl, —[(C=O)O$_r$]$_s(C_1$-$C_8)$alkyl or heterocyclyl, wherein the aryl, alkyl and heterocyclyl may be optionally substituted with one or more $R_{50}$'s;

or $R_{28a}$ and $R_{29a}$ are taken together with the nitrogen to which both are attached to form a 3- to 8-membered ring, which may optionally contain 1-4 heteroatoms selected from N, O, and S and be optionally substituted with one or more $R_{50}$'s;

$R_{28b}$ and $R_{29b}$ are independently hydrogen, alkyl or haloalkyl;

$R_{46}$ is (a) aryl, which may optionally be substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-$C_6)$-alkyl-, cyano, nitro, —COOH, —$(C_1$-$C_6)$-alkyl-COOH, —$(C_1$-$C_6)$-alkyl$(NH_2)$COOH, —$(C_1$-$C_6)$-alkyl-$CO_2(C_1$-$C_6)$-alkyl, —$CO_2(C_1$-$C_6)$-alkyl, —O$(C_1$-$C_6)$-alkylaryl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (b) heteroaryl optionally substituted with one or more substituents selected from the group consisting of: halo, —OH, $(C_1$-$C_6)$-alkyl, halo$(C_1$-$C_6)$alkyl, halo$(C_1$-$C_6)$alkyloxy, $(C_1$-$C_6)$-alkyloxy, (OH)—$(C_1$-

$C_6$)-alkyl-, cyano, nitro, —COOH, —($C_1$-$C_6$)-alkyl-COOH, —($C_1$-$C_6$)-alkyl($NH_2$)COOH, —($C_1$-$C_6$)-alkyl-$CO_2$($C_1$-$C_6$)-alkyl, —$CO_2$($C_1$-$C_6$)-alkyl, —O($C_1$-$C_6$)-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (c) —($C_1$-$C_{10}$)-alkyl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, —COOH, —($C_1$-$C_6$)-alkylCOOH, —($C_1$-$C_6$)-alkyl($NH_2$)COOH, —($C_1$-$C_6$)-alkyl-$CO_2$($C_1$-$C_6$)-alkyl, —$CO_2$($C_1$-$C_6$)-alkyl, —O($C_1$-$C_6$)-alkylaryl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_{50}$ is (a) hydrogen, (b) halo, (c) —OH, (d) ($C_1$-$C_6$)-alkyl, (e) halo($C_1$-$C_6$)-alkyl, (f) —O[(C=O)]$_q$($C_1$-$C_6$)-alkyl, (g) cyano, (h) nitro, (i) —COOH, (j) —CO($C_1$-$C_6$)-alkyl, (k) —$CO_2$($C_1$-$C_6$)-alkyl, (l) (OH)—($C_1$-$C_6$)-alkyl-, (m) —($C_1$-$C_6$)-alkylCOOH, (n) —($C_1$-$C_6$)-alkyl($NH_2$)COOH, or (o) —($C_3$-$C_6$)-cycloalkyl;

$R_{50a}$ is halo, —OH, —O[(C=O)]$_s$($C_1$-$C_6$)-alkyl, cyano, nitro, —COOH, —CO($C_1$-$C_6$)-alkyl, —$CO_2$($C_1$-$C_6$)-alkyl, —($C_1$-$C_6$)-haloalkyl, —($C_3$-$C_6$)-cycloalkyl or —($C_1$-$C_6$)-alkyl;

n is 0 to 2;
q is 1;
r is 0 or 1; and
s is 0 or 1.

3. The compound of claim 1, wherein:
A is

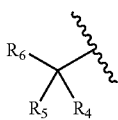

or heterocyclyl, which may be optionally substituted with one or more $R_{10a}$'s;

X is $CR_{20}R_{20}$;

$R_1$ is —C(O)$R_7$, —C(O)O$R_7$, —S(O)$_n$$R_7$ or —C(O)NR$_{28}$R$_{29}$;

$R_{2a}$, $R_{2b}$ and $R_{2c}$ are independently hydrogen, halo, —($C_1$-$C_6$)-alkyl or halo($C_1$-$C_6$)-alkyl-;

$R_{3a}$ is hydrogen, ($C_1$-$C_8$)alkyl or aryl, wherein the alkyl and aryl may be optionally substituted with one or more halo, —($C_1$-$C_6$)-alkyl, halo($C_1$-$C_6$)-alkyl, OH, —O($C_1$-$C_6$)-alkyl, halo($C_1$-$C_6$)alkyloxy, cyano, or nitro;

$R_{3b}$ is (a) hydrogen, (b) —OH, (c) $R_{46}$—S(O)$_n$—, (d) aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (e)-($C_1$-$C_8$)-alkyl, which may optionally be substituted with one or more substituents selected from the group consisting of: halo, —OH, halo($C_1$-$C_6$)alkyloxy, ($C_1$-$C_6$)-alkyloxy, (OH)—($C_1$-$C_6$)-alkyl-, cyano, ($C_3$-$C_6$)-cycloalkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (f) —O[(C=O)]$_s$aryl, which may optionally be substituted with one or more substituents selected from the group consisting of: halo, ($C_1$-$C_6$)-alkyl, halo($C_1$-$C_6$)alkyl, halo($C_1$-$C_6$)alkyloxy, ($C_1$-$C_6$)-alkyloxy, —COOH, —($C_1$-$C_6$)-alkylCOOH, —($C_1$-$C_6$)-alkyl($NH_2$)COOH, —($C_1$-$C_6$)-alkyl-$CO_2$($C_1$-$C_6$)-alkyl, —$CO_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (g) —O[(C=O)]$_s$heteroaryl, which may optionally be substituted with one or more substituents selected from the group consisting of: halo, ($C_1$-$C_6$)-alkyl, halo($C_1$-$C_6$)alkyl, halo($C_1$-$C_6$)alkyloxy, ($C_1$-$C_6$)-alkyloxy, —COOH, —($C_1$-$C_6$)-alkylCOOH, —($C_1$-$C_6$)-alkyl($NH_2$)COOH, —($C_1$-$C_6$)-alkyl-$CO_2$($C_1$-$C_6$)-alkyl, —$CO_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_4$, $R_5$ and $R_6$ are independently hydroxy or halo($C_1$-$C_4$)-alkyl; provided that (i) only one of $R_4$, $R_5$ or $R_6$ is hydroxy and (ii) $R_5$ and $R_6$ are halo($C_1$-$C_4$)-alkyl when $R_{3a}$ and $R_{3b}$ are hydrogen and $R_4$ is hydroxy;

$R_7$ is alkyl, cycloalkyl, aryl or heterocyclyl, wherein the alkyl, cycloalkyl, aryl, or heterocyclyl may be optionally substituted with one or more $R_{10b}$'s;

$R_{10a}$ is halo, —OH, —O[(C=O)]$_s$($C_1$-$C_6$)-alkyl, cyano, nitro, —COOH, —CO($C_1$-$C_6$)-alkyl, —$CO_2$($C_1$-$C_6$)-alkyl, —($C_1$-$C_6$)-haloalkyl, —($C_3$-$C_6$)-cycloalkyl or —($C_1$-$C_6$)-alkyl;

$R_{10b}$ is (a) halo; (b) —OH; (c) —O[(C=O)]$_s$($C_1$-$C_6$)-alkyl; (d) —O[(C=O)]$_s$($C_1$-$C_6$)-alkylaryl; (e) $R_{46}$—S(O)$_n$—; (f) —$CO_2$($C_1$-$C_6$)-alkyl; (g) aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, ($C_1$-$C_6$)-alkyl-S(O)$_n$—, cyano, nitro, —O($C_1$-$C_6$)-alkylaryl, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (h) heteroaryl optionally substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, —O($C_1$-$C_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (i) heterocyclo, other than heteroaryl, which is optionally substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (j) —($C_1$-$C_6$)-alkyl, which may optionally be substituted with one or more substituents selected from the group consisting of: halo, —OH, halo($C_1$-$C_6$)alkyloxy, ($C_1$-$C_6$)-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (k) —($C_3$-$C_8$)-cycloalkyl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; or (l) —O[(C=O)]$_s$aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, and (OH)—($C_1$-$C_6$)-alkyl-;

$R_{20}$ is hydrogen or ($C_1$-$C_4$)-alkyl;

$R_{28}$ and $R_{29}$ are independently hydrogen, aryl, ($C_1$-$C_6$) alkyl, halo($C_1$-$C_6$)alkyl, aryl($C_1$-$C_3$)alkyl or heterocyclyl, wherein the aryl, alkyl, arylalkyl and heterocyclyl may be optionally substituted with one or more $R_{50a}$'s;

or $R_{28}$ and $R_{29}$ are taken together with the nitrogen to which both are attached to form a 3- to 8-membered ring, which may optionally contain 1-4 heteroatoms selected from N, O, and S and be optionally substituted with one or more $R_{50a}$'s;

$R_{46}$ is (a) aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, —COOH, —($C_1$-$C_6$)-alkylCOOH, —($C_1$-$C_6$)-alkyl(NH$_2$)COOH, —($C_1$-$C_6$)-alkyl-CO$_2$($C_1$-$C_6$)-alkyl, —CO$_2$($C_1$-$C_6$)-alkyl, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (b) heteroaryl optionally substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, —COOH, —($C_1$-$C_6$)-alkylCOOH, —($C_1$-$C_6$)-alkyl(NH$_2$)COOH, —($C_1$-$C_6$)-alkyl-CO$_2$($C_1$-$C_6$)-alkyl, —CO$_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (c) —($C_1$-$C_6$)-alkyl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, —COOH, —($C_1$-$C_6$)-alkyl-COOH, —($C_1$-$C_6$)-alkyl(NH$_2$)COOH, —($C_1$-$C_6$)-alkyl-CO$_2$($C_1$-$C_6$)-alkyl, —CO$_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s;

$R_{50}$ is (a) hydrogen, (b) halo, (c) —OH, (d) ($C_1$-$C_6$)-alkyl, (e) halo($C_1$-$C_6$)-alkyl, (f) —O[(C=O)]$_s$($C_1$-$C_6$)-alkyl, or (g) (OH)—($C_1$-$C_6$)-alkyl-;

$R_{50a}$ is halo, —OH, —O[(C=O)]$_s$($C_1$-$C_6$)-alkyl, cyano, nitro, —COOH, —CO($C_1$-$C_6$)-alkyl, —CO$_2$($C_1$-$C_6$)-alkyl, —($C_1$-$C_6$)-haloalkyl, —($C_3$-$C_6$)-cycloalkyl or —($C_1$-$C_6$)-alkyl;

n is 0 to 2;

q is 1; and s is 0 or 1.

4. The compound of claim 1, wherein:

A is

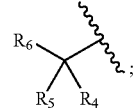

X is CH$_2$;

$R_1$ is —C(O)R$_7$, —C(O)OR$_7$ or —S(O)$_n$R$_7$;

$R_{2a}$, $R_{2b}$ and $R_{2c}$ are independently hydrogen, halo or —($C_1$-$C_6$)-alkyl;

$R_{3a}$ is hydrogen, ($C_1$-$C_8$)alkyl or aryl, wherein the alkyl and aryl may be optionally substituted with one or more halo, —($C_1$-$C_6$)-alkyl, halo($C_1$-$C_6$)-alkyl, OH, —O($C_1$-$C_6$)-alkyl, halo($C_1$-$C_6$)alkyloxy, cyano, or nitro;

$R_{3b}$ is (a) hydrogen, (b) —OH, (c) aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, cyano, nitro, aryl, which may be optionally substituted with one or more $R_{50}$'s; heteroaryl, which may be optionally substituted with one or more $R_{50}$'s, and heterocyclo, which may be optionally substituted with one or more $R_{50}$'s; (d) —($C_1$-$C_8$)-alkyl, which may be optionally substituted with one or more substituents selected from the group consisting of: halo, —OH, halo($C_1$-$C_6$)alkyloxy, ($C_1$-$C_6$)-alkyloxy, (OH)—($C_1$-$C_6$)-alkyl-, cyano, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (e) —O[(C=O)]$_s$aryl, which may optionally be substituted with one or more substituents selected from the group consisting of: halo, ($C_1$-$C_6$)-alkyl, halo($C_1$-$C_6$)alkyl, halo($C_1$-$C_6$)alkyloxy, ($C_1$-$C_6$)-alkyloxy, —COOH, —($C_1$-$C_6$)-alkylCOOH, —($C_1$-$C_6$)-alkyl-CO$_2$($C_1$-$C_6$)-alkyl, —CO$_2$($C_1$-$C_6$)-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; (f) —O[(C=O)]$_s$heteroaryl, which may optionally be substituted with one or more substituents selected from the group consisting of:

halo, $(C_1-C_6)$-alkyl, halo$(C_1-C_6)$alkyl, halo$(C_1-C_6)$alkyloxy, $(C_1-C_6)$-alkyloxy, —COOH, —$(C_1-C_6)$-alkyl COOH, —$(C_1-C_6)$-alkyl-CO$_2$$(C_1-C_6)$-alkyl, —CO$_2$$(C_1-C_6)$-alkyl, aryl, which may be optionally substituted with one or more $R_{50}$'s, heteroaryl, which may be optionally substituted with one or more $R_{50}$'s, and heterocyclo, which may be optionally substituted with one or more $R_{50}$'s; or (g) $R_{46}$—S(O)$_n$—;

$R_4$, $R_5$ and $R_6$ are independently hydroxy or halo$(C_1-C_4)$-alkyl; provided that (i) only one of $R_4$, $R_5$ or $R_6$ is hydroxy and (ii) $R_5$ and $R_6$ are halo$(C_1-C_4)$-alkyl when $R_{3a}$ and $R_{3b}$ are hydrogen and $R_4$ is hydroxy;

$R_7$ is alkyl, cycloalkyl, aryl or heterocyclyl, wherein the alkyl, cycloalkyl, aryl, or heterocyclyl may be optionally substituted with one or more $R_{10b}$'s;

$R_{10b}$ is (a) halo; (b) —OH; (c) —O[(C═O)]$_s$$(C_1-C_6)$-alkyl; (d) —O[(C═O)]$_s$$(C_1-C_6)$-alkylaryl; (e) $R_{46}$—S(O)$_n$—; (f) —CO$_2$$(C_1-C_6)$-alkyl; (g) aryl, which may optionally be substituted with one or more substituents selected from the group consisting of: halo, $(C_1-C_6)$-alkyl, halo$(C_1-C_6)$alkyl, $(C_1-C_6)$-alkyloxy, halo$(C_1-C_6)$alkyloxy, cyano, nitro, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (h) heteroaryl optionally substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, cyano, nitro, —O$(C_1-C_6)$-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (i) —$(C_1-C_6)$-alkyl, which may optionally be substituted with one or more substituents selected from the group consisting of: halo, halo$(C_1-C_6)$alkyloxy, $(C_1-C_6)$-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (j) —$(C_3-C_8)$-cycloalkyl, which may optionally be substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; or (k) —O[(C═O)]$_s$aryl, which may optionally be substituted with one or more substituents selected from the group consisting of: halo, $(C_1-C_6)$-alkyl, halo$(C_1-C_6)$alkyl, halo$(C_1-C_6)$alkyloxy, and $(C_1-C_6)$-alkyloxy;

$R_{46}$ is (a) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, —COOH, —$(C_1-C_6)$-alkylCOOH, —$(C_1-C_6)$-alkyl(NH$_2$)COOH, —$(C_1-C_6)$-alkyl-CO$_2$$(C_1-C_6)$-alkyl, —CO$_2$$(C_1-C_6)$-alkyl, aryl, heteroaryl, and heterocyclo; (b) heteroaryl optionally substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, —COOH, —$(C_1-C_6)$-alkylCOOH, —$(C_1-C_6)$-alkyl(NH$_2$)COOH, —$(C_1-C_6)$-alkyl-CO$_2$$(C_1-C_6)$-alkyl, —CO$_2$$(C_1-C_6)$-alkyl, aryl, heteroaryl and heterocyclo; or (c) —$(C_1-C_{10})$-alkyl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, aryl, heteroaryl, and heterocyclo;

$R_{50}$ is (a) hydrogen, (b) halo, (c) —OH, (d) $(C_1-C_6)$-alkyl, (e) halo$(C_1-C_6)$-alkyl, (f) —O[(C═O)]$_s$$(C_1-C_6)$-alkyl, or (g) (OH)—$(C_1-C_6)$-alkyl-;

n is 0 to 2;

q is 1; and s is 0 or 1.

5. The compound of claim 1, wherein:

A is

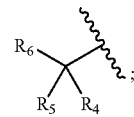

X is CH$_2$;

$R_1$ is —C(O)R$_7$ or —S(O)$_n$R$_7$;

$R_{2a}$, $R_{2b}$ and $R_2$ are independently hydrogen, halo or —$(C_1-C_6)$-alkyl;

$R_{3a}$ is hydrogen, $(C_1-C_8)$alkyl or aryl, wherein the alkyl and aryl may be optionally substituted with one or more halo, —$(C_1-C_6)$-alkyl, halo$(C_1-C_6)$-alkyl, OH, —O$(C_1-C_6)$-alkyl, halo$(C_1-C_6)$alkyloxy, cyano, or nitro;

$R_{3b}$ is (a) hydrogen, (b) —OH, (c) aryl, which may optionally be substituted with one or more substituents selected from the group consisting of: halo, —OH, $(C_1-C_6)$-alkyl, halo$(C_1-C_6)$alkyl, halo$(C_1-C_6)$alkyloxy, $(C_1-C_6)$-alkyloxy, (OH)—$(C_1-C_6)$-alkyl-, cyano, nitro, aryl, heteroaryl, and heterocyclo; (d) —$(C_1-C_8)$-alkyl, which may optionally be substituted with one or more substituents selected from the group consisting of: halo, —OH, halo$(C_1-C_6)$alkyloxy, $(C_1-C_6)$-alkyloxy, (OH)—$(C_1-C_6)$-alkyl-, cyano, aryl, heteroaryl, and heterocyclo; (e) —O[(C═O)]$_s$aryl, which may optionally be substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, —COOH, —$(C_1-C_6)$-alkylCOOH, —$(C_1-C_6)$-alkyl-CO$_2$$(C_1-C_6)$-alkyl, —CO$_2$$(C_1-C_6)$-alkyl, aryl, heteroaryl and heterocyclo; (f) —O[(C═O)]$_s$heteroaryl, which may optionally be substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, —COOH, —$(C_1-C_6)$-alkylCOOH, —$(C_1-C_6)$-alkyl-CO$_2$$(C_1-C_6)$-alkyl, —CO$_2$$(C_1-C_6)$-alkyl, aryl, heteroaryl, and heterocyclo; or (g) $R_{46}$—S(O)$_n$—;

$R_4$ and $R_6$ are halo($C_1$-$C_4$)-alkyl;

$R_5$ is hydroxy;

$R_7$ is alkyl, cycloalkyl, aryl or heterocyclyl, wherein the alkyl, cycloalkyl, aryl, or heterocyclyl may be optionally substituted with one or more $R_{10b}$'s;

$R_{10b}$ is (a) halo; (b) —OH; (c) —O[(C═O)]$_s$($C_1$-$C_6$)-alkyl; (d) —O[(C═O)]$_s$($C_1$-$C_6$)-alkylaryl; (e) —CO$_2$($C_1$-$C_6$)-alkyl; (f) aryl, which may optionally be substituted with one or more substituents selected from the group consisting of: halo, ($C_1$-$C_6$)-alkyl, halo($C_1$-$C_6$)alkyl, ($C_1$-$C_6$)-alkyloxy, halo($C_1$-$C_6$)alkyloxy, cyano, nitro, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (g) heteroaryl optionally substituted with one or more substituents selected from the group consisting of: halo, ($C_1$-$C_6$)-alkyl, halo($C_1$-$C_6$)alkyl, OH, halo($C_1$-$C_6$)alkyloxy, ($C_1$-$C_6$)-alkyloxy, cyano, nitro, —O($C_1$-$C_6$)-alkylaryl, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, haloalkyloxy, cyano, or nitro; (h) —($C_1$-$C_6$)-alkyl, which may optionally be substituted with one or more substituents selected from the group consisting of: halo, halo($C_1$-$C_6$)alkyloxy, ($C_1$-$C_6$)-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (i) —($C_3$-$C_8$)-cycloalkyl, which may optionally be substituted with one or more substituents selected from the group consisting of: halo, ($C_1$-$C_6$)-alkyl, halo($C_1$-$C_6$)alkyl, halo($C_1$-$C_6$)alkyloxy, ($C_1$-$C_6$)-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; or (j) —O[(C═O)]$_s$aryl, which may optionally be substituted with one or more substituents selected from the group consisting of: halo, ($C_1$-$C_6$)-alkyl, halo($C_1$-$C_6$)alkyl, halo($C_1$-$C_6$)alkyloxy, and ($C_1$-$C_6$)-alkyloxy;

$R_{46}$ is (a) aryl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, aryl, heteroaryl, and heterocyclo; (b) heteroaryl optionally substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, aryl, heteroaryl and heterocyclo; or (c)-($C_1$-$C_{10}$)-alkyl, which may optionally be substituted with one or more substituents selected from the group consisting of: halo, —OH, ($C_1$-$C_6$)-alkyl, halo($C_1$-$C_6$)alkyl, halo($C_1$-$C_6$)alkyloxy, ($C_1$-$C_6$)-alkyloxy, (OH)—($C_1$-$C_6$)-alkyl-, aryl, heteroaryl, and heterocyclo;

n is 0 to 2;

q is 1; and s is 0 or 1.

6. A compound of formula I:

or stereoisomers or pharmaceutically acceptable salts or N-oxides thereof, wherein:

A is

X is CH$_2$;

$R_1$ is —C(O)$R_7$;

$R_{2a}$, $R_{2b}$ and $R_{2c}$ are independently hydrogen or —($C_1$-$C_6$)-alkyl;

$R_{3a}$ is hydrogen, ($C_1$-$C_8$)alkyl or aryl, wherein the alkyl and aryl may be optionally substituted with one or more halo, —($C_1$-$C_6$)-alkyl, halo($C_1$-$C_6$)-alkyl, OH, —O($C_1$-$C_6$)-alkyl, halo($C_1$-$C_6$)alkyloxy, cyano, or nitro;

$R_{3b}$ is (a) hydrogen, (b) —OH, (c) aryl, which may optionally be substituted with one or more substituents selected from the group consisting of: halo, ($C_1$-$C_6$)-alkyl, halo($C_1$-$C_6$)alkyl, ($C_1$-$C_6$)-alkyloxy, cyano and nitro; (d)-($C_1$-$C_8$)-alkyl, which may optionally be substituted with one or more substituents selected from the group consisting of: halo, —OH, halo($C_1$-$C_6$)alkyloxy, ($C_1$-$C_6$)-alkyloxy, aryl and heteroaryl; (e) —O[(C═O)]$_s$aryl, which may optionally be substituted with one or more substituents selected from the group consisting of: halo, ($C_1$-$C_6$)-alkyl, halo($C_1$-$C_6$)alkyl, ($C_1$-$C_6$)-alkyloxy, —COOH, —($C_1$-$C_6$)-alkylCOOH, —($C_1$-$C_6$)-alkyl-CO$_2$($C_1$-$C_6$)-alkyl, —CO$_2$($C_1$-$C_6$)-alkyl and aryl; or (f) —O[(C═O)]$_s$heteroaryl, which may optionally be substituted with one or more substituents selected from the group consisting of: halo, ($C_1$-$C_6$)-alkyl, halo($C_1$-$C_6$)alkyl, ($C_1$-$C_6$)-alkyloxy, —COOH, —($C_1$-$C_6$)-alkylCOOH, —($C_1$-$C_6$)-alkyl-CO$_2$($C_1$-$C_6$)-alkyl, —CO$_2$($C_1$-$C_6$)-alkyl and aryl;

$R_4$ and $R_6$ are halo($C_1$-$C_4$)-alkyl;

$R_5$ is hydroxy;

$R_7$ is alkyl, aryl or heterocyclyl, wherein the alkyl, aryl, or heterocyclyl may be optionally substituted with one or more $R_{10b}$'s;

$R_{10b}$ is (a) halo; (b) —OH; (c) —O[(C═O)]$_s$($C_1$-$C_6$)-alkyl; (d) —O[(C═O)]$_s$($C_1$-$C_6$)-alkylaryl; (e) —CO$_2$($C_1$-$C_6$)-alkyl; (f) aryl, which may optionally be substituted with one or more substituents selected from the group consisting of: halo, $(C_1-C_6)$-alkyl, halo$(C_1-C_6)$ alkyl, $(C_1-C_6)$-alkyloxy, halo$(C_1-C_6)$-alkyloxy, cyano, nitro, aryl, which may be optionally substituted with one or more halo, alkyl, haloalkyl, OH, alkyloxy, haloalkyoxy, cyano, or nitro, heteroaryl, which may be optionally substituted with one or more halo, alkyl, haloalkyl, OH, alkyloxy, haloalkyoxy, cyano, or nitro; and heterocyclo, which may be optionally substituted with one or more halo, alkyl, haloalkyl, OH, alkyloxy, cyano, or nitro; (g) heteroaryl optionally substituted with one or more substituents selected from the group consisting of: halo, $(C_1-C_6)$-alkyl, halo$(C_1-C_6)$alkyl, —OH, $(C_1-C_6)$-alkyloxy, halo$(C_1-C_6)$-alkyloxy, cyano, nitro, —O$(C_1-C_6)$-alkylaryl, aryl, which may be optionally substituted with one or more halo, alkyl, haloalkyl, OH, alkyloxy, haloalkyoxy, cyano, or nitro; heteroaryl, which may be optionally substituted with one or more halo, alkyl, haloalkyl, OH, alkyloxy, haloalkyoxy, cyano, or nitro; and heterocyclo, which may be optionally substituted with one or more halo, alkyl, haloalkyl, OH, alkyloxy, haloalkyoxy, cyano, or nitro; (h) —$(C_1-C_6)$-alkyl, which may optionally be substituted with one or more substituents selected from the group consisting of: halo, halo$(C_1-C_6)$ alkyloxy, $(C_1-C_6)$-alkyloxy, aryl, which may be optionally substituted with one or more halo, alkyl, haloalkyl, OH, alkyloxy, haloalkyoxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; (i) —$(C_3-C_8)$-cycloalkyl, which may optionally be substituted with one or more substituents selected from the group consisting of: halo, $(C_1-C_6)$-alkyl, halo$(C_1-C_6)$alkyl, halo$(C_1-C_6)$alkyloxy, $(C_1-C_6)$-alkyloxy, aryl, which may be optionally substituted with one or more halo, alkyl, haloalkyl, OH, alkyloxy, haloalkyloxy, cyano, or nitro; heteroaryl, which may be optionally substituted with one or more halo, alkyl, haloalkyl, OH, alkyloxy, haloalkyloxy, cyano, or nitro, and heterocyclo, which may be optionally substituted with one or more halo, alkyl, haloalkyl, OH, alkyloxy, haloalkyloxy, cyano, or nitro; or (j) —O[(C=O)]$_s$aryl, which may optionally be substituted with one or more substituents selected from the group consisting of: halo, $(C_1-C_6)$-alkyl, halo$(C_1-C_6)$alkyl, halo$(C_1-C_6)$alkyloxy, and $(C_1-C_6)$-alkyloxy;

q is 1; and s is 0 or 1;

excluding compounds wherein: $R_{2a}$ is hydrogen, methyl or ethyl; $R_{2b}$, $R_{2c}$, $R_{3a}$ and $R_{3b}$ are hydrogen; $R_4$ and $R_6$ are $CF_3$; and $R_7$ is $C_{1-5}$ alkyl or cycloalkyl.

7. A compound of formula I:

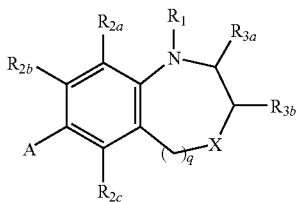

I or stereoisomers or pharmaceutically acceptable salts or N-oxides thereof, wherein:

A is

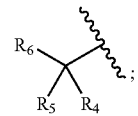

X is $CH_2$;

$R_1$ is —C(O)$R_7$;

$R_{2a}$, $R_{2b}$ and $R_{2c}$ are hydrogen;

$R_{3a}$ is hydrogen, $(C_1-C_8)$alkyl or aryl, wherein the alkyl and aryl may be optionally substituted with one or more halo, —$(C_1-C_6)$-alkyl, halo$(C_1-C_6)$-alkyl, OH, —O$(C_1-C_6)$-alkyl, halo$(C_1-C_6)$alkyloxy, cyano, or nitro;

$R_{3b}$ is (a) hydrogen, (b) —OH, (c) aryl, which may optionally be substituted with one or more substituents selected from the group consisting of: halo, $(C_1-C_6)$-alkyl, halo$(C_1-C_6)$alkyl, and $(C_1-C_6)$-alkyloxy; (d)-$(C_1-C_8)$-alkyl; (e) —Oaryl, which may optionally be substituted with one or more substituents selected from the group consisting of: halo, $(C_1-C_6)$-alkyl, halo$(C_1-C_6)$ alkyl, $(C_1-C_6)$-alkyloxy, —COOH, —$(C_1-C_6)$-alkyl-COOH, —$(C_1-C_6)$-alkyl-$CO_2(C_1-C_6)$-alkyl, —$CO_2(C_1-C_6)$-alkyl and aryl; or (f) —Oheteroaryl, which may optionally be substituted with one or more substituents selected from the group consisting of: halo, $(C_1-C_6)$-alkyl, halo$(C_1-C_6)$alkyl, $(C_1-C_6)$-alkyloxy, —COOH, —$(C_1-C_6)$-alkylCOOH, —$(C_1-C_6)$-alkyl-$CO_2(C_1-C_6)$-alkyl, —$CO_2(C_1-C_6)$-alkyl and aryl;

$R_4$ and $R_6$ are halo$(C_1-C_4)$-alkyl;

$R_5$ is hydroxy;

$R_7$ is alkyl or aryl, wherein the alkyl or aryl may be optionally substituted with one or more $R_{10b}$'s;

$R_{10b}$ is (a) halo; (b) —OH; (c) —O$(C_1-C_6)$-alkyl; (d) —$CO_2(C_1-C_6)$-alkyl; (e) aryl, which may optionally be substituted with one or more substituents selected from the group consisting of: halo, $(C_1-C_6)$-alkyl, halo$(C_1-C_6)$alkyl, $(C_1-C_6)$-alkyloxy, halo$(C_1-C_6)$-alkyloxy, cyano, nitro, aryl, which may be optionally substituted with one or more halo, alkyl, haloalkyl, OH, alkyloxy, haloalkyloxy, cyano, or nitro, heteroaryl, which may be optionally substituted with one or more halo, alkyl, haloalkyl, OH, alkyloxy, haloalkyloxy, cyano, or nitro; and heterocyclo, which may be optionally substituted with one or more halo, alkyl, haloalkyl, OH, alkyloxy, cyano, or nitro; (f) heteroaryl which may be optionally substituted with one or more halo, $(C_1-C_6)$-alkyl, halo $(C_1-C_6)$alkyl, —OH, $(C_1-C_6)$-alkyloxy, halo$(C_1-C_6)$-alkyloxy, cyano or nitro; (g) —$(C_1-C_6)$-alkyl, which may optionally be substituted with one or more substituents selected from the group consisting of: halo, halo $(C_1-C_6)$alkyloxy, and $(C_1-C_6)$-alkyloxy; (h) —$(C_3-C_8)$-cycloalkyl; or (i) —Oaryl; and q is 1; excluding compounds wherein $R_{3a}$ and $R_{3b}$ are hydrogen; $R_4$ and $R_6$ are —$CF_3$; and $R_7$ is $C_{1-5}$ alkyl.

8. A compound of claim 1, wherein the compound is selected from the group consisting of:
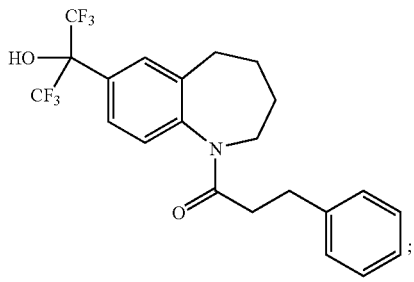
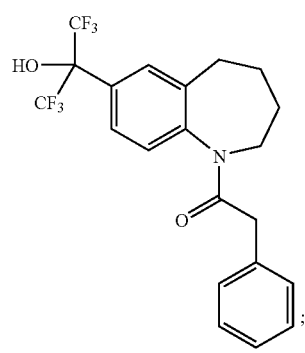
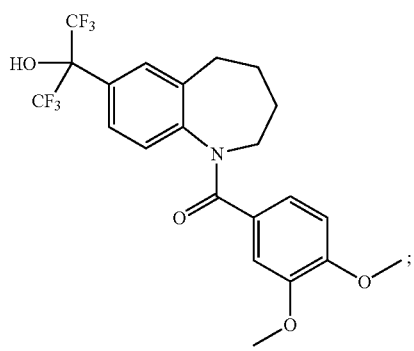
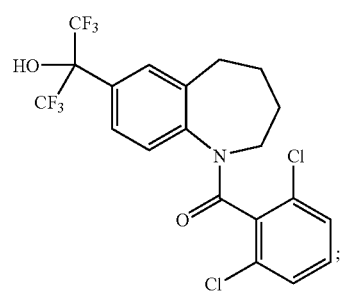
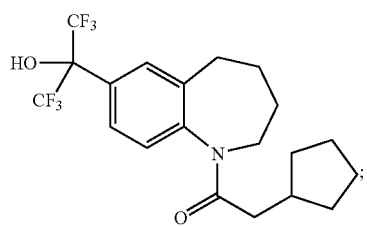
-continued
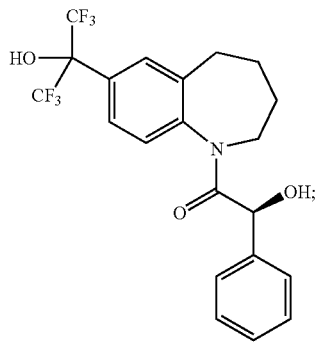
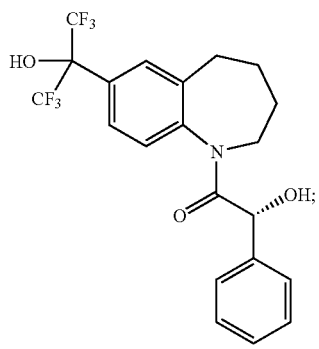
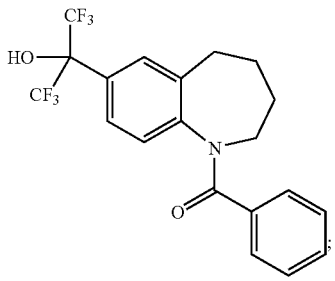
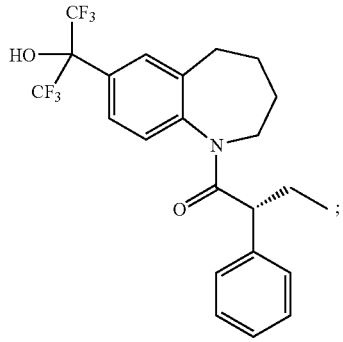
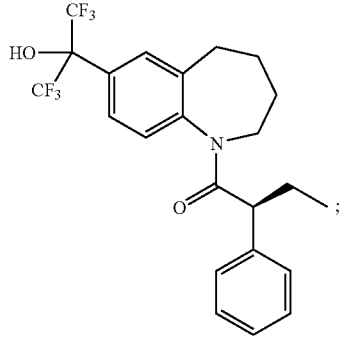

231
-continued
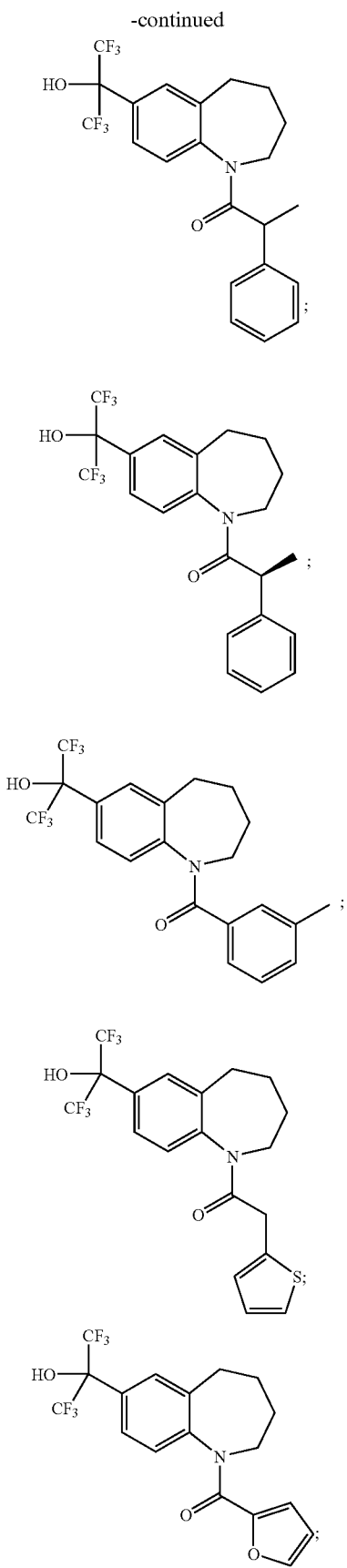
232
-continued
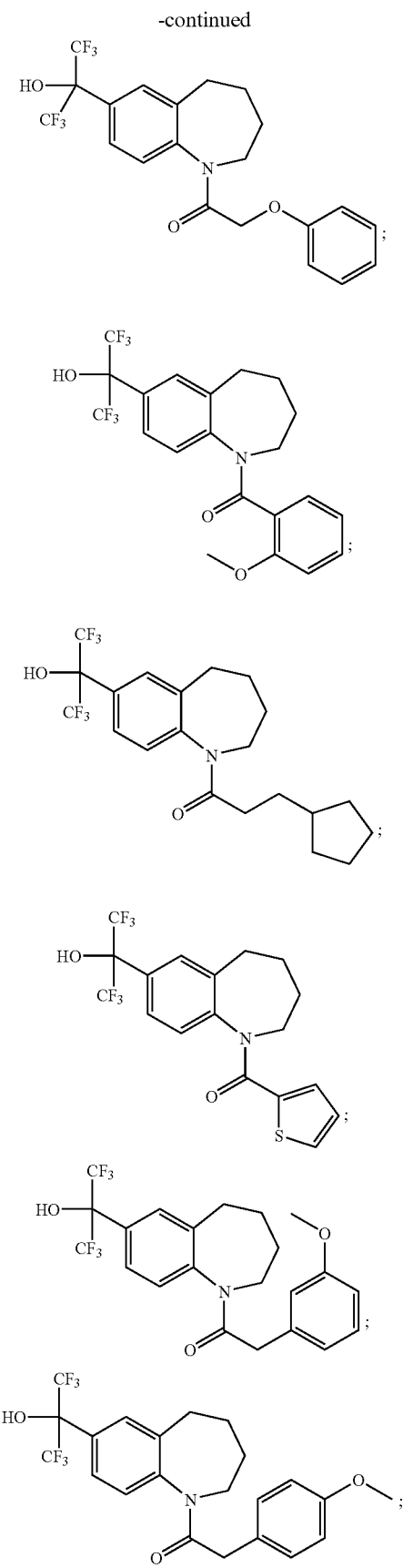

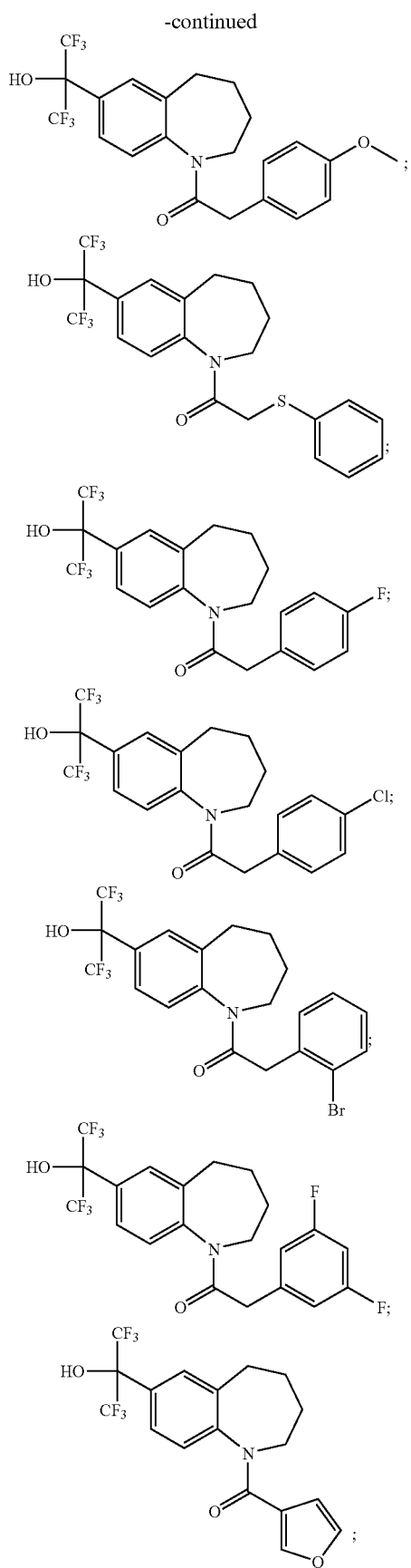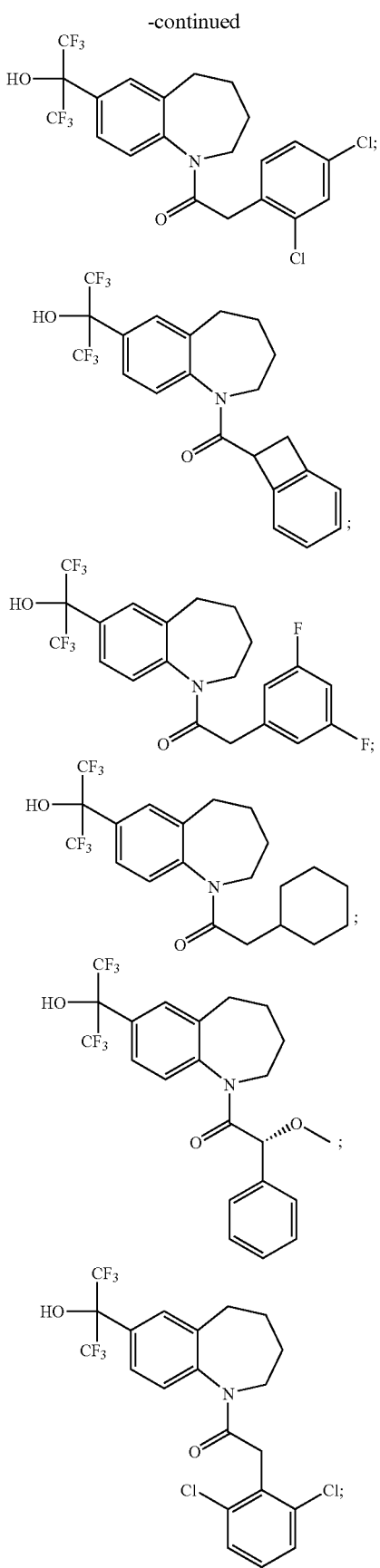

-continued
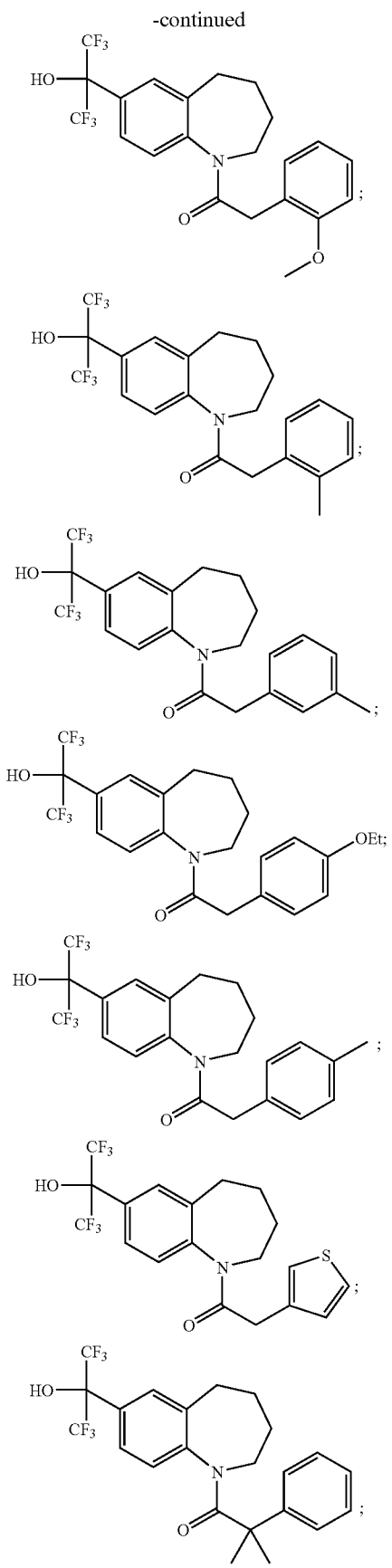
-continued
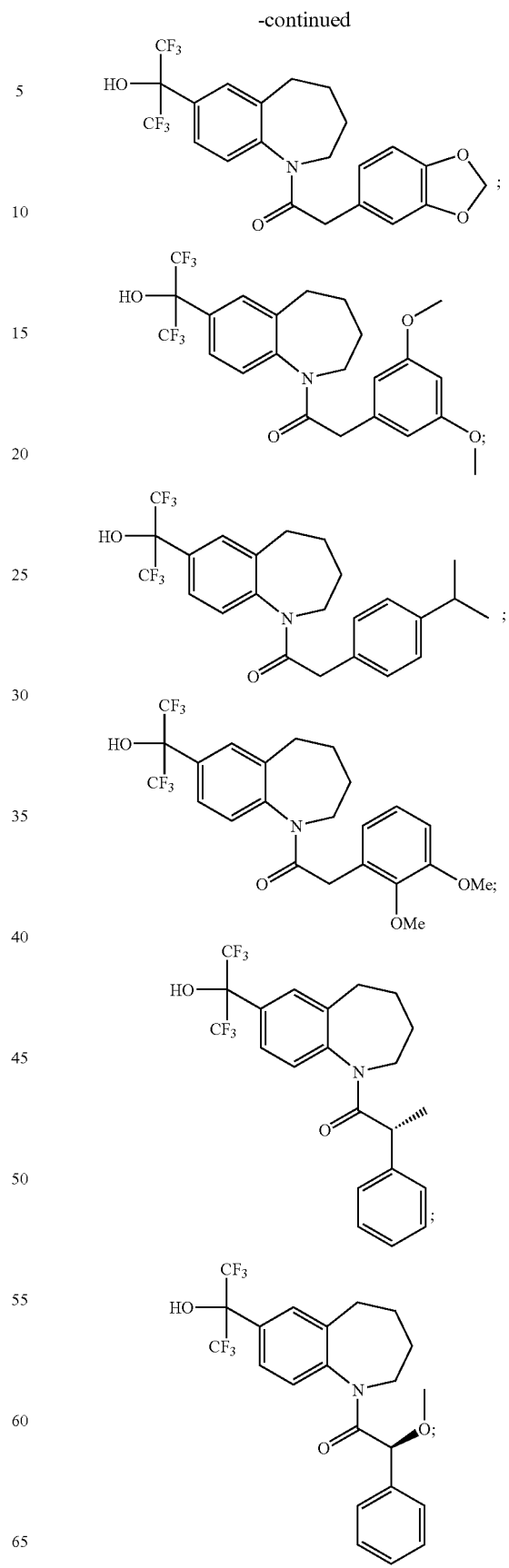

-continued
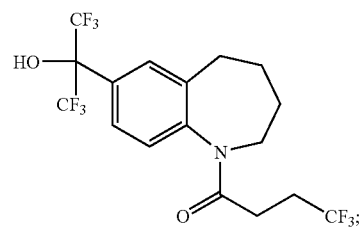
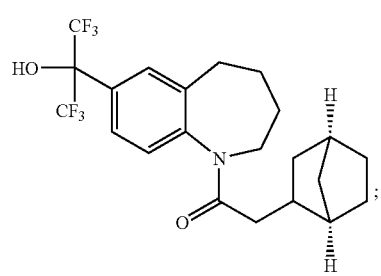
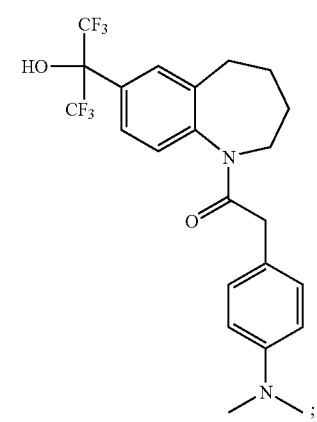
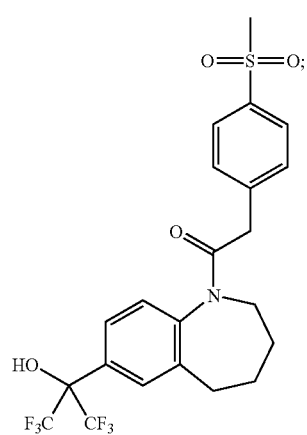
-continued
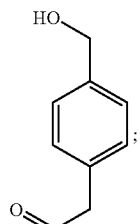
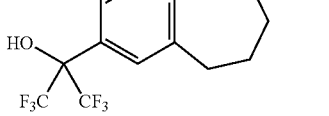
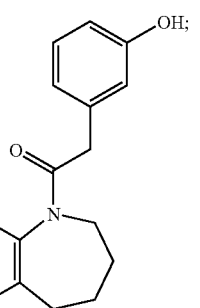
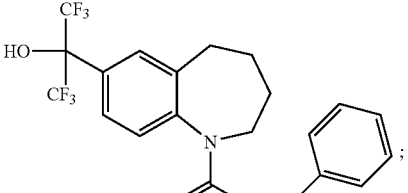
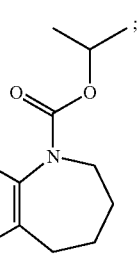
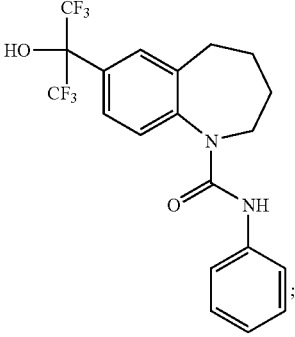

-continued
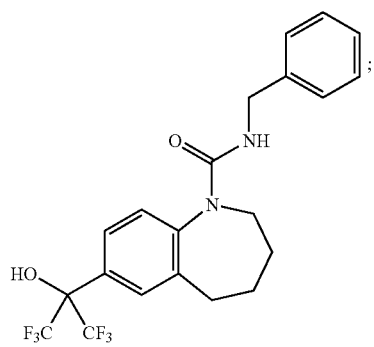
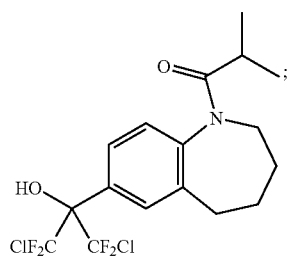
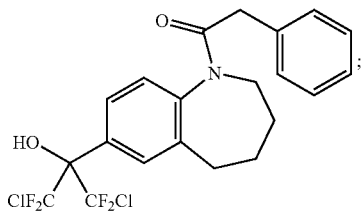
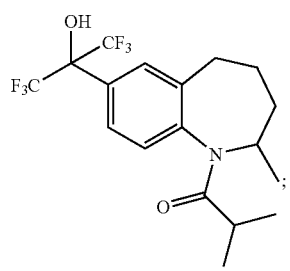
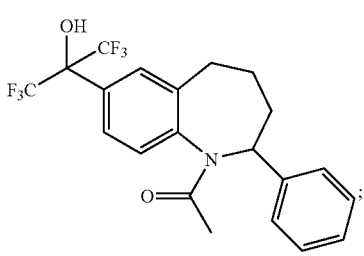
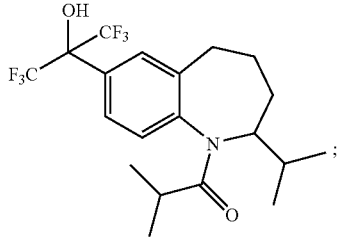
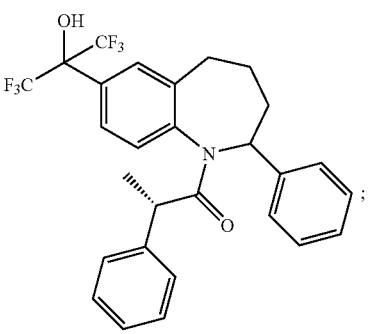

241
-continued
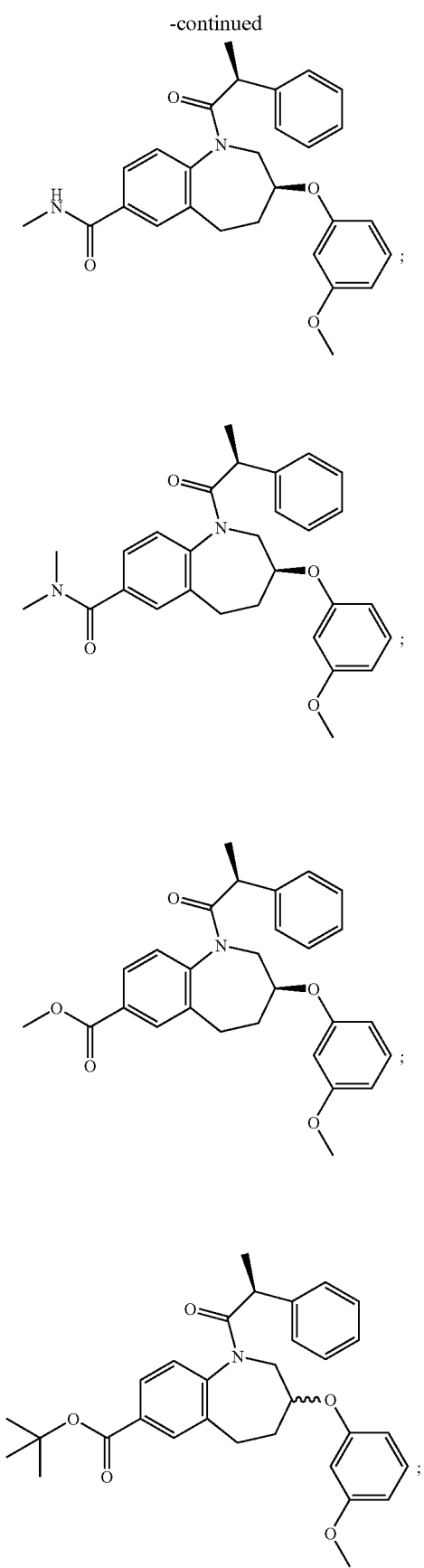
242
-continued
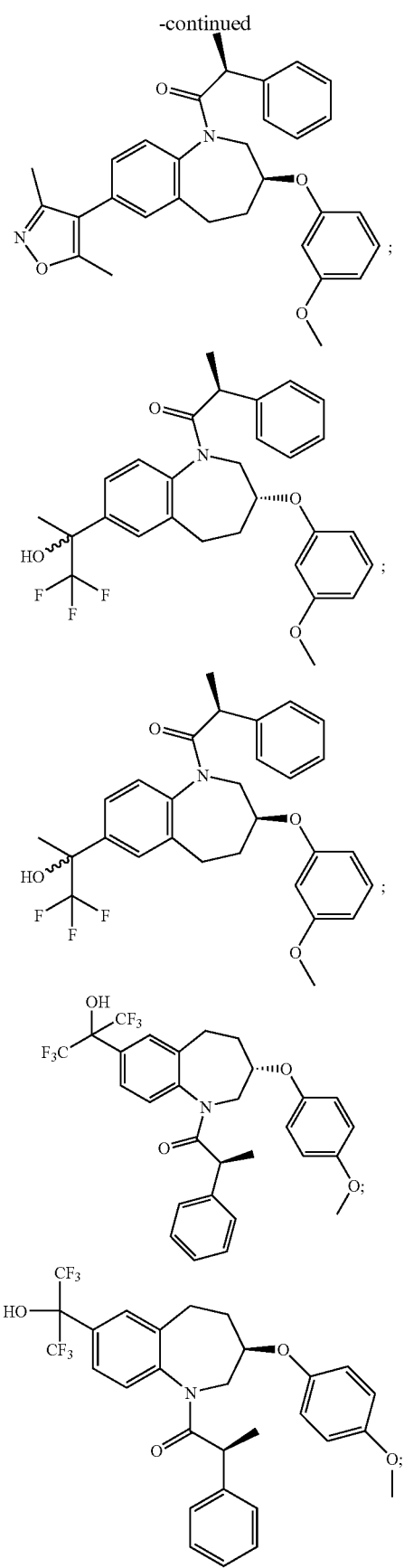

-continued
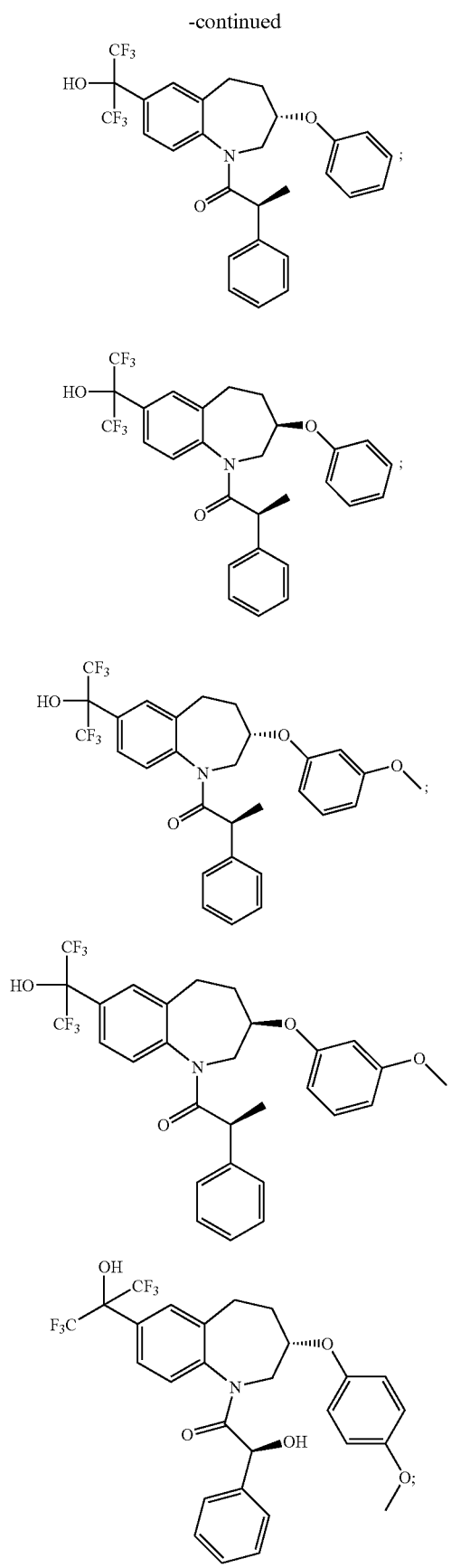
-continued
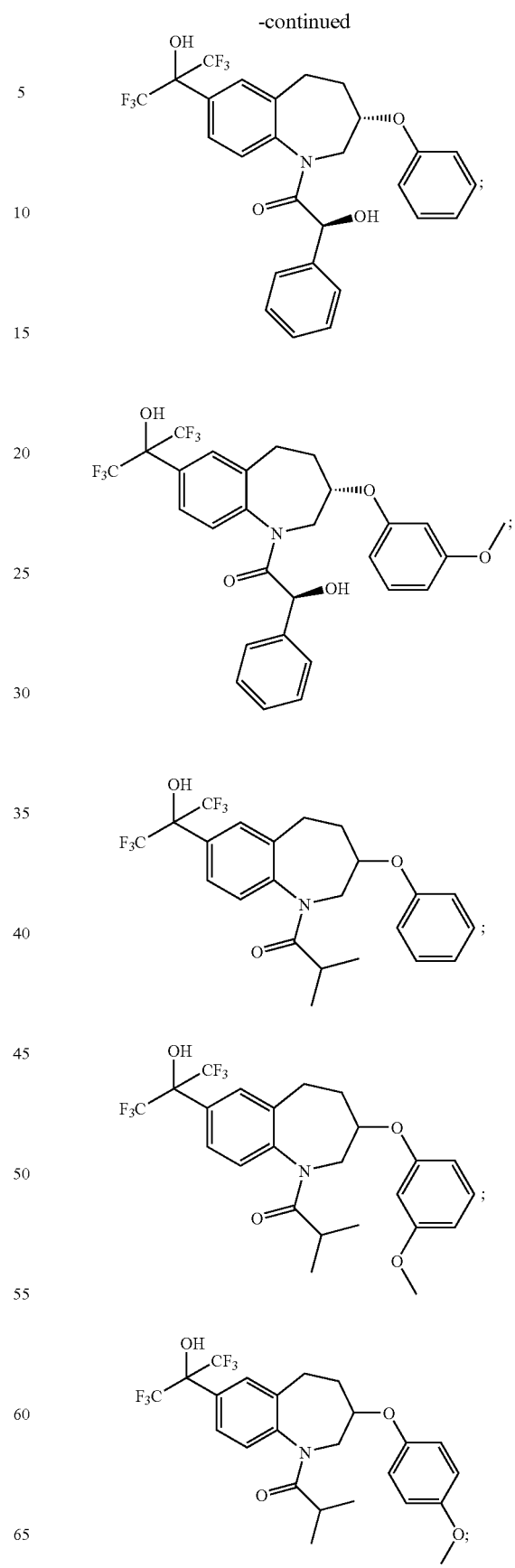

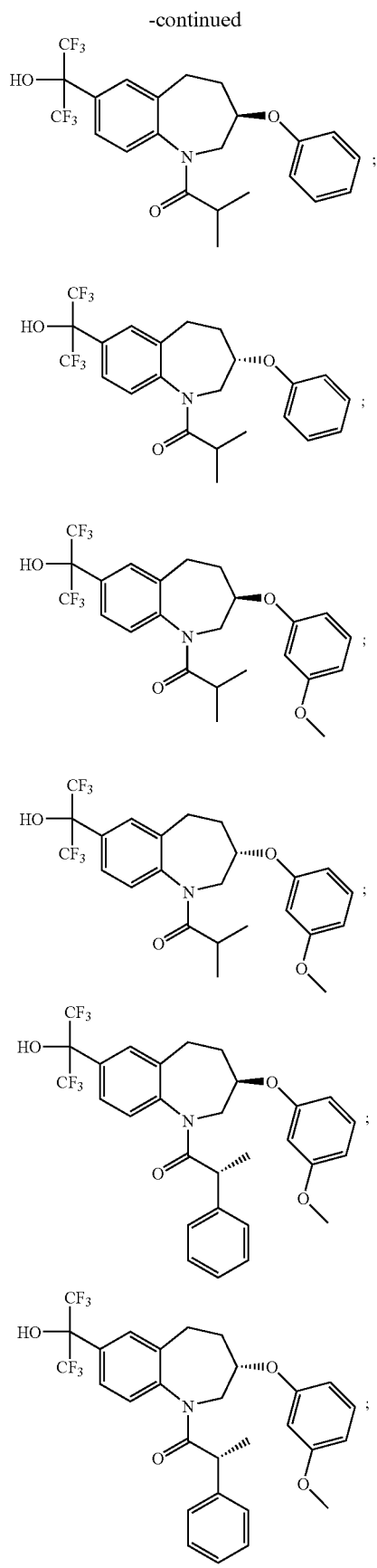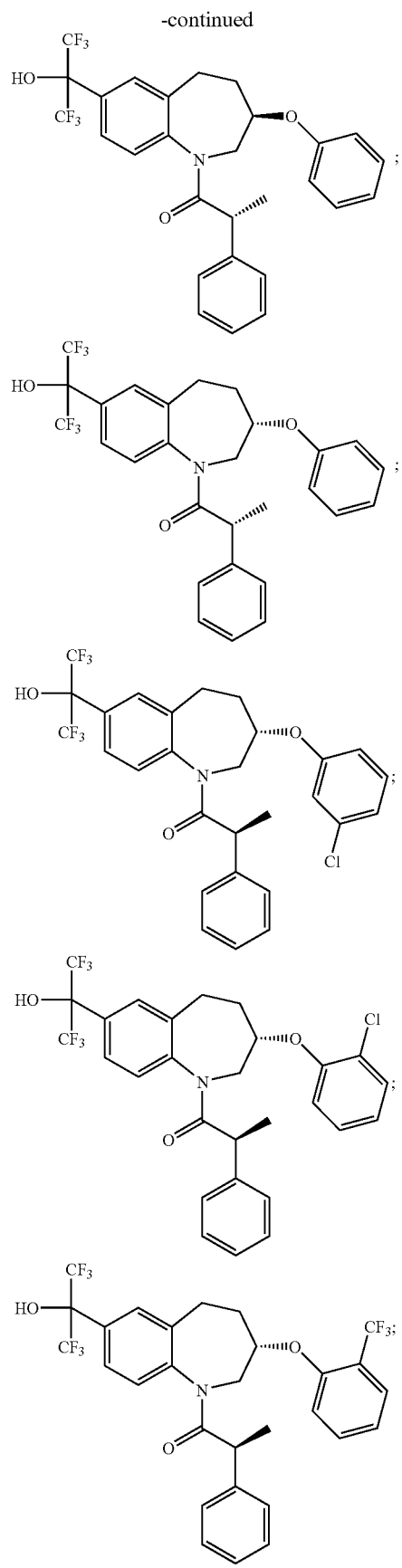

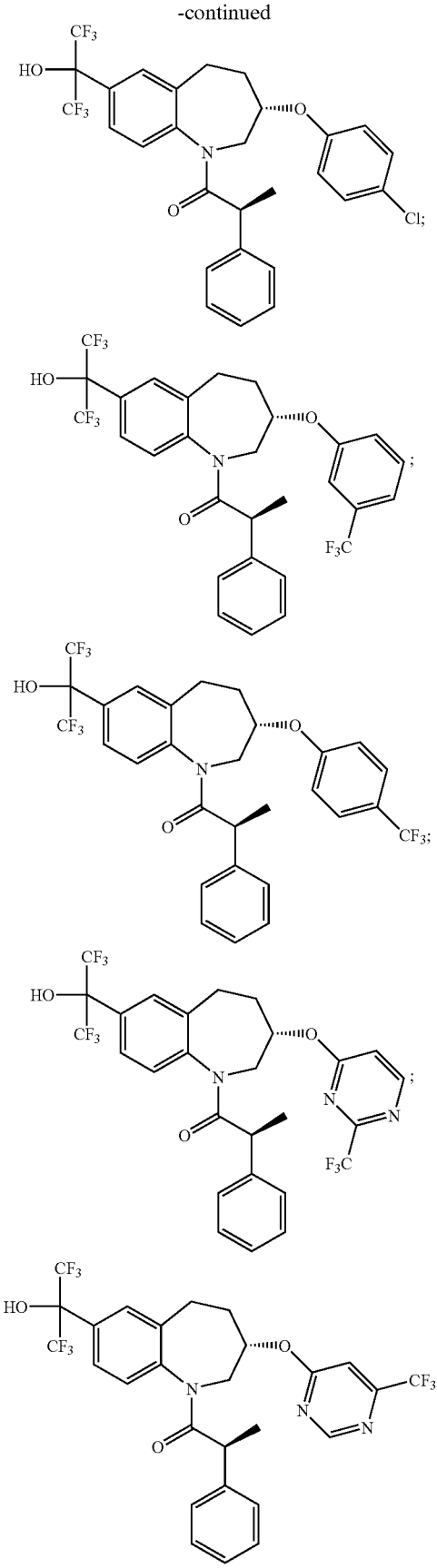
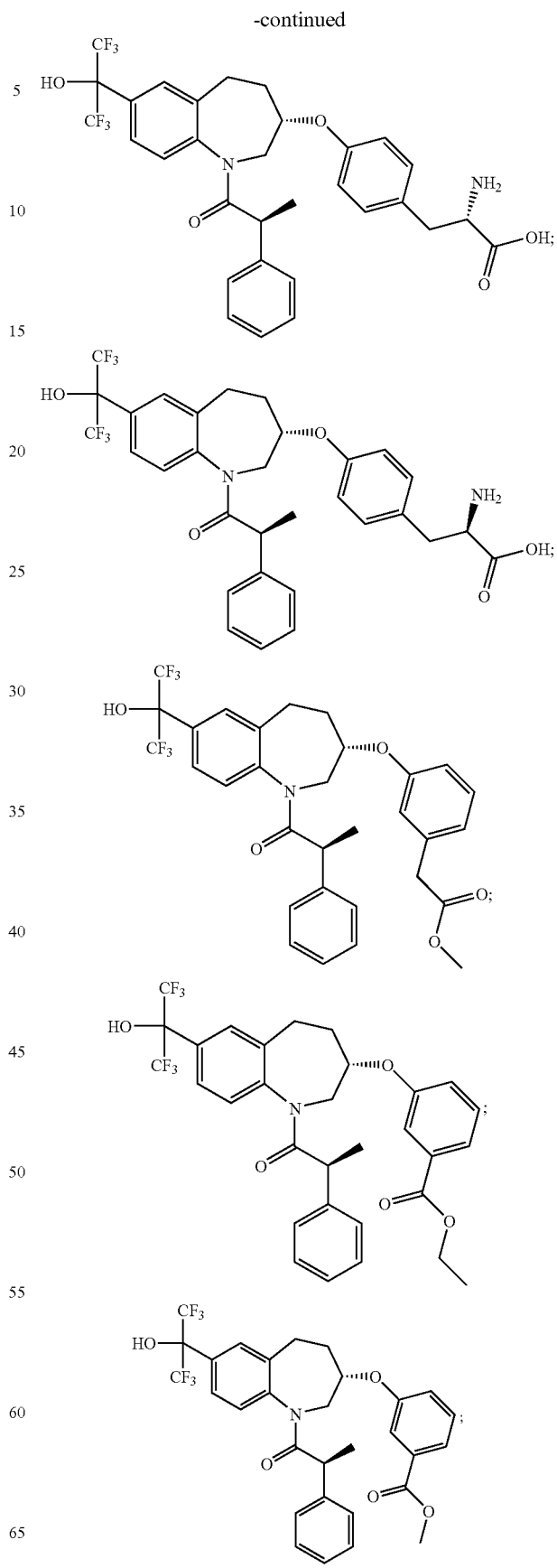

249
-continued
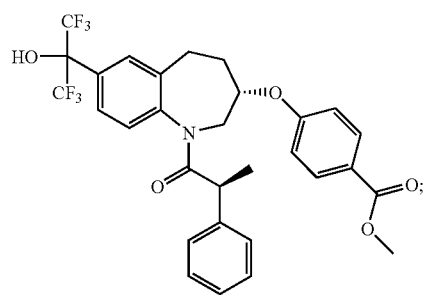
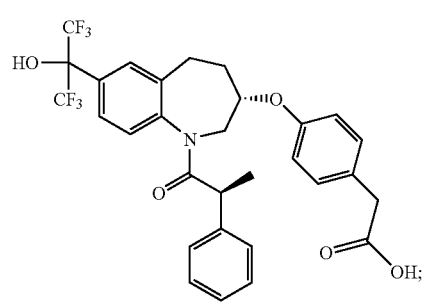
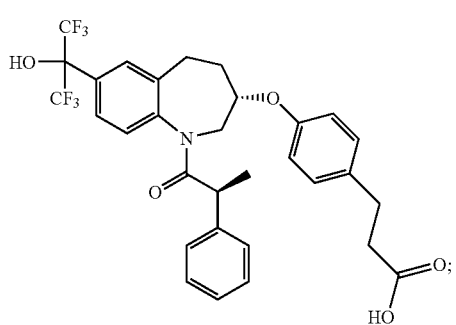
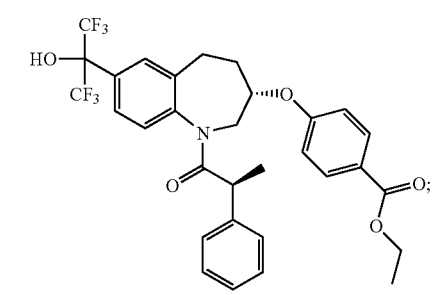
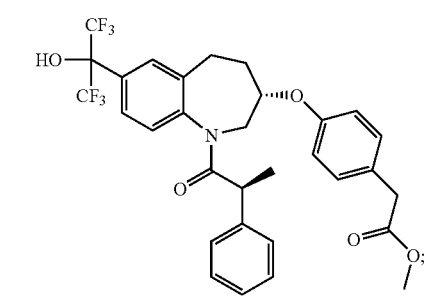
250
-continued
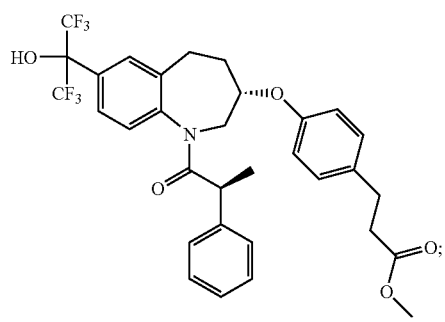
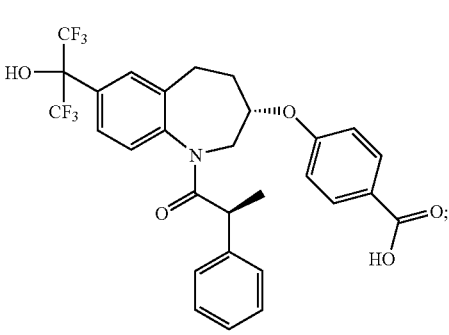
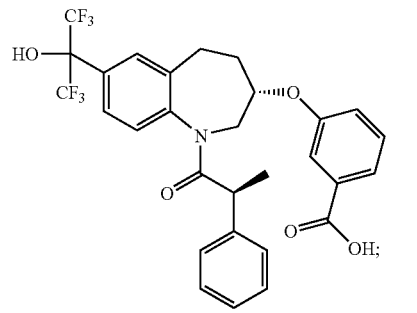
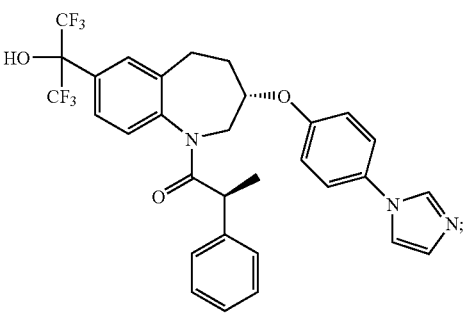
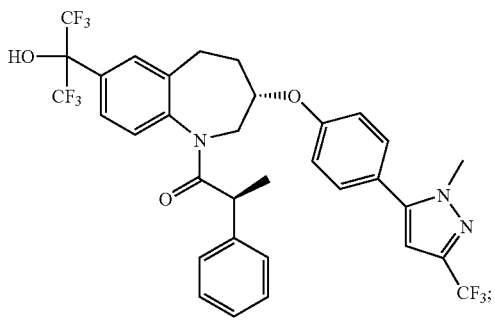

251
-continued
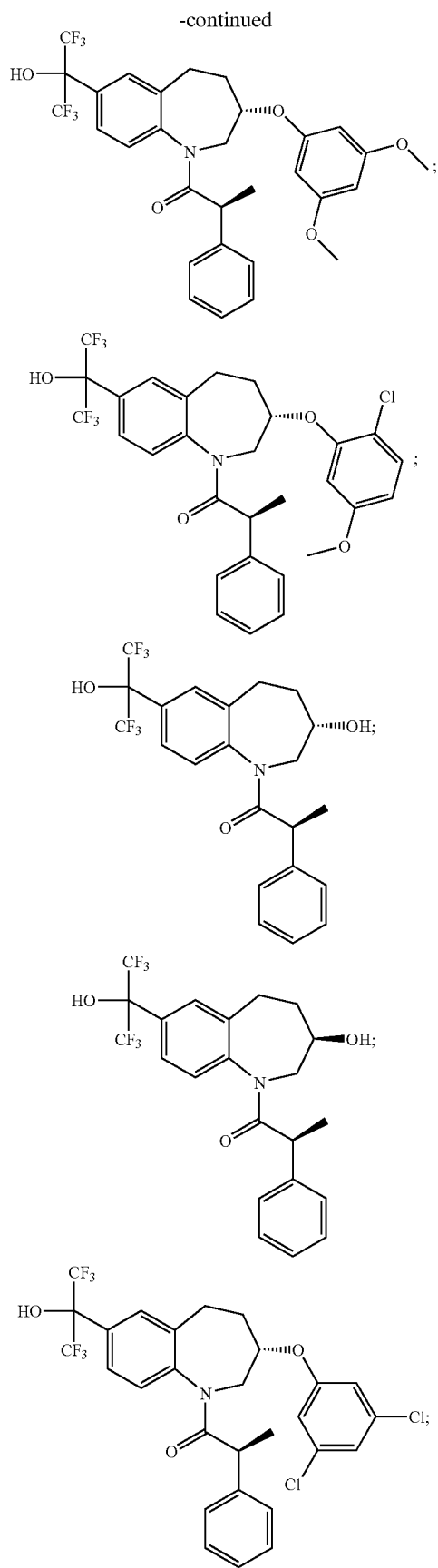
252
-continued
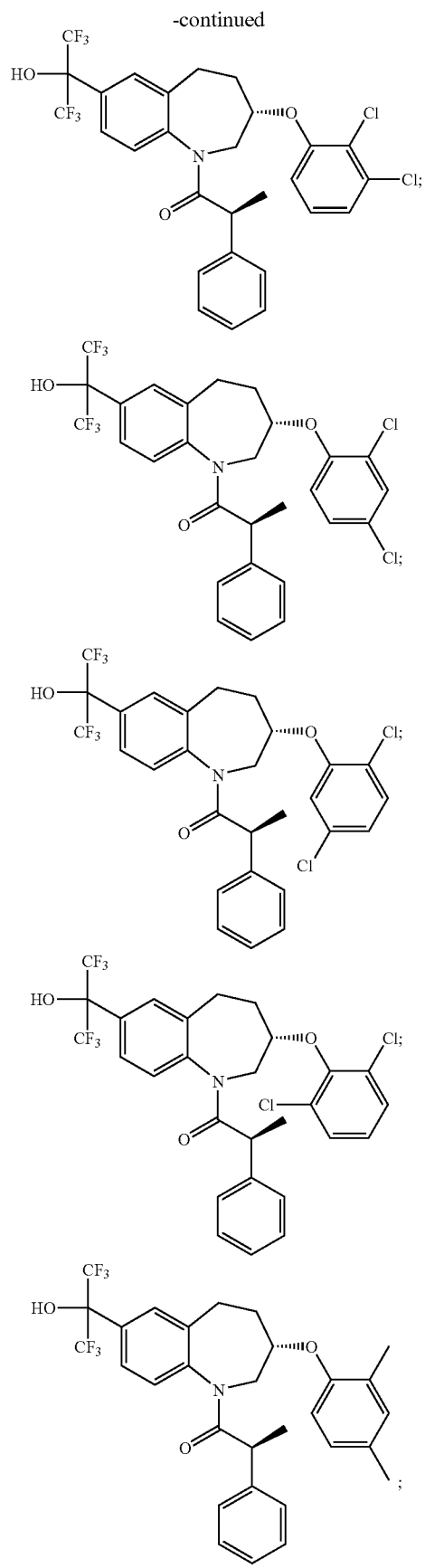

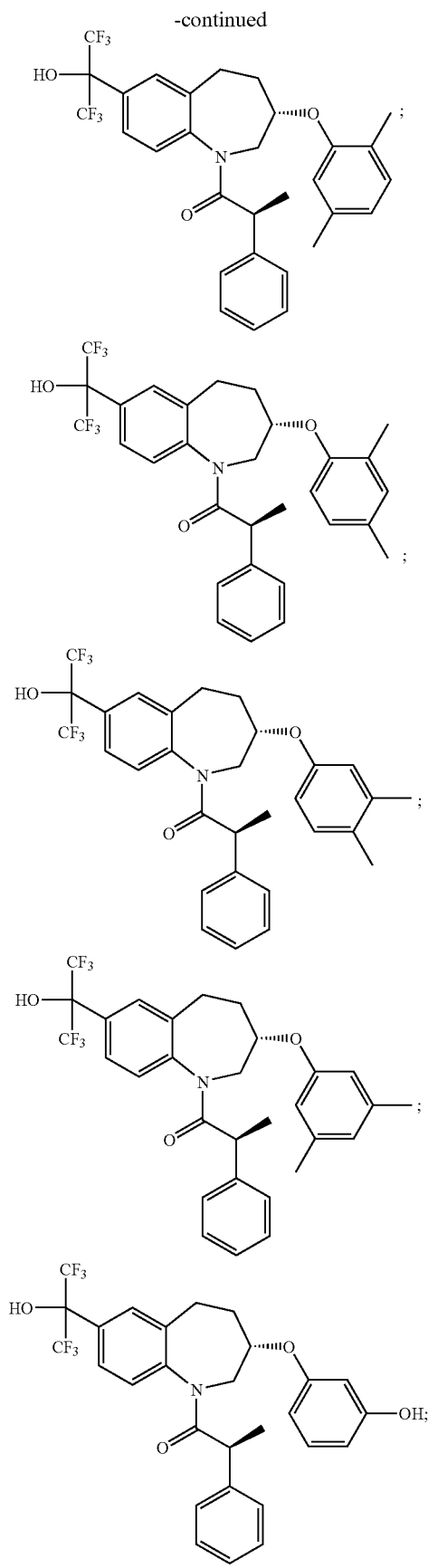
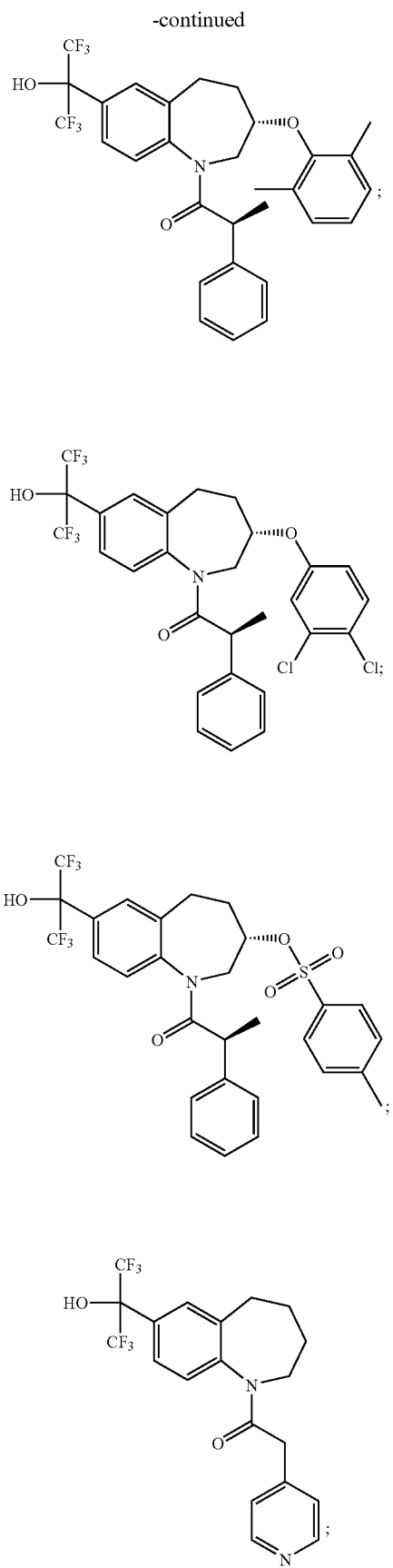

-continued
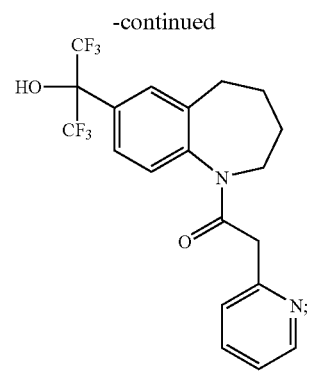
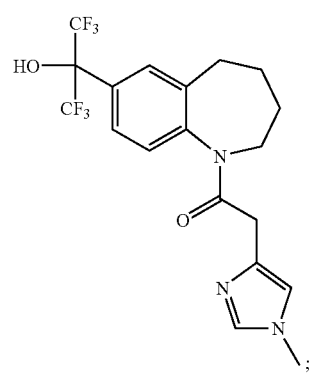
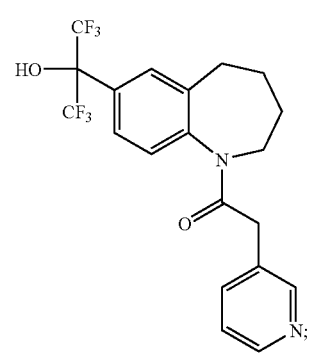
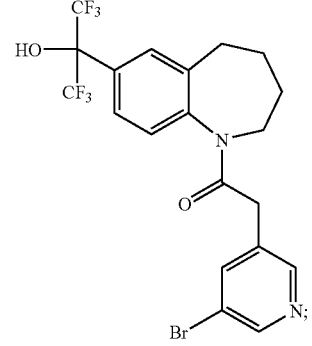
-continued
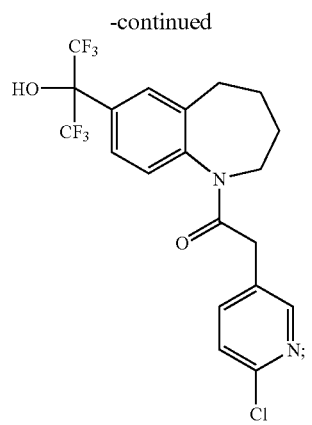
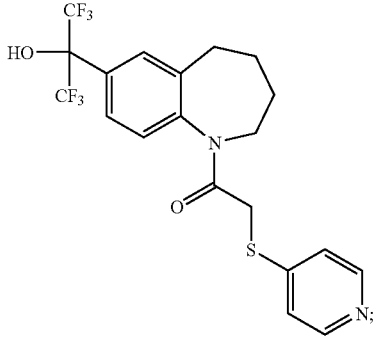
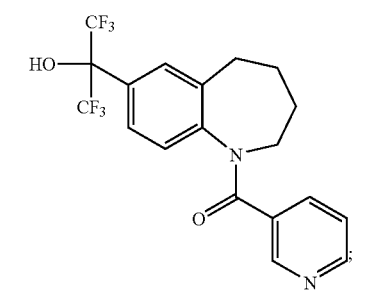
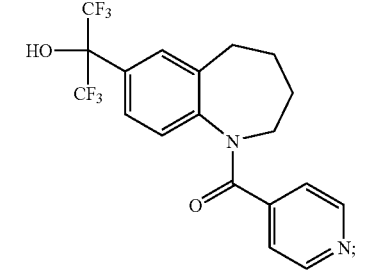

-continued
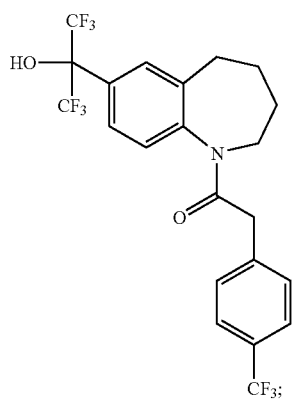
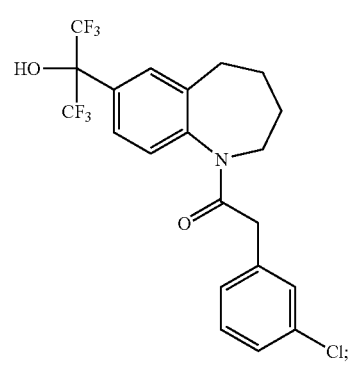
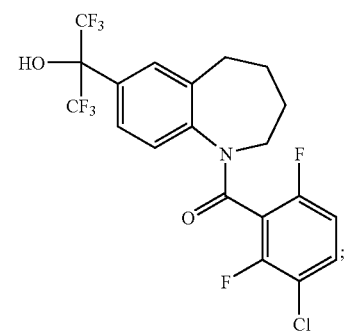
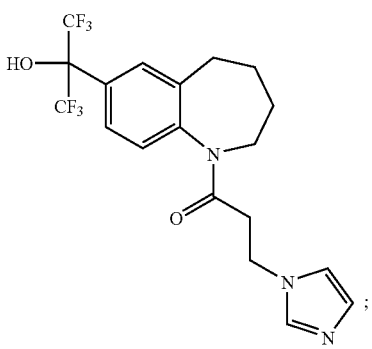
-continued
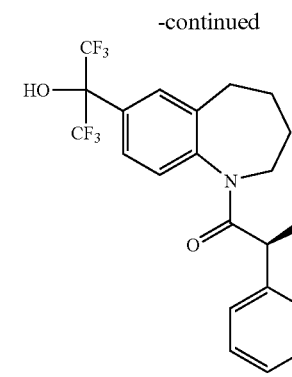
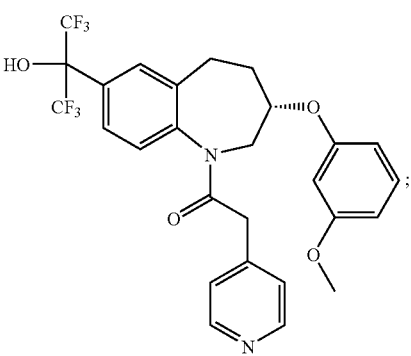
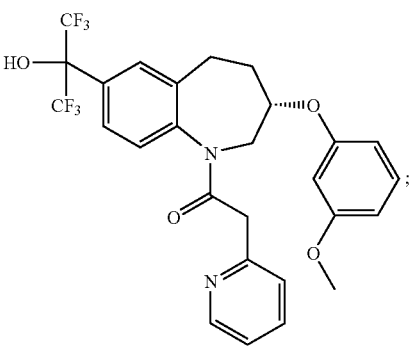
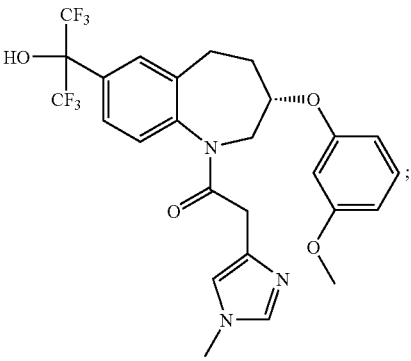

259
-continued
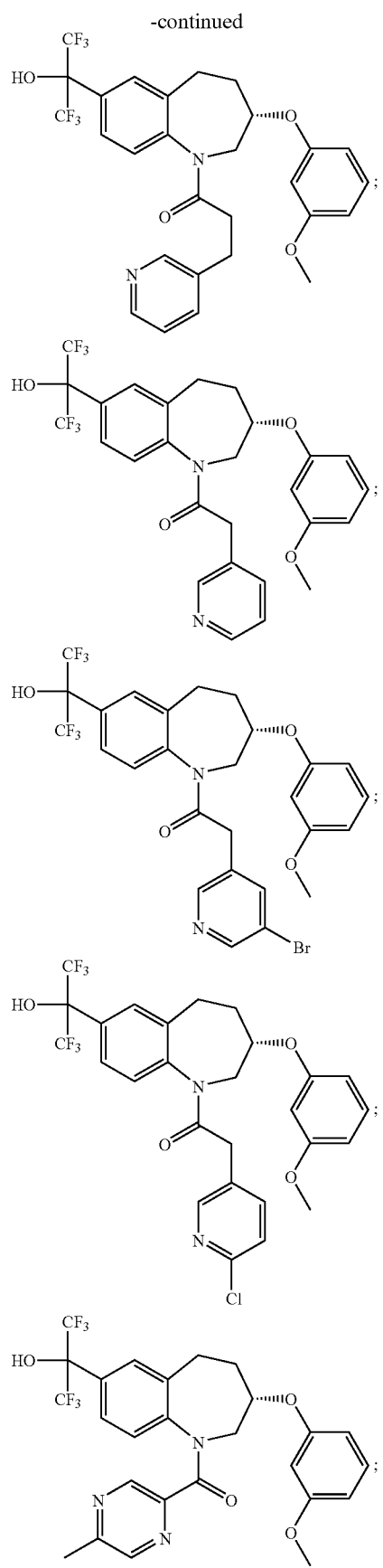
260
-continued
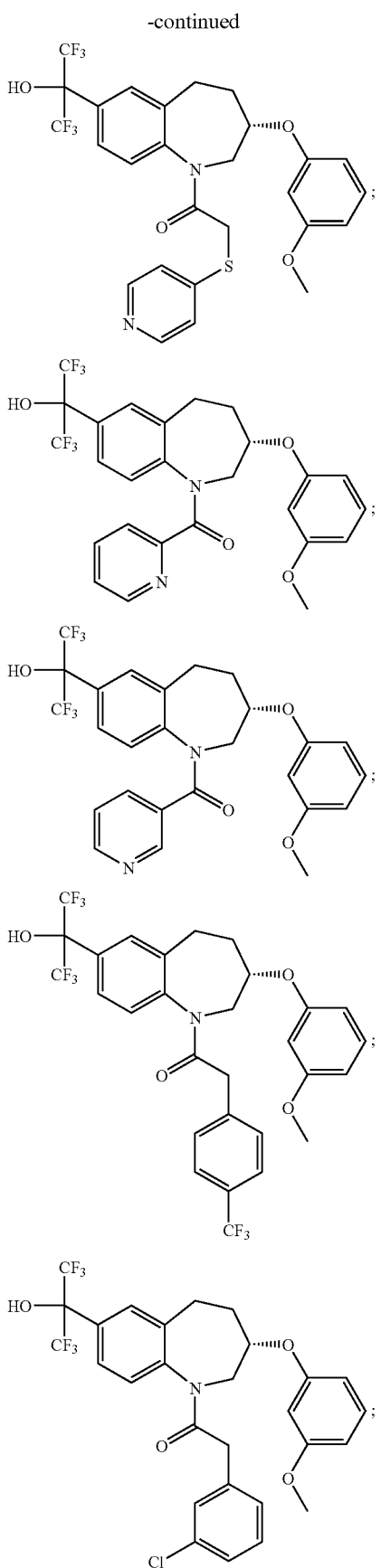

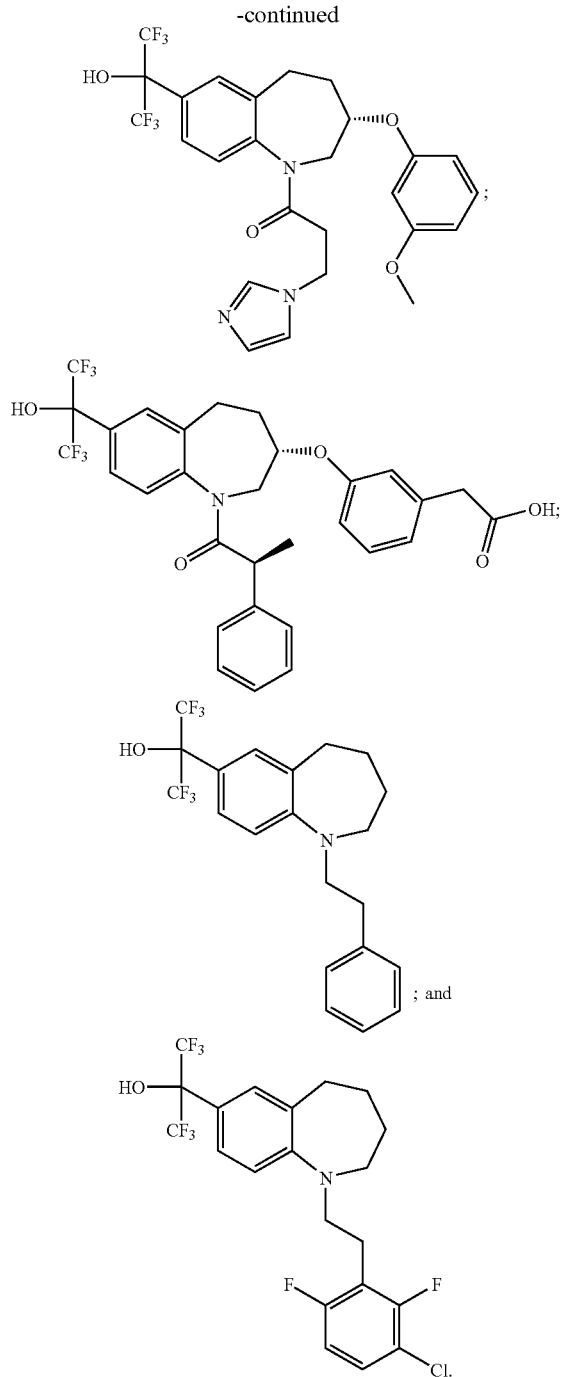

9. A pharmaceutical composition comprising at least one compound of claim 1.

10. The pharmaceutical composition of claim 9 further comprising a pharmaceutically acceptable carrier.

11. A pharmaceutical composition comprising at least one compound of claim 6.

12. The pharmaceutical composition of claim 11 further comprising a pharmaceutically acceptable carrier.

13. A pharmaceutical composition comprising at least one compound of claim 7.

14. The pharmaceutical composition of claim 13 further comprising a pharmaceutically acceptable carrier.

15. A pharmaceutical composition comprising at least one compound of claim 8.

16. The pharmaceutical composition of claim 15 further comprising a pharmaceutically acceptable carrier.

17. A compound of the formula

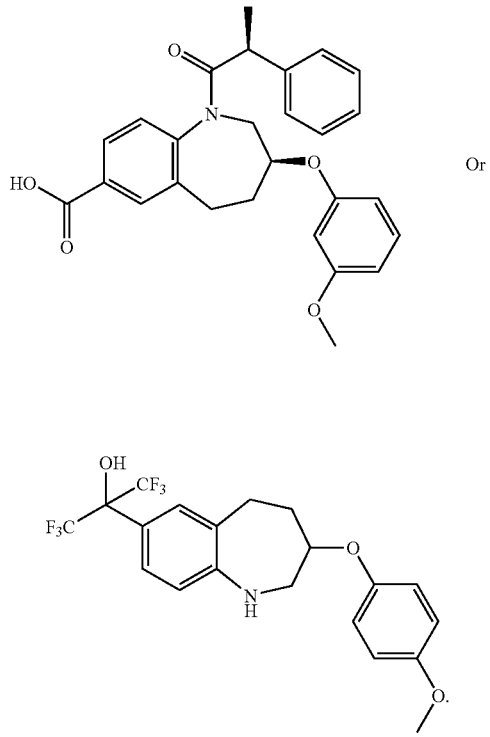

* * * * *

UNITED STATES PATENT AND TRADEMARK OFFICE
CERTIFICATE OF CORRECTION

| | | |
|---|---|---|
| PATENT NO. | : 7,741,317 B2 | |
| APPLICATION NO. | : 11/582673 | |
| DATED | : June 22, 2010 | |
| INVENTOR(S) | : Hannguang J. Chao et al. | |

It is certified that error appears in the above-identified patent and that said Letters Patent is hereby corrected as shown below:

On the Title Page:

Item (56), References Cited under FOREIGN PATENT DOCUMENTS:
    Delete "WO    WO 0054759    *    9/2000".

Claim 1:

Column 210, line 50, change "C(O)NR$_{28}$R$_{29}$" to -- —C(O)NR$_{28}$R$_{29}$ --.

Column 210, line 54, change "—S(O)R$_7$" to -- —S(O)$_n$R$_7$ --.

Column 215, line 42, change S(O)R$_7$" to -- —S(O)$_n$R$_7$ --.

Claim 2:
    Column 215, line 55, change "CO$_2$(C$_1$-C$_6$)-alkyl" to -- —CO$_2$(C$_1$-C$_6$)-alkyl --.

Claim 6:
    Column 227, line 52, change "CF$_3$" to -- —CF$_3$ --.

Signed and Sealed this
Fifteenth Day of November, 2011

David J. Kappos
*Director of the United States Patent and Trademark Office*

CERTIFICATE OF CORRECTION (continued)
U.S. Pat. No. 7,741,317 B2

In the Claims:

Claim 8 :

Column 234, lines 25 to 32, change " 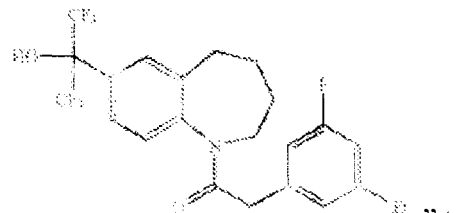 " to

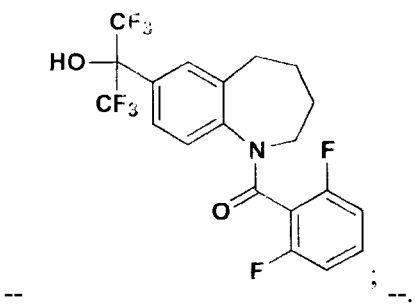

-- ; --.

Column 250, lines 55 to 66, change " 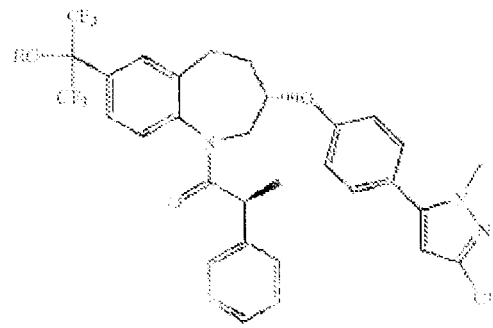 " to

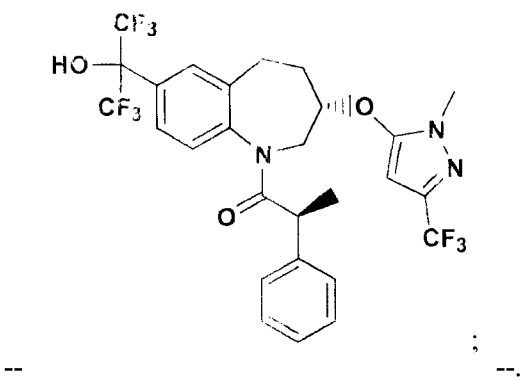

-- ; --.

CERTIFICATE OF CORRECTION (continued)
U.S. Pat. No. 7,741,317 B2

Column 254, line 50, after " 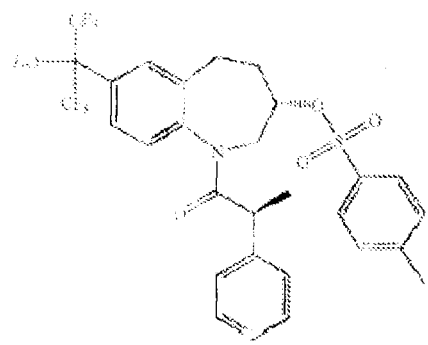 ' " insert

-- 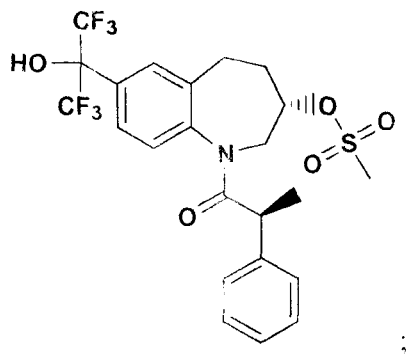 --.